US007998965B2

(12) United States Patent
Sum et al.

(10) Patent No.: US 7,998,965 B2
(45) Date of Patent: *Aug. 16, 2011

(54) GLUTAMATE AGGRECANASE INHIBITORS

(75) Inventors: Phaik-Eng Sum, Pomona, NY (US); Jerauld Stanley Skotnicki, Westfield, NJ (US); Steve Yik-Kai Tam, Wellesley, MA (US); Tarek Suhayl Mansour, New City, NY (US); David Brian How, Nyack, NY (US); Joshua James Sabatini, White Plains, NY (US); Jason Shaoyun Xiang, Winchester, MA (US); Eric Feyfant, Lexington, MA (US)

(73) Assignee: Wyeth LLC, Madison, NJ (US)

( * ) Notice: Subject to any disclaimer, the term of this patent is extended or adjusted under 35 U.S.C. 154(b) by 33 days.

This patent is subject to a terminal disclaimer.

(21) Appl. No.: 12/465,840

(22) Filed: May 14, 2009

(65) Prior Publication Data

US 2010/0010012 A1 Jan. 14, 2010

Related U.S. Application Data

(62) Division of application No. 11/484,005, filed on Jul. 11, 2006, now Pat. No. 7,553,873.

(60) Provisional application No. 60/697,590, filed on Jul. 11, 2005.

(51) Int. Cl.
| | | |
|---|---|---|
| A61K 31/4965 | (2006.01) | |
| A61K 31/16 | (2006.01) | |
| A61K 31/34 | (2006.01) | |
| A61K 31/44 | (2006.01) | |
| A61K 31/38 | (2006.01) | |
| C07C 237/00 | (2006.01) | |
| C07D 307/87 | (2006.01) | |
| C07D 333/02 | (2006.01) | |
| C07D 241/02 | (2006.01) | |

(52) U.S. Cl. ............. 514/255.06; 514/616; 514/469; 514/355; 514/438; 564/153; 549/462; 549/29; 544/336

(58) Field of Classification Search ............. 514/255.06, 514/616, 469, 355, 438; 564/153; 549/462; 549/29; 544/336
See application file for complete search history.

(56) References Cited

U.S. PATENT DOCUMENTS

| | | | |
|---|---|---|---|
| 4,769,389 A | 9/1988 | Makovec et al. | |
| 5,563,127 A | 10/1996 | Amparo et al. | |
| 5,597,825 A | 1/1997 | Himmelsbach et al. | |
| 5,602,179 A | 2/1997 | Makovec et al. | |
| 5,618,825 A | 4/1997 | Baldwin et al. | |
| 5,648,368 A | 7/1997 | Egbertson et al. | |
| 5,698,538 A | 12/1997 | Amparo et al. | |
| 5,736,559 A | 4/1998 | Himmelsbach et al. | |
| 5,756,810 A | 5/1998 | Baldwin et al. | |
| 5,852,007 A | 12/1998 | Chatterjee | |
| 5,922,763 A | 7/1999 | Himmelsbach et al. | |
| 6,242,422 B1 | 6/2001 | Karanewsky et al. | |
| 6,306,840 B1 | 10/2001 | Adams et al. | |
| 6,376,538 B1 | 4/2002 | Adams et al. | |
| 6,605,608 B1 | 8/2003 | Seko et al. | |
| 6,624,152 B2 | 9/2003 | Adams et al. | |
| 6,630,512 B2 | 10/2003 | Adams et al. | |
| 6,723,711 B2 | 4/2004 | Biediger et al. | |
| 2002/0019416 A1 | 2/2002 | Fukami et al. | |
| 2002/0091089 A1 | 7/2002 | Karanewsky et al. | |
| 2002/0169326 A1 | 11/2002 | Fukami et al. | |
| 2003/0013725 A1 | 1/2003 | Seko et al. | |
| 2003/0018016 A1 | 1/2003 | Adams et al. | |
| 2003/0083267 A1 | 5/2003 | Adams et al. | |
| 2003/0199692 A1 | 10/2003 | Biediger et al. | |
| 2003/0232806 A1 | 12/2003 | Seko et al. | |
| 2004/0009956 A1 | 1/2004 | Pei et al. | |
| 2004/0063959 A1 | 4/2004 | Fukami et al. | |
| 2004/0259804 A1 | 12/2004 | Karanewsky | |
| 2005/0049242 A1 | 3/2005 | Robinson et al. | |

FOREIGN PATENT DOCUMENTS

| | | |
|---|---|---|
| DE | 3332633 | 4/1985 |
| EP | 496378 | 7/1992 |
| EP | 751765 | 1/1997 |
| EP | 805796 | 11/1997 |
| EP | 854863 | 7/1998 |
| EP | 997147 | 5/2000 |
| EP | 1090912 | 4/2001 |
| EP | 1142867 | 10/2001 |
| EP | 1189881 | 3/2002 |
| EP | 1213288 | 6/2002 |
| GB | 1 108 819 | 4/1968 |
| GB | 2292149 | 2/1996 |
| JP | 06192199 | 7/1994 |
| JP | 11080191 | 3/1999 |
| JP | 11116541 | 4/1999 |
| JP | 2002145849 | 5/2002 |
| WO | WO-94/12181 | 6/1994 |
| WO | WO-95/24186 | 9/1995 |
| WO | WO-96/20689 | 7/1996 |
| WO | WO-96/22966 | 8/1996 |
| WO | WO-97/03951 | 2/1997 |
| WO | WO-97/21690 | 6/1997 |
| WO | WO-99/02146 | 1/1999 |

(Continued)

OTHER PUBLICATIONS

Baker et al., Journal of Pharmaceutical Sciences (1966), 55(3), p. 295-302.*
"Poster at the OARSI World Congress on Osteoarthritis 2007 held from Dec. 6-9, 2007 in Fort Lauderdale, Florida".
F. Makovec et al. "New glutamic and aspartic derivatives with potent CCK-antagonistic activity" Eur. J. Med. Chem.-Chim. Ther., vol. 21, No. 1, 1986, pp. 9-20, XP009082343.
Baker et al., Journal of Pharmaceutical Science, 1966, 55(3), pp. 295-300, Abstract from STN search report.
Kerwin, et al., "Hybrid Cholecystokinin (CCK) Antagonists: New Implications in the Design and Modification of CCK Antagonists", J. Med. Chem., 32:739-742 (1989).

(Continued)

*Primary Examiner* — Yong Chu
(74) *Attorney, Agent, or Firm* — Ram W. Sabnis

(57) ABSTRACT

The present invention relates to modulators of metalloproteinase activity.

10 Claims, 2 Drawing Sheets

FOREIGN PATENT DOCUMENTS

| | | |
|---|---|---|
| WO | WO-99/48371 | 9/1999 |
| WO | WO-00/00470 | 1/2000 |
| WO | WO-00/23421 | 4/2000 |
| WO | WO-00/27808 | 5/2000 |
| WO | WO-00/68188 | 11/2000 |
| WO | WO-01/83445 | 11/2001 |
| WO | WO-01/90077 | 11/2001 |
| WO | WO 03/093498 | 11/2003 |
| WO | WO-2005/019167 | 3/2005 |
| WO | WO-2005/040355 | 5/2005 |
| WO | WO-2005/058808 | 6/2005 |
| WO | WO-2005/060456 | 7/2005 |

OTHER PUBLICATIONS

Kuefner, et al., "Carboxypeptidase-Mediated Release of Methotrexate from Methotrexate α-Peptides", Biochemistry, 28:2288-2297 (1989).

International Search Report, Issued Apr. 27, 2007, in PCT/US2006/027066.

Augeri, et al., "Potent and Selective Non-Cysteine-Containing Inhibitors of Protein Farnesyltransferase", Journal of Medicinal Chemistry, 41(22):4288-4300 (1998).

Boger, et al., "Conformationally Restricted Analogues Designed for Selective Inhibition of GAR Tfase Versus Thymidylate Synthase or Dihydrofolate Reductase", Bioorg. Med. Chem., 8:1075-1086 (2000).

Database Caplus [Online], XP002413088, "Inhibitory Effect of Methotrexate on Matrix Metalloproteinase-1 (Collagenase) Production by Synovial Fibroblasts", Database Accession No. 1997:137341.

Makovec, et al., "Structure-Antigastrin Activity Relationships of New (R)-4-Benzamido-5-oxopentanoic Acid Derivatives", Journal of Medicinal Chemistry, 35(1):28-38 (1992).

Martinelli. et al., "Methotrexate Analogues. 12. Synthesis and Biological Properties of Some Aza Homologues", Journal of Medicinal Chemistry, 22(7):869-874 (1979).

Piper, et al., "Syntheses of α- and γ-Substituted Amides, Peptides, and Esters of Methotrexate and Their Evaluation as Inhibitors of Folate Metabolism", Journal of Medicinal Chemistry, 25(2):182-187 (1982).

Springer, et al., "Optimization of Alkylating Agent Prodrugs Derived from Phenol and Aniline Mustards: A New Clinical Candidate Prodrug (ZD2767) for Antibody-Directed Enzyme Prodrug Therapy (ADEPT)", Journal of Medicinal Chemistry, 38(26):5051-5065 (1995).

PCT Invitation to Pay Additional Fees with Partial International Search Report from PCT Application No. PCT/US2006/027066, (2006).

Beyermann, et al., "Rapid Continuous Peptide Synthesis via FMOC Amino Acid Chloride Coupling and 4-(aminomethyl)piperidine Deblocking", Journal of Organic Chemistry, 55(2):721-728 (1990).

Habermehl, et al., "Synthesis of N-[(3-ethoxycarbonylmethyl)-cyclohexyl]-azetidin-2-yl-propionic Acid Hydrochloride"; Zeitschrift Fuer Naturforschung, B: Chemical Sciences, 47(2):1779-1784 (1992).

Jobron, et al., "Solid-Phase Synthesis of New S-Glycoamino Acid Building Blocks", Organic Letters, 2(15):2265-2267 (2000).

Moroder, et al., "Cytochrome C. Part I.: Synthesis of the Protected Hexadecapeptide (Sequence 1-16) of Baker's Yeast Iso-1-Cytochrome C", Biopolymers, 12(3):477-492 (1973).

Okada, et al., "Amino Acids and Peptides LVI: Synthesis of Pyrazinone Ring-Containing Opioid Mimetics and Examination of Their Opioid Receptor Binding Activity", Tetrahedron, 55(50):14391-14406 (1999).

Suresh Babu, et al., "(Fluoren-9-ylmethoxy)carbonyl (Fmoc) Amino Acid Azides: Synthesis, Isolation, Characterisation, Stability and Application to Synthesis of Peptides", J. Chem. Soc., Perkin Trust, 1:4328-4331 (2000).

Takahashi, et al., "Novel Matrix Metalloproteinase Inhibitors: Generation of Lead Compounds by the in Silico Fragment-Based Approach", Bioorganic & Medicinal Chemistry, 13(14):4527-4543 (2005).

Wen, et al., "Synthesis of 9-Fluorenylmethoxycarbonyl-Protected Amino Aldehydes", Tetrahedron: Asymmetry, 9(11):1855-1858 (1998).

Abbaszade, I. et al., "Cloning anc Characterization of ADAMTS11, an Aggrecanase from the ADAMTS Family", *J Biol Chem*, 274(33):23443-23450 (1999).

Colige, A. et al., "cDNA Cloning and Expression of Bovine Procollagen I N-Proteinase: A New Member of the Superfamily of Zinc-Metalloproteinases with Binding Sites for Cells and Other Matrix Components", *Proc Natl Acad Sci USA*, 94:2374-2379 (1997).

Kuno, et al., "Molecular Cloning of a Gene Encoding a New Type of Metalloproteinase-disintegrin Family Protein with Thrombospondin Motifs as an Inflammation Associated Gene", *Journal of Biological Chemistry*, 272(1):556-562 (1997).

Tang, BL, "ADAMTS: a Novel Family of Extracellular Matrix Proteases", *Int J. Biochem Cell Biol*, 33:33-44 (2001).

Vazquez, F. et al., "Meth-1, a Human Ortholog of ADAMTS-1, and METH-2 are Members of a New Family of Proteins with Angio-Inhibitory Activity", *J Biol Chem*, 274(33):23349-23357 (1999).

\* cited by examiner

Figure 1: Inhibition of aggrecan degradation by test compound 8OO
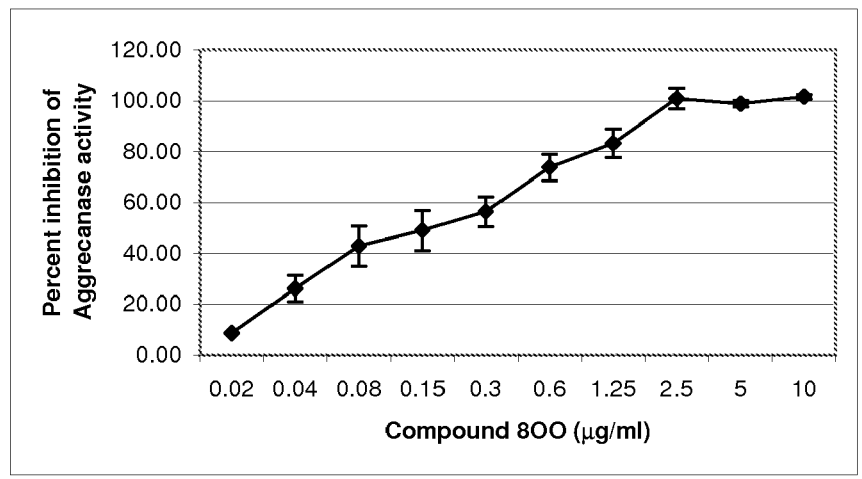

Figure 2: Test compound 8OO and Aggrecan metabolism
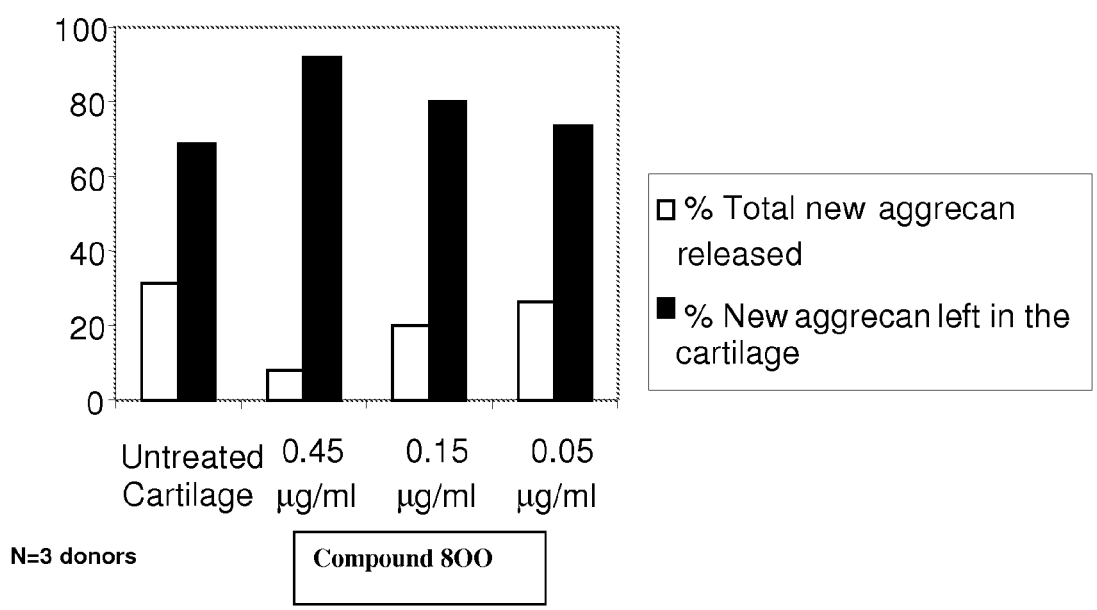

GLUTAMATE AGGRECANASE INHIBITORS

CROSS-REFERENCE TO RELATED APPLICATIONS

This is a Divisional Application of U.S. Ser. No. 11/484,005, filed Jul. 11, 2006, which claims the benefit under 35 U.S.C. §119(e) of U.S. Ser. No. 60/697,590, filed Jul. 11, 2005, all of which are incorporated by reference herein in their entirety.

Throughout this application, various publications are referenced. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure, as it appears in the U.S. Patent and Trademark Office patent file or records, but otherwise reserves any and all copyright rights whatsoever.

FIELD OF THE INVENTION

The present invention relates to compounds and their use as, for example, metalloproteinase inhibitors.

BACKGROUND OF THE INVENTION

Metalloproteinases, including matrix metalloproteinases and aggrecanases, are known to have a role in the breakdown of connective tissue. Matrix metalloproteinases ("MMPs") constitute a superfamily of proteolytic enzymes that are genetically related and capable of degrading almost all the constituents of extracellular matrix and basement membrane that restrict cell movement. Aggrecanases are members of the ADAMTS (A disintegrin and metalloproteinase with thrombospondin motifs) family of proteins. Aggrecanase-1 and aggrecanase-2 have been designated ADAMTS-4 and ADAMTS-5, respectively (Tang B L, *Int J Biochem Cell Biol* 2001, 33, 33-44).

The ADAMTS family is involved in cleaving aggrecan, a cartilage component also known as the large aggregating chondroitin sulphate proteoglycan (Abbaszade I et al., *J Biol Chem* 1999, 274, 23443-23450), procollagen processing (Colige A et al., *Proc Natl Acad Sci USA* 1997, 94, 2374-2379), angiogenesis (Vazquez F et al., *J Biol Chem* 1999, 274, 23349-23357), inflammation (Kuno K et al., *J Biol Chem* 1997, 272, 556-562) and tumor invasion (Masui T. et al., *J Biol Chem* 1997, 272, 556-562). MMPs have been shown to cleave aggrecan as well.

The loss of aggrecan has been implicated in the degradation of articular cartilage in arthritic diseases, for example osteoarthritis is a debilitating disease which affects at least 30 million Americans. Degradation of articular cartilage and the resulting chronic pain can severely reduce quality of life. An early and important characteristic of the osteoarthritic process is loss of aggrecan from the extracellular matrix, resulting in deficiencies in the biomechanical characteristics of the cartilage. Likewise, MMPs and aggrecanases are known to play a role in many disorders in which extracellular protein degradation or destruction occurs, such as cancer, asthma, chronic obstructive pulmonary disease ("COPD"), atherosclerosis, age-related macular degeneration, myocardial infarction, corneal ulceration and other ocular surface diseases, hepatitis, aortic aneurysms, tendonitis, central nervous system diseases, abnormal wound healing, angiogenesis, restenosis, cirrhosis, multiple sclerosis, glomerulonephritis, graft versus host disease, diabetes, inflammatory bowel disease, shock, invertebral disc degeneration, stroke, osteopenia, and periodontal diseases.

Therefore, metalloproteinase inhibitors, including inhibitors of MMPs and aggrecanases, are needed.

The present invention is directed to these and other important ends.

SUMMARY OF THE INVENTION

In one embodiment, the invention provides compounds of the Formula (I):

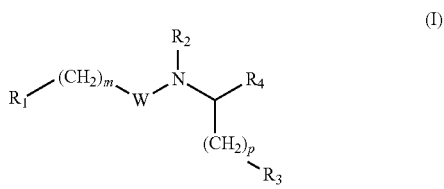

and pharmaceutically acceptable salts thereof,
wherein
W is —C(O)—, —OC(O)—, —NHC(O)—, —C(O)O—, or —C(O)NH—;
$R_1$ is phenyl, heteroaryl, biphenyl, bicyclic aryl, tricyclic aryl, bicyclic heteroaryl, or tricyclic heteroaryl, each optionally substituted with one or more of $R_5$ or $R_6$, and when $R_1$ is substituted with more than one of $R_5$ or $R_6$, the substituents can be identical or different;
$R_2$ is hydrogen, ($C_1$-$C_6$) alkyl, ($C_2$-$C_6$) alkenyl, ($C_2$-$C_6$) alkynyl, —$(CH_2)_n R_{11}$, —OH, or —O—($C_1$-$C_6$) alkyl;
$R_3$ is —$CO_2H$, —$CONH_2$, —CONHOH, —$CONHSO_2R_7$, tetrazole, —$SO_2NHR_7$, —$SO_3H$, —PO(OH)$NH_2$, —PO(OH)$OR_7$, —$CONHR_7$, —$COOR_7$, an acid mimetic group, or a 5 or 6-membered heterocycloalkyl or heteroaryl containing 1 to 4 heteroatoms selected from O, N, S;
$R_4$ is —$CO_2H$, —$CONH_2$, —$(CH_2)_n OR_7$, or —$CONR_9 R_{10}$;
$R_5$ is aryl, heteroaryl, —$(CH_2)_n$-aryl, —$(CH_2)_n$-heteroaryl, —O-aryl, —O-heteroaryl, —S-aryl, —S-heteroaryl, —NH-aryl, —NH-heteroaryl, —CO—($C_1$-$C_6$) alkyl, —CO-aryl, —CO-heteroaryl, —$SO_2$—($C_1$-$C_6$) alkyl, —$SO_2$-aryl, —$SO_2$-heteroaryl, —$SO_2NH$-aryl, —$SO_2NH$-heteroaryl, —$NHSO_2$—($C_1$-$C_6$) alkyl, —$NHSO_2$-aryl, —$NHSO_2$-heteroaryl, —NHCO-aryl, —NHCO-heteroaryl, —CONH-aryl, —CONH-heteroaryl, ($C_1$-$C_6$) alkyl, —O—($C_1$-$C_6$) alkyl, —S—($C_1$-$C_6$) alkyl, —NH—($C_1$-$C_6$) alkyl, —NHCO—($C_1$-$C_6$) alkyl, —CONH—($C_1$-$C_6$) alkyl, —O—($C_3$-$C_6$) cycloalkyl, —S—($C_3$-$C_6$) cycloalkyl, —NH—($C_3$-$C_6$) cycloalkyl, —NHCO—($C_3$-$C_6$) cycloalkyl, or —CONH—($C_3$-$C_6$) cycloalkyl; each alkyl, aryl, cycloalkyl, or heteroaryl optionally substituted with one or more of $R_6$, and when $R_5$ is substituted with more than one $R_6$, the substituents can be identical or different;
$R_6$ and $R_{12}$ are each independently hydrogen, halogen, —CN, —$OCF_3$, —$CF_3$, —$NO_2$, —OH, —SH, —$NR_7 R_8$, —$CONR_7 R_8$, —$NR_8 COR_7$, —$NR_8 CO_2 R_7$, —$CO_2 R_7$, —$COR_7$, —$SO_2$—($C_1$-$C_6$) alkyl, —$SO_2$-aryl, —$SO_2$-heteroaryl, —$SO_2 R_7$, —$NR_7 SO_2 R_8$, —$SO_2 NR_7 R_8$, ($C_1$-$C_6$) alkyl, —O—($C_1$-$C_6$) alkyl, —S—$(C_1-C_6)$ alkyl, —NH—$(C_1-C_6)$ alkyl, —NHCO—$(C_1-C_6)$ alkyl, —CONH—$(C_1-C_6)$ alkyl, —O—$(C_3-C_6)$ cycloalkyl, —S—$(C_3-C_6)$ cycloalkyl, —NH—$(C_3-C_6)$ cycloalkyl, —NHCO—$(C_3-C_6)$ cycloalkyl, —CONH—$(C_3-C_6)$ cycloalkyl, heterocloalkyl, —$(C_1-C_6)$ alkyl-OR$_7$, $(C_2-C_6)$ alkynyl, $(C_2-C_6)$ alkenyl, —O—$(C_1-C_6)$ alkyl-$(C_3-C_6)$ cycloalkyl, —O-alkenyl, —O—$(C_1-C_6)$ alkyl substituted with aryl, aryl, heteroaryl, —$(CH_2)_n$-aryl, —$(CH_2)_n$-heteroaryl, —O-aryl, —O-heteroaryl, —S-aryl, or —S-heteroaryl; each alkyl, aryl, cycloalkyl, heterocycloalkyl, heteroaryl, alkenyl, or alkynyl optionally substituted with one or more of $R_{13}$;

$R_7$ and $R_8$ are each independently hydrogen, $(C_1-C_6)$ alkyl, aryl, heteroaryl, $(C_2-C_6)$ alkenyl, $(C_2-C_6)$ alkynyl, cycloalkyl, —$(CH_2)_n$-aryl, or —$(CH_2)_n$-heteroaryl; or $R_7$ and $R_8$ together with the atom to which they are attached may form a five- to seven-membered cyclic group containing up to 3 heteroatoms selected from N, O, or S;

$R_9$ and $R_{10}$ are each independently hydrogen, $(C_1-C_6)$ alkyl, $(C_1-C_6)$ alkyl-OH, $(C_1-C_6)$ alkyl-O—$(C_1-C_6)$ alkyl, aryl, cycloalkyl, heteroaryl, $(C_2-C_6)$ alkenyl, $(C_2-C_6)$ alkynyl, bicyclic aryl, tricyclic aryl, bicyclic heteroaryl, or tricyclic heteroaryl, each alkyl, aryl, cycloalkyl, or heteroaryl optionally substituted with one or more $R_{12}$; or $R_9$ and $R_{10}$ together may form a five- to seven-membered cyclic group containing up to 3 heteroatoms selected from N, O, or S;

$R_{11}$ is aryl, heteroaryl, or cycloalkyl;

$R_{13}$ is halogen, —O—$(C_1-C_6)$ alkyl, —$CO_2H$, —OH, —$CF_3$, hydrogen, $(C_1-C_6)$ alkyl, aryl, heteroaryl, $(C_2-C_6)$ alkenyl, $(C_2-C_6)$ alkynyl, cycloalkyl, cycloalkyl substituted with —OH, aryl substituted with —$NH_2$, aryl substituted with —O—$(C_1-C_6)$ alkyl, —$(CH_2)_n$-aryl, or —$(CH_2)_n$-heteroaryl;

m is 0-4;
n is 0-4; and
p is 0-2.

In another embodiment, the invention provides compounds of the Formula (II):

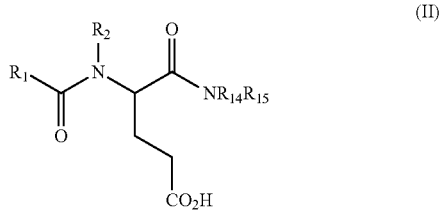

(II)

and pharmaceutically acceptable salts thereof, wherein $R_2$ is hydrogen, $(C_1-C_6)$ alkyl, $(C_2-C_6)$ alkenyl, $(C_2-C_6)$ alkynyl, —$(CH_2)_pR_{11}$, —OH, or —O—$(C_1-C_6)$ alkyl;

$R_{14}$ and $R_{15}$ are each independently hydrogen, $(C_1-C_6)$ alkyl, aryl, heteroaryl, $(C_2-C_6)$ alkenyl, $(C_2-C_6)$ alkynyl, cycloalkyl, heterocycloalkyl —$(CH_2)_n$-aryl, bicyclic aryl, tricyclic aryl, bicyclic heteroaryl, or tricyclic heteroaryl; each alkyl, aryl, cycloalkyl, heterocycloalkyl, or heteroaryl optionally substituted with one or more $R_{12}$; or $R_{14}$ and $R_{15}$ together may form a five- to seven-membered cyclic group containing up to 3 heteroatoms selected from N, O, or S;

p is 0-2, and $R_1$, $R_{11}$, $R_{12}$, and n are as described above for compounds of the Formula (I).

In another embodiment, the compounds or pharmaceutically acceptable salts of the compounds of Formula (I) or Formula (II) are useful as pharmaceutical compositions comprising compounds or pharmaceutically acceptable salts of compounds of Formula (I) or Formula (II) and a pharmaceutically acceptable carrier.

In one embodiment, the compounds or pharmaceutically acceptable salts of the compounds of the Formula (I) or Formula (II) are useful as metalloproteinase modulators.

In one embodiment, the invention provides methods for treating a metalloproteinase-related disorder, comprising administering to an animal in need thereof the compounds or pharmaceutically acceptable salts of compounds of Formula (I) or Formula (II) in an amount effective to treat a metalloproteinase-related disorder.

In one embodiment, the invention provides methods of synthesizing the compounds or pharmaceutically acceptable salts of compounds of Formula (I) or Formula (II). In another embodiment, the invention provides compounds or pharmaceutically acceptable salts of compounds of Formula (I) or Formula (II) made by particular processes.

BRIEF DESCRIPTION OF THE DRAWINGS

FIG. 1 illustrates inhibition of aggecan degradation by test compound 8OO.

FIG. 2 illustrates the effect of test compound 8OO on aggreecan metabolism.

DESCRIPTION OF THE INVENTION

All recitations of a group, such as alkyl, are understood for the purposes of this specification to encompass both substituted and unsubstituted forms.

The term "alkyl", as used herein, whether used alone or as part of another group, refers to a substituted or unsubstituted aliphatic hydrocarbon chain and includes, but is not limited to, straight and branched chains containing from 1 to 12 carbon atoms, or in some instances, from 1 to 6 carbon atoms, unless explicitly specified otherwise. For example, methyl, ethyl, propyl, isopropyl, butyl, i-butyl and t-butyl are encompassed by the term "alkyl." $(C_1-C_6)$-alkyl includes straight and branched chain aliphatic groups having from 1 to 6 carbons. Specifically included within the definition of "alkyl" are those aliphatic hydrocarbon chains that are optionally substituted. The alkyl may suitably be a $(C_1-C_3)$-alkyl. In one embodiment, an alkyl is optionally substituted with one or more of the following groups: —V-halogen, —V—$(C_1-C_6)$-alkyl, —V—$(C_2-C_6)$-alkenyl, —V—$(C_2-C_6)$-alkynyl, —V—$N(R')_2$, methylenedioxo, ethylenedioxo, —V—$NHSO_2R'$, —V—$NR'COR'$, —V—$NHCO_2R'$, —V—$NO_2$, —V—$SO_2N(R')_2$, —V—$SO_2R'$, —V—$OR'$, —V—$COR'$, —V—$CO_2R'$, —V—$CON(R')_2$, or —V—CN, wherein each R' is independently hydrogen, unsubstituted $(C_1-C_6)$-alkyl, or unsubstituted aryl; and wherein each V is independently a bond or $(C_1-C_6)$-alkyl.

The carbon number as used in the definitions herein refers to carbon backbone and carbon branching, but does not include carbon atoms of the substituents, such as alkoxy substitutions and the like.

The term "alkenyl", as used herein, whether used alone or as part of another group, refers to a substituted or unsubstituted hydrocarbon chain and includes, but is not limited to, straight and branched chains having 2 to 8 carbon atoms e.g. 2 to 6 carbon atoms and containing at least one double bond.

In one embodiment, the alkenyl moiety has 1 or 2 double bonds. Such alkenyl moieties may exist in the E or Z conformations and the compounds of this invention include both conformations. ($C_2$-$C_6$) alkenyl includes a 2 to 6 carbon straight or branched chain having at least one carbon-carbon double bond. Specifically included within the definition of "alkenyl" are those aliphatic hydrocarbon chains that are optionally substituted. In one embodiment, a heteroatom, such as O, S or N, attached to an alkenyl is not attached to a carbon atom that is bonded to a double bond. In one embodiment, an alkenyl is optionally substituted with one or more of the following groups: —V-halogen, —V—($C_1$-$C_6$)-alkyl, —V—($C_2$-$C_6$)-alkenyl, —V—($C_2$-$C_6$)-alkynyl, —V—N(R')$_2$, methylenedioxo, ethylenedioxo, —V—NHSO$_2$R', —V—NR'COR', —V—NHCO$_2$R', —V—NO$_2$, —V—SO$_2$N(R')$_2$, —V—SO$_2$R', —V—OR', —V—COR', —V—CO$_2$R', —V—CON(R')$_2$, or —V—CN, wherein each R' is independently hydrogen, unsubstituted ($C_1$-$C_6$)-alkyl, or unsubstituted aryl; and wherein each V is independently a bond or ($C_1$-$C_6$)-alkyl.

The term "alkynyl", as used herein, whether used alone or as part of another group, refers to a hydrocarbon moiety containing at least one carbon-carbon triple bond. ($C_2$-$C_6$) alkynyl includes a 2 to 6 carbon straight or branched chain having at least one carbon-carbon triple bond. In one embodiment, an alkynyl is optionally substituted with one or more of the following groups: —V-halogen, —V—($C_1$-$C_6$)-alkyl, —V—($C_2$-$C_6$)-alkenyl, —V—($C_2$-$C_6$)-alkynyl, —V—N(R')$_2$, methylenedioxo, ethylenedioxo, —V—NHSO$_2$R', —V—NR'COR', —V—NHCO$_2$R', —V—NO$_2$, —V—SO$_2$N(R')$_2$, —V—SO$_2$R', —V—OR', —V—COR', —V—CO$_2$R', —V—CON(R')$_2$, or —V—CN, wherein each R' is independently hydrogen, unsubstituted ($C_1$-$C_6$)-alkyl, or unsubstituted aryl; and wherein each V is independently a bond or ($C_1$-$C_6$)-alkyl.

The term "cycloalkyl" refers to a monocyclic, bicyclic, tricyclic, fused, bridged, or spiro monovalent saturated or unsaturated non-aromatichydrocarbon ring system of 3-15 carbon atoms e.g. 3 to 6 carbon atoms. Any suitable ring position of the cycloalkyl moiety may be covalently linked to the defined chemical structure. Examples of cycloalkyl moieties include, but are not limited to, cyclopropyl, cyclopropylmethyl, cyclobutyl, cyclopentyl, cyclohexyl, cycloheptyl, norbornyl, adamantyl, spiro[4.5]decanyl, and homologs, isomers, and the like. $C_3$-$C_6$ cycloalkyl includes monocyclic, saturated rings of 3 to 6 carbons. In one embodiment, a cycloalkyl is optionally substituted with one or more of the following groups: —V-halogen, —V—($C_1$-$C_6$)-alkyl, —V—($C_2$-$C_6$)-alkenyl, —V—($C_2$-$C_6$)-alkynyl, —V—N(R')$_2$, methylenedioxo, ethylenedioxo, —V—NHSO$_2$R', —V—NR'COR', —V—NHCO$_2$R', —V—NO$_2$, —V—SO$_2$N(R')$_2$, —V—SO$_2$R', —V—OR', —V—COR', —V—CO$_2$R', —V—CON(R')$_2$, or —V—CN, wherein each R' is independently hydrogen, unsubstituted ($C_1$-$C_6$)-alkyl, or unsubstituted aryl; and wherein each V is independently a bond or ($C_1$-$C_6$)-alkyl. Cycloalkylalkyl when used herein refers to a ($C_1$-$C_6$)-alkyl group as defined above substituted by a $C_3$ to $C_{15}$ cycloalkyl group as defined above e.g. cyclohexylmethyl and cyclohexylethyl.

"Heteroaryl" refers to a 5 to 6 membered aromatic heterocyclic ring which contains from 1 to 4 heteroatoms selected from the group consisting of oxygen, nitrogen, and sulfur atoms in the ring and may be fused with a carbocyclic or heterocyclic ring at any possible position (e.g. fused to one or more carbocyclic or heterocyclic rings, each having 5-8 ring atoms, the fused heterocyclic ring containing from 1 to 4 heteroatoms selected from the group consisting of oxygen, nitrogen, and sulfur atoms in the ring) e.g. it is suitably a bicyclic or tricyclic ring. Exemplary heteroaryl groups include, but are not limited to, furanyl, furazanyl, homopiperazinyl, imidazolinyl, isothiazolyl, isoxazolyl, oxadiazolyl, oxazolyl, pyrimidinyl, phenanthridinyl, pyranyl, pyrazinyl, pyrazolinyl, pyrazolyl, pyridazinyl, pyridooxazolyl, pyridoimidazolyl, pyridothiazolyl, pyridinyl, pyrimidinyl, pyrrolinyl, thiadiazinyl, thiadiazolyl, thienyl, thienothiazolyl, thienooxazolyl, thienoimidazolyl, thiophenyl, triazinyl, and triazolyl. In one embodiment, a heteroaryl is optionally substituted with one or more of the following groups: —V-halogen, —V—($C_1$-$C_6$)-alkyl, —V—($C_2$-$C_6$)-alkenyl, —V—($C_2$-$C_6$)-alkynyl, —V—N(R')$_2$, methylenedioxo, ethylenedioxo, —V—NHSO$_2$R', —V—NR'COR', —V—NHCO$_2$R', —V—NO$_2$, —V—SO$_2$N(R')$_2$, —V—SO$_2$R', —V—OR', —V—COR', —V—CO$_2$R', —V—CON(R')$_2$, or —V—CN, wherein each R' is independently hydrogen, unsubstituted ($C_1$-$C_6$)-alkyl, or unsubstituted aryl; and wherein each V is independently a bond or ($C_1$-$C_6$)-alkyl.

"Heterocycloalkyl" refers to a 5 to 7-membered saturated or unsaturated non aromatic ring containing carbon atoms and from 1 to 4 heteroatoms selected from N, O, and S which may suitably be monocyclic or may be fused to one or more further rings to provide a polycyclic moiety e.g. a bicyclic or tricyclic moiety. The further ring(s) may be carbocyclic rings(s) or they may contain from 1 to 4 further heteroatoms selected from N, O and S, preferably they are carbocyclic rings. The further ring(s) may be saturated, unsaturated or aromatic rings(s), preferably they are non-aromatic rings) Exemplary heterocycloalkyl groups include, but are not limited to, azepanyl, azetidinyl, aziridinyl, imidazolidinyl, morpholinyl, oxazolidinyl, oxazolidinyl, piperazinyl, piperidinyl, pyrazolidinyl, pyrrolidinyl, quinuclidinyl, tetrahydrofuranyl, and thiomorpholinyl. In one embodiment, a heterocycloalkyl is optionally substituted with one or more of the following: —V-halogen, —V—($C_1$-$C_6$)-alkyl, —V—($C_2$-$C_6$)-alkenyl, —V—($C_2$-$C_6$)-alkynyl, —V—N(R')$_2$, methylenedioxo, ethylenedioxo, —V—NHSO$_2$R', —V—NR'COR', —V—NHCO$_2$R', —V—NO$_2$, —V—SO$_2$N(R')$_2$, —V—SO$_2$R', —V—OR', —V—COR', —V—CO$_2$R', —V—CON(R')$_2$, or —V—CN, wherein each R' is independently hydrogen, unsubstituted ($C_1$-$C_6$)-alkyl, or unsubstituted aryl; and wherein each V is independently a bond or ($C_1$-$C_6$)-alkyl.

The term "aryl" as used herein as a group or part of a group refers to an aromatic carbocyclic ring system, e.g., of from 6 to 14 carbon atoms such as phenyl, which may be optionally substituted. An aryl group may be fused with a carbocyclic or heterocyclic ring at any possible position (e.g. fused to one or more carbocyclic or heterocyclic rings, each having 5-8 ring atoms, the fused heterocyclic ring containing from 1 to 4 heteroatoms selected from the group consisting of oxygen, nitrogen, and sulfur atoms in the ring). "Phenyl", as used herein, whether used alone or as part of another group, refers to a substituted or unsubstituted phenyl group. The aryl fused with a carbocyclic ring may suitably be a bicyclic aryl or a tricyclic aryl. In one embodiment, an aryl group such as phenyl is optionally substituted with one or more of the following: —V-halogen, —V—($C_1$-$C_6$)-alkyl, —V—($C_2$-$C_6$)-alkenyl, —V—($C_2$-$C_6$)-alkynyl, —V—N(R')$_2$, methylenedioxo, ethylenedioxo, —V—NHSO$_2$R', —V—NR'COR', —V—NHCO$_2$R', —V—NO$_2$, —V—SO$_2$N(R')$_2$, —V—SO$_2$R', —V—OR', —V—COR', —V—CO$_2$R', —V—CON(R')$_2$, or —V—CN, wherein each R' is independently hydrogen, unsubstituted $(C_1-C_6)$-alkyl, or unsubstituted aryl; and wherein each V is independently a bond or $(C_1-C_6)$-alkyl.

The term "biphenyl" as used herein refers to two phenyl groups connected at one carbon site on each ring. In one embodiment, one or both phenyl groups is independently optionally substituted with one or more of the following groups: —V-halogen, —V—$(C_1-C_6)$-alkyl, —V—$(C_2-C_6)$-alkenyl, —V—$(C_2-C_6)$-alkynyl, —V—$N(R')_2$, methylenedioxo, ethylenedioxo, —V—$NHSO_2R'$, —V—NR'COR', —V—$NHCO_2R'$, —V—$NO_2$, —V—$SO_2N(R')_2$, —V—$SO_2R'$, —V—OR', —V—COR', —V—$CO_2R'$, —V—$CON(R')_2$, or —V—CN, wherein each R' is independently hydrogen, unsubstituted $(C_1-C_6)$-alkyl, or unsubstituted aryl; and wherein each V is independently a bond or $(C_1-C_6)$-alkyl.

The term "biaryl" as used herein refers to two aryl groups connected at one carbon site on each ring. In one embodiment, one or both aryl groups is independently optionally substituted with one or more of the following groups: —V-halogen, —V—$(C_1-C_6)$-alkyl, —V—$(C_2-C_6)$-alkenyl, —V—$(C_2-C_6)$-alkynyl, —V—$N(R')_2$, methylenedioxo, ethylenedioxo, —V—$NHSO_2R'$, —V—NR'COR', —V—$NHCO_2R'$, —V—$NO_2$, —V—$SO_2N(R')_2$, —V—$SO_2R'$, —V—OR', —V—COR', —V—$CO_2R'$, —V—$CON(R')_2$, or —V—CN, wherein each R' is independently hydrogen, unsubstituted $(C_1-C_6)$-alkyl, or unsubstituted aryl; and wherein each V is independently a bond or $(C_1-C_6)$-alkyl.

The term "bicyclic aryl" as used herein refers to two fused carbocyclic groups, wherein one or both of the carbocyclic groups is aromatic. For example, a bicyclic aryl can contain from 8 to 12 ring atoms. In one embodiment, one or both carbocyclic groups of the bicyclic aryl is independently optionally substituted with one or more of the following groups: —V-halogen, —V—$(C_1-C_6)$-alkyl, —V—$(C_2-C_6)$-alkenyl, —V—$(C_2-C_6)$-alkynyl, —V—$N(R')_2$, methylenedioxo, ethylenedioxo, —V—$NHSO_2R'$, —V—NR'COR', —V—$NHCO_2R'$, —V—$NO_2$, —V—$SO_2N(R')_2$, —V—$SO_2R'$, —V—OR', —V—COR', —V—$CO_2R'$, —V—$CON(R')_2$, or —V—CN, wherein each R' is independently hydrogen, unsubstituted $(C_1-C_6)$-alkyl, or unsubstituted aryl; and wherein each V is independently a bond or $(C_1-C_6)$-alkyl.

The term "tricyclic aryl" as used herein refers to three fused carbocyclic groups, wherein two or three of the carbocyclic groups is aromatic. For example, a tricyclic aryl can contain from 13 to 18 ring atoms. In one embodiment, one or more of the carbocyclic groups of the tricyclic aryl are independently optionally substituted with one or more of the following groups: —V-halogen, —V—$(C_1-C_6)$-alkyl, —V—$(C_2-C_6)$-alkenyl, —V—$(C_2-C_6)$-alkynyl, —V—$N(R')_2$, methylenedioxo, ethylenedioxo, —V—$NHSO_2R'$, —V—NR'COR', —V—$NHCO_2R'$, —V—$NO_2$, —V—$SO_2N(R')_2$, —V—$SO_2R'$, —V—OR', —V—COR', —V—$CO_2R'$, —V—$CON(R')_2$, or —V—CN, wherein each R' is independently hydrogen, unsubstituted $(C_1-C_6)$-alkyl, or unsubstituted aryl; and wherein each V is independently a bond or $(C_1-C_6)$-alkyl.

The term "bicyclic heteroaryl" as used herein refers to two fused cyclic groups, wherein one or both of the cyclic groups is aromatic and contains one to four heteroatoms selected from O, S, and N. For example, a bicyclic heteroaryl can contain from 8 to 12 ring atoms, and from 1 to 3 heteroatoms selected from O, N, and S in each ring. In one embodiment, one or both cyclic groups is independently optionally substituted with one or more of the following groups: —V-halogen, —V—$(C_1-C_6)$-alkyl, —V—$(C_2-C_6)$-alkenyl, —V—$(C_2-C_6)$-alkynyl, —V—$N(R')_2$, methylenedioxo, ethylenedioxo, —V—$NHSO_2R'$, —V—NR'COR', —V—$NHCO_2R'$, —V—$NO_2$, —V—$SO_2N(R')_2$, —V—$SO_2R'$, —V—OR', —V—COR', —V—$CO_2R'$, —V—$CON(R')_2$, or —V—CN, wherein each R' is independently hydrogen, unsubstituted $(C_1-C_6)$-alkyl, or unsubstituted aryl; and wherein each V is independently a bond or $(C_1-C_6)$-alkyl.

The term "tricyclic heteroaryl" as used herein refers to three fused cyclic groups, wherein two or three of the cyclic groups is aromatic and at least one aromatic group contains 1 to 4 heteroatoms selected from O, S, and N. For example, a tricyclic aryl can contain from 13 to 18 ring atoms, and from 1 to 3 heteroatoms selected from O, N, and S in each ring. In one embodiment, the cyclic groups are independently substituted with one or more of the following groups: —V-halogen, —V—$(C_1-C_6)$-alkyl, —V—$(C_2-C_6)$-alkenyl, —V—$(C_2-C_6)$-alkynyl, —V—$N(R')_2$, methylenedioxo, ethylenedioxo, —V—$NHSO_2R'$, —V—NR'COR', —V—$NHCO_2R'$, —V—$NO_2$, —V—$SO_2N(R')_2$, —V—$SO_2R'$, —V—OR', —V—COR', —V—$CO_2R'$, —V—$CON(R')_2$, or —V—CN, wherein each R' is independently hydrogen, unsubstituted $(C_1-C_6)$-alkyl, or unsubstituted aryl; and wherein each V is independently a bond or $(C_1-C_6)$-alkyl.

An optionally substituted moiety may be substituted with one or more substituents, examples of which are as illustrated herein. In one embodiment, an "optionally substituted" moiety is substituted with one or more of the following: —V-halogen, —V—$(C_1-C_6)$-alkyl, —V—$(C_2-C_6)$-alkenyl, —V—$(C_2-C_6)$-alkynyl, —V—$N(R')_2$, methylenedioxo, ethylenedioxo, —V—$NHSO_2R'$, —V—NR'COR', —V—$NHCO_2R'$, —V—$NO_2$, —V—$SO_2N(R')_2$, —V—$SO_2R'$, —V—OR', —V—COR', —V—$CO_2R'$, —V—$CON(R')_2$, or —V—CN, wherein each R' is independently hydrogen, unsubstituted $(C_1-C_6)$-alkyl, or unsubstituted aryl; and wherein each V is independently a bond or $(C_1-C_6)$-alkyl.

When such moieties are substituted, for example, they may typically be mono-, di-, tri- or persubstituted. Examples for a halogen substituent include 1-bromo vinyl, 1-fluoro vinyl, 1,2-difluoro vinyl, 2,2-difluorovinyl, 1,2,2-trifluorovinyl, 1,2-dibromo ethane, 1,2 difluoro ethane, 1-fluoro-2-bromo ethane, $CF_2F_3$, $CF_2CF_2CF_3$, and the like.

The term halogen includes bromine, chlorine, fluorine, and iodine.

For the sake of simplicity, connection points ("-") are not depicted. When an atom or compound is described to define a variable, it is understood that it is intended to replace the variable in a manner to satisfy the valency of the atom or compound. For example, if "X*" was C(R*)=C(R*), both carbon atoms form a part of the ring in order to satisfy their respective valences. Likewise, when divalent substituents are presented, it is understood that they are not limited to the order listed, for example, as used in this specification "$OCH_2$" encompasses $CH_2O$ and $OCH_2$.

The term "administer", "administering", or "administration", as used herein refers to either directly administering a compound or pharmaceutically acceptable salt of the compound or a composition to a animal, or administering a prodrug derivative or analog of the compound or pharmaceutically acceptable salt of the compound or composition to the animal, which can form an equivalent amount of active compound within the animal's body.

The term "animal" as used herein includes, without limitation, a human, mouse, rat, guinea pig, dog, cat, horse, cow, pig, monkey, chimpanzee, baboon, or rhesus. In one embodiment, the animal is a mammal. In another embodiment, the animal is a human.

The term "amine protecting group" as used herein refers to a moiety that temporarily blocks an amine reactive site in a compound. Generally, this is done so that a chemical reaction can be carried out at another reactive site in a multifunctional compound or to otherwise stabilize the amine. In one embodiment, an amine protecting group is selectively removable by a chemical reaction. An exemplary amine protecting group is a 9-fluorenylmethoxycarbonyl protecting group. Another exemplary amine protecting group is a carbamate protecting group. Carbamate protecting groups include, without limitation, t-butyl carbamate, methyl carbamate, ethyl carbamate, 2,2,2-trichloroethyl carbamate, 2-(trimethylsilyl)ethyl carbamate, 1,1-dimethyl-2,2,2-trichloroethyl carbamate, benzyl carbamate, p-methoxybenzyl carbamate, p-nitrobenzylcarbamate, p-bromobenzyl carbamate, p-chlorobenzyl carbamate, and 2,4-dichlorobenzyl carbamate. See, Greene and Wuts, *Protecting Groups in Organic Synthesis*, Second Edition, John Wiley & Sons (1991).

The term "carboxylic acid protecting group" as used herein refers to a moiety that temporarily blocks a carboxylic acid reactive site in a compound. Generally, this is done so that a chemical reaction can be carried out at another reactive site in a multifunctional compound or to otherwise stabilize the carboxylic acid. In one embodiment, a carboxylic acid protecting group is selectively removable by a chemical reaction. An exemplary carboxylic acid protecting group is an alkyl ester protecting group, such as a tert-butyl ester.

The term "acid mimetic group" as used herein refers to a moiety that has chemical and physical similarities producing broadly similar biological properties to an acid. In one embodiment, an acid mimetic group is a 5 or 6-membered heterocycle containing 1 to 4 heteroatoms selected from O, N, S. Exemplary acid mimetic groups include:

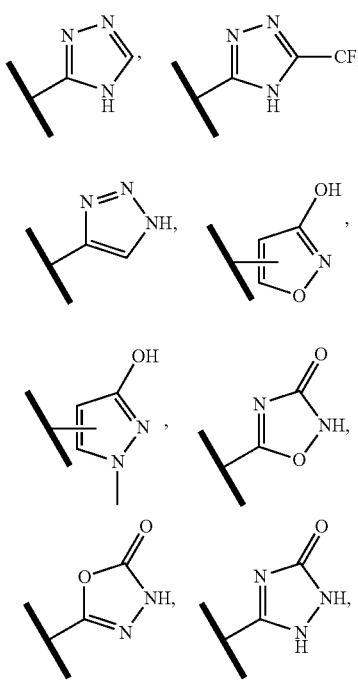

-continued

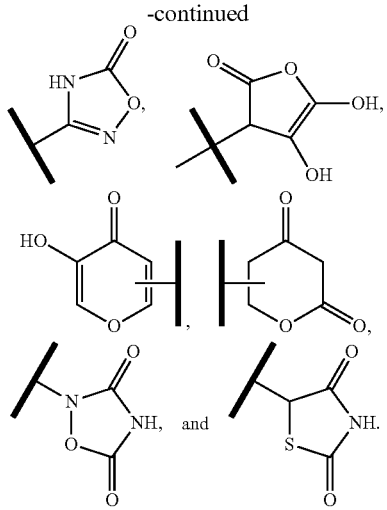

The term "conditions effective to" as used herein refers to synthetic reaction conditions which will be apparent to those skilled in the art of synthetic organic chemistry.

The term "effective amount" as used herein refers to an amount of a compound or pharmaceutically acceptable salt of a compound that, when administered to an animal, is effective to prevent, to at least partially ameliorate, or to cure, a condition from which the animal suffers or is suspected to suffer.

The term "metalloproteinase-related disorder" used herein refers to a condition for which it would be beneficial to modulate activity of the metalloproteinase. Exemplary metalloproteinase-related disorders include, without limitation, arthritic disorders, osteoarthritis, cancer, rheumatoid arthritis, asthma, chronic obstructive pulmonary disease, atherosclerosis, age-related macular degeneration, myocardial infarction, corneal ulceration and other ocular surface diseases, hepatitis, aortic aneurysms, tendonitis, central nervous system diseases, abnormal wound healing, angiogenesis, restenosis, cirrhosis, multiple sclerosis, glomerulonephritis, graft versus host disease, diabetes, inflammatory bowel disease, shock, invertebral disc degeneration, stroke, osteopenia, and periodontal diseases.

The term "metalloproteinase modulator" refers to a compound that is capable of modulating the expression of a metalloproteinase. For example, a metalloproteinase modulator may enhance metalloproteinase expression. A metalloproteinase modulator may also be an inhibitor of a metalloproteinase.

The term "isolated and purified" as used herein refers to an isolate that is separate from other components of a reaction mixture or a natural source. In certain embodiments, the isolate contains at least about 50%, at least about 55%, at least about 60%, at least about 65%, at least about 70%, at least about 75%, at least about 80%, at least about 85%, at least about 90%, at least about 95%, or at least about 98% of the compound or pharmaceutically acceptable salt of the compound by weight of the isolate.

As used herein, a compound of the invention includes a pharmaceutically acceptable salt thereof. The term "pharmaceutically acceptable salt" as used herein refers to a salt of an acid and a basic nitrogen atom of a compound of the present invention. Exemplary salts include, but are not limited to, sulfate, citrate, acetate, oxalate, chloride, hydrochloride, bromide, hydrobromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, napthalenesulfonate, propionate, succinate, fumarate, maleate, malonate, mandelate, malate, phthalate, and pamoate. The term "pharmaceutically acceptable salt" as used herein also refers to a salt of a compound of the present invention having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like. The term "pharmaceutically acceptable salt" also includes a hydrate of a compound of the present invention.

The term "substantially free of its corresponding opposite enantiomer" as used herein means that the compound contains no more than about 10% by weight of its corresponding opposite enantiomer. In other embodiments, the compound that is substantially free of its corresponding opposite enantiomer contains no more than about 5%, no more than about 1%, no more than about 0.5%, or no more than about 0.1% by weight of its corresponding opposite enantiomer. An enantiomer that is substantially free of its corresponding opposite enantiomer includes a compound that has been isolated and purified or has been prepared substantially free of its corresponding opposite enantiomer.

The term "tautomer" as used herein refers to compounds produced by the phenomenon wherein a proton of one atom of a molecule shifts to another atom. See, Jerry March, *Advanced Organic Chemistry: Reactions, Mechanisms and Structures*, Fourth Edition, John Wiley & Sons, pages 69-74 (1992).

The following abbreviations as used herein mean: Ac is acetate; boc is t-butyl carbamate; Bu is butyl; DIEA is diisopropylethylamine; DMF is dimethylformamide; DMSO is dimethylsulfoxide; ESI is electrospray ionization; Et is ethyl; HPLC is high pressure liquid chromatography; HRMS is high resolution mass spectrometry; Me is methyl; MS is mass spectrometry; m/z is mass-to-charge ratio; r.t. is retention time; TFA is trifluoroacetic acid; THF is tetrahydrofuran; FMOC is 9-fluorenylmethoxycarbonyl; DEA is diethylamine; DME is dimethoxyethane; Bop is benzotriazole-1-yl-oxy-tris-(dimethylamino)-phosphonium hexafluorophosphate; PyBop is benzotriazole-1-yl-oxy-tris-pyrrolidino-phosphonium hexafluorophosphate; HBTU is O-benzotriazole-N,N,N',N'-tetramethyl-uronium-hexafluoro-phosphate; and EDC is 1-(3-dimethylaminopropyl)-3-ethyl-carbodiimide hydrochloride.

Compounds and Pharmaceutically Acceptable Salts of Compounds of the Invention

The compounds or pharmaceutically acceptable salts of compounds of the present invention can contain an asymmetric carbon atom and some of the compounds or pharmaceutically acceptable salts of compounds of the invention can contain one or more asymmetric centers, and can thus give rise to optical isomers and diastereomers. While depicted without respect to stereochemistry in the compounds or pharmaceutically acceptable salts of compounds of the present invention, the present invention includes such optical isomers and diastereomers, as well as racemic and resolved, enantiomerically pure R and S stereoisomers, and also other mixtures of the R and S stereoisomers and pharmaceutically acceptable salts thereof. Where a stereoisomer is provided, it can in some embodiments be provided substantially free of its corresponding opposite enantiomer.

In addition, the compounds and pharmaceutically acceptable salts of compounds of the present invention can exist as tautomers. Such tautomers can be transient or isolatable as a stable product. These tautomers are within the scope of the present invention.

Prodrugs of the compounds or pharmaceutically acceptable salts of compounds are also within the scope of the present invention.

Compounds of the Formula (I)

In one embodiment, the present invention is directed to compounds of the Formula (I):

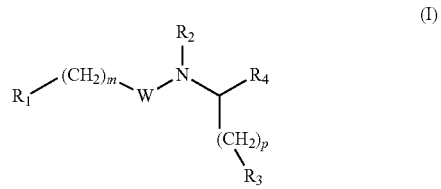

and pharmaceutically acceptable salts thereof,
wherein
W is —C(O)—, —OC(O)—, —NHC(O)—, —C(O)O—, or —C(O)NH—;
$R_1$ is phenyl, heteroaryl, biphenyl, bicyclic aryl, tricyclic aryl, bicyclic heteroaryl, or tricyclic heteroaryl, each optionally substituted with one or more of $R_5$ or $R_6$, and when $R_1$ is substituted with more than one of $R_5$ or $R_6$, the substituents can be identical or different;
$R_2$ is hydrogen, ($C_1$-$C_6$) alkyl, ($C_2$-$C_6$) alkenyl, ($C_2$-$C_6$) alkynyl, —$(CH_2)_n R_{11}$, —OH, or —O—($C_1$-$C_6$) alkyl;
$R_3$ is —$CO_2H$, —$CONH_2$, —CONHOH, —$CONHSO_2 R_7$, tetrazole, —$SO_2 NHR_7$, —$SO_3 H$, —$PO(OH)NH_2$, —$PO(OH)OR_7$, —$CONHR_7$, —$COOR_7$, an acid mimetic group, or a 5 or 6-membered heterocycloalkyl or heteroaryl containing 1 to 4 heteroatoms selected from O, N, S;
$R_4$ is —$CO_2H$, —$CONH_2$, —$(CH_2)_n OR_7$, or —$CONR_9 R_{10}$;
$R_5$ is aryl, heteroaryl, —$(CH_2)_n$-aryl, —$(CH_2)_n$-heteroaryl, —O-aryl, —O-heteroaryl, —S-aryl, —S-heteroaryl, —NH-aryl, —NH-heteroaryl, —CO—($C_1$-$C_6$) alkyl, —CO-aryl, —CO-heteroaryl, —$SO_2$—($C_1$-$C_6$) alkyl, —$SO_2$-aryl, —$SO_2$-heteroaryl, —$SO_2 NH$-aryl, —$SO_2 NH$-heteroaryl, —$NHSO_2$—($C_1$-$C_6$) alkyl, —$NHSO_2$-aryl, —$NHSO_2$-heteroaryl, —NHCO-aryl, —NHCO-heteroaryl, —CONH-aryl, —CONH-heteroaryl, ($C_1$-$C_6$) alkyl, —O—($C_1$-$C_6$) alkyl, —S—($C_1$-$C_6$) alkyl, —NH—($C_1$-$C_6$) alkyl, —NHCO—($C_1$-$C_6$) alkyl, —CONH—($C_1$-$C_6$) alkyl, —O—($C_3$-$C_6$) cycloalkyl, —S—($C_3$-$C_6$) cycloalkyl, —NH—($C_3$-$C_6$) cycloalkyl, —NHCO—($C_3$-$C_6$) cycloalkyl, or —CONH—($C_3$-$C_6$) cycloalkyl; each alkyl, aryl, cycloalkyl, or heteroaryl optionally substituted with one or more of $R_6$, and when $R_5$ is substituted with more than one $R_6$, the substituents can be identical or different;
$R_6$ and $R_{12}$ are each independently hydrogen, halogen, —CN, —$OCF_3$, —$CF_3$, —$NO_2$, —OH, —SH, —NR$_7$R$_8$, —CONR$_7$R$_8$, —NR$_8$COR$_7$, —NR$_8$CO$_2$R$_7$, —CO$_2$R$_7$, —COR$_7$, —SO$_2$—(C$_1$-C$_6$) alkyl, —SO$_2$-aryl, —SO$_2$-heteroaryl, —SO$_2$R$_7$, —NR$_7$SO$_2$R$_8$, —SO$_2$NR$_7$R$_8$; (C$_1$-C$_6$) alkyl, —O—(C$_1$-C$_6$) alkyl, —S—(C$_1$-C$_6$) alkyl, —NH—(C$_1$-C$_6$) alkyl, —NHCO—(C$_1$-C$_6$) alkyl, —CONH—(C$_1$-C$_6$) alkyl, —O—(C$_3$-C$_6$) cycloalkyl, —S—(C$_3$-C$_6$) cycloalkyl, —NH—(C$_3$-C$_6$) cycloalkyl, —NHCO—(C$_3$-C$_6$) cycloalkyl, —CONH—(C$_3$-C$_6$) cycloalkyl, heterocycloalkyl, —(C$_1$-C$_6$) alkyl-OR$_7$, (C$_2$-C$_6$) alkynyl, (C$_2$-C$_6$) alkenyl, —O—(C$_1$-C$_6$) alkyl-(C$_3$-C$_6$) cycloalkyl, —O-alkenyl, —O—(C$_1$-C$_6$) alkyl substituted with aryl, aryl, heteroaryl, —(CH$_2$)$_n$-aryl, —(CH$_2$)$_n$-heteroaryl, —O-aryl, —O-heteroaryl, —S-aryl, or —S-heteroaryl; each alkyl, aryl, cycloalkyl, heterocycloalkyl, heteroaryl, alkenyl, or alkynyl optionally substituted with one or more of R$_{13}$;

R$_7$ and R$_8$ are each independently hydrogen, (C$_1$-C$_6$) alkyl, aryl, heteroaryl, (C$_2$-C$_6$) alkenyl, (C$_2$-C$_6$) alkynyl, cycloalkyl, —(CH$_2$)$_n$-aryl, or —(CH$_2$)$_n$-heteroaryl; or R$_7$ and R$_8$ together with the atom to which they are attached may form a five- to seven-membered cyclic group containing up to 3 heteroatoms selected from N, O, or S;

R$_9$ and R$_{10}$ are each independently hydrogen, (C$_1$-C$_6$) alkyl, (C$_1$-C$_6$) alkyl-OH, (C$_1$-C$_6$) alkyl-O—(C$_1$-C$_6$) alkyl, aryl, cycloalkyl, heteroaryl, (C$_2$-C$_6$) alkenyl, (C$_2$-C$_6$) alkynyl, bicyclic aryl, tricyclic aryl, bicyclic heteroaryl, or tricyclic heteroaryl, each alkyl, aryl, cycloalkyl, or heteroaryl optionally substituted with one or more R$_{12}$; or R$_9$ and R$_{10}$ together may form a five- to seven-membered cyclic group containing up to 3 heteroatoms selected from N, O, or S;

R$_{11}$ is aryl, heteroaryl, or cycloalkyl;

R$_{13}$ is halogen, —O—(C$_1$-C$_6$) alkyl, —CO$_2$H, —OH, —CF$_3$, hydrogen, (C$_1$-C$_6$) alkyl, aryl, heteroaryl, (C$_2$-C$_6$) alkenyl, (C$_2$-C$_6$) alkynyl, cycloalkyl, cycloalkyl substituted with —OH, aryl substituted with —NH$_2$, aryl substituted with —O—(C$_1$-C$_6$) alkyl, —(CH$_2$)$_n$-aryl, or —(CH$_2$)$_n$-heteroaryl;

m is 0-4;
n is 0-4; and
p is 0-2.

In one embodiment, W is —CO.
In another embodiment, R$_3$ is —CO$_2$H.
In one embodiment, R$_1$ is bicyclic aryl optionally substituted with one or more of R$_5$ and R$_6$.
In another embodiment, R$_1$ is tricyclic aryl optionally substituted with one or more of R$_5$ and R$_6$.
In one embodiment, R$_1$ is biphenyl optionally substituted with one or more of R$_5$ and R$_6$.
In one embodiment, m is 0-2. In another embodiment, m is 0.
In one embodiment, p is 0-2. In another embodiment, p is 2.
In another embodiment, m is 0 and p is 2.
In another embodiment, R$_3$ is

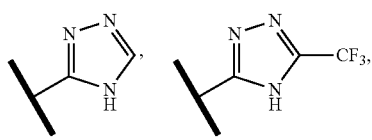

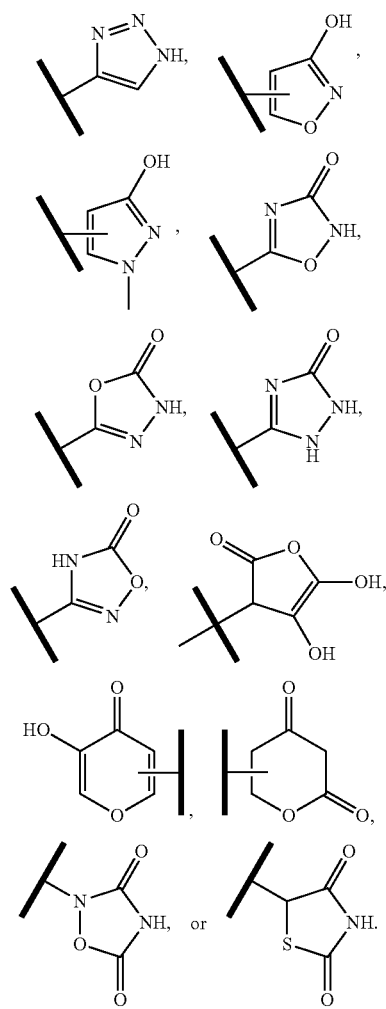

In another embodiment, R$_5$ is

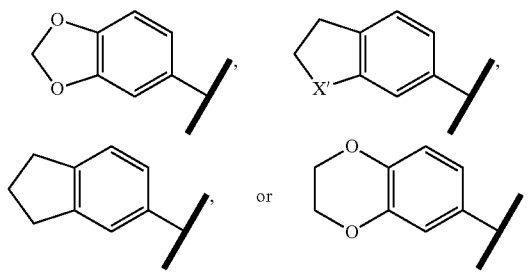

wherein X' is O, S, or NH.

In one embodiment, R$_4$ is —CO$_2$H, —CONH$_2$, —(CH$_2$)$_n$OR$_7$, or —CONR$_9$R$_{10}$.

In one embodiment, W is —CO, R$_2$ is hydrogen, R$_3$ is —CO$_2$H, R$_1$ is biphenyl optionally substituted with one or more of R$_5$ and R$_6$, R$_4$ is —CONR$_9$R$_{10}$, m is 0, and p is 2.

In another embodiment, when R$_4$ is other than hydrogen, the compound or pharmaceutically acceptable salt of the compound is the S-enantiomer with respect to the carbon to which R$_4$ is bound.

In one embodiment, $R_2$ is hydrogen, $R_4$ is

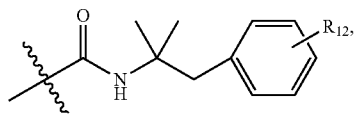

and $R_{12}$ is —F.

In one embodiment, $R_2$ is hydrogen, $R_4$ is

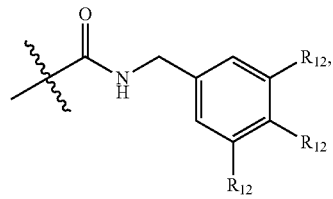

and each $R_{12}$ is —OCH$_3$.

In another embodiment, $R_2$ is hydrogen; and $R_4$ is

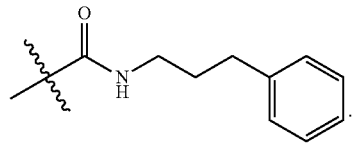

Compounds of the Formula (Ia)

In one embodiment, the invention is directed to compounds of the Formula (Ia):

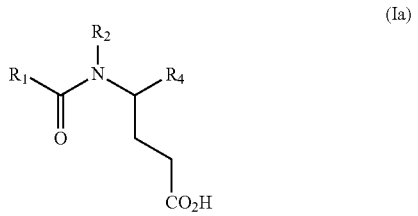

(Ia)

and pharmaceutically acceptable salts thereof, wherein $R_1$ is phenyl, heteroaryl, biphenyl, bicyclic aryl, tricyclic aryl, bicyclic heteroaryl, or tricyclic heteroaryl, each optionally substituted with one or more of $R_5$ or $R_6$, and when $R_1$ is substituted with more than one of $R_5$ or $R_6$, the substituents can be identical or different;

$R_2$ is hydrogen, ($C_1$-$C_6$) alkyl, ($C_2$-$C_6$) alkenyl, ($C_2$-$C_6$) alkynyl, —(CH$_2$)$_n$R$_{11}$, —OH, or —O—($C_1$-$C_6$) alkyl;

$R_4$ is —CO$_2$H, —CONH$_2$, —(CH$_2$)$_n$OR$_7$, or —CONR$_9$R$_{10}$;

$R_5$ is aryl, heteroaryl, —(CH$_2$)$_n$-aryl, —(CH$_2$)$_n$-heteroaryl, —O-aryl, —O-heteroaryl, —S-aryl, —S-heteroaryl, —NH-aryl, —NH-heteroaryl, —CO—($C_1$-$C_6$) alkyl, —CO-aryl, —CO-heteroaryl, —SO$_2$—($C_1$-$C_6$) alkyl, —SO$_2$-aryl, —SO$_2$-heteroaryl, —SO$_2$NH-aryl, —SO$_2$NH-heteroaryl, —NHSO$_2$—($C_1$-$C_6$) alkyl, —NHSO$_2$-aryl, —NHSO$_2$-heteroaryl, —NHCO-aryl, —NHCO-heteroaryl, —CONH-aryl, —CONH-heteroaryl, ($C_1$-$C_6$) alkyl, —O—($C_1$-$C_6$) alkyl, —S—($C_1$-$C_6$) alkyl, —NH—($C_1$-$C_6$) alkyl, —NHCO—($C_1$-$C_6$) alkyl, —CONH—($C_1$-$C_6$) alkyl, —O—($C_3$-$C_6$) cycloalkyl, —S—($C_3$-$C_6$) cycloalkyl, —NH—($C_3$-$C_6$) cycloalkyl, —NHCO—($C_3$-$C_6$) cycloalkyl, or —CONH—($C_3$-$C_6$) cycloalkyl; each alkyl, aryl, cycloalkyl, or heteroaryl optionally substituted with one or more of $R_6$, and when $R_5$ is substituted with more than one $R_6$, the substituents can be identical or different;

$R_6$ and $R_{12}$ are each independently hydrogen, halogen, —CN, —OCF$_3$, —CF$_3$, —NO$_2$, —OH, —SH, —NR$_7$R$_8$, —CONR$_7$R$_8$, —NR$_8$COR$_7$, —NR$_8$CO$_2$R$_7$, —CO$_2$R$_7$, —COR$_7$, —SO$_2$—($C_1$-$C_6$) alkyl, —SO$_2$-aryl, —SO$_2$-heteroaryl, —SO$_2$R$_7$, —NR$_7$SO$_2$R$_8$, —SO$_2$NR$_7$R$_8$; ($C_1$-$C_6$) alkyl, —O—($C_1$-$C_6$) alkyl, —S—($C_1$-$C_6$) alkyl, —NH—($C_1$-$C_6$) alkyl, —NHCO—($C_1$-$C_6$) alkyl, —CONH—($C_1$-$C_6$) alkyl, —O—($C_3$-$C_6$) cycloalkyl, —S—($C_3$-$C_6$) cycloalkyl, —NH—($C_3$-$C_6$) cycloalkyl, —NHCO—($C_3$-$C_6$) cycloalkyl, —CONH—($C_3$-$C_6$) cycloalkyl, heterocycloalkyl, —($C_1$-$C_6$) alkyl-OR$_7$, ($C_2$-$C_6$) alkynyl, ($C_2$-$C_6$) alkenyl, —O—($C_1$-$C_6$) alkyl-($C_3$-$C_6$) cycloalkyl, —O-alkenyl, —O—($C_1$-$C_6$) alkyl substituted with aryl, aryl, heteroaryl, —(CH$_2$)$_n$-aryl, —(CH$_2$)$_n$-heteroaryl, —O-aryl, —O-heteroaryl, —S-aryl, or —S-heteroaryl; each alkyl, aryl, cycloalkyl, heterocycloalkyl, heteroaryl, alkenyl, or alkynyl optionally substituted with one or more of $R_{13}$;

$R_7$ and $R_8$ are each independently hydrogen, ($C_1$-$C_6$) alkyl, aryl, heteroaryl, ($C_2$-$C_6$) alkenyl, ($C_2$-$C_6$) alkynyl, cycloalkyl, —(CH$_2$)$_n$-aryl, or —(CH$_2$)$_n$-heteroaryl; or $R_7$ and $R_8$ together with the atom to which they are attached may form a five- to seven-membered cyclic group containing up to 3 heteroatoms selected from N, O, or S;

$R_9$ and $R_{10}$ are each independently hydrogen, ($C_1$-$C_6$) alkyl, ($C_1$-$C_6$) alkyl-OH, ($C_1$-$C_6$) alkyl-O—($C_1$-$C_6$) alkyl, aryl, cycloalkyl, heteroaryl, ($C_2$-$C_6$) alkenyl, ($C_2$-$C_6$) alkynyl, bicyclic aryl, tricyclic aryl, bicyclic heteroaryl, or tricyclic heteroaryl, each alkyl, aryl, cycloalkyl, or heteroaryl optionally substituted with one or more $R_{12}$; or $R_9$ and $R_{10}$ together may form a five- to seven-membered cyclic group containing up to 3 heteroatoms selected from N, O, or S;

$R_{11}$ is aryl, heteroaryl, or cycloalkyl;

$R_{13}$ is halogen, —O—($C_1$-$C_6$) alkyl, —CO$_2$H, —OH, —CF$_3$, hydrogen, ($C_1$-$C_6$) alkyl, aryl, heteroaryl, ($C_2$-$C_6$) alkenyl, ($C_2$-$C_6$) alkynyl, cycloalkyl, cycloalkyl substituted with —OH, aryl substituted with —NH$_2$, aryl substituted with —O—($C_1$-$C_6$) alkyl, —(CH$_2$)$_n$-aryl, or —(CH$_2$)$_n$-heteroaryl; and n is 0-4.

In one embodiment, $R_1$ is bicyclic aryl optionally substituted with one or more of $R_5$ and $R_6$.

In another embodiment, $R_1$ is tricyclic aryl optionally substituted with one or more of $R_5$ and $R_6$.

In one embodiment, $R_1$ is biphenyl optionally substituted with one or more of $R_5$ and $R_6$.

In one embodiment, $R_4$ is —CO$_2$H, —CONH$_2$, —(CH$_2$)$_n$OR$_7$, or —CONR$_9$R$_{10}$.

In one embodiment, $R_1$ is biphenyl optionally substituted with one or more of $R_5$ and $R_6$, and $R_4$ is —CONR$_9$R$_{10}$.

In another embodiment, $R_5$ is

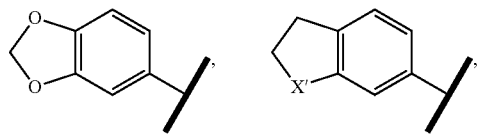

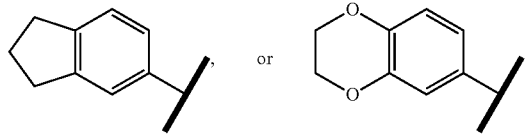

wherein X' is O, S, or NH.

In another embodiment, when $R_4$ is other than hydrogen, the compound or pharmaceutically acceptable salt of the compound is the S-enantiomer with respect to the carbon to which $R_4$ is bound.

In one embodiment, $R_2$ is hydrogen, $R_4$ is

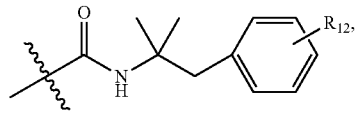

and $R_{12}$ is —F.

In one embodiment, $R_2$ is hydrogen, $R_4$ is

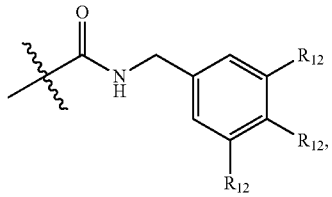

and each $R_{12}$ is —OCH$_3$.

In another embodiment, $R_2$ is hydrogen; and $R_4$ is

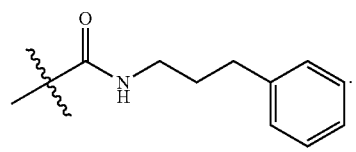

Compounds of the Formula (Ib)

In one embodiment, the invention is directed to compounds of the Formula (Ib):

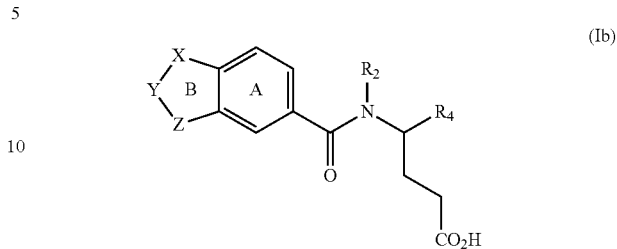

and pharmaceutically acceptable salts thereof,
wherein
X, Y, and Z are each independently (CH$_2$)$_n$, O, S, NR$_7$, CO, or SO$_2$; or X, Y, and Z form a benzene in ring B; ring A and ring B are each independently optionally substituted with one or more of $R_5$ and $R_6$;
$R_2$ is hydrogen, (C$_1$-C$_6$) alkyl, (C$_2$-C$_6$) alkenyl, (C$_2$-C$_6$) alkynyl, —(CH$_2$)$_n$R$_{11}$, —OH, or —O—(C$_1$-C$_6$) alkyl;
$R_4$ is —CO$_2$H, —CONH$_2$, —(CH$_2$)$_n$OR$_7$, or —CONR$_9$R$_{10}$;
$R_5$ is aryl, heteroaryl, —(CH$_2$)$_n$-aryl, —(CH$_2$)$_n$-heteroaryl, —O-aryl, —O-heteroaryl, —S-aryl, —S-heteroaryl, —NH-aryl, —NH-heteroaryl, —CO—(C$_1$-C$_6$) alkyl, —CO-aryl, —CO-heteroaryl, —SO$_2$—(C$_1$-C$_6$) alkyl, —SO$_2$-aryl, —SO$_2$-heteroaryl, —SO$_2$NH-aryl, —SO$_2$NH-heteroaryl, —NHSO$_2$—(C$_1$-C$_6$) alkyl, —NHSO$_2$-aryl, —NHSO$_2$-heteroaryl, —NHCO-aryl, —NHCO-heteroaryl, —CONH-aryl, —CONH-heteroaryl, (C$_1$-C$_6$) alkyl, —O—(C$_1$-C$_6$) alkyl, —S—(C$_1$-C$_6$) alkyl, —NH—(C$_1$-C$_6$) alkyl, —NHCO—(C$_1$-C$_6$) alkyl, —CONH—(C$_1$-C$_6$) alkyl, —O—(C$_3$-C$_6$) cycloalkyl, —S—(C$_3$-C$_6$) cycloalkyl, —NH—(C$_3$-C$_6$) cycloalkyl, —NHCO—(C$_3$-C$_6$) cycloalkyl, or —CONH—(C$_3$-C$_6$) cycloalkyl; each alkyl, aryl, cycloalkyl, or heteroaryl optionally substituted with one or more of $R_6$, and when $R_5$ is substituted with more than one $R_6$, the substituents can be identical or different;
$R_6$ and $R_{12}$ are each independently hydrogen, halogen, —CN, —OCF$_3$, —CF$_3$, —NO$_2$, —OH, —SH, —NR$_7$R$_8$, —CONR$_7$R$_8$, —NR$_8$COR$_7$, —NR$_8$CO$_2$R$_7$, —CO$_2$R$_7$, —COR$_7$, —SO$_2$—(C$_1$-C$_6$) alkyl, —SO$_2$-aryl, —SO$_2$-heteroaryl, —SO$_2$R$_7$, —NR$_7$SO$_2$R$_8$, —SO$_2$NR$_7$R$_8$; (C$_1$-C$_6$) alkyl, —O—(C$_1$-C$_6$) alkyl, —S—(C$_1$-C$_6$) alkyl, —NH—(C$_1$-C$_6$) alkyl, —NHCO—(C$_1$-C$_6$) alkyl, —CONH—(C$_1$-C$_6$) alkyl, —O—(C$_3$-C$_6$) cycloalkyl, —S—(C$_3$-C$_6$) cycloalkyl, —NH—(C$_3$-C$_6$) cycloalkyl, —NHCO—(C$_3$-C$_6$) cycloalkyl, —CONH—(C$_3$-C$_6$) cycloalkyl, heterocycloalkyl, —(C$_1$-C$_6$) alkyl-OR$_7$, (C$_2$-C$_6$) alkynyl, (C$_2$-C$_6$) alkenyl, —O—(C$_1$-C$_6$) alkyl-(C$_3$-C$_6$) cycloalkyl, —O-alkenyl, —O—(C$_1$-C$_6$) alkyl substituted with aryl, aryl, heteroaryl, —(CH$_2$)$_n$-aryl, —(CH$_2$)$_n$-heteroaryl, —O-aryl, —O-heteroaryl, —S-aryl, or —S-heteroaryl; each alkyl, aryl, cycloalkyl, heterocycloalkyl, heteroaryl, alkenyl, or alkynyl optionally substituted with one or more of $R_{13}$;
$R_7$ and $R_8$ are each independently hydrogen, (C$_1$-C$_6$) alkyl, aryl, heteroaryl, (C$_2$-C$_6$) alkenyl, (C$_2$-C$_6$) alkynyl, cycloalkyl, —(CH$_2$)$_n$-aryl, or —(CH$_2$)$_n$-heteroaryl; or $R_7$ and $R_8$ together with the atom to which they are attached may form a five- to seven-membered cyclic group containing up to 3 heteroatoms selected from N, O, or S;

$R_9$ and $R_{10}$ are each independently hydrogen, $(C_1-C_6)$ alkyl, $(C_1-C_6)$ alkyl-OH, $(C_1-C_6)$ alkyl-O—$(C_1-C_6)$ alkyl, aryl, cycloalkyl, heteroaryl, $(C_2-C_6)$ alkenyl, $(C_2-C_6)$ alkynyl, bicyclic aryl, tricyclic aryl, bicyclic heteroaryl, or tricyclic heteroaryl, each alkyl, aryl, cycloalkyl, or heteroaryl optionally substituted with one or more $R_{12}$; or $R_9$ and $R_{10}$ together may form a five- to seven-membered cyclic group containing up to 3 heteroatoms selected from N, O, or S;

$R_{11}$ is aryl, heteroaryl, or cycloalkyl;

$R_{13}$ is halogen, —O—$(C_1-C_6)$ alkyl, —$CO_2H$, —OH, —$CF_3$, hydrogen, $(C_1-C_6)$ alkyl, aryl, heteroaryl, $(C_2-C_6)$ alkenyl, $(C_2-C_6)$ alkynyl, cycloalkyl, cycloalkyl substituted with —OH, aryl substituted with —$NH_2$, aryl substituted with —O—$(C_1-C_6)$ alkyl, —$(CH_2)_n$-aryl, or —$(CH_2)_n$-heteroaryl; and n is 0-4.

In one embodiment, $R_4$ is —$CO_2H$, —$CONH_2$, —$(CH_2)_n OR_7$, or —$CONR_9R_{10}$.

In another embodiment, when $R_4$ is other than hydrogen, the compound or pharmaceutically acceptable salt of the compound is the S-enantiomer with respect to the carbon to which $R_4$ is bound.

In one embodiment, $R_2$ is hydrogen, $R_4$ is

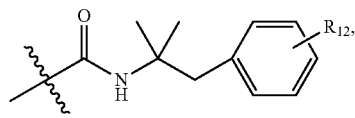

and $R_{12}$ is —F.

In one embodiment, $R_2$ is hydrogen; $R_4$ is

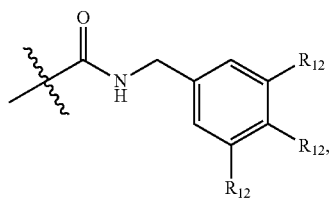

And each $R_{12}$ is —$OCH_3$.

In another embodiment, $R_2$ is hydrogen; and $R_4$ is

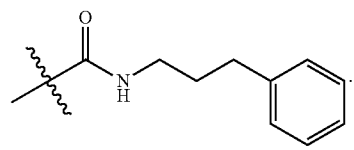

Compounds of the Formula (Ic)

In one embodiment, the invention is directed to compounds of the Formula (Ic):

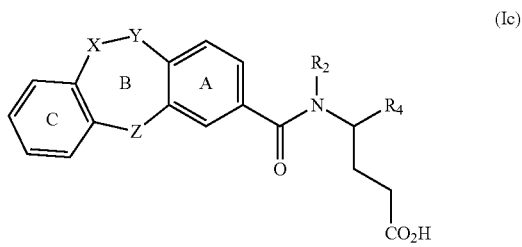

and pharmaceutically acceptable salts thereof,
wherein
X, Y, and Z are each independently $(CH_2)_n$, O, S, $NR_7$, CO, or $SO_2$; or X, Y, and Z form a benzene in ring B; ring A, ring B, and ring C are each independently optionally substituted with one or more of $R_5$ and $R_6$;

$R_2$ is hydrogen, $(C_1-C_6)$ alkyl, $(C_2-C_6)$ alkenyl, $(C_2-C_6)$ alkynyl, —$(CH_2)_nR_{11}$, —OH, or —O—$(C_1-C_6)$ alkyl;

$R_4$ is —$CO_2H$, —$CONH_2$, —$(CH_2)_nOR_7$, or —$CONR_9R_{10}$;

$R_5$ is aryl, heteroaryl, —$(CH_2)_n$-aryl, —$(CH_2)_n$-heteroaryl, —O-aryl, —O-heteroaryl, —S-aryl, —S-heteroaryl, —NH-aryl, —NH-heteroaryl, —CO—$(C_1-C_6)$ alkyl, —CO-aryl, —CO-heteroaryl, —$SO_2$—$(C_1-C_6)$ alkyl, —$SO_2$-aryl, —$SO_2$-heteroaryl, —$SO_2NH$-aryl, —$SO_2NH$-heteroaryl, —$NHSO_2$—$(C_1-C_6)$ alkyl, —$NHSO_2$-aryl, —$NHSO_2$-heteroaryl, —NHCO-aryl, —NHCO-heteroaryl, —CONH-aryl, —CONH-heteroaryl, $(C_1-C_6)$ alkyl, —O—$(C_1-C_6)$ alkyl, —S—$(C_1-C_6)$ alkyl, —NH—$(C_1-C_6)$ alkyl, —NHCO—$(C_1-C_6)$ alkyl, —CONH—$(C_1-C_6)$ alkyl, —O—$(C_3-C_6)$ cycloalkyl, —S—$(C_3-C_6)$ cycloalkyl, —NH—$(C_3-C_6)$ cycloalkyl, —NHCO—$(C_3-C_6)$ cycloalkyl, or —CONH—$(C_3-C_6)$ cycloalkyl; each alkyl, aryl, cycloalkyl, or heteroaryl optionally substituted with one or more of $R_6$, and when $R_5$ is substituted with more than one $R_6$, the substituents can be identical or different;

$R_6$ and $R_{12}$ are each independently hydrogen, halogen, —CN, —$OCF_3$, —$CF_3$, —$NO_2$, —OH, —SH, —$NR_7R_8$, —$CONR_7R_8$, —$NR_8COR_7$, —$NR_8CO_2R_7$, —$CO_2R_7$, —$COR_7$, —$SO_2$—$(C_1-C_6)$ alkyl, —$SO_2$-aryl, —$SO_2$-heteroaryl, —$SO_2R_7$, —$NR_7SO_2R_8$, —$SO_2NR_7R_8$; $(C_1-C_6)$ alkyl, —O—$(C_1-C_6)$ alkyl, —S—$(C_1-C_6)$ alkyl, —NH—$(C_1-C_6)$ alkyl, —NHCO—$(C_1-C_6)$ alkyl, —CONH—$(C_1-C_6)$ alkyl, —O—$(C_3-C_6)$ cycloalkyl, —S—$(C_3-C_6)$ cycloalkyl, —NH—$(C_3-C_6)$ cycloalkyl, —NHCO—$(C_3-C_6)$ cycloalkyl, —CONH—$(C_3-C_6)$ cycloalkyl, heterocycloalkyl, —$(C_1-C_6)$ alkyl-$OR_7$, $(C_2-C_6)$ alkynyl, $(C_2-C_6)$ alkenyl, —O—$(C_1-C_6)$ alkyl-$(C_3-C_6)$ cycloalkyl, —O-alkenyl, —O—$(C_1-C_6)$ alkyl substituted with aryl, aryl, heteroaryl, —$(CH_2)_n$-aryl, —$(CH_2)_n$-heteroaryl, —O-aryl, —O-heteroaryl, —S-aryl, or —S-heteroaryl; each alkyl, aryl, cycloalkyl, heterocycloalkyl, heteroaryl, alkenyl, or alkynyl optionally substituted with one or more of $R_{13}$;

$R_7$ and $R_8$ are each independently hydrogen, $(C_1-C_6)$ alkyl, aryl, heteroaryl, $(C_2-C_6)$ alkenyl, $(C_2-C_6)$ alkynyl, cycloalkyl, —$(CH_2)_n$-aryl, or —$(CH_2)_n$-heteroaryl; or $R_7$ and $R_8$ together with the atom to which they are attached may form a five- to seven-membered cyclic group containing up to 3 heteroatoms selected from N, O, or S;

$R_9$ and $R_{10}$ are each independently hydrogen, $(C_1-C_6)$ alkyl, $(C_1-C_6)$ alkyl-OH, $(C_1-C_6)$ alkyl-O—$(C_1-C_6)$ alkyl, aryl, cycloalkyl, heteroaryl, $(C_2-C_6)$ alkenyl, $(C_2-C_6)$ alkynyl, bicyclic aryl, tricyclic aryl, bicyclic heteroaryl, or tricyclic heteroaryl, each alkyl, aryl, cycloalkyl, or heteroaryl optionally substituted with one or more $R_{12}$; or $R_9$ and $R_{10}$ together may form a five- to seven-membered cyclic group containing up to 3 heteroatoms selected from N, O, or S;

$R_{11}$ is aryl, heteroaryl, or cycloalkyl;

$R_{13}$ is halogen, —O—$(C_1-C_6)$ alkyl, —$CO_2H$, —OH, —$CF_3$, hydrogen, $(C_1-C_6)$ alkyl, aryl, heteroaryl, $(C_2-C_6)$ alkenyl, $(C_2-C_6)$ alkynyl, cycloalkyl, cycloalkyl substituted with —OH, aryl substituted with —$NH_2$, aryl substituted with —O—$(C_1-C_6)$ alkyl, —$(CH_2)_n$-aryl, or —$(CH_2)_n$-heteroaryl; and n is 0-4.

In one embodiment, $R_4$ is —$CO_2H$, —$CONH_2$, —$(CH_2)_n OR_7$, or —$CONR_9R_{10}$.

In another embodiment, when $R_4$ is other than hydrogen, the compound or pharmaceutically acceptable salt of the compound is the S-enantiomer with respect to the carbon to which $R_4$ is bound.

In one embodiment, $R_2$ is hydrogen, $R_4$ is

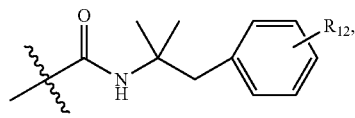

and $R_{12}$ is —F.

In one embodiment, $R_2$ is hydrogen; $R_4$ is

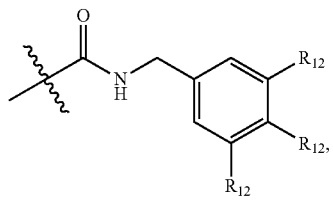

and each $R_{12}$ is —$OCH_3$.

In another embodiment, $R_2$ is hydrogen; and $R_4$ is

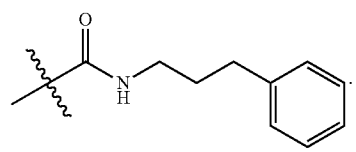

Compounds of the Formula (Id)

In one embodiment, the invention is directed to compounds of the Formula (Id):

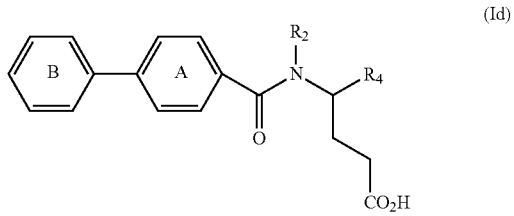

and pharmaceutically acceptable salts thereof,
wherein
ring A and ring B are each independently optionally substituted with one or more of $R_5$ and $R_6$;

$R_2$ is hydrogen, $(C_1-C_6)$ alkyl, $(C_2-C_6)$ alkenyl, $(C_2-C_6)$ alkynyl, —$(CH_2)_n R_{11}$, —OH, or —O—$(C_1-C_6)$ alkyl;

$R_4$ is —$CO_2H$, —$CONH_2$, —$(CH_2)_n OR_7$, or —$CONR_9R_{10}$;

$R_5$ is aryl, heteroaryl, —$(CH_2)_n$-aryl, —$(CH_2)_n$-heteroaryl, —O-aryl, —O-heteroaryl, —S-aryl, —S-heteroaryl, —NH-aryl, —NH-heteroaryl, —CO—$(C_1-C_6)$ alkyl, —CO-aryl, —CO-heteroaryl, —$SO_2$—$(C_1-C_6)$ alkyl, —$SO_2$-aryl, —$SO_2$-heteroaryl, —$SO_2$NH-aryl, —$SO_2$NH-heteroaryl, —$NHSO_2$—$(C_1-C_6)$ alkyl, —$NHSO_2$-aryl, —$NHSO_2$-heteroaryl, —NHCO-aryl, —NHCO-heteroaryl, —CONH-aryl, —CONH-heteroaryl, $(C_1-C_6)$ alkyl, —O—$(C_1-C_6)$ alkyl, —S—$(C_1-C_6)$ alkyl, —NH—$(C_1-C_6)$ alkyl, —NHCO—$(C_1-C_6)$ alkyl, —CONH—$(C_1-C_6)$ alkyl, —O—$(C_3-C_6)$ cycloalkyl, —S—$(C_3-C_6)$ cycloalkyl, —NH—$(C_3-C_6)$ cycloalkyl, —NHCO—$(C_3-C_6)$ cycloalkyl, or —CONH—$(C_3-C_6)$ cycloalkyl; each alkyl, aryl, cycloalkyl, or heteroaryl optionally substituted with one or more of $R_6$, and when $R_5$ is substituted with more than one $R_6$, the substituents can be identical or different;

$R_6$ and $R_{12}$ are each independently hydrogen, halogen, —CN, —$OCF_3$, —$CF_3$, —$NO_2$, —OH, —SH, —$NR_7R_8$, —$CONR_7R_8$, —$NR_8COR_7$, —$NR_8CO_2R_7$, —$CO_2R_7$, —$COR_7$, —$SO_2$—$(C_1-C_6)$ alkyl, —$SO_2$-aryl, —$SO_2$-heteroaryl, —$SO_2R_7$, —$NR_7SO_2R_8$, —$SO_2NR_7R_8$; $(C_1-C_6)$ alkyl, —O—$(C_1-C_6)$ alkyl, —S—$(C_1-C_6)$ alkyl, —NH—$(C_1-C_6)$ alkyl, —NHCO—$(C_1-C_6)$ alkyl, —CONH—$(C_1-C_6)$ alkyl, —O—$(C_3-C_6)$ cycloalkyl, —S—$(C_3-C_6)$ cycloalkyl, —NH—$(C_3-C_6)$ cycloalkyl, —NHCO—$(C_3-C_6)$ cycloalkyl, —CONH—$(C_3-C_6)$ cycloalkyl, heterocycloalkyl, —$(C_1-C_6)$ alkyl-$OR_7$, $(C_2-C_6)$ alkynyl, $(C_2-C_6)$ alkenyl, —O—$(C_1-C_6)$ alkyl-$(C_3-C_6)$ cycloalkyl, —O-alkenyl, —O—$(C_1-C_6)$ alkyl substituted with aryl, aryl, heteroaryl, —$(CH_2)_n$-aryl, —$(CH_2)_n$-heteroaryl, —O-aryl, —O-heteroaryl, —S-aryl, or —S-heteroaryl; each alkyl, aryl, cycloalkyl, heterocycloalkyl, heteroaryl, alkenyl, or alkynyl optionally substituted with one or more of $R_{13}$;

$R_7$ and $R_8$ are each independently hydrogen, $(C_1-C_6)$ alkyl, aryl, heteroaryl, $(C_2-C_6)$ alkenyl, $(C_2-C_6)$ alkynyl, cycloalkyl, —$(CH_2)_n$-aryl, or —$(CH_2)_n$-heteroaryl; or $R_7$ and $R_8$ together with the atom to which they are attached may form a five- to seven-membered cyclic group containing up to 3 heteroatoms selected from N, O, or S;

$R_9$ and $R_{10}$ are each independently hydrogen, $(C_1\text{-}C_6)$ alkyl, $(C_1\text{-}C_6)$ alkyl-OH, $(C_1\text{-}C_6)$ alkyl-O—$(C_1\text{-}C_6)$ alkyl, aryl, cycloalkyl, heteroaryl, $(C_2\text{-}C_6)$ alkenyl, $(C_2\text{-}C_6)$ alkynyl, bicyclic aryl, tricyclic aryl, bicyclic heteroaryl, or tricyclic heteroaryl, each alkyl, aryl, cycloalkyl, or heteroaryl optionally substituted with one or more $R_{12}$; or $R_9$ and $R_{10}$ together may form a five- to seven-membered cyclic group containing up to 3 heteroatoms selected from N, O, or S;

$R_{11}$ is aryl, heteroaryl, or cycloalkyl;

$R_{13}$ is halogen, —O—$(C_1\text{-}C_6)$ alkyl, —$CO_2H$, —OH, —$CF_3$, hydrogen, $(C_1\text{-}C_6)$ alkyl, aryl, heteroaryl, $(C_2\text{-}C_6)$ alkenyl, $(C_2\text{-}C_6)$ alkynyl, cycloalkyl, cycloalkyl substituted with —OH, aryl substituted with —$NH_2$, aryl substituted with —O—$(C_1\text{-}C_6)$ alkyl, —$(CH_2)_n$-aryl, or —$(CH_2)_n$-heteroaryl; and n is 0-4.

In one embodiment, $R_4$ is —$CO_2H$, —$CONH_2$, —$(CH_2)_n$ $OR_7$, or —$CONR_9R_{10}$.

In another embodiment, when $R_4$ is other than hydrogen, the compound or pharmaceutically acceptable salt of the compound is the S-enantiomer with respect to the carbon to which $R_4$ is bound.

In one embodiment, $R_2$ is hydrogen, $R_4$ is

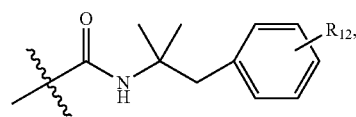

and $R_{12}$ is —F.

In one embodiment, $R_2$ is hydrogen; $R_4$ is

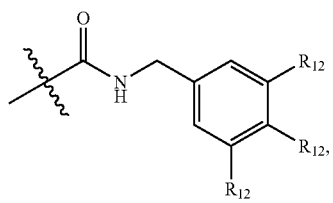

and each $R_{12}$ is —$OCH_3$.

In another embodiment, $R_2$ is hydrogen; and $R_4$ is

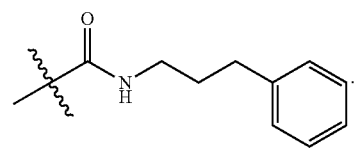

Compounds of the Formula (II)

In another embodiment, the invention provides compounds of the Formula (II):

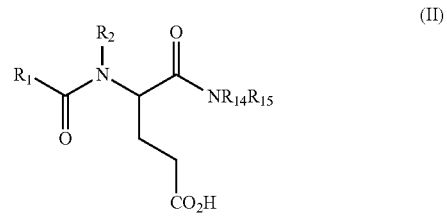

and pharmaceutically acceptable salts thereof, wherein $R_1$ is phenyl, $(C_1\text{-}C_6)$ alkyl substituted with phenyl, heteroaryl, biphenyl, bicyclic aryl, tricyclic aryl, bicyclic heteroaryl, or tricyclic heteroaryl, each optionally substituted with one or more of $R_5$ or $R_6$, and when $R_1$ is substituted with more than one of $R_5$ or $R_6$, the substituents can be identical or different;

$R_2$ is hydrogen, $(C_1\text{-}C_6)$ alkyl, $(C_2\text{-}C_6)$ alkenyl, $(C_2\text{-}C_6)$ alkynyl, —$(CH_2)_pR_{11}$, —OH, or —O—$(C_1\text{-}C_6)$ alkyl;

$R_5$ is aryl, heteroaryl, —$(CH_2)_n$-aryl, —$(CH_2)_n$-heteroaryl, —O-aryl, —O-heteroaryl, —S-aryl, —S-heteroaryl, —NH-aryl, —NH-heteroaryl, —CO—$(C_1\text{-}C_6)$ alkyl, —CO-aryl, —CO-heteroaryl, —$SO_2$—$(C_1\text{-}C_6)$ alkyl, —$SO_2$-aryl, —$SO_2$-heteroaryl, —$SO_2$NH-aryl, —$SO_2$NH-heteroaryl, —$NHSO_2$—$(C_1\text{-}C_6)$ alkyl, —$NHSO_2$-aryl, —$NHSO_2$-heteroaryl, —NHCO-aryl, —NHCO-heteroaryl, —CONH-aryl, —CONH-heteroaryl, $(C_1\text{-}C_6)$ alkyl, —O—$(C_1\text{-}C_6)$ alkyl, —S—$(C_1\text{-}C_6)$ alkyl, —NH—$(C_1\text{-}C_6)$ alkyl, —NHCO—$(C_1\text{-}C_6)$ alkyl, —CONH—$(C_1\text{-}C_6)$ alkyl, —O—$(C_3\text{-}C_6)$ cycloalkyl, —S—$(C_3\text{-}C_6)$ cycloalkyl, —NH—$(C_3\text{-}C_6)$ cycloalkyl, —NHCO—$(C_3\text{-}C_6)$ cycloalkyl, or —CONH—$(C_3\text{-}C_6)$ cycloalkyl; each alkyl, aryl, cycloalkyl, or heteroaryl optionally substituted with one or more of $R_6$, and when $R_5$ is substituted with more than one $R_6$, the substituents can be identical or different;

$R_6$ and $R_{12}$ are each independently hydrogen, halogen, —CN, —$OCF_3$, —$CF_3$, —$NO_2$, —OH, —SH, —$NR_7R_8$, —$CONR_7R_8$, —$NR_8COR_7$, —$NR_8CO_2R_7$, —$CO_2R_7$, —$COR_7$, —$SO_2$—$(C_1\text{-}C_6)$ alkyl, —$SO_2$-aryl, —$SO_2$-heteroaryl, —$SO_2R_7$, —$NR_7SO_2R_8$, —$SO_2NR_7R_8$; $(C_1\text{-}C_6)$ alkyl, —O—$(C_1\text{-}C_6)$ alkyl, —S—$(C_1\text{-}C_6)$ alkyl, —NH—$(C_1\text{-}C_6)$ alkyl, —NHCO—$(C_1\text{-}C_6)$ alkyl, —CONH—$(C_1\text{-}C_6)$ alkyl, —O—$(C_3\text{-}C_6)$ cycloalkyl, —S—$(C_3\text{-}C_6)$ cycloalkyl, —NH—$(C_3\text{-}C_6)$ cycloalkyl, —NHCO—$(C_3\text{-}C_6)$ cycloalkyl, —CONH—$(C_3\text{-}C_6)$ cycloalkyl, heterocycloalkyl, —$(C_1\text{-}C_6)$ alkyl-$OR_7$, $(C_2\text{-}C_6)$ alkynyl, $(C_2\text{-}C_6)$ alkenyl, —O— $(C_1\text{-}C_6)$ alkyl-$(C_3\text{-}C_6)$ cycloalkyl, —O-alkenyl, —O— $(C_1\text{-}C_6)$ alkyl substituted with aryl, aryl, heteroaryl, —$(CH_2)_n$-aryl, —$(CH_2)_n$-heteroaryl, —O-aryl, —O-heteroaryl, —S-aryl, or —S-heteroaryl; each alkyl, aryl, cycloalkyl, heterocycloalkyl, heteroaryl, alkenyl, or alkynyl optionally substituted with one or more of $R_{13}$;

$R_7$ and $R_8$ are each independently hydrogen, $(C_1\text{-}C_6)$ alkyl, aryl, heteroaryl, $(C_2\text{-}C_6)$ alkenyl, $(C_2\text{-}C_6)$ alkynyl, cycloalkyl, —$(CH_2)_n$-aryl, or —$(CH_2)_n$-heteroaryl; or $R_7$ and $R_8$ together with the atom to which they are attached may form a five- to seven-membered cyclic group containing up to 3 heteroatoms selected from N, O, or S;

$R_{11}$ is aryl, heteroaryl, or cycloalkyl;

$R_{13}$ is halogen, —O—$(C_1\text{-}C_6)$ alkyl, —$CO_2H$, —OH, —$CF_3$, hydrogen, $(C_1\text{-}C_6)$ alkyl, aryl, heteroaryl, $(C_2$-

$C_6$) alkenyl, ($C_2$-$C_6$) alkynyl, cycloalkyl, cycloalkyl substituted with —OH, aryl substituted with —$NH_2$, aryl substituted with —O—($C_1$-$C_6$) alkyl, —$(CH_2)_n$-aryl, or —$(CH_2)_n$-heteroaryl;

$R_{14}$ and $R_{15}$ are each independently hydrogen, ($C_1$-$C_6$) alkyl, aryl, heteroaryl, ($C_2$-$C_6$) alkenyl, ($C_2$-$C_6$) alkynyl, cycloalkyl, heterocycloalkyl —$(CH_2)_n$-aryl, bicyclic aryl, tricyclic aryl, bicyclic heteroaryl, or tricyclic heteroaryl; each alkyl, aryl, cycloalkyl, heterocycloalkyl, or heteroaryl optionally substituted with one or more $R_{12}$; or $R_{14}$ and $R_{15}$ together may form a five- to seven-membered cyclic group containing up to 3 heteroatoms selected from N, O, or S;

n is 0-4, and
p is 0-2.

In one embodiment, $R_1$ is bicyclic aryl optionally substituted with one or more of $R_5$ and $R_6$.

In another embodiment, $R_1$ is tricyclic aryl optionally substituted with one or more of $R_5$ and $R_6$.

In one embodiment, $R_1$ is biphenyl optionally substituted with one or more of $R_5$ and $R_6$.

In another embodiment, $R_5$ is

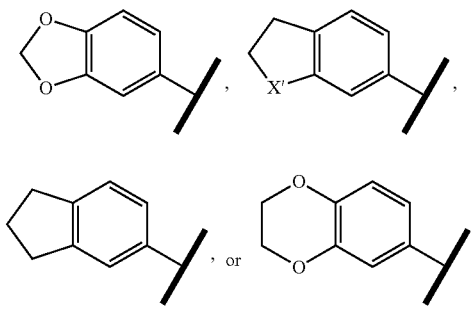

wherein X' is O, S, or NH.

In another embodiment, $R_2$ is hydrogen.

In one embodiment, the compound of Formula (I) is $N^2$-(4-benzoylbenzoyl)-$N^1$-benzyl-L-α-glutamine, N-(4-benzoylbenzoyl)-L-glutamic acid, $N^1$-(1,3-benzodioxol-5-ylmethyl)-$N^2$-(1,1'-biphenyl-4-ylcarbonyl)-L-α-glutamine, $N^2$-(1,1'-biphenyl-4-ylcarbonyl)-$N^1$-butyl-L-α-glutamine, $N^2$-(1,1'-biphenyl-4-ylcarbonyl)-$N^1$-cyclopropyl-L-α-glutamine, $N^2$-(1,1'-biphenyl-4-ylcarbonyl)-$N^1$-cyclohexyl-L-α-glutamine, $N^1$-benzyl-$N^2$-(4-thien-2-ylbenzoyl)-L-α-glutamine, $N^1$-benzyl-$N^2$-[4-(2-furyl)benzoyl]-L-α-glutamine, $N^1$-benzyl-$N^2$-[(4'-ethynyl-1,1'-biphenyl-4-yl)carbonyl]-L-α-glutamine, $N^2$-(1,1'-biphenyl-4-ylcarbonyl)-$N^1$-(4-fluorobenzyl)-L-α-glutamine, $N^2$-(1,1'-biphenyl-4-ylcarbonyl)-$N^1$-cyclooctyl-L-α-glutamine, $N^1$-benzyl-$N^2$-(4-bromobenzoyl)-L-α-glutamine, $N^1$-benzyl-$N^2$-[(2',5'-dimethyl-1,1'-biphenyl-4-yl)carbonyl]-L-α-glutamine, $N^2$-(1,1'-biphenyl-4-ylcarbonyl)-$N^1$-(3,4-dimethoxybenzyl)-L-α-glutamine, $N^1$-benzyl-$N^2$-(4-pyridin-4-ylbenzoyl)-L-α-glutamine, $N^1$-benzyl-$N^2$-[(3',5'-dimethyl-1,1'-biphenyl-4-yl)carbonyl]-L-α-glutamine, $N^1$-benzyl-$N^2$-[(4'-ethyl-1,1'-biphenyl-4-yl)carbonyl]-L-α-glutamine, $N^1$-benzyl-$N^2$-[(3'-ethoxy-1,1'-biphenyl-4-yl)carbonyl]-L-α-glutamine, $N^1$-benzyl-$N^2$-[(2'-ethoxy-1,1'-biphenyl-4-yl)carbonyl]-L-α-glutamine, $N^1$-benzyl-$N^2$-[(2',6'-dimethyl-1,1'-biphenyl-4-yl)carbonyl]-L-α-glutamine, $N^2$-(1,1'-biphenyl-4-ylcarbonyl)-$N^1$-cyclopentyl-L-α-glutamine, $N^1$-[2-(acetylamino)ethyl]-$N^2$-(1,1'-biphenyl-4-ylcarbonyl)-L-α-glutamine, $N^1$-2-adamantyl-$N^2$-(1,1'-biphenyl-4-ylcarbonyl)-L-α-glutamine, $N^1$-(2-adamantylmethyl)-$N^2$-(1,1'-biphenyl-4-ylcarbonyl)-L-α-glutamine, $N^1$-benzyl-$N^2$-(4-pyridin-2-ylbenzoyl)-L-α-glutamine, $N^1$-benzyl-$N^2$-(4-pyridin-3-ylbenzoyl)-L-α-glutamine, $N^1$-benzyl-$N^2$-[4-(1,3-thiazol-2-yl)benzoyl]-L-α-glutamine, $N^2$-(1,1'-biphenyl-4-ylcarbonyl)-$N^1$-(4-methoxybenzyl)-L-α-glutamine, $N^2$-(1,1'-biphenyl-4-ylcarbonyl)-$N^1$-[2-(3,4-dimethoxyphenyl)ethyl]-L-α-glutamine, $N^2$-(1,1'-biphenyl-4-ylcarbonyl)-$N^1$-(2-methoxyethyl)-L-α-glutamine, $N^2$-(1,1'-biphenyl-4-ylcarbonyl)-$N^1$-[2-(4-methoxyphenyl)ethyl]-L-α-glutamine, $N^2$-(1,1'-biphenyl-4-ylcarbonyl)-$N^1$-(1-naphthylmethyl)-L-α-glutamine, $N^2$-(1,1'-biphenyl-4-ylcarbonyl)-$N^1$-(3-methylbenzyl)-L-α-glutamine, $N^2$-(1,1'-biphenyl-4-ylcarbonyl)-$N^1$-(2-furylmethyl)-L-α-glutamine, $N^2$-(1,1'-biphenyl-4-ylcarbonyl)-$N^1$-(3-methoxybenzyl)-L-α-glutamine, $N^2$-(1,1'-biphenyl-4-ylcarbonyl)-$N^1$-(3,4,5-trimethoxybenzyl)-L-α-glutamine, $N^2$-(1,1'-biphenyl-4-ylcarbonyl)-$N^1$-(2,4-dichlorobenzyl)-L-α-glutamine, $N^2$-(1,1'-biphenyl-4-ylcarbonyl)-$N^1$-[4-(trifluoromethoxy)benzyl]-L-α-glutamine, $N^2$-(1,1'-biphenyl-4-ylcarbonyl)-$N^1$-[3-(trifluoromethoxy)benzyl]-L-α-glutamine, $N^2$-(1,1'-biphenyl-4-ylcarbonyl)-$N^1$-[4-(methylthio)benzyl]-L-α-glutamine, $N^2$-(1,1'-biphenyl-4-ylcarbonyl)-$N^1$-(4-phenoxybenzyl)-L-α-glutamine, $N^2$-(1,1'-biphenyl-4-ylcarbonyl)-$N^1$-[2-(3-methoxyphenyl)ethyl]-L-α-glutamine, $N^2$-(1,1'-biphenyl-4-ylcarbonyl)-$N^1$-(2,4-dimethoxybenzyl)-L-α-glutamine, $N^2$-(1,1'-biphenyl-4-ylcarbonyl)-$N^1$-(2-methoxybenzyl)-L-α-glutamine, $N^2$-(1,1'-biphenyl-4-ylcarbonyl)-$N^1$-(3,4-dichlorobenzyl)-L-α-glutamine, $N^2$-(1,1'-biphenyl-4-ylcarbonyl)-$N^1$-(3,5-difluorobenzyl)-L-α-glutamine, $N^2$-(1,1'-biphenyl-4-ylcarbonyl)-$N^5$-hydroxy-$N^1$-[3-(trifluoromethoxy)benzyl]-L-glutamamide, $N^2$-(1,1'-biphenyl-4-ylcarbonyl)-$N^5$-hydroxy-$N^1$-[2-(3-methoxyphenyl)ethyl]-L-glutamamide, $N^2$-(1,1'-biphenyl-4-ylcarbonyl)-$N^5$-hydroxy-$N^1$-(3,4,5-trimethoxybenzyl)-L-glutamamide, $N^2$-(1,1'-biphenyl-4-ylcarbonyl)-$N^1$-(3,5-dimethoxybenzyl)-L-α-glutamine, $N^2$-(1,1'-biphenyl-4-ylcarbonyl)-$N^1$-(3,5-dimethoxybenzyl)-$N^5$-hydroxy-L-glutamamide, $N^1$-benzyl-$N^2$-[(4'-vinyl-1,1'-biphenyl-4-yl)carbonyl]-L-α-glutamine, $N^2$-(1,1'-biphenyl-4-ylcarbonyl)-$N^1$-(3,4-dimethylbenzyl)-L-α-glutamine, $N^1$-benzyl-$N^2$-[(4'-ethoxy-1,1'-biphenyl-4-yl)carbonyl]-L-α-glutamine, $N^1$-benzyl-$N^2$-[(4'-propoxy-1,1'-biphenyl-4-yl)carbonyl]-L-α-glutamine, $N^1$-benzyl-$N^2$-[(4'-butoxy-1,1'-biphenyl-4-yl)carbonyl]-L-α-glutamine, $N^1$-benzyl-$N^2$-{[4'-(cyclobutylmethoxy)-1,1'-biphenyl-4-yl]carbonyl}-L-α-glutamine, $N^1$-benzyl-$N^2$-{[4'-(cyclohexylmethoxy)-1,1'-biphenyl-4-yl]carbonyl}-L-α-glutamine, $N^2$-{[4'-(allyloxy)-1,1'-biphenyl-4-yl]carbonyl}-$N^1$-benzyl-L-α-glutamine, $N^2$-(1,1'-biphenyl-4-ylcarbonyl)-$N^1$-(3,4-dimethylbenzyl)-$N^5$-hydroxy-L-glutamamide, $N^2$-(1,1'-biphenyl-4-ylacetyl)-$N^1$-(3-methoxybenzyl)-L-α-glutamine, $N^2$-[(3-fluorophenyl)acetyl]-$N^1$-(3-methoxybenzyl)-L-α-glutamine, $N^2$-{[4'-(acetylamino)-1,1'-biphenyl-4-yl]carbonyl}-$N^1$-benzyl-L-α-glutamine, $N^1$-benzyl-$N^2$-{[4'-(2-furoylamino)-1,1'-biphenyl-4-yl]carbonyl}-L-α-glutamine, $N^1$-benzyl-$N^2$-({4'-[(4-fluorobenzoyl)amino]-1,1'-biphenyl-4-yl}carbonyl)-L-α-glutamine, $N^2$-{[4'-(benzoylamino)-1,1'-biphenyl-4-yl]carbonyl}-$N^1$-benzyl-L-α-glutamine, $N^1$-benzyl-$N^2$-(5-phenyl-2-furoyl)-L-α-glutamine, $N^1$-benzyl-$N^2$-[5-(3-ethoxyphenyl)-2-furoyl]-L-α-glutamine, $N^1$-benzyl-$N^2$-[5-(3,5-dimethylphenyl)-2-furoyl]-L-α-glutamine, $N^1$-benzyl-$N^2$-(2,2'-bifuran-5-ylcarbonyl)-L-α-glutamine, $N^1$-benzyl-$N^2$-(5-thien-2-yl-2-furoyl)-L-α-glutamine, $N^2$-[(2,2'-dimethyl-1,1'-biphenyl-4-yl)carbonyl]-

$N^1$-(3-methoxybenzyl)-L-α-glutamine, $N^2$-(1,1'-biphenyl-4-ylcarbonyl)-$N^1$-(2-phenylethyl)-L-α-glutamine, $N^2$-(1,1'-biphenyl-4-ylcarbonyl)-$N^1$-[3-(trifluoromethyl)benzyl]-L-α-glutamine, $N^1$-(4-aminobenzyl)-$N^2$-(1,1'-biphenyl-4-ylcarbonyl)-L-α-glutamine, $N^1$-(3-aminobenzyl)-$N^2$-(1,1'-biphenyl-4-ylcarbonyl)-L-α-glutamine, $N^2$-(1,1'-biphenyl-4-ylcarbonyl)-$N^1$-[2-(trifluoromethyl)benzyl]-L-α-glutamine, $N^1$-benzyl-$N^2$-[(2-fluoro-1,1'-biphenyl-4-yl)carbonyl]-L-α-glutamine, $N^2$-(1,1'-biphenyl-4-ylcarbonyl)-$N^1$-(3-fluorobenzyl)-L-α-glutamine, $N^2$-(1,1'-biphenyl-4-ylcarbonyl)-$N^1$-(3-phenylpropyl)-L-α-glutamine, $N^1$-benzyl-$N^2$-(1,1'-biphenyl-3-ylcarbonyl)-L-α-glutamine, $N^1$-benzyl-$N^2$-(3-thien-2-ylbenzoyl)-L-α-glutamine, $N^1$-benzyl-$N^2$-[(3-chloro-1,1'-biphenyl-4-yl)carbonyl]-L-α-glutamine, $N^1$-benzyl-$N^2$-[(3-fluoro-1,1'-biphenyl-4-yl)carbonyl]-L-α-glutamine, $N^1$-benzyl-$N^2$-[(2,6-dimethoxy-1,1'-biphenyl-4-yl)carbonyl]-L-α-glutamine, $N^2$-(1,1'-biphenyl-4-ylcarbonyl)-$N^1$-[2-(3-chlorophenyl)ethyl]-L-α-glutamine, $N^2$-(1,1'-biphenyl-4-ylcarbonyl)-$N^1$-(2-fluorobenzyl)-L-α-glutamine, $N^2$-(1,1'-biphenyl-4-ylcarbonyl)-$N^1$-(3,4-difluorobenzyl)-L-α-glutamine, $N^2$-(1,1'-biphenyl-4-ylcarbonyl)-$N^1$-(2-methylbenzyl)-L-α-glutamine, $N^1$-benzyl-$N^2$-({4'-[(3-methoxybenzyl)oxy]-1,1'-biphenyl-4-yl}carbonyl)-L-α-glutamine, $N^1$-benzyl-$N^2$-({4'-[(3,5-dimethoxybenzyl)oxy]-1,1'-biphenyl-4-yl}carbonyl)-L-α-glutamine, $N^1$-benzyl-$N^2$-{[4'-(2-naphthylmethoxy)-1,1'-biphenyl-4-yl]carbonyl}-L-α-glutamine, $N^2$-(1,1'-biphenyl-4-ylcarbonyl)-$N^1$-2,3-dihydro-1H-inden-2-yl-L-α-glutamine, $N^2$-(1,1'-biphenyl-4-ylcarbonyl)-$N^1$-(2,3-dimethylbenzyl)-L-α-glutamine, $N^2$-(1,1'-biphenyl-4-ylcarbonyl)-$N^1$-(4-phenylbutyl)-L-α-glutamine, $N^1$-(2-benzylphenyl)-$N^2$-(1,1'-biphenyl-4-ylcarbonyl)-L-α-glutamine, $N^2$-(1,1'-biphenyl-4-ylcarbonyl)-$N^1$-(4-methoxy-1,1'-biphenyl-3-yl)-L-α-glutamine, $N^2$-(1,1'-biphenyl-4-ylcarbonyl)-$N^1$-(4-methylbenzyl)-L-α-glutamine, $N^2$-(1,1'-biphenyl-4-ylcarbonyl)-$N^1$-[4-fluoro-3-(trifluoromethyl)benzyl]-L-α-glutamine, $N^2$-(1,1'-biphenyl-4-ylcarbonyl)-$N^1$-heptyl-L-α-glutamine, $N^2$-(1,1'-biphenyl-4-ylcarbonyl)-$N^1$-(3-iodobenzyl)-L-α-glutamine, $N^2$-(1,1'-biphenyl-4-ylcarbonyl)-$N^1$-(3-vinylbenzyl)-L-α-glutamine, $N^2$-(1,1'-biphenyl-4-ylcarbonyl)-$N^1$-(3-thien-2-ylbenzyl)-L-α-glutamine, $N^2$-(1,1'-biphenyl-4-ylcarbonyl)-$N^1$-[2-(4-fluorophenyl)-1,1-dimethylethyl]-L-α-glutamine, $N^1$-benzyl-$N^2$-[(6-phenylpyridin-3-yl)carbonyl]-L-α-glutamine, $N^1$-(3-methoxybenzyl)-$N^2$-[(6-phenylpyridin-3-yl)carbonyl]-L-α-glutamine, $N^2$-(1,1'-biphenyl-4-ylcarbonyl)-$N^1$-(4-tert-butylbenzyl)-L-α-glutamine, $N^2$-(1,1'-biphenyl-4-ylcarbonyl)-$N^1$-(4-iodobenzyl)-L-α-glutamine, $N^2$-(1,1'-biphenyl-4-ylcarbonyl)-$N^1$-(4-vinylbenzyl)-L-α-glutamine, $N^2$-(1,1'-biphenyl-4-ylcarbonyl)-$N^1$-(sec-butyl)-L-α-glutamine, $N^2$-(1,1'-biphenyl-4-ylcarbonyl)-$N^1$-(cyclopropylmethyl)-L-α-glutamine, $N^2$-(biphenyl-4-ylcarbonyl)-$N^1$-[4-(dimethylamino)benzyl]-L-α-glutamine, $N^2$-(biphenyl-4-ylcarbonyl)-$N^1$-[2-(4-bromophenyl)ethyl]-L-α-glutamine, $N^2$-(biphenyl-4-ylcarbonyl)-$N^1$-(2-biphenyl-4-ylethyl)-L-α-glutamine, $N^2$-(biphenyl-4-ylcarbonyl)-$N^1$-[2-(2'-ethoxybiphenyl-4-yl)ethyl]-L-α-glutamine, $N^2$-(biphenyl-4-ylcarbonyl)-$N^1$-[2-(4'-ethynylbiphenyl-4-yl)ethyl]-L-α-glutamine, $N^2$-(biphenyl-4-ylcarbonyl)-$N^1$-{2-[4-(2-thienyl)phenyl]ethyl}-L-α-glutamine, $N^2$—(biphenyl-4-ylcarbonyl)-$N^1$-[2-(4-pyridin-2-ylphenyl)ethyl]-L-α-glutamine, $N^2$-(biphenyl-4-ylcarbonyl)-$N^1$-[3-(dimethylamino)benzyl]-L-α-glutamine, $N^2$-(biphenyl-4-ylcarbonyl)-$N^1$-(3,3-diphenylpropyl)-L-α-glutamine, $N^2$-(biphenyl-4-ylcarbonyl)-$N^1$-(3,3-dimethylbutyl)-L-α-glutamine, $N^2$-(biphenyl-4-ylcarbonyl)-$N^1$-isopropyl-L-α-glutamine, $N^2$-(biphenyl-4-ylcarbonyl)-$N^1$-(pyridin-4-ylmethyl)-L-α-glutamine, $N^2$-(biphenyl-4-ylcarbonyl)-$N^1$,$N^1$-diethyl-L-α-glutamine, $N^2$-(biphenyl-4-ylcarbonyl)-$N^1$-(1,1-dimethylpropyl)-L-α-glutamine, $N^2$-(biphenyl-4-ylcarbonyl)-$N^1$-[2-(4'-formylbiphenyl-4-yl)ethyl]-L-α-glutamine, $N^2$-(biphenyl-4-ylcarbonyl)-$N^1$-{2-[4'-(trifluoromethyl)biphenyl-4-yl]ethyl}-L-α-glutamine, $N^2$-(biphenyl-4-ylcarbonyl)-$N^1$-[2-(4'-formylbiphenyl-3-yl)ethyl]-L-α-glutamine, $N^2$-(biphenyl-4-ylcarbonyl)-$N^1$-{2-[4'-(trifluoromethyl)biphenyl-3-yl]ethyl}-L-α-glutamine, $N^2$-(biphenyl-4-ylcarbonyl)-$N^1$-[2-(4'-methoxybiphenyl-3-yl)ethyl]-L-α-glutamine, $N^2$-(biphenyl-4-ylcarbonyl)-$N^1$-[2-(4'-methoxybiphenyl-4-yl)ethyl]-L-α-glutamine, $N^2$-(biphenyl-4-ylcarbonyl)-$N^1$-[2-(3-bromophenyl)ethyl]-L-α-glutamine, $N^2$-(biphenyl-4-ylcarbonyl)-$N^1$-pentyl-L-α-glutamine, $N^2$-(biphenyl-4-ylcarbonyl)-$N^1$-[2-(4-pyridin-4-ylphenyl)ethyl]-L-α-glutamine, $N^2$-(biphenyl-4-ylcarbonyl)-$N^1$-(tert-butyl)-L-α-glutamine, $N^2$-(biphenyl-4-ylcarbonyl)-$N^1$-{[4'-(trifluoromethyl)biphenyl-3-yl]methyl}-L-α-glutamine, $N^2$-(biphenyl-4-ylcarbonyl)-$N^1$-(2,2-dimethylpropyl)-L-α-glutamine, $N^2$-(biphenyl-4-ylcarbonyl)-$N^1$-[(4'-ethynylbiphenyl-3-yl)methyl]-L-α-glutamine, $N^2$-(biphenyl-4-ylcarbonyl)-$N^1$-(3-pyridin-2-ylbenzyl)-L-α-glutamine, $N^2$-(biphenyl-4-ylcarbonyl)-$N^1$-(1,1-dimethyl-2-phenylethyl)-L-α-glutamine, $N^2$-(biphenyl-4-ylcarbonyl)-$N^1$-[2-(4-chlorophenyl)-1,1-dimethylethyl]-L-α-glutamine, $N^2$-(biphenyl-4-ylcarbonyl)-$N^1$-hexyl-L-α-glutamine, $N^2$-(biphenyl-4-ylcarbonyl)-$N^1$-(1-methyl-1-phenylethyl)-L-α-glutamine, $N^2$-(biphenyl-4-ylcarbonyl)-$N^1$-(1,3,3-tetramethylbutyl)-L-α-glutamine, $N^2$-(biphenyl-4-ylcarbonyl)-$N^1$-(2-morpholin-4-ylethyl)-L-α-glutamine, $N^2$-(biphenyl-4-ylcarbonyl)-$N^1$-(2-hydroxy-1,1-dimethylethyl)-L-α-glutamine, $N^2$-(biphenyl-4-ylcarbonyl)-$N^1$-[2-(4-fluorophenyl)ethyl]-L-α-glutamine, $N^2$-(biphenyl-4-ylcarbonyl)-$N^1$-[2-(2-fluorophenyl)ethyl]-L-α-glutamine, $N^2$-(biphenyl-4-ylcarbonyl)-$N^1$-[2-(4-chlorophenyl)ethyl]-L-α-glutamine, $N^2$-(biphenyl-4-ylcarbonyl)-$N^1$-[2-(2-thienyl)ethyl]-L-α-glutamine, $N^2$-(biphenyl-4-ylcarbonyl)-$N^1$-[2-(2-chlorophenyl)ethyl]-L-α-glutamine, $N^2$-(biphenyl-4-ylcarbonyl)-$N^1$-(6-hydroxyhexyl)-L-α-glutamine, $N^2$-(biphenyl-4-ylcarbonyl)-$N^1$-(5-hydroxypentyl)-L-α-glutamine, 3-[(biphenyl-4-ylmethyl)amino]-3-oxopropanoic acid, $N^2$-(biphenyl-4-ylcarbonyl)-$N^1$-propyl-L-α-glutamine, $N^2$-(biphenyl-4-ylcarbonyl)-$N^1$-[2-(4-fluorophenyl)-1,1-dimethylethyl]-α-glutamine, $N^2$-(biphenyl-4-ylcarbonyl)-$N^1$-[2-(4-fluorophenyl)-1,1-dimethylethyl]-D-α-glutamine, $N^2$-(biphenyl-4-ylcarbonyl)-$N^1$-[2-(3-pyridin-2-ylphenyl)ethyl]-L-α-glutamine, $N^2$-2-naphthoyl-$N^1$-(3-phenylpropyl)-L-α-glutamine, $N^2$-(9H-fluoren-2-ylcarbonyl)-$N^1$-(3,4,5-trimethoxybenzyl)-L-α-glutamine, $N^2$-(9H-fluoren-1-ylcarbonyl)-$N^1$-(3,4,5-trimethoxybenzyl)-L-α-glutamine, $N^2$-[(9-oxo-9H-fluoren-2-yl)carbonyl]-$N^1$-(3,4,5-trimethoxybenzyl)-L-α-glutamine, $N^2$-(9H-fluoren-2-ylcarbonyl)-$N^1$-(3-phenylpropyl)-L-α-glutamine, $N^2$-(9H-fluoren-1-ylcarbonyl)-$N^1$-(3-phenylpropyl)-L-α-glutamine, $N^2$-(4-phenoxybenzoyl)-$N^1$-(3,4,5-trimethoxybenzyl)-L-α-glutamine, $N^2$-(9H-fluoren-2-ylcarbonyl)-$N^1$-hexyl-L-α-glutamine, $N^2$-(9H-fluoren-1-ylcarbonyl)-$N^1$-hexyl-L-α-glutamine, $N^1$-hexyl-$N^2$-(4-phenoxybenzoyl)-L-α-glutamine, $N^1$-hexyl-$N^2$-[(9-oxo-9H-fluoren-2-yl)carbonyl]-L-α-glutamine, $N^2$-[(9-oxo-9H-fluoren-2-yl)carbonyl]-$N^1$-(3-phenylpropyl)-L-α-glutamine, $N^2$-(4-phenoxybenzoyl)-$N^1$-(3-phenylpropyl)-L-α-glutamine, N-[4-(pyrimidin-2-ylamino)benzoyl]-L-glutamic acid, N-(1,1'-biphenyl-4-ylcarbonyl)-D-glutamic acid, N-[4-(pyrimidin-2-ylamino)benzoyl]-L-α-glutamine, $N^2$-(1,1'-biphenyl-4-ylcarbonyl)-D-α-glutamine, $N^2$-(1,1'-biphenyl-4-ylcarbonyl)-$N^1$-(4-hydroxybutyl)-L-α-glutamine, $N^1$-benzyl-$N^2$-(1,1-biphenyl-4-ylcarbonyl)-L-α-glutamine, $N^1$-benzyl-$N^2$-[4-(pyrimidin-2-ylamino)benzoyl]-L-α-glutamine, (4S)-4-[(1,1'-biphenyl-4-ylcarbonyl)amino]-5-hydroxypentanoic acid, N-({4'-[(phenylacetyl)amino]-1,1'-biphenyl-4-yl}carbonyl)-L-glutamic acid, N-[(4'-{[(3-methyl-1-benzofuran-2-yl)carbonyl]amino}-1,1'-biphenyl-4-yl)carbonyl]-L-glutamic acid, N-{[4'-(2-furoylamino)-1,1'-biphenyl-4-yl]carbonyl}-L-glutamic acid, N-{[4'-(acetylamino)-1,1'-biphenyl-4-yl]carbonyl}-L-glutamic acid, N-{[4'-(benzoylamino)-1,1'-biphenyl-4-yl]carbonyl}-L-glutamic acid, N-({4'-[(1-benzofuran-2-ylcarbonyl)amino]-1,1'-biphenyl-4-yl}carbonyl)-L-glutamic acid, $N^1$-(1,1-dimethyl-2-phenylethyl)-$N^2$-(9H-fluoren-2-ylcarbonyl)-L-α-glutamine, $N^1$-[2-(4-chlorophenyl)-1,1-dimethylethyl]-$N^2$-(9H-fluoren-2-ylcarbonyl)-L-α-glutamine, $N^2$-(9H-fluoren-2-ylcarbonyl)-$N^1$-(6-hydroxyhexyl)-L-α-glutamine, $N^1$-(6-hydroxyhexyl)-$N^2$-(4-phenoxybenzoyl)-L-α-glutamine, $N^2$-(9H-fluoren-9-ylcarbonyl)-$N^1$-(6-hydroxyhexyl)-L-α-glutamine, $N^2$-(9H-fluoren-9-ylcarbonyl)-$N^1$-(3,4,5-trimethoxybenzyl)-L-α-glutamine, $N^2$-(3-phenoxybenzoyl)-$N^1$-(3,4,5-trimethoxybenzyl)-L-α-glutamine, $N^2$-(9H-fluoren-4-ylcarbonyl)-$N^1$-(3,4,5-trimethoxybenzyl)-L-α-glutamine, $N^1$-1-adamantyl-$N^2$-[(9-oxo-9H-fluoren-2-yl)carbonyl]-L-α-glutamine, $N^1$-1-adamantyl-$N^2$-(4-phenoxybenzoyl)-L-α-glutamine, $N^1$-1-adamantyl-$N^2$-(9H-fluoren-2-ylcarbonyl)-L-α-glutamine, $N^1$-1-adamantyl-$N^2$-(9H-fluoren-9-ylcarbonyl)-L-α-glutamine, $N^2$-(9H-fluoren-2-ylcarbonyl)-$N^1$-(3-methylbenzyl)-L-α-glutamine, $N^1$-(3-methylbenzyl)-$N^2$-[(9-oxo-9H-fluoren-2-yl)carbonyl]-L-α-glutamine, $N^2$-(9H-fluoren-9-ylcarbonyl)-$N^1$-(3-methylbenzyl)-L-α-glutamine, $N^2$-(9H-fluoren-2-ylcarbonyl)-$N^1$-propyl-L-α-glutamine, $N^1$-benzyl-$N^2$-[(9-oxo-9H-fluoren-2-yl)carbonyl]-L-α-glutamine, $N^1$-benzyl-$N^2$-(9H-fluoren-2-ylcarbonyl)-L-α-glutamine, $N^1$-benzyl-$N^2$-(9H-fluoren-9-ylcarbonyl)-L-α-glutamine, $N^1$-benzyl-$N^2$-(3-phenoxybenzoyl)-L-α-glutamine, $N^1$-(1-methyl-1-phenylethyl)-$N^2$-[(9-oxo-9H-fluoren-2-yl)carbonyl]-L-α-glutamine, $N^2$-(9H-fluoren-9-ylcarbonyl)-$N^1$-(1-methyl-1-phenylethyl)-L-α-glutamine, $N^1$-(1-methyl-1-phenylethyl)-$N^2$-(3-phenoxybenzoyl)-L-α-glutamine, $N^2$—(biphenyl-4-ylcarbonyl)-$N^1$-[(1S)-1-phenylethyl]-L-α-glutamine, $N^2$-(9H-fluoren-2-ylcarbonyl)-$N^1$-[(1S)-1-phenylethyl]-L-α-glutamine, $N^2$-(biphenyl-4-ylcarbonyl)-$N^1$-[(1S)-1-(4-fluorophenyl)ethyl]-L-α-glutamine, tert-butyl $N^2$-(biphenyl-4-ylcarbonyl)-$N^1$-(1-phenylethyl)-L-α-glutaminate, $N^2$-(biphenyl-4-ylcarbonyl)-$N^1$-[(1R)-1-(4-fluorophenyl)ethyl]-L-α-glutamine, $N^2$-(biphenyl-4-ylcarbonyl)-$N^1$-[(1R)-1-phenylethyl]-L-α-glutamine, $N^2$-(9H-fluoren-2-ylcarbonyl)-$N^1$-[(1R)-1-phenylethyl]-L-α-glutamine, $N^2$-(9H-fluoren-1-ylcarbonyl)-$N^1$-(6-hydroxyhexyl)-L-α-glutamine, $N^1$-(6-hydroxyhexyl)-$N^2$-[(9-oxo-9H-fluoren-2-yl)carbonyl]-L-α-glutamine, $N^2$-(biphenyl-4-ylcarbonyl)-$N^1$-9H-fluoren-9-yl-L-α-glutamine, $N^2$-(9H-fluoren-2-ylcarbonyl)-$N^1$-[2-(4-fluorophenyl)-1,1-dimethylethyl]-L-α-glutamine, $N^2$-[(3'-ethoxybiphenyl-4-yl)carbonyl]-N-(3,4,5-trimethoxybenzyl)-L-α-glutamine, $N^2$-[(2'-ethoxybiphenyl-4-yl)carbonyl]-N-(3,4,5-trimethoxybenzyl)-L-α-glutamine, $N^2$-[(4'-methoxybiphenyl-4-yl)carbonyl]-N-(3,4,5-trimethoxybenzyl)-L-α-glutamine, $N^2$-(4-bromobenzoyl)-N-(3,4,5-trimethoxybenzyl)-L-α-glutamine, $N^2$-[(3'-methoxybiphenyl-4-yl)carbonyl]-N-(3,4,5-trimethoxybenzyl)-L-α-glutamine, 4'-{[((1S)-3-carboxy-1-{[(3,4,5-trimethoxybenzyl)amino]carbonyl}propyl)amino]carbonyl}biphenyl-3-carboxylic acid, $N^2$-[(4'-ethylbiphenyl-4-yl)carbonyl]-N-(3,4,5-trimethoxybenzyl)-L-α-glutamine, N-benzyl-$N^2$-[4-(2-naphthyl)benzoyl]-L-α-glutamine, $N^2$-[(3',4'-dimethoxybiphenyl-4-yl)carbonyl]-N-(3,4,5-trimethoxybenzyl)-L-α-glutamine, $N^2$-[(2',4'-dimethoxybiphenyl-4-yl)carbonyl]-N-(3,4,5-trimethoxybenzyl)-L-α-glutamine, N-(3,4,5-trimethoxybenzyl)-$N^2$-[(3',4',5'-trimethoxybiphenyl-4-yl)carbonyl]-L-α-glutamine, N-(1-adamantylmethyl)-$N^2$-(biphenyl-4-ylcarbonyl)-L-α-glutamine, N-(1,1-dimethyl-2-phenylethyl)-$N^2$-[(3'-methoxybiphenyl-4-yl)carbonyl]-L-α-glutamine, $N^2$-[(3',4'-dimethoxybiphenyl-4-yl)carbonyl]-N-(1,1-dimethyl-2-phenylethyl)-L-α-glutamine, N-(1,1-dimethyl-2-phenylethyl)-$N^2$-[(2'-ethoxybiphenyl-4-yl)carbonyl]-L-α-glutamine, N-(1,1-dimethyl-2-phenylethyl)-$N^2$-[(3'-fluoro-4'-methylbiphenyl-4-yl)carbonyl]-L-α-glutamine, $N^2$-(4-bromobenzoyl)-N-(1,1-dimethyl-2-phenylethyl)-L-α-glutamine, N-[(1S)-1-benzyl-2-hydroxyethyl]-$N^2$-(biphenyl-4-ylcarbonyl)-L-α-glutamine, N-[(1S)-1-benzyl-2-hydroxyethyl]-$N^2$-(9H-fluoren-2-ylcarbonyl)-L-α-glutamine, N-(1-adamantylmethyl)-$N^2$-(4-bromobenzoyl)-L-α-glutamine, N-(1-adamantylmethyl)-$N^2$-[(4'-hydroxybiphenyl-4-yl)carbonyl]-L-α-glutamine, $N^2$-[4-(1,3-benzodioxol-5-yl)benzoyl]-N-(1,1-dimethyl-2-phenylethyl)-L-α-glutamine, $N^2$-[(2',4'-dimethoxybiphenyl-4-yl)carbonyl]-N-(1,1-dimethyl-2-phenylethyl)-L-α-glutamine, $N^2$-[(3'-fluoro-4'-methylbiphenyl-4-yl)carbonyl]-N-(3,4,5-trimethoxybenzyl)-L-α-glutamine, $N^2$-({4'-[(3,5-dimethoxybenzyl)oxy]biphenyl-4-yl}carbonyl)-N-(3,4,5-trimethoxybenzyl)-L-α-glutamine, N-(1-adamantylmethyl)-$N^2$-({4'-[(3-methoxybenzyl)oxy]biphenyl-4-yl}carbonyl)-L-α-glutamine, N-(1-adamantylmethyl)-$N^2$-({4'-[(3,5-dimethoxybenzyl)oxy]biphenyl-4-yl}carbonyl)-L-α-glutamine, $N^2$-(biphenyl-4-ylcarbonyl)-N-methyl-N-(2-phenylethyl)-L-α-glutamine, $N^2$-[(4'-sec-butylbiphenyl-4-yl)carbonyl]-N-(1,1-dimethyl-2-phenylethyl)-L-α-glutamine, N-(1,1-dimethyl-2-phenylethyl)-$N^2$-[(4'-isopropylbiphenyl-4-yl)carbonyl]-L-α-glutamine, N-(1,1-dimethyl-2-phenylethyl)-$N^2$-(1,1':4',1"-terphenyl-4-ylcarbonyl)-L-α-glutamine, $N^2$-({4'-[(3,5-dimethoxybenzyl)oxy]biphenyl-4-yl}carbonyl)-N-(1,1-dimethyl-2-phenylethyl)-L-α-glutamine, $N^2$-[(4'-hydroxybiphenyl-4-yl)carbonyl]-N-(3,4,5-trimethoxybenzyl)-L-α-glutamine, N-(1-adamantylmethyl)-$N^2$-({3'-[(dimethylamino)carbonyl]biphenyl-4-yl}carbonyl)-L-α-glutamine, N-(1-adamantylmethyl)-$N^2$-[(3',5'-dimethylbiphenyl-4-yl)carbonyl]-L-α-glutamine, $N^2$-(9H-fluoren-2-ylcarbonyl)-N-methyl-N-(2-phenylethyl)-L-α-glutamine, N-[2-(4-fluorophenyl)-1,1-dimethylethyl]-$N^2$-[(3'-methylbiphenyl-4-yl)carbonyl]-L-α-glutamine, $N^2$-({4'-[(3,5-dimethylbenzyl)oxy]biphenyl-4-yl}carbonyl)-N-(3,4,5-trimethoxybenzyl)-L-α-glutamine, $N^2$-[(4'-{[3,5-bis(trifluoromethyl)benzyl]oxy}biphenyl-4-yl)carbonyl]-N-(3,4,5-trimethoxybenzyl)-L-α-glutamine, $N^2$-[(3'-isopropylbiphenyl-4-yl)carbonyl]-N-(3,4,5-trimethoxybenzyl)-L-α-glutamine, $N^2$-[(4'-isopropylbiphenyl-4-yl)carbonyl]-N-(3,4,5-trimethoxybenzyl)-L-α-glutamine, N-(1-adamantylmethyl)-$N^2$-[4-(1-benzofuran-5-yl)benzoyl]-L-α-glutamine, N-(1-adamantylmethyl)-$N^2$-[4-(1H-indol-5-yl)benzoyl]-L-α-glutamine, $N^2$-[(3'-ethoxybiphenyl-4-yl)carbonyl]-N-[2-(4-fluorophenyl)-1,1-dimethylethyl]-L-α-glutamine, N-[2-(4-fluorophenyl)-1,1-dimethylethyl]-$N^2$-[(3'-methoxybiphenyl-4-yl)carbonyl]-L-α-glutamine, N-[2-(4-fluorophenyl)-1,1-dimethylethyl]-$N^2$-[(3'-isopropylbiphenyl-4-yl)carbonyl]-L-α-glutamine, $N^2$-[(3'-fluoro-4'-methylbiphenyl-4-yl)carbonyl]-N-[2-(4-fluorophenyl)-1,1-dimethylethyl]-L-α-glutamine, N-[2-(4-fluorophenyl)-1,1-dimethylethyl]-$N^2$-[(4'-isobutylbiphenyl-4-yl)carbonyl]-L-α-glutamine, $N^2$-(1,1:4',1 terphenyl-4- ylcarbonyl)-N-(3,4,5-trimethoxybenzyl)-L-α-glutamine, N-benzyl-$N^2$-{[3'-(hydroxymethyl)biphenyl-4-yl]carbonyl}-L-α-glutamine, N-benzyl-$N^2$-({4'-[(3-fluorobenzyl)oxy]biphenyl-4-yl}carbonyl)-L-α-glutamine, N-benzyl-$N^2$-{[4'-(benzyloxy)biphenyl-4-yl]carbonyl}-L-α-glutamine, N-benzyl-$N^2$-[4-(phenylethynyl)benzoyl]-L-α-glutamine, N-benzyl-$N^2$-{4-[(9-hydroxy-9H-fluoren-9-yl)ethynyl]benzoyl}-L-α-glutamine, N-benzyl-$N^2$-{4-[(1E)-3-oxo-3-phenylprop-1-en-1-yl]benzoyl}-L-α-glutamine, N-(3,4,5-trimethoxybenzyl)-$N^2$-[(2',4',6'-trimethylbiphenyl-4-yl)carbonyl]-L-α-glutamine, N-(1,1-dimethyl-2-phenylethyl)-$N^2$-({4'-[(3-methoxybenzyl)oxy]biphenyl-4-yl}carbonyl)-L-α-glutamine, N-(1,1-dimethyl-2-phenylethyl)-$N^2$-[(4'-hydroxybiphenyl-4-yl)carbonyl]-L-α-glutamine, N-(1,1-dimethyl-2-phenylethyl)-$N^2$-[(3'-ethoxybiphenyl-4-yl)carbonyl]-L-α-glutamine, $N^2$-({4'-[(3,5-dimethoxybenzyl)oxy]biphenyl-4-yl}carbonyl)-N-(6-hydroxyhexyl)-L-α-glutamine, $N^2$-({4'-[(3-methoxybenzyl)oxy]biphenyl-4-yl}carbonyl)-N-(3,4,5-trimethoxybenzyl)-L-α-glutamine, $N^2$-(4-bromobenzoyl)-N-(3-methylbenzyl)-L-α-glutamine, $N^2$-[4-(1,3-benzodioxol-5-yl)benzoyl]-N-(3-methylbenzyl)-L-α-glutamine, $N^2$-(biphenyl-4-ylcarbonyl)-N-butyl-N-methyl-L-α-glutamine, N-[2-(4-fluorophenyl)-1,1-dimethylethyl]-$N^2$-[(4'-hydroxybiphenyl-4-yl)carbonyl]-L-α-glutamine, N-butyl-$N^2$-(9H-fluoren-2-ylcarbonyl)-N-methyl-L-α-glutamine, $N^2$-(biphenyl-4-ylcarbonyl)-N-[2-(3,4-dimethoxyphenyl)ethyl]-N-methyl-L-α-glutamine, $N^2$-[4-(1,3-benzodioxol-5-yl)benzoyl]-N-[2-(4-fluorophenyl)-1,1-dimethylethyl]-L-α-glutamine, N-[2-(3,4-dimethoxyphenyl)ethyl]-$N^2$-(9H-fluoren-2-ylcarbonyl)-N-methyl-L-α-glutamine, $N^2$-(9H-fluoren-2-ylcarbonyl)-N-[(2R)-2-phenylpropyl]-L-α-glutamine, $N^2$-(biphenyl-4-ylcarbonyl)-N-[(2R)-2-phenylpropyl]-L-α-glutamine, N-benzyl-$N^2$-{4-[(4-hydroxycyclohexyl)ethynyl]benzoyl}-L-α-glutamine, $N^2$-{4-[(3-aminophenyl)ethynyl]benzoyl}-N-benzyl-L-α-glutamine, N-benzyl-$N^2$-[4-(3-hydroxy-3,3-diphenylprop-1-yn-1-yl)benzoyl]-L-α-glutamine, N-benzyl-$N^2$-{4-[(3-methoxyphenyl)ethynyl]benzoyl}-L-α-glutamine, $N^2$-[(3'-hydroxybiphenyl-4-yl)carbonyl]-N-(3,4,5-trimethoxybenzyl)-L-α-glutamine, N-(1,1-dimethyl-2-phenylethyl)-$N^2$-{[4'-(hydroxymethyl)biphenyl-4-yl]carbonyl}-L-α-glutamine, N-(1,1-dimethyl-2-phenylethyl)-$N^2$-[(4'-methylbiphenyl-4-yl)carbonyl]-L-α-glutamine, $N^2$-(biphenyl-4-ylcarbonyl)-$N^1$-[2-(4-fluorophenyl)-1,1-dimethylethyl]-L-glutamamide, $N^2$-({4'-[(3-tert-butylphenoxy)methyl]biphenyl-4-yl}carbonyl)-N-(1,1-dimethyl-2-phenylethyl)-L-α-glutamine, $N^2$-({4'-[(3,5-di-tert-butylphenoxy)methyl]biphenyl-4-yl}carbonyl)-N-(1,1-dimethyl-2-phenylethyl)-L-α-glutamine, N-(1,1-dimethyl-2-phenylethyl)-$N^2$-({4'-[(3-ethylphenoxy)methyl]biphenyl-4-yl}carbonyl)-L-α-glutamine, N-(1,1-dimethyl-2-phenylethyl)-$N^2$-({4'-[(3-methoxyphenoxy)methyl]biphenyl-4-yl}carbonyl)-L-α-glutamine, N-[2-(4-fluorophenyl)-1,1-dimethylethyl]-$N^2$-[(3'-hydroxybiphenyl-4-yl)carbonyl]-L-α-glutamine, $N^2$-(biphenyl-4ylcarbonyl)-$N^1$-[2-(4-fluorophenyl)-1,2-dimethylethyl]-$N^5$-hydroxy-L-glutamanide, $N^2$-[4-(5-bromo-2-thienyl)benzoyl]-N-[2-(4-fluorophenyl)-1,1-dimethylethyl]-L-α-glutamine, N-[2-(5-chloro-2-thienyl)-1,1-dimethylethyl]-$N^2$-[(3'-fluorobiphenyl-4-yl)carbonyl]-L-α-glutamine, $N^2$-[(3',4'-difluorobiphenyl-4-yl)carbonyl]-N-[2-(4-fluorophenyl)-1,1-dimethylethyl]-L-α-glutamine, N-[2-(4-chlorophenyl)-1,1-dimethylethyl]-$N^2$-[(3',4'-difluorobiphenyl-4-yl)carbonyl]-L-α-glutamine, N-[2-(4-chlorophenyl)-1,1-dimethylethyl]-$N^2$-[(2',4'-difluorobiphenyl-4-yl)carbonyl]-L-α-glutamine, N-[2-(4-chlorophenyl)-1,1-dimethylethyl]-$N^2$-[(2',5'-difluorobiphenyl-4-yl)carbonyl]-L-α-glutamine, N-[2-(4-chlorophenyl)-1,1-dimethylethyl]-$N^2$-[(2',6'-difluorobiphenyl-4-yl)carbonyl]-L-α-glutamine, N-[2-(4-chlorophenyl)-1,1-dimethylethyl]-$N^2$-[(3',5'-difluorobiphenyl-4-yl)carbonyl]-L-α-glutamine, N-[2-(4-chlorophenyl)-1,1-dimethylethyl]-$N^2$-[(2',3'-difluorobiphenyl-4-yl)carbonyl]-L-α-glutamine, N-(1,1-dimethyl-2-phenylethyl)-$N^2$-(4-pyrimidin-5-ylbenzoyl)-L-α-glutamine, $N^2$-[(3',4'-difluorobiphenyl-4-yl)carbonyl]-N-(1,1-dimethyl-2-phenylethyl)-L-α-glutamine, $N^2$-[(3',5'-difluorobiphenyl-4-yl)carbonyl]-N-(1,1-dimethyl-2-phenylethyl)-L-α-glutamine, N-[2-(5-chloro-2-thienyl)-1,1-dimethylethyl]-$N^2$-[(3',4'-difluorobiphenyl-4-yl)carbonyl]-L-α-glutamine, $N^2$-(biphenyl-4-ylcarbonyl)-N-[2-(5-chloro-2-thienyl)-1,1-dimethylethyl]-L-α-glutamine, $N^2$-{[5-(3-chloro-4-fluorophenyl)-2-thienyl]carbonyl}-N-[2-(5-chloro-2-thienyl)-1,1-dimethylethyl]-L-α-glutamine, $N^2$-{[4'-(hydroxymethyl)biphenyl-4-yl]carbonyl}-N-(3,4,5-trimethoxybenzyl)-L-α-glutamine, $N^2$-{[4'-(bromomethyl)biphenyl-4-yl]carbonyl}-N-(3,4,5-trimethoxybenzyl)-L-α-glutamine, N-[2-(4-fluorophenyl)-1,1-dimethylethyl]-$N^2$-[4-(2-thienyl)benzoyl]-L-α-glutamine, N-[2-(4-fluorophenyl)-1,1-dimethylethyl]-$N^2$-[4-(2-furyl)benzoyl]-L-α-glutamine, $N^2$-{[4'-(hydroxymethyl)biphenyl-4-yl]carbonyl}-N-(3-methylbenzyl)-L-α-glutamine, $N^2$-{[3'-(hydroxymethyl)biphenyl-4-yl]carbonyl}-N-(3-methylbenzyl)-L-α-glutamine, $N^2$-[4-(2,3-dihydro-1-benzofuran-5-yl)benzoyl]-N-[2-(4-fluorophenyl)-1,1-dimethylethyl]-L-α-glutamine, $N^2$-[(3'-chloro-4'-fluorobiphenyl-4-yl)carbonyl]-N-[2-(4-fluorophenyl)-1,1-dimethylethyl]-L-α-glutamine, $N^2$-{[3'-(bromomethyl)biphenyl-4-yl]carbonyl}-N-(3-methylbenzyl)-L-α-glutamine, N-[2-(4-fluorophenyl)-1,1-dimethylethyl]-$N^2$-[4-(3-thienyl)benzoyl]-L-α-glutamine, N-[2-(4-fluorophenyl)-1,1-dimethylethyl]-$N^2$-[4-(5-methyl-2-thienyl)benzoyl]-L-α-glutamine, $N^2$-[4-(5-chloro-2-thienyl)benzoyl]-N-[2-(4-fluorophenyl)-1,1-dimethylethyl]-L-α-glutamine, N-[2-(4-chlorophenyl)-1,1-dimethylethyl]-$N^2$-[4-(2-thienyl)benzoyl]-L-α-glutamine, N-[2-(4-chlorophenyl)-1,1-dimethylethyl]-$N^2$-{[5-(3-methoxyphenyl)-2-thienyl]carbonyl}-L-α-glutamine, N-[2-(4-chlorophenyl)-1,1-dimethylethyl]-$N^2$-[(5-phenyl-2-thienyl)carbonyl]-L-α-glutamine, $N^2$-(2,2'-bithien-5-ylcarbonyl)-N-[2-(4-chlorophenyl)-1,1-dimethylethyl]-L-α-glutamine, $N^2$-[4-(2,3-dihydro-1-benzofuran-6-yl)benzoyl]-N-[2-(4-fluorophenyl)-1,1-dimethylethyl]-L-α-glutamine, N-[2-(4-fluorophenyl)-1,1-dimethylethyl]-$N^2$-{[6-(3-methoxyphenyl)pyridin-3-yl]carbonyl}-L-α-glutamine, N-[2-(4-fluorophenyl)-1,1-dimethylethyl]-$N^2$-[(6-phenylpyridin-3-yl)carbonyl]-L-α-glutamine, N-[2-(4-fluorophenyl)-1,1-dimethylethyl]-$N^2$-[(5-phenyl-2-thienyl)carbonyl]-L-α-glutamine, $N^2$-[(3-fluorobiphenyl-4-yl)carbonyl]-N-[2-(4-fluorophenyl)-1,1-dimethylethyl]-L-α-glutamine, N-[2-(4-chlorophenyl)-1,1-dimethylethyl]-$N^2$-[(5-pyridin-4-yl-2-thienyl)carbonyl]-L-α-glutamine, $N^2$-{[5-(3-chloro-4-fluorophenyl)-2-thienyl]carbonyl}-N-[2-(4-chlorophenyl)-1,1-dimethylethyl]-L-α-glutamine, N-[2-(4-chlorophenyl)-1,1-dimethylethyl]-$N^2$-[4-(2,3-dihydro-1-benzofuran-6-yl)benzoyl]-L-α-glutamine, N-[2-(4-chlorophenyl)-1,1-dimethylethyl]-$N^2$-[(5-pyridin-3-yl-2-thienyl)carbonyl]-L-α-glutamine, $N^2$-[4-(2,3-dihydro-1-benzofuran-6-yl)benzoyl]-N-(1,1-dimethyl-2-phenylethyl)-L-α-glutamine, $N^2$-{[5-(3-chloro-4-fluorophenyl)-2-thienyl]carbonyl}-N-(1,1-dimethyl-2-phenylethyl)-L-α-glutamine, N-(1,1-dimethyl-2-phenylethyl)-$N^2$-[4-(2-thienyl)benzoyl]-L-α-glutamine, N-(1,1-dimethyl-2-phenylethyl)-$N^2$-{[5-(3-methoxyphenyl)-2-thienyl]carbonyl}-L-α-glutamine, N-(1,1-dimethyl-2-phenylethyl)-$N^2$-[(5-phenyl-2-thienyl)

carbonyl]-L-α-glutamine, N²-(2,2'-bithien-5-ylcarbonyl)-N-(1,1-dimethyl-2-phenylethyl)-L-α-glutamine, N-(1,1-dimethyl-2-phenylethyl)-N²-[(5-pyridin-4-yl-2-thienyl)carbonyl]-L-α-glutamine, N-(1,1-dimethyl-2-phenylethyl)-N²-[(5-pyridin-3-yl-2-thienyl)carbonyl]-L-α-glutamine, N-[2-(4-chlorophenyl)-1,1-dimethylethyl]-N²-[4-(5-chloro-2-thienyl)benzoyl]-L-α-glutamine, N²-{[6-(5-chloro-2-thienyl)pyridin-3-yl]carbonyl}-N-(1,1-dimethyl-2-phenylethyl)-L-α-glutamine, N-(1,1-dimethyl-2-phenylethyl)-N²-[(6-phenylpyridin-3-yl)carbonyl]-L-α-glutamine, N-[2-(4-chlorophenyl)-1,1-dimethylethyl]-N²-(5-phenyl-2-furoyl)-L-α-glutamine, N-[2-(4-chlorophenyl)-1,1-dimethylethyl]-N²-{[6-(5-chloro-2-thienyl)pyridin-3-yl]carbonyl}-L-α-glutamine, N-[2-(4-chlorophenyl)-1,1-dimethylethyl]-N²-[(6-phenylpyridin-3-yl)carbonyl]-L-α-glutamine, N-[2-(4-fluorophenyl)-1,1-dimethylethyl]-N²-{[5-(3-methoxyphenyl)-2-thienyl]carbonyl}-L-α-glutamine, N-[2-(4-fluorophenyl)-1,1-dimethylethyl]-N²-[(5-pyridin-3-yl-2-thienyl)carbonyl]-L-α-glutamine, N²-{[5-(3-chloro-4-fluorophenyl)-2-thienyl]carbonyl}-N-[2-(4-fluorophenyl)-1,1-dimethylethyl]-L-α-glutamine, N²-(2,2'-bithien-5-ylcarbonyl)-N-[2-(4-fluorophenyl)-1,1-dimethylethyl]-L-α-glutamine, N-[2-(4-chlorophenyl)-1,1-dimethylethyl]-N²-[4-(5-formyl-2-thienyl)benzoyl]-L-α-glutamine, N²-[4-(5-acetyl-2-thienyl)benzoyl]-N-[2-(4-chlorophenyl)-1,1-dimethylethyl]-L-α-glutamine, N-[2-(4-chlorophenyl)-1,1-dimethylethyl]-N²-[4-(1,3-thiazol-2-yl)benzoyl]-L-α-glutamine, N-(1,1-dimethyl-2-phenylethyl)-N²-[4-(1,3-thiazol-2-yl)benzoyl]-L-α-glutamine, N-(1,1-dimethyl-2-phenylethyl)-N²-(5-phenyl-2-furoyl)-L-α-glutamine, N-(1,1-dimethyl-2-phenylethyl)-N²-[4-(5-formyl-2-thienyl)benzoyl]-L-α-glutamine, N²-[4-(5-acetyl-2-thienyl)benzoyl]-N-(1,1-dimethyl-2-phenylethyl)-L-α-glutamine, N-[2-(4-chlorophenyl)-1,1-dimethylethyl]-N²-[3-(5-chloro-2-thienyl)benzoyl]-L-α-glutamine, N-[2-(4-chlorophenyl)-1,1-dimethylethyl]-N²-[3-(2-thienyl)benzoyl]-L-α-glutamine, N-[2-(4-chlorophenyl)-1,1-dimethylethyl]-N²-{[5-(4-chlorophenyl)-2-thienyl]carbonyl}-L-α-glutamine, N-[2-(4-chlorophenyl)-1,1-dimethylethyl]-N²-{[5-(4-fluorophenyl)-2-thienyl]carbonyl}-L-α-glutamine, N²-[4-(5-bromo-2-thienyl)benzoyl]-N-[2-(4-chlorophenyl)-1,1-dimethylethyl]-L-α-glutamine, N²-[4-(5-bromo-2-thienyl)benzoyl]-N-(1,1-dimethyl-2-phenylethyl)-L-α-glutamine, N-(1,1-dimethyl-2-phenylethyl)-N²-{[5-(4-fluorophenyl)-2-thienyl]carbonyl}-L-α-glutamine, N²-[3-(5-chloro-2-thienyl)benzoyl]-N-(1,1-dimethyl-2-phenylethyl)-L-α-glutamine, N-(1,1-dimethyl-2-phenylethyl)-N²-[3-(2-thienyl)benzoyl]-L-α-glutamine, N²-[(3'-chlorobiphenyl-4-yl)carbonyl]-N-[2-(4-fluorophenyl)-1,1-dimethylethyl]-L-α-glutamine, N²-[(4'-chlorobiphenyl-4-yl)carbonyl]-N-[2-(4-fluorophenyl)-1,1-dimethylethyl]-L-α-glutamine, N²-[(4'-fluorobiphenyl-4-yl)carbonyl]-N-[2-(4-fluorophenyl)-1,1-dimethylethyl]-L-α-glutamine, N²-[(3'-fluorobiphenyl-4-yl)carbonyl]-N-[2-(4-fluorophenyl)-1,1-dimethylethyl]-L-α-glutamine, N-[2-(4-chlorophenyl)-1,1-dimethylethyl]-N²-[(3-phenyl-2-thienyl)carbonyl]-L-α-glutamine, N²-[(4'-chlorobiphenyl-4-yl)carbonyl]-N-[2-(4-chlorophenyl)-1,1-dimethylethyl]-L-α-glutamine, N²-[(3'-chlorobiphenyl-4-yl)carbonyl]-N-[2-(4-chlorophenyl)-1,1-dimethylethyl]-L-α-glutamine, N-[2-(4-fluorophenyl)-1,1-dimethylethyl]-N²-{[5-(4-fluorophenyl)-2-thienyl]carbonyl}-L-α-glutamine, N²-{[5-(4-chlorophenyl)-2-thienyl]carbonyl}-N-(1,1-dimethyl-2-phenylethyl)-L-α-glutamine, N-(1,1-dimethyl-2-phenylethyl)-N²-[(3-phenyl-2-thienyl)carbonyl]-L-α-glutamine, N²-(4-bromobenzoyl)-N-[2-(4-fluorophenyl)-1,1-dimethylethyl]-L-α-glutamine, N-(1,1-dimethyl-2-phenylethyl)-N²-[(4'-fluorobiphenyl-4-yl)carbonyl]-L-α-glutamine, N-(1,1-dimethyl-2-phenylethyl)-N²-[(3'-fluorobiphenyl-4-yl)carbonyl]-L-α-glutamine, N²-[4-(5-chloro-2-thienyl)benzoyl]-N-[2-(4-fluorophenyl)-1,1-dimethylethyl]-D-α-glutamine, N²-{[6-(5-chloro-2-thienyl)pyridin-3-yl]carbonyl}-N-[2-(4-fluorophenyl)-1,1-dimethylethyl]-L-α-glutamine, N²-{[5-(4-chlorophenyl)-2-thienyl]carbonyl}-N-[2-(4-fluorophenyl)-1,1-dimethylethyl]-L-α-glutamine, N²-{[5-(3,4-difluorophenyl)-2-thienyl]carbonyl}-N-[2-(4-fluorophenyl)-1,1-dimethylethyl]-L-α-glutamine, N²-[(4'-{[3,5-bis(trifluoromethyl)phenoxy]methyl}biphenyl-4-yl)carbonyl]-N-(1,1-dimethyl-2-phenylethyl)-L-α-glutamine, N²-({4'-[(1,3-benzodioxol-5-yloxy)methyl]biphenyl-4-yl}carbonyl)-N-(1,1-dimethyl-2-phenylethyl)-L-α-glutamine, N²-{[3'-(benzyloxy)biphenyl-4-yl]carbonyl}-N-(3,4,5-trimethoxybenzyl)-L-α-glutamine, N²-({3'-[(3,5-dimethoxybenzyl)oxy]biphenyl-4-yl}carbonyl)-N-(3,4,5-trimethoxybenzyl)-L-α-glutamine, N²-({3'-[(3-methoxybenzyl)oxy]biphenyl-4-yl}carbonyl)-N-(3,4,5-trimethoxybenzyl)-L-α-glutamine, N²-({4'-[(3,5-dimethoxybenzyl)oxy]biphenyl-4-yl}carbonyl)-N-[2-(4-fluorophenyl)-1,1-dimethylethyl]-L-α-glutamine, N-benzyl-N²-{[4'-(biphenyl-3-ylmethoxy)biphenyl-4-yl]carbonyl}-L-α-glutamine, N-benzyl-N²-({4'-[(3'-methoxybiphenyl-3-yl)methoxy]biphenyl-4-yl}carbonyl)-L-α-glutamine, N²-({4'-[(3,5-dimethoxyphenoxy)methyl]biphenyl-4-yl}carbonyl)-N-(3-methylbenzyl)-L-α-glutamine, N²-({3'-[(3,5-dimethoxyphenoxy)methyl]biphenyl-4-yl}carbonyl)-N-(3-methylbenzyl)-L-α-glutamine, N²-[(3'-{[3,5-bis(trifluoromethyl)phenoxy]methyl}biphenyl-4-yl)carbonyl]-N-(3-methylbenzyl)-L-α-glutamine, N²-({3'-[(3-ethylphenoxy)methyl]biphenyl-4-yl}carbonyl)-N-(3-methylbenzyl)-L-α-glutamine, N-benzyl-N²-{[4'-(biphenyl-2-ylmethoxy)biphenyl-4-yl]carbonyl}-L-α-glutamine, or N-benzyl-N²-({4'-[(3'-methoxybiphenyl-2-yl)methoxy]biphenyl-4-yl}carbonyl)-L-α-glutamine.

Methods for Making the Compounds and Pharmaceutically Acceptable Salts of Compounds of the Invention The compounds and pharmaceutically acceptable salts of compounds of the present invention can be prepared using a variety of methods starting from commercially available compounds, known compounds, or compounds prepared by known methods. General synthetic routes to many of the compounds of the invention are included in the following schemes. It is understood by those skilled in the art that protection and deprotection steps not shown in the Schemes may be required for these syntheses, and that the order of steps may be changed to accommodate functionality in the target molecule.

As used in the schemes, $PG_1$ is an amine protecting group; $PG_2$ is a carboxylic acid protecting group; and $R_1$, $R_2$, $R_6$, $R_{12}$, $R_{13}$, $R_{14}$, and $R_{15}$ are defined as above.

General Synthetic Schemes for Preparation of Compounds

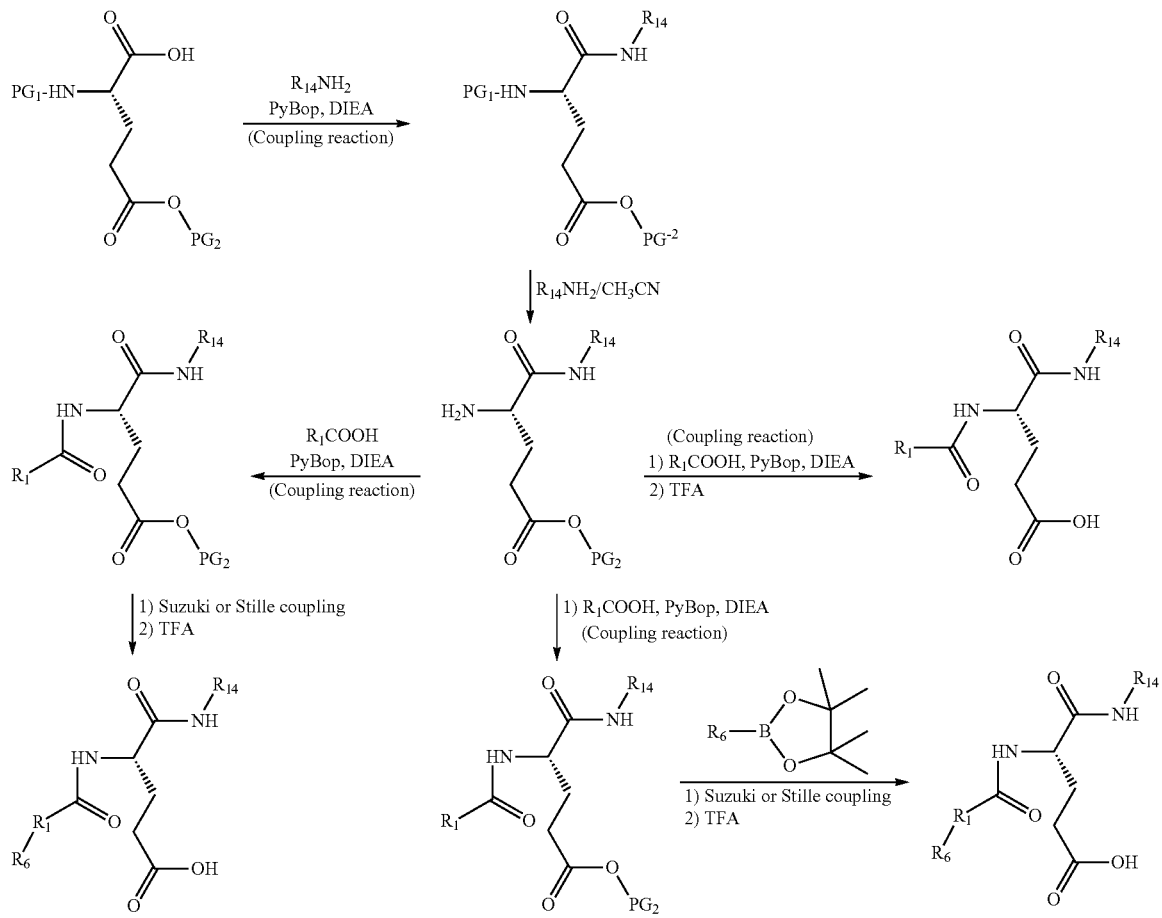

The amide formation between a carboxylic acid and an amine is carried out using a coupling reagent in a solvent such as DMF. Coupling reagents that may be used include benzotriazole-1-yl-oxy-tris-(dimethylamino)-phosphonium hexafluorophosphate (Bop reagent), benzotriazole-1-yl-oxy-tris-pyrrolidino-phosphonium hexafluorophosphate (PyBop reagent), O-benzotriazole-N,N,N',N'-tetramethyl-uronium-hexafluoro-phosphate (HBTU), 1-(3-dimethylaminopropyl)-3-ethyl-carbodiimide hydrochloride (EDC), and other known or commercially available coupling reagents.

Cross coupling is generally referred to as Suzuki or Stille coupling reactions.

The amine protecting group is cleaved under mild conditions with an amine base to afford the free amine. A variety of amine bases may be used, including for example, diethylamine, piperidine, morpholine, dicyclohexylamine, p-dimethylaminopyridine, or diisopropylethylamine in a solvent, such as acetonitrile or DMF.

Hydrolysis of the carboxylic acid protecting group is carried out using TFA, NaOH, LiOH, potassium carbonate, or the like.

Scheme 1 demonstrates the preparation of compounds of the invention in two steps from N-(4-aminobenzoyl)-L-glutamic diethyl ester (1). Heating an aryl or heteroaryl chloride such as chloropyridine with N-(4-aminobenzoyl)-L-glutamic diethyl ester gave the diethyl ester (2), which was hydrolyzed with bases such as NaOH, LiOH, or the like to provide (3).

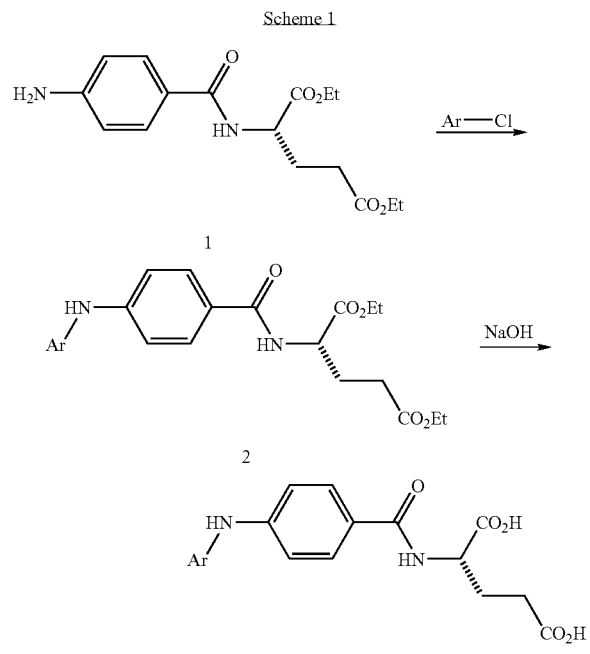

Scheme 2 provides the preparation of a compound of the invention in two steps from biphenylcarboxylic acid (4). Amide formation was carried out using a coupling reagent, such as EDC. Hydrolysis of the diethyl ester (5) under basic conditions gave the final product dicarboxylic acid (6).

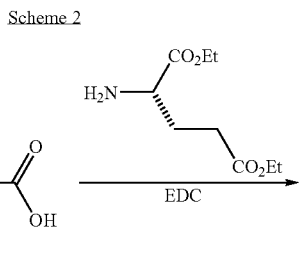

Scheme 3 provides the preparation of compounds of the invention in two steps. Coupling of the amine and carboxylic acid (7) was carried out using a coupling reagent such as EDC. The tert-butyl protecting group on (8) was hydrolyzed in acidic conditions (TFA in dichloromethane) to provide the product (9).

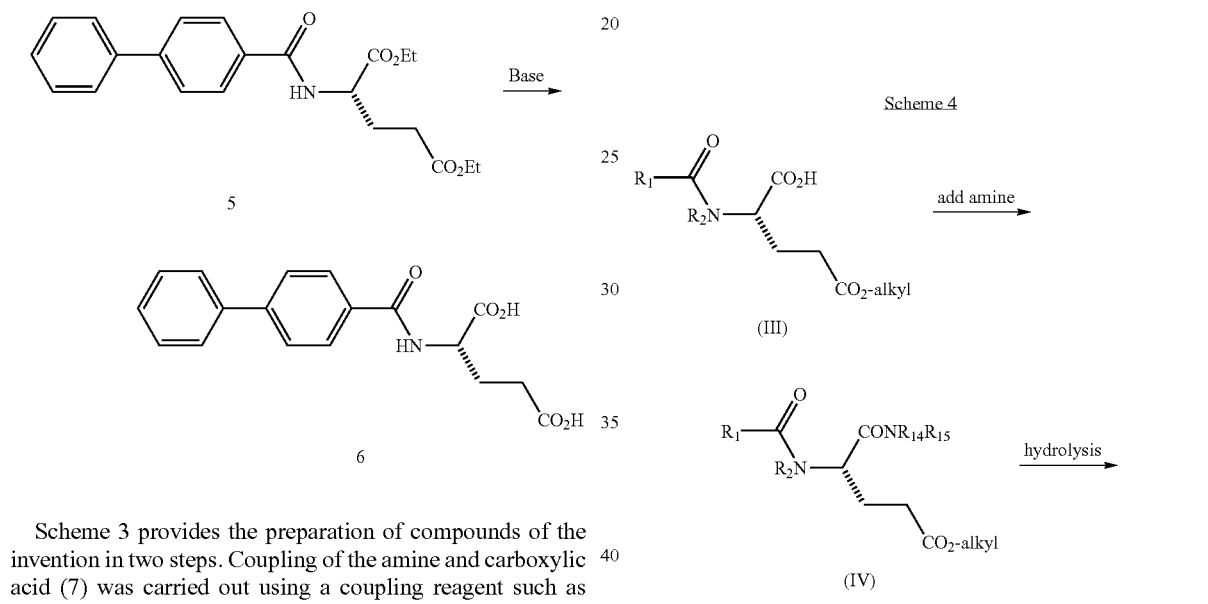

Scheme 4 demonstrates the synthesis of a compound or pharmaceutically acceptable salt of a compound of the Formula (II). As shown in Scheme 4, a compound of the Formula (III) is treated with an amine under conditions effective to provide a compound of the Formula (IV). Hydrolysis of the alkyl ester provides a compound of the Formula (II).

Scheme 5 provides the synthesis of compounds of the Formula (II) following the general procedures set forth in Scheme 4. Coupling of commercially available amines, amines known in the literature, or other amines with biphenylcarboxylic acid (4, or fluorenecarboxylic acids or other carboxylic acids) can be carried out in EDC, PyBop/DIEA, or other coupling reagents as described above in the general scheme. Hydrolysis of the tert-butyl ester (10) was carried out using TFA. The second coupling reaction of the carboxylic acid (11) with a variety of amines was carried out using a similar procedure as employed in the first step. Finally, the methyl ester (12) was hydrolyzed with NaOH/MeOH in THF to provide (13).

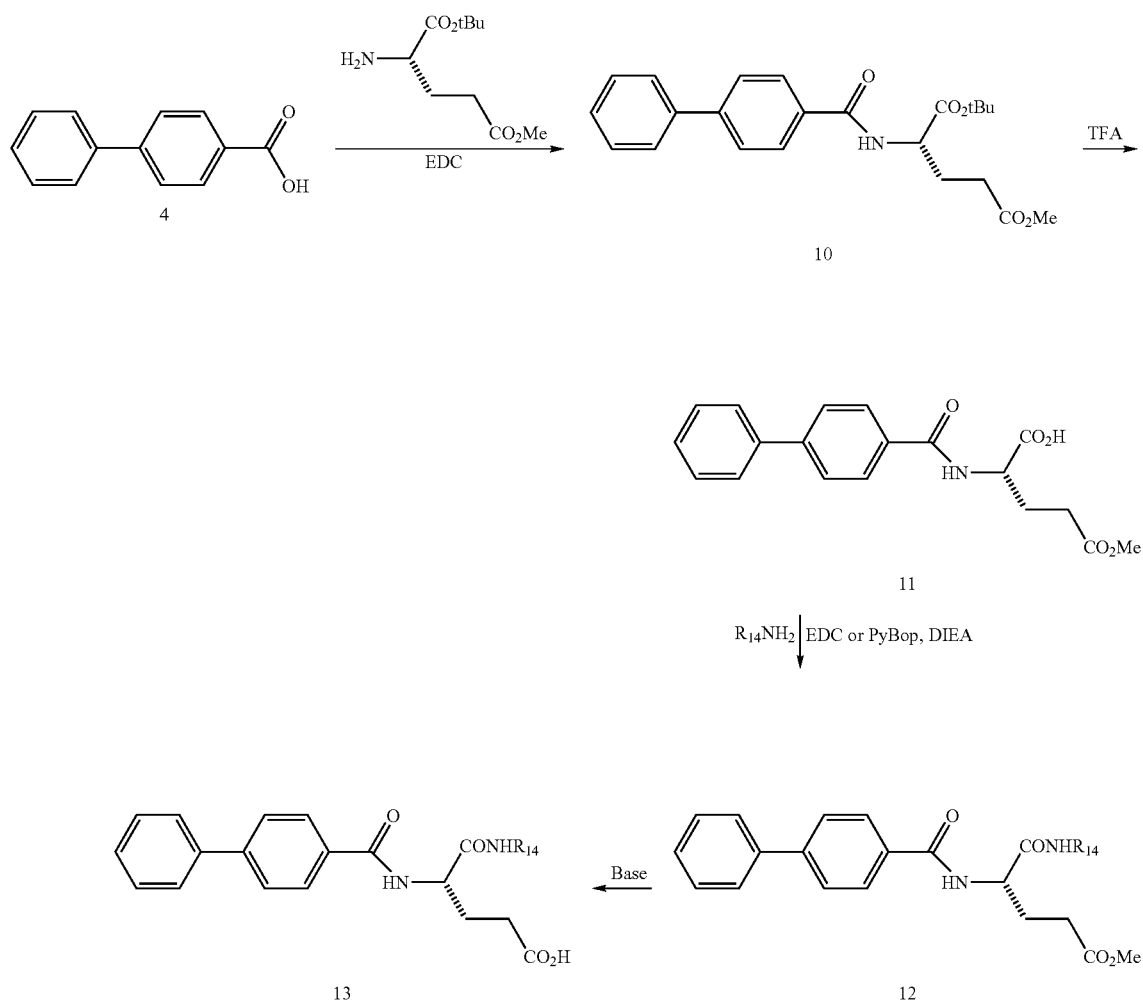

Scheme 6 demonstrates the synthesis of a compound or pharmaceutically acceptable salt of a compound of the Formula (II). As shown in Scheme 6, a compound of the Formula (V) is treated with an amine under conditions effective to provide a compound of the Formula (VI). Hydrolysis of the amine protecting group provides a compound of the Formula (VII), which is coupled with a carboxylic acid under conditions effective to provide a compound of the Formula (VIII). Hydrolysis of the protected carboxylic acid provides a compound of the Formula (II).

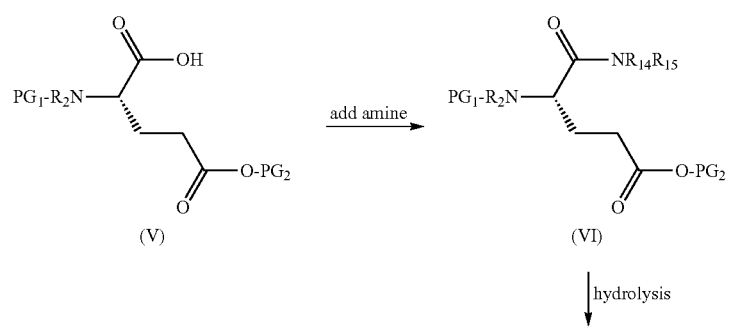

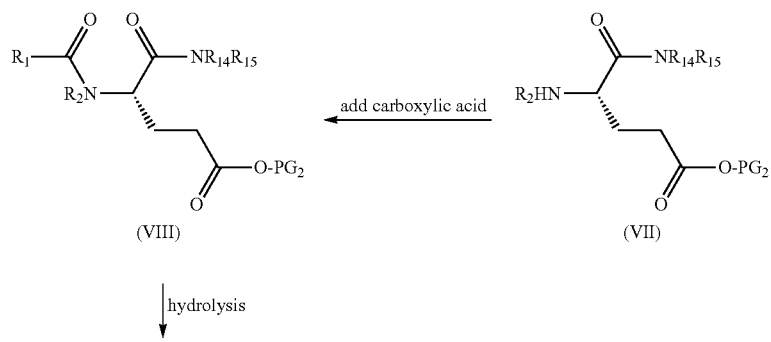

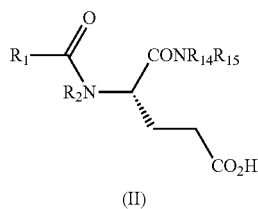

Scheme 7 provides the synthesis of compounds of the Formula (II) following the general procedures set forth in Scheme 6. In scheme 7, Fmoc-glu(Obut)OH (14) was reacted with a known or commercially available primary or secondary amine. Hydrolysis of the Fmoc protecting group of (15) was carried out with diethylamine in acetonitrile. The amine (16) was then coupled with a carboxylic acid (e.g. 4-biphenylcarboxylic acid or fluorenecarboxylic acid) and the resulting tert-butyl ester (17) was hydrolyzed using TFA in dichloromethane to provide (18).

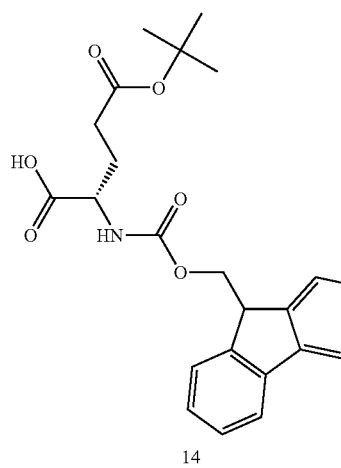

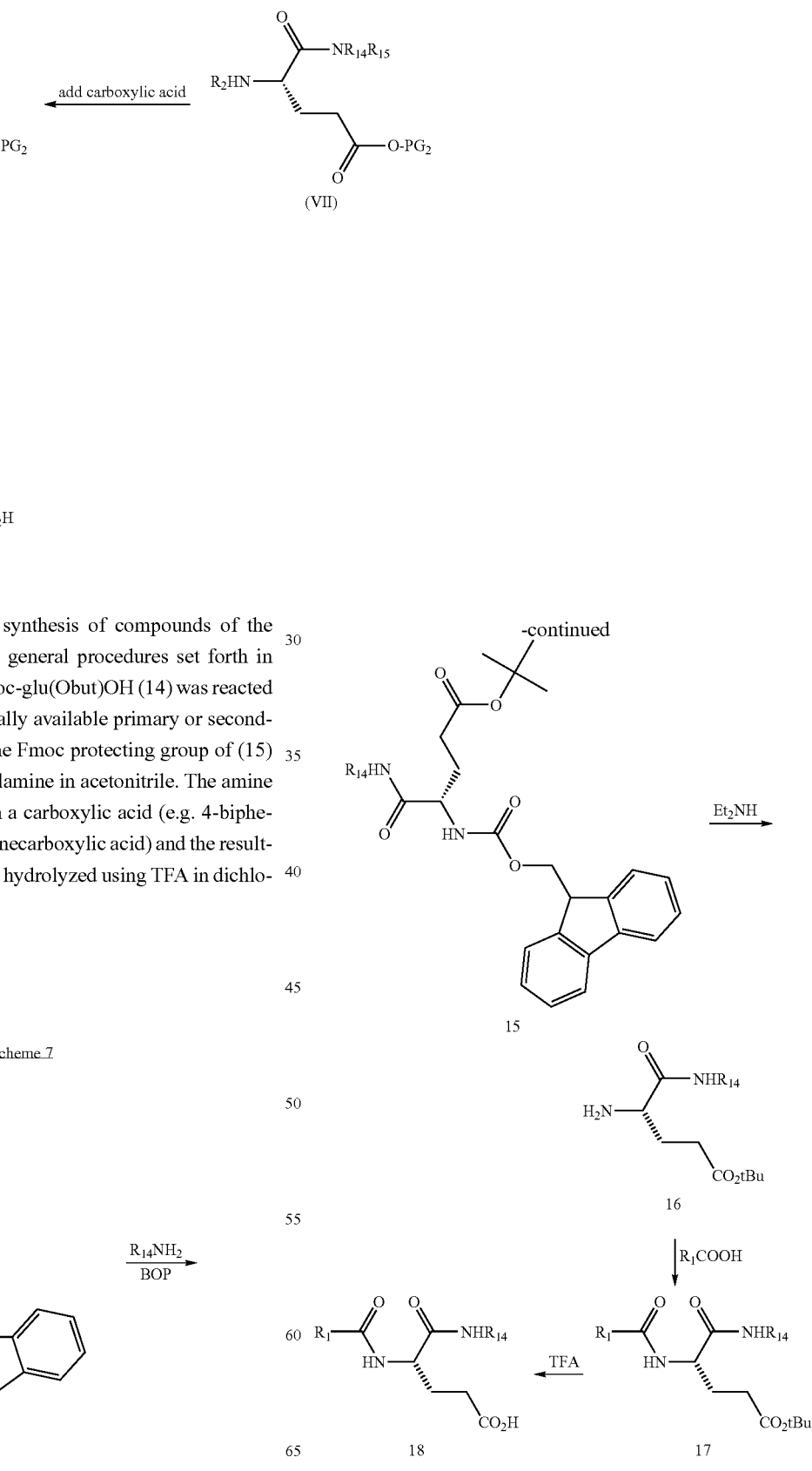

Scheme 8 demonstrates the preparation of compounds of the invention similar to the procedure described in scheme 7. Bromo or iodophenethylamine (or bromo or iodo benzylamine) was coupled with the Fmoc protected amino acid (14). Removal of the Fmoc protecting group of (19) was carried out in base and the resulting compound (20) was reacted with 4-biphenylcarboxylic acid (or fluorenecarboxylic acid or other carboxylic acid). Cross-coupling of the bromo or iodo intermediate (21) with a boronic ester or stannyl reagent (via Suzuki or Stille method) gave the coupling product t-butyl ester (22), which was then hydrolyzed to give the final carboxylic acid product (23).

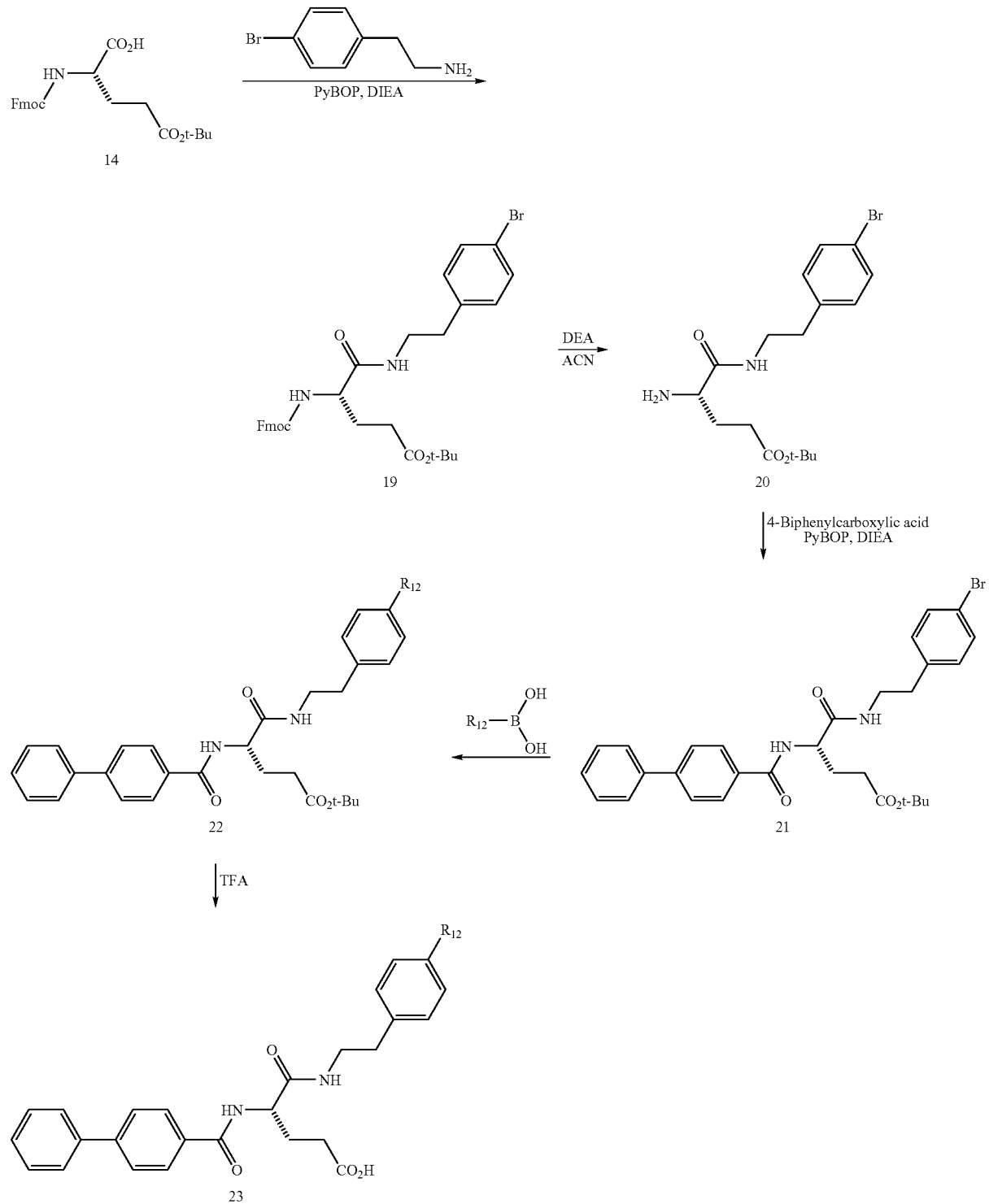

Scheme 9 demonstrates the preparation of compounds of the invention in three steps from bromo compounds. Cross coupling of (25) with either a boronic ester or a stannyl compound using either Suzuki or Stille coupling gave the tert-butyl ester (26), which was then hydrolyzed to the carboxylic acid (27).

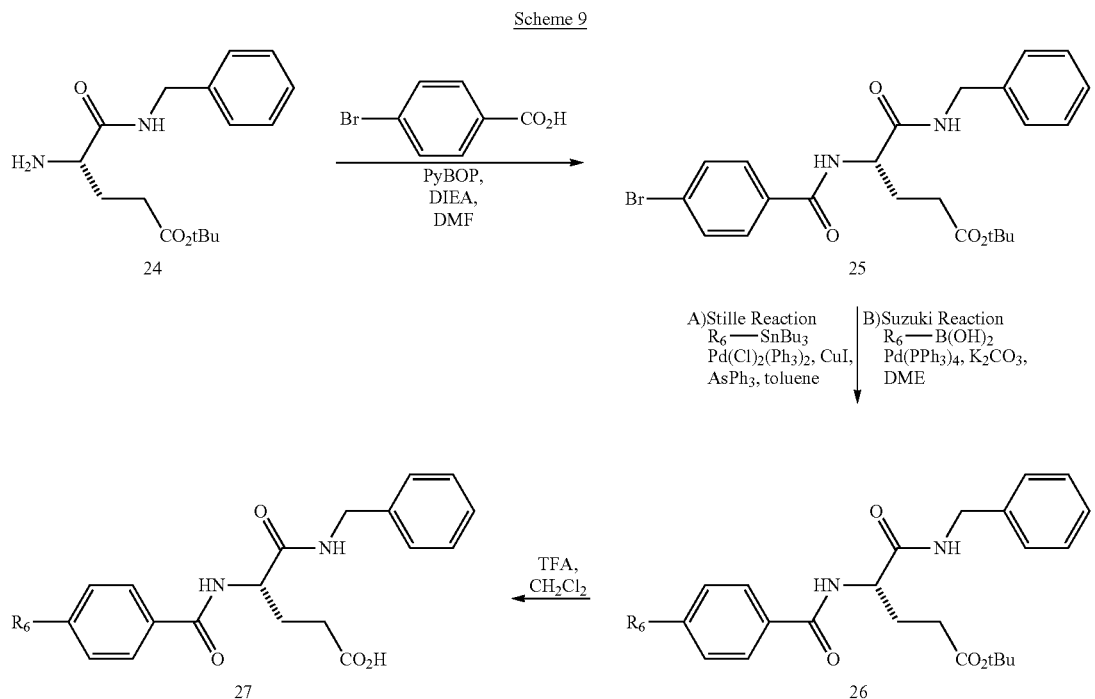

Scheme 9

Scheme 10 provides compounds of the invention prepared in three or four steps from bromo compounds. Suzuki coupling of (25) with the 4-hydroxyphenylboronic acid gave the intermediate (28). Path A: Alkylation of the phenolic compound with an alkylhalide or benzyl halide provided (29), followed by acid hydrolysis to give the carboxylic acid (30).

Path B: The brominated compound (31) was treated with an alcohol to give (32), followed by acid hydrolysis to give the carboxylic acid (33). Path C: The intermediate (28) was treated a bromobenzylbromide compound to provide (52), followed by treatment with phenylboronic acid to provide (53), which was then acid hydrolized to give (54).

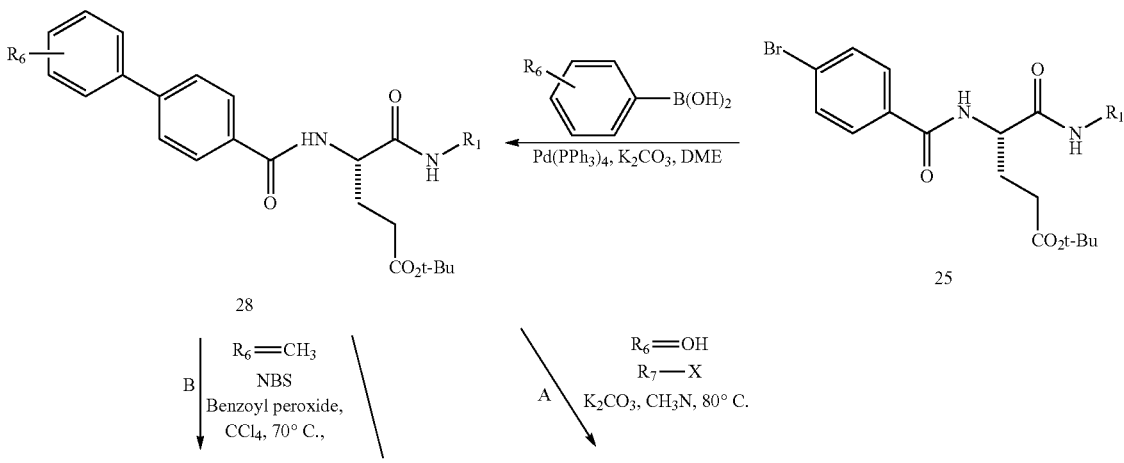

Scheme 10

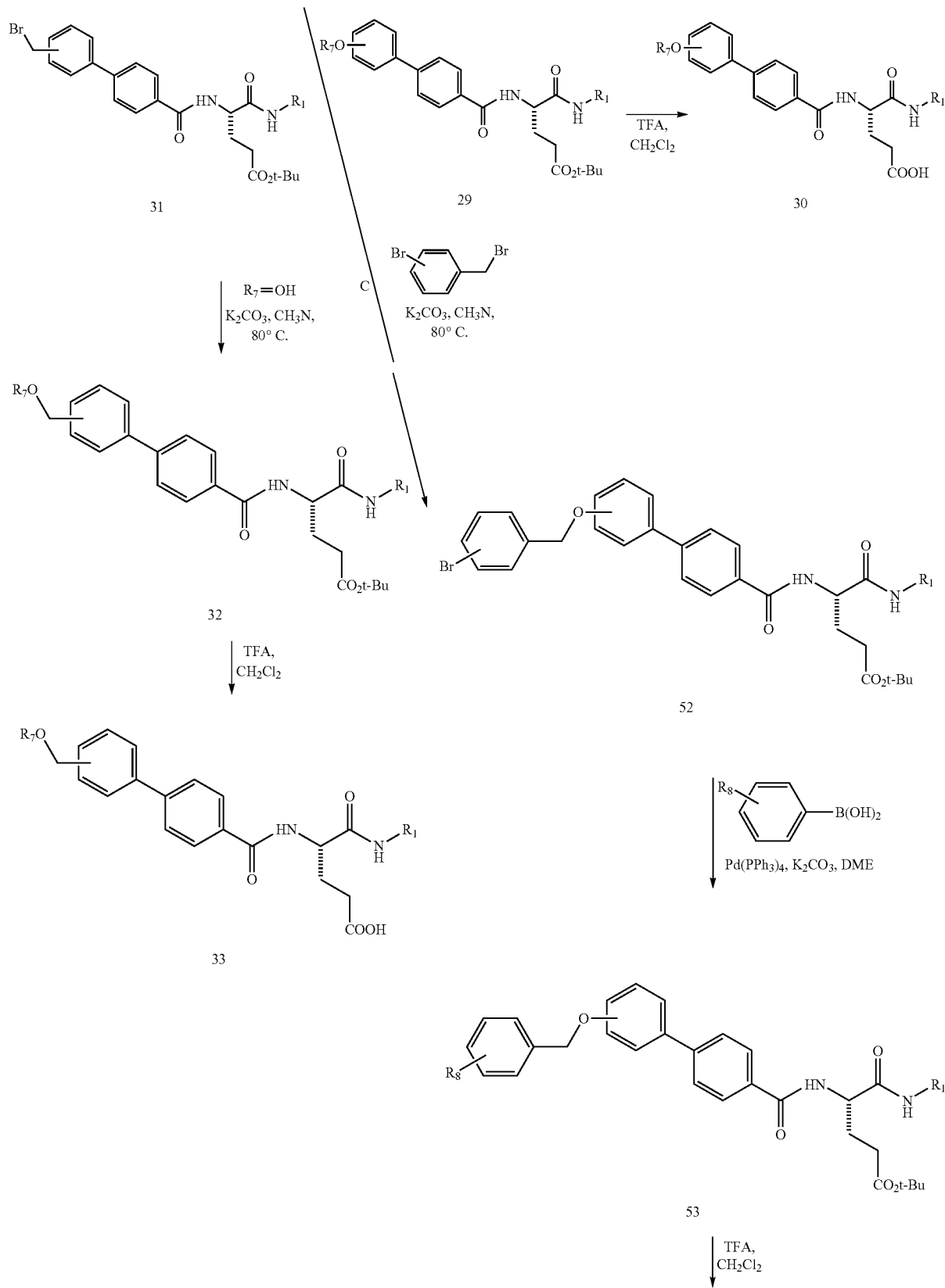

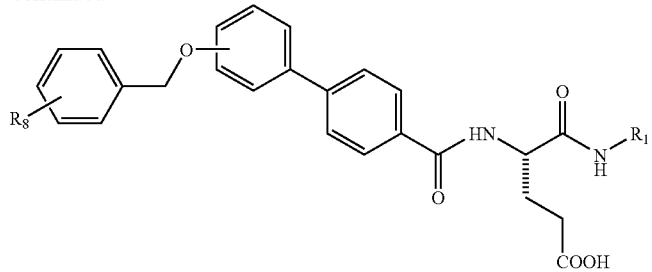

54

Scheme 11 provides compounds of the invention prepared in a similar manner described in scheme 10, except 5-bromofuroic acid was used in the first coupling reaction step. The bromo intermediate (34) was then reacted with a boronic acid and hydrolysis of the resulting tert-butyl ester (35) in acid provided the carboxylic acid (36).

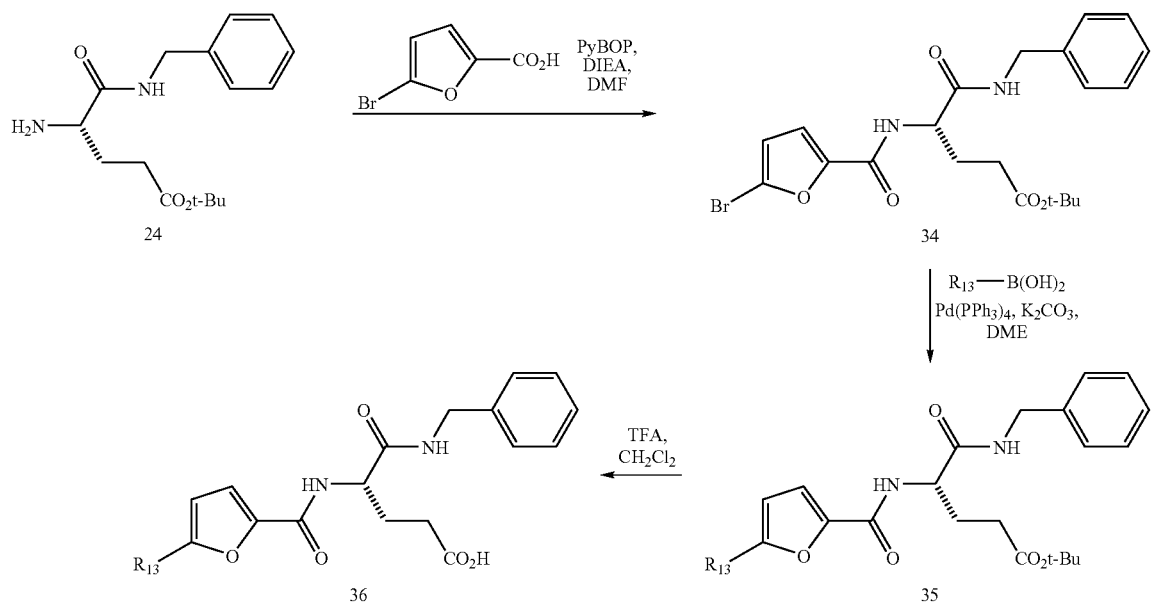

Scheme 12 provides compounds of the invention prepared according to the procedure described in scheme 11, except 6-bromonicotinic acid was used to couple with the amino intermediate (37) to afford (38).

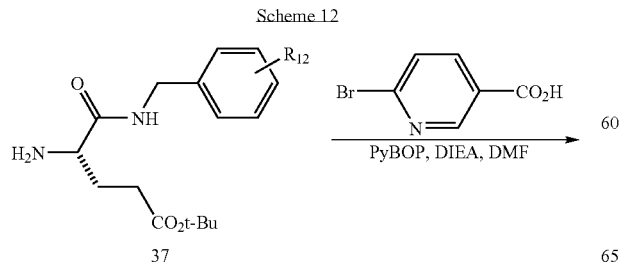

-continued

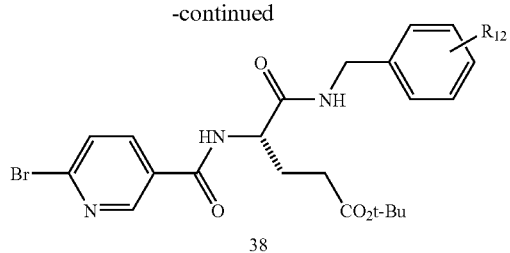

Scheme 13 provides compounds of the invention prepared according to the procedure described in scheme 10, except 4-(4,4,5,5)-tetramethyl-1,3,2-dioxoborolan-2-yl)aniline was used in the Suzuki coupling reaction with (25). The amino intermediate (39) was then acylated with an acid chloride and the tert-butyl ester (40) was hydrolyzed in acidic conditions to give the desired carboxylic acid (41).

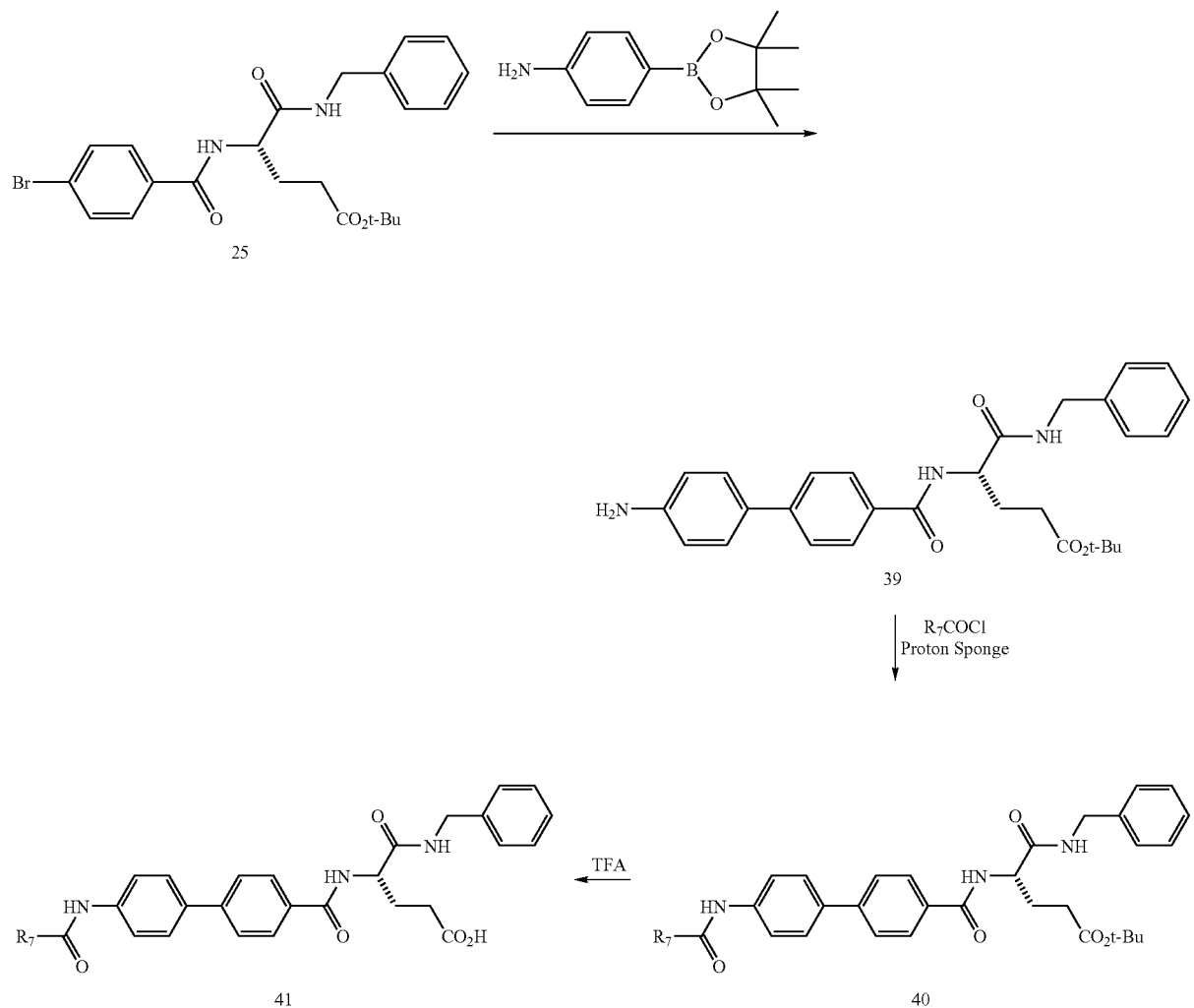

Scheme 14 demonstrates the preparation of compounds of the invention in four steps. The L-glutamic acid α-tert-butyl ester γ-ethyl ester was reacted with 4-biphenylcarboxylic acid (4, or other carboxylic acid) using EDC, PyBop, Bop, or other coupling agent. Hydrolysis of the alpha tert-butyl ester (42) in trifluoroacetic acid gave the alpha carboxylic acid intermediate (43) in good yield. Treatment of the acid with a base (e.g. triethylamine) and ethyl chloroformate followed by sodium borohydride gave the corresponding alcohol (44). The ethyl ester was then hydrolyzed in basic conditions to give the final product (45).

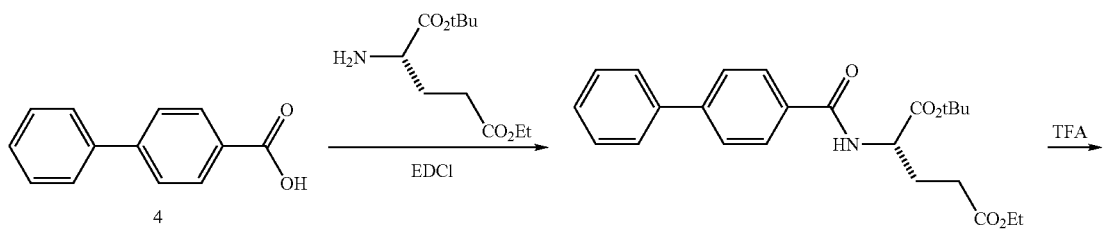

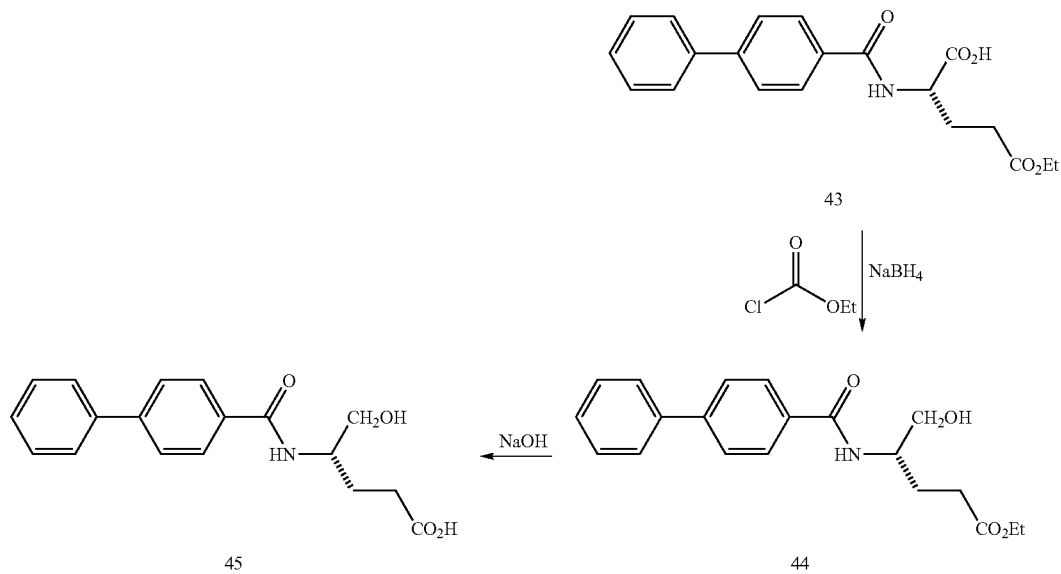

Scheme 15 provides compounds of the invention prepared in four steps from bromobenzoic acid. L-glutamic acid di-tert butyl ester was coupled with the bromobenzoic acid (46). Suzuki coupling of the bromo compound (47) with 4-(4,4,5,5)-tetramethyl-1,3,2-dioxoborolan-2-yl)aniline gave the amino intermediate (48) in good yield. Acylation of the amine with an acid chloride gave the acylated product (49), and hydrolysis of the tert-butyl ester in acidic conditions gave the final dicarboxylic acid (50).

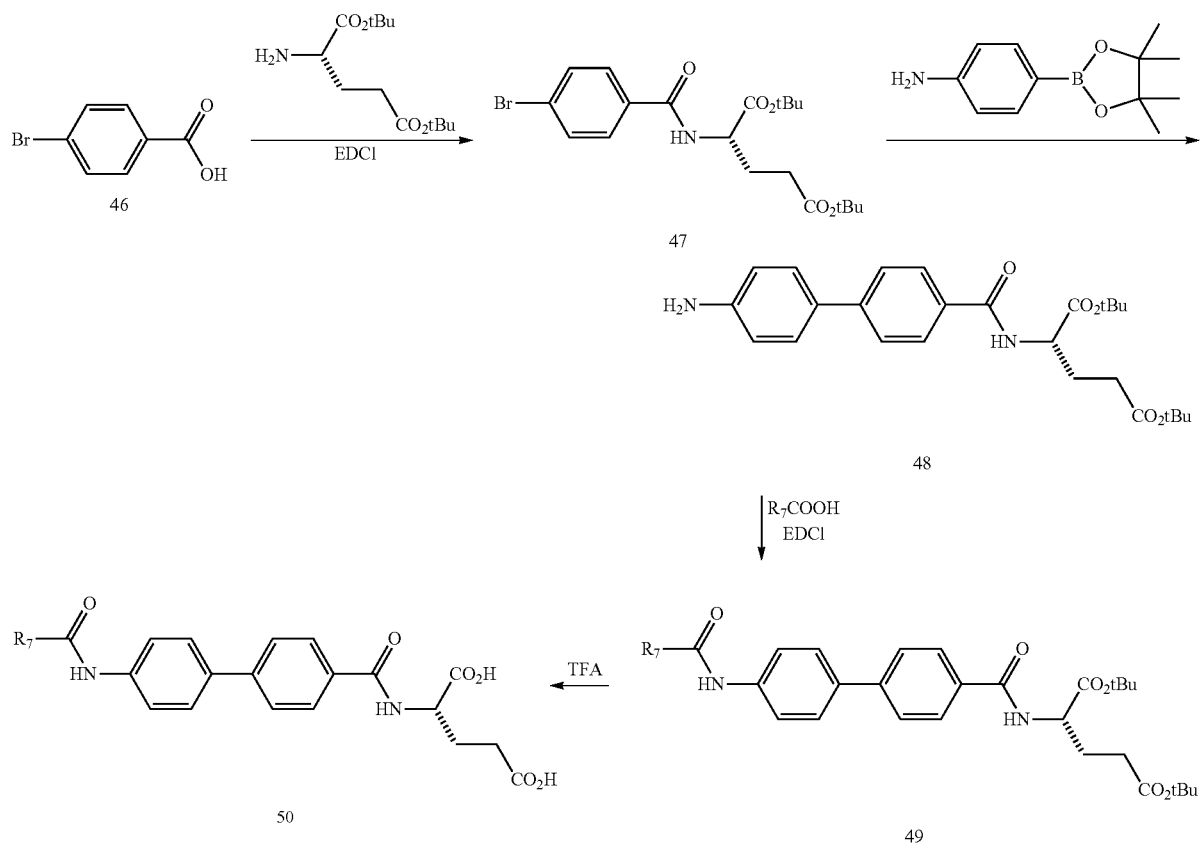

Scheme 16 provides compounds of the invention prepared in a single step from a carboxylic acid. A carboxylic acid of the invention (17) is reacted with Bop, hydroxylamine hydrochloride, and DIEA to afford the hydroxamic acid (51).

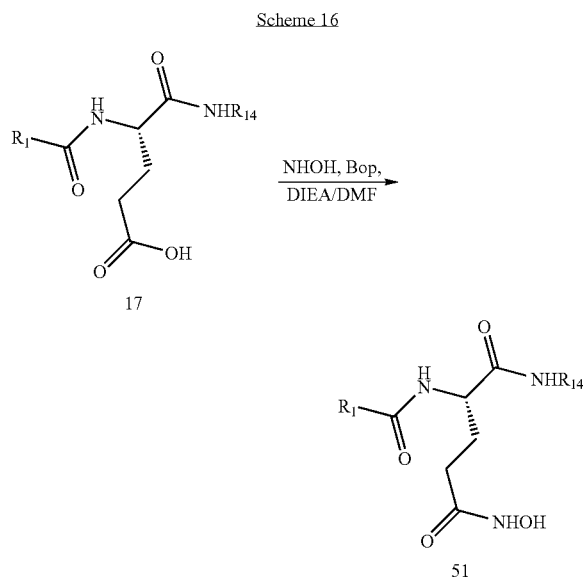

One of skill in the art will recognize that Schemes 1-16 can be adapted to produce other compounds and pharmaceutically acceptable salts of compounds according to the present invention.

Therapeutic Administration

When administered to an animal, the compounds or pharmaceutically acceptable salts of the compounds of the invention can be administered neat or as a component of a composition that comprises a physiologically acceptable carrier or vehicle. A composition of the invention can be prepared using a method comprising admixing the compound or a pharmaceutically acceptable salt of the compound and a physiologically acceptable carrier, excipient, or diluent. Admixing can be accomplished using methods well known for admixing a compound or a pharmaceutically acceptable salt of the compound and a physiologically acceptable carrier, excipient, or diluent.

The present compositions, comprising compounds or pharmaceutically acceptable salts of the compounds of the invention can be administered orally. The compounds or pharmaceutically acceptable salts of compounds of the invention can also be administered by any other convenient route, for example, by infusion or bolus injection, by absorption through epithelial or mucocutaneous linings (e.g., oral, rectal, vaginal, and intestinal mucosa, etc.) and can be administered together with another therapeutic agent. Administration can be systemic or local. Various known delivery systems, including encapsulation in liposomes, microparticles, microcapsules, and capsules, can be used.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. In some instances, administration will result of release of the compound or a pharmaceutically acceptable salt of the compound into the bloodstream. The mode of administration is left to the discretion of the practitioner.

In one embodiment, the compound or a pharmaceutically acceptable salt of the compound is administered orally.

In another embodiment, the compound or a pharmaceutically acceptable salt of the compound is administered intravenously.

In another embodiment, it may be desirable to administer the compound or a pharmaceutically acceptable salt of the compound locally. This can be achieved, for example, by local infusion during surgery, topical application, e.g., in conjunction with a wound dressing after surgery, by injection, by means of a catheter, by means of a suppository or edema, or by means of an implant, said implant being of a porous, non-porous, or gelatinous material, including membranes, such as sialastic membranes, or fibers.

In certain embodiments, it can be desirable to introduce the compound or a pharmaceutically acceptable salt of the compound into the central nervous system, circulatory system or gastrointestinal tract by any suitable route, including intraventricular, intrathecal injection, paraspinal injection, epidural injection, enema, and by injection adjacent to the peripheral nerve. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compound or a pharmaceutically acceptable salt of the compound can be formulated as a suppository, with traditional binders and excipients such as triglycerides.

In another embodiment, the compound or a pharmaceutically acceptable salt of the compound can be delivered in a vesicle, in particular a liposome (see Langer, *Science* 1990, 249, 1527-1533 and Treat et al., *Liposomes in the Therapy of Infectious Disease and Cancer* 1989, 317-327 and 353-365.

In yet another embodiment, the compound or a pharmaceutically acceptable salt of the compound can be delivered in a controlled-release system or sustained-release system (see, e.g., Goodson, in *Medical Applications of Controlled Release* 1984, vol. 2, 115-138). Other controlled or sustained-release systems discussed in the review by Langer, *Science* 1990, 249, 1527-1533 can be used. In one embodiment, a pump can be used (Langer, *Science* 1990, 249, 1527-1533; Sefton, *CRC Crit. Ref. Biomed. Eng.* 1987, 14, 201; Buchwald et al., *Surgery* 1980, 88, 507; and Saudek et al., *N. Engl. J Med.* 1989, 321, 574). In another embodiment, polymeric materials can be used (see *Medical Applications of Controlled Release* (Langer and Wise, eds., 1974); *Controlled Drug Bioavailability, Drug Product Design and Performance* (Smolen and Ball, eds., 1984); Ranger and Peppas, *J. Macromol. Sci. Rev. Macromol. Chem.* 1983, 2, 61; Levy et al., *Science* 1935, 228, 190; During et al., *Ann. Neural.* 1989, 25, 351; and Howard et al., *J. Neurosurg.* 1989, 71, 105).

In yet another embodiment, a controlled- or sustained-release system can be placed in proximity of a target of the compound or a pharmaceutically acceptable salt of the compound, e.g., the reproductive organs, thus requiring only a fraction of the systemic dose.

The present compositions can optionally comprise a suitable amount of a physiologically acceptable excipient.

Such physiologically acceptable excipients can be liquids, such as water and oils, including those of petroleum, animal, vegetable, or synthetic origin, such as peanut oil, soybean oil, mineral oil, sesame oil and the like. The physiologically acceptable excipients can be saline, gum acacia, gelatin, starch paste, talc, keratin, colloidal silica, urea and the like. In addition, auxiliary, stabilizing, thickening, lubricating, and coloring agents can be used. In one embodiment the physiologically acceptable excipients are sterile when administered to an animal. The physiologically acceptable excipient should be stable under the conditions of manufacture and storage and should be preserved against the contaminating action of microorganisms. Water is a particularly useful excipient when the compound or a pharmaceutically acceptable salt of the compound is administered intravenously. Saline solutions and aqueous dextrose and glycerol solutions can also be employed as liquid excipients, particularly for injectable solutions. Suitable physiologically acceptable excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

Liquid carriers may be used in preparing solutions, suspensions, emulsions, syrups, and elixirs. The compound or pharmaceutically acceptable salt of the compound of this invention can be dissolved or suspended in a pharmaceutically acceptable liquid carrier such as water, an organic solvent, a mixture of both, or pharmaceutically acceptable oils or fat. The liquid carrier can contain other suitable pharmaceutical additives including solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particular containing additives as above, e.g., cellulose derivatives, including sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule. Other examples of suitable physiologically acceptable excipients are described in *Remington's Pharmaceutical Sciences* 1447-1676 (Alfonso R. Gennaro, ed., 19th ed. 1995).

In one embodiment, the compound or a pharmaceutically acceptable salt of the compound is formulated in accordance with routine procedures as a composition adapted for oral administration to humans. Compositions for oral delivery can be in the form of tablets, lozenges, buccal forms, troches, aqueous or oily suspensions or solutions, granules, powders, emulsions, capsules, syrups, or elixirs for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. In powders, the carrier can be a finely divided solid, which is an admixture with the finely divided compound or pharmaceutically acceptable salt of the compound. In tablets, the compound or pharmaceutically acceptable salt of the compound is mixed with a carrier having the necessary compression properties in suitable proportions and compacted in the shape and size desired. The powders and tablets can contain up to about 99% of the compound or pharmaceutically acceptable salt of the compound.

Capsules may contain mixtures of the compounds or pharmaceutically acceptable salts of the compounds with inert fillers and/or diluents such as pharmaceutically acceptable starches (e.g., corn, potato, or tapioca starch), sugars, artificial sweetening agents, powdered celluloses (such as crystalline and microcrystalline celluloses), flours, gelatins, gums, etc.

Tablet formulations can be made by conventional compression, wet granulation, or dry granulation methods and utilize pharmaceutically acceptable diluents, binding agents, lubricants, disintegrants, surface modifying agents (including surfactants), suspending or stabilizing agents (including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrroldine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine.

Moreover, when in a tablet or pill form, the compositions can be coated to delay disintegration and absorption in the gastrointestinal tract, thereby providing a sustained action over an extended period of time. Selectively permeable membranes surrounding an osmotically active driving compound or a pharmaceutically acceptable salt of the compound are also suitable for orally administered compositions. In these latter platforms, fluid from the environment surrounding the capsule can be imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment the excipients are of pharmaceutical grade.

In another embodiment, the compound or a pharmaceutically acceptable salt of the compound can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lignocaine to lessen pain at the site of the injection. Generally, the ingredients are supplied either separately or mixed together in unit dosage form, for example, as a dry lyophilized powder or water-free concentrate in a hermetically sealed container such as an ampule or sachette indicating the quantity of active agent. Where the compound or a pharmaceutically acceptable salt of the compound is to be administered by infusion, it can be dispensed, for example, with an infusion bottle containing sterile pharmaceutical grade water or saline. Where the compound or a pharmaceutically acceptable salt of the compound is administered by injection, an ampule of sterile water for injection or saline can be provided so that the ingredients can be mixed prior to administration.

In another embodiment, the compound or pharmaceutically acceptable salt of the compound can be administered transdermally through the use of a transdermal patch. Transdermal administrations include administrations across the surface of the body and the inner linings of the bodily passages including epithelial and mucosal tissues. Such administrations can be carried out using the present compounds or pharmaceutically acceptable salts of the compounds, in lotions, creams, foams, patches, suspensions, solutions, and suppositories (e.g., rectal or vaginal).

Transdermal administration can be accomplished through the use of a transdermal patch containing the compound or pharmaceutically acceptable salt of the compound and a carrier that is inert to the compound or pharmaceutically acceptable salt of the compound, is non-toxic to the skin, and allows delivery of the agent for systemic absorption into the blood stream via the skin. The carrier may take any number of forms such as creams or ointments, pastes, gels, or occlusive devices. The creams or ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the compound or pharmaceutically acceptable salt of the compound into the blood stream, such as a semi-permeable membrane covering a reservoir containing the compound or pharmaceutically acceptable salt of the compound with or without a carrier, or a matrix containing the active ingredient.

The compounds or pharmaceutically acceptable salts of the compounds of the invention may be administered rectally or vaginally in the form of a conventional suppository. Suppository formulations may be made from traditional materials, including cocoa butter, with or without the addition of waxes to alter the suppository's melting point, and glycerin. Water-soluble suppository bases, such as polyethylene glycols of various molecular weights, may also be used.

The compound or a pharmaceutically acceptable salt of the compound can be administered by controlled-release or sustained-release means or by delivery devices that are known to those of ordinary skill in the art. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

In one embodiment a controlled- or sustained-release composition comprises a minimal amount of the compound or a pharmaceutically acceptable salt of the compound to treat or prevent a metalloproteinase-related disorder in a minimal amount of time. Advantages of controlled- or sustained-release compositions include extended activity of the drug, reduced dosage frequency, and increased compliance by the animal being treated. In addition, controlled- or sustained-release compositions can favorably affect the time of onset of action or other characteristics, such as blood levels of the compound or a pharmaceutically acceptable salt of the compound, and can thus reduce the occurrence of adverse side effects.

Controlled- or sustained-release compositions can initially release an amount of the compound or a pharmaceutically acceptable salt of the compound that promptly produces the desired therapeutic or prophylactic effect, and gradually and continually release other amounts of the compound or a pharmaceutically acceptable salt of the compound to maintain this level of therapeutic or prophylactic effect over an extended period of time. To maintain a constant level of the compound or a pharmaceutically acceptable salt of the compound in the body, the compound or a pharmaceutically acceptable salt of the compound can be released from the dosage form at a rate that will replace the amount of the compound or a pharmaceutically acceptable salt of the compound being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

In certain embodiments, the present invention is directed to prodrugs of the compounds or pharmaceutically acceptable salts of compounds of the present invention. Various forms of prodrugs are known in the art, for example as discussed in Bundgaard, ed., *Design of Prodrugs*, Elsevier (1985); Widder et al., ed., *Methods in Enzymology*, vol. 4, Academic Press (1985); Kgrogsgaard-Larsen et al., ed., "*Design and Application of Prodrugs*", Textbook of Drug Design and Development, Chapter 5, 113-191 (1991); Bundgaard et al., *Journal of Drug Delivery Reviews* 1992, 8, 1-38; Bundgaard et al., *J. Pharmaceutical Sciences* 1988, 77, 285 et seq.; and Higuchi and Stella, eds., *Prodrugs as Drug Delivery Systems*, American Chemical Society (1975).

The amount of the compound or a pharmaceutically acceptable salt of the compound is an amount that is effective for treating or preventing a metalloproteinase-related disorder. In addition, in vitro or in vivo assays can optionally be employed to help identify optimal dosage ranges. The precise dose to be employed can also depend on the route of administration, the condition, the seriousness of the condition being treated, as well as various physical factors related to the individual being treated, and can be decided according to the judgment of a health-care practitioner. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The number and frequency of dosages corresponding to a completed course of therapy will be determined according to the judgment of a health-care practitioner. The effective dosage amounts described herein refer to total amounts administered; that is, if more than one compound or a pharmaceutically acceptable salt of the compound is administered, the effective dosage amounts correspond to the total amount administered.

The amount of the compound or a pharmaceutically acceptable salt of the compound that is effective for treating or preventing a metalloproteinase-related disorder will typically range from about 0.001 mg/kg to about 250 mg/kg of body weight per day, in one embodiment, from about 1 mg/kg to about 250 mg/kg body weight per day, in another embodiment, from about 1 mg/kg to about 50 mg/kg body weight per day, and in another embodiment, from about 1 mg/kg to about 20 mg/kg of body weight per day.

In one embodiment, the pharmaceutical composition is in unit dosage form, e.g., as a tablet, capsule, powder, solution, suspension, emulsion, granule, or suppository. In such form, the composition is sub-divided in unit dose containing appropriate quantities of the active ingredient; the unit dosage form can be packaged compositions, for example, packeted powders, vials, ampoules, prefilled syringes or sachets containing liquids. The unit dosage form can be, for example, a capsule or tablet itself, or it can be the appropriate number of any such compositions in package form. Such unit dosage form may contain from about 1 mg/kg to about 250 mg/kg, and may be given in a single dose or in two or more divided doses.

The compound or a pharmaceutically acceptable salt of the compound can be assayed in vitro or in vivo for the desired therapeutic or prophylactic activity prior to use in humans. Animal model systems can be used to demonstrate safety and efficacy.

Thus, in one embodiment, the invention provides a composition comprising an effective amount of the compound or a pharmaceutically acceptable salt of the compound of the present invention and a pharmaceutically acceptable carrier.

In another embodiment, the pharmaceutically acceptable carrier is suitable for oral administration and the composition comprises an oral dosage form.

Therapeutic or Prophylactic Uses

In one embodiment, the compounds or pharmaceutically acceptable salts of the compounds of the present invention are useful as metalloproteinase modulators. Accordingly, the compounds and pharmaceutically acceptable salts of the compounds of the present invention are useful for treating an animal with a metalloproteinase-related disorder.

In one embodiment, the invention provides a method for treating a metalloproteinase-related disorder, comprising administering to an animal in need thereof a compound or a pharmaceutically acceptable salt of the compound of Formula (I) or Formula (II) in an amount effective to treat a metalloproteinase-related disorder. In another embodiment, the compound or pharmaceutically acceptable salt of the compound is of the Formula (Ia), (Ib), (Ic), or (Id).

In one embodiment, the metalloproteinase is a matrix metalloproteinase or an aggrecanase.

In another embodiment, the aggrecanase is aggrecanase-1 or aggrecanase-2.

In one embodiment, the metalloproteinase-related disorder is selected from the group consisting of arthritic disorders, osteoarthritis, cancer, rheumatoid arthritis, asthma, chronic obstructive pulmonary disease, atherosclerosis, age-related macular degeneration, myocardial infarction, corneal ulceration and other ocular surface diseases, hepatitis, aortic aneurysms, tendonitis, central nervous system diseases, abnormal wound healing, angiogenesis, restenosis, cirrhosis, multiple sclerosis, glomerulonephritis, graft versus host disease, diabetes, inflammatory bowel disease, shock, invertebral disc degeneration, stroke, osteopenia, and periodontal diseases.

In another embodiment, the metalloproteinase-related disorder is osteoarthritis.

In one embodiment, the present invention is directed to a method for modulating the activity of a metalloproteinase in an animal in need thereof, comprising contacting the metalloproteinase with an effective amount of a compound or pharmaceutically acceptable salt of the compound of Formula (I) or Formula (II). In one embodiment, the method further comprises determining the activity of the metalloproteinase. In one embodiment, the step of determining the activity of the metalloproteinase is performed before the step of contacting the metalloproteinase with the compound or a pharmaceutically acceptable salt of the compound. In another embodiment, the step of determining the activity of the metalloproteinase is performed after the step of contacting the metalloproteinase with the compound or a pharmaceutically acceptable salt of the compound. In another embodiment, the compound or pharmaceutically acceptable salt of the compound is of the Formula (Ia), (Ib), (Ic), or (Id).

The compounds and pharmaceutically acceptable salts of the compounds of Formula (I) or Formula (II) are also useful in the manufacture of medicaments for treating a metalloproteinase-related disorder in an animal. In another embodiment, the compound or pharmaceutically acceptable salt of the compound is of the Formula (Ia), (Ib), (Ic), or (Id).

Accordingly, in one embodiment, the invention provides the use of a compound or pharmaceutically acceptable salt of the compound of Formula (I) or Formula (II) for the manufacture of a medicament for treating a metalloproteinase-related disorder. In another embodiment, the compound or pharmaceutically acceptable salt of the compound is of the Formula (Ia), (Ib), (Ic), or (Id).

In one embodiment, the metalloproteinase is a matrix metalloproteinase or an aggrecanase.

In another embodiment, the aggrecanase is aggrecanase-1 or aggrecanase-2.

In one embodiment, the metalloproteinase-related disorder is selected from the group consisting of arthritic disorders, osteoarthritis, cancer, rheumatoid arthritis, asthma, chronic obstructive pulmonary disease, atherosclerosis, age-related macular degeneration, myocardial infarction, corneal ulceration and other ocular surface diseases, hepatitis, aortic aneurysms, tendonitis, central nervous system diseases, abnormal wound healing, angiogenesis, restenosis, cirrhosis, multiple sclerosis, glomerulonephritis, graft versus host disease, diabetes, inflammatory bowel disease, shock, invertebral disc degeneration, stroke, osteopenia, and periodontal diseases.

In another embodiment, the metalloproteinase-related disorder is osteoarthritis.

In one embodiment, the present invention is directed to the use of a compound or pharmaceutically acceptable salt of the compound of Formula (I) or Formula (II) for the manufacture of a medicament for modulating the activity of a metalloproteinase. In one embodiment, the medicament is also for determining the activity of the receptor. In another embodiment, the compound or pharmaceutically acceptable salt of the compound is of the Formula (Ia), (Ib), (Ic), or (Id).

EXAMPLES

Scheme 1

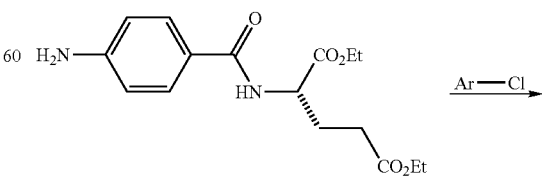

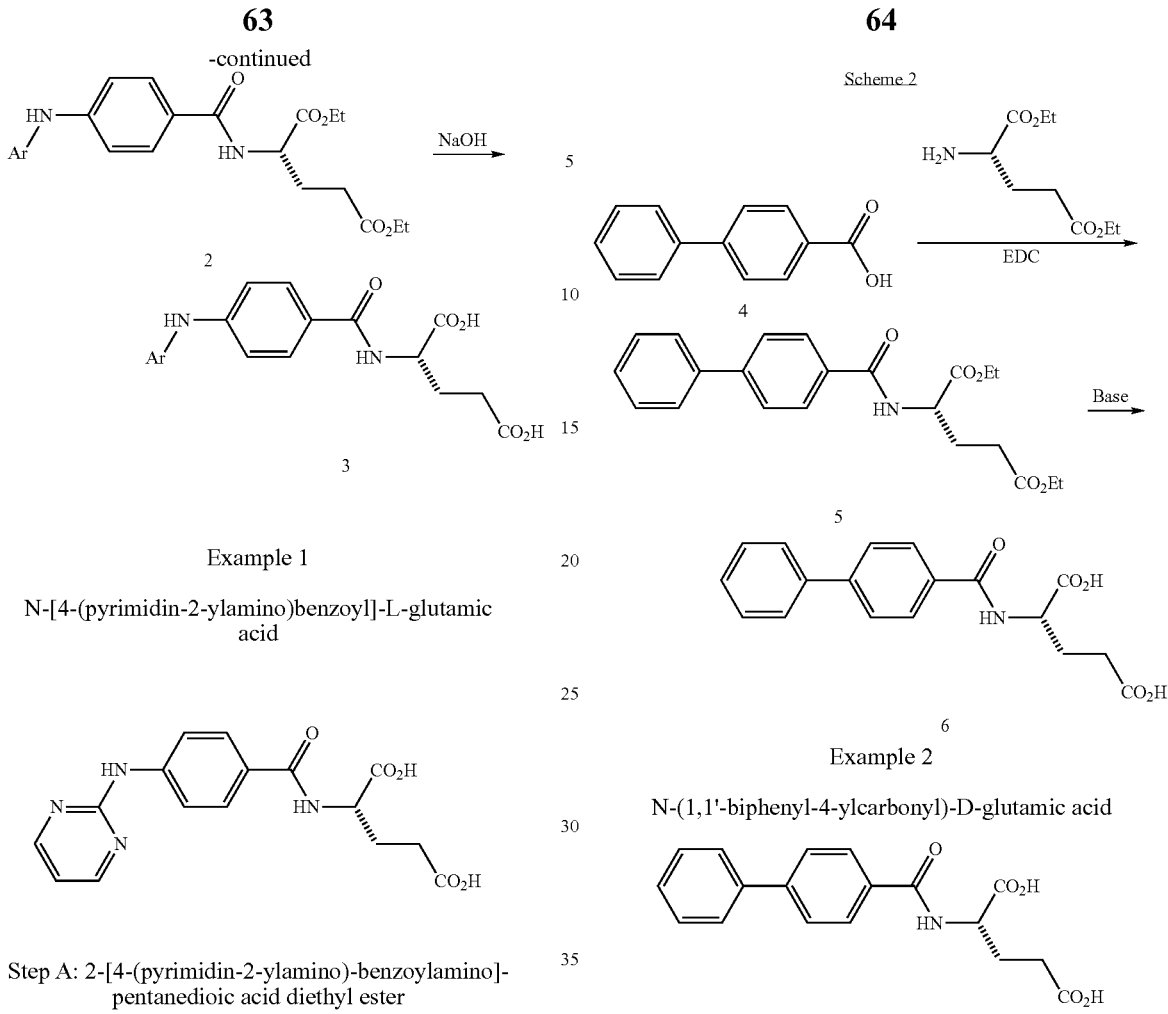

Example 1

N-[4-(pyrimidin-2-ylamino)benzoyl]-L-glutamic acid

Step A: 2-[4-(pyrimidin-2-ylamino)-benzoylamino]-pentanedioic acid diethyl ester 2-Chloropyrimidine (0.72 g, 6.3 mmol) and N-(4-aminobenzoyl)-L-glutamic acid diethyl ester (2.04 g, 6.3 mmol, 1 equiv.) were dissolved in DMF (4 mL) and the resulting mixture was heated to 110° C. for 3 hrs. Reaction was complete as determined by TLC. The mixture was cooled to room temperature and partitioned between ethyl acetate and water. The organic phase was washed with brine, dried over $MgSO_4$, and concentrated by rotavap. The residue was purified by column chromatography (silica gel, 50% EtOAc/hexane) to afford 1.75 g of desired product 2-[4-(pyrimidin-2-ylamino)-benzoylamino]-pentanedioic acid diethyl ester in 69% yield. MS (ESI) m/z 399.

Step B: N-[4-(pyrimidin-2-ylamino)benzoyl]-L-glutamic acid

A solution of 2-[4-(pyrimidin-2-ylamino)-benzoylamino]-pentanedioic acid diethyl ester (250 mg, 0.62 mmol) in THF (4 mL) was added to MeOH (4 mL), followed by the addition of 1N NaOH solution (5 mL, 5 mmol, 8 equiv.). The mixture was stirred at room temperature overnight. Reaction was complete as determined by HPLC. Solvents were removed by rotavap and a small amount of water (5 mL) was added to make a homogeneous solution. 1N HCl was added dropwise until the solution reached a pH of 4. The solid precipitate was collected by filtration, washed with EtOAc, and dried in vacuum oven. The product N-[4-(pyrimidin-2-ylamino)benzoyl]-L-glutamic acid (120 mg) was isolated in 45% yield. MS (ESI) m/z 343.

Example 2

N-(1,1'-biphenyl-4-ylcarbonyl)-D-glutamic acid

Step A: 2-[(Biphenyl-4-carbonyl)-amino]-pentanedioic acid diethyl ester

A solution of 4-biphenylcarboxylic acid (670 mg, 3.4 mmol) and (809 mg, 3.4 mmol, 1 equiv.) in dry DMF (20 mL) was added to EDCI (801 mg, 5.1 mmol, 1.5 equiv.), triethylamine (853 mg, 8.4 mmol, 2.5 equiv.) and DMAP (82 mg, 0.7 mmol, 20%). The mixture was stirred at room temperature overnight. Reaction was complete as determined by TLC. The mixture was diluted with EtOAc and washed with $H_2O$, brine, and dried over magnesium sulfate. Solvent was removed and the residue subject to column chromatography (silica gel, 50% EtOAc/hexane). 660 mg of desired product 2-[(Biphenyl-4-carbonyl)-amino]-pentanedioic acid diethyl ester was isolated in 51% yield. MS (ESI) m/z 382.

Step B: N-(1,1'-biphenyl-4-ylcarbonyl)-D-glutamic acid

A solution of 2-[(Biphenyl-4-carbonyl)-amino]-pentanedioic acid diethyl ester (250 mg, 0.65 mmol) in THF (6 mL) was added to MeOH (6 mL), followed by the addition of 1N NaOH solution (5.2 mL, 5.2 mmol, 8 eq.). The mixture was stirred at room temperature overnight. Reaction was complete as determined by HPLC. Solvents were removed by rotavap and a small amount of water (5 mL) was added to make a homogeneous solution. 1N HCl was added dropwise until the solution reached a pH of 4. The solid precipitate was collected by filtration, washed with EtOAc, and dried in vacuum oven. Product N-(1,1'-biphenyl-4-ylcarbonyl)-D- glutamic acid (189 mg) was isolated in 89% yield. MS (ESI) m/z 326.

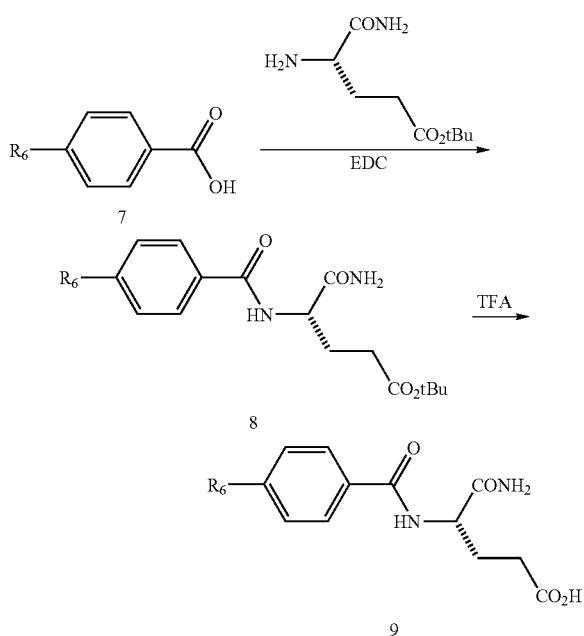

Scheme 3

Example 3

$N^2$-[4-(pyrimidin-2-ylamino)benzoyl]-L-alpha-glutamine

Step A: 4-Carbamoyl-4-[4-(pyrimidin-2-ylamino)-benzoylamino]-butyric acid tert-butyl ester 4-(Pyrimidin-2-ylamino)-benzoic acid (1.80 g, 8.4 mmol, 1 equiv.) and EDCI (2.41 g, 12.6 mmol, 1.5 equiv.) were dissolved in DMF (60 mL) under $N_2$. The mixture was stirred at room temperature for 20 minutes, followed by the addition of H-Glu (OtBu)—$NH_2$ (2 g, 8.4 mmol, 1 equiv), $Et_3N$ (2.92 mL, 20.9 mmol, 2.5 equiv.), and DMAP (0.512 g, 4.2 mmol, 0.5 equiv). The mixture was allowed to stir at room temperature overnight. Reaction was complete as determined by TLC. DMF was removed by rotovap and the residue was dissolved in EtOAc. The organic layer was washed with brine and dried over $MgSO_4$. Most of the solvent was removed by rotavap and a solid was precipitated from the mixture during solvent evaporation. The solid was collected by filtration and washed with EtOAc. 823 mg of 4-Carbamoyl-4-[4-(pyrimidin-2-ylamino)-benzoylamino]-butyric acid tert-butyl ester was obtained in 25% yield. MS (ESI) m/z 400.

Step B: $N^2$-[4-(pyrimidin-2-ylamino)benzoyl]-L-alpha-glutamine

4-Carbamoyl-4-[4-(pyrimidin-2-ylamino)-benzoylamino]-butyric acid tert-butyl ester was dissolved in dichloroethane (10 mL), followed by the addition of TFA (5 mL). The mixture was stirred at room temperature for 4 hrs. TLC indicated the reaction was complete. Solvents were then removed by rotavap and the residue was washed with EtOAc. A solid was collected by filtration and dried in vacuum oven overnight. 4-Carbamoyl-4-[4-(pyrimidin-2-ylamino)-benzoylamino]-butyric acid was obtained in quantitative yield (285 mg). MS (ESI) m/z 344.

Example 4

$N^2$-(1,1'-biphenyl-4-ylcarbonyl)-D-alpha-glutamine

The title compound was prepared according to the procedures similar to that described for Example 3. Yield 95%, MS (ESI) m/z 327.

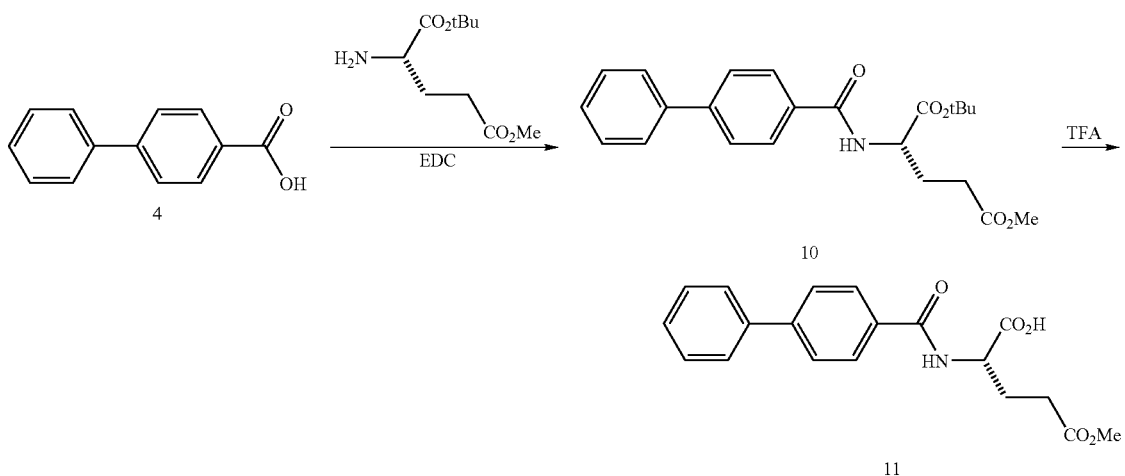

Scheme 5

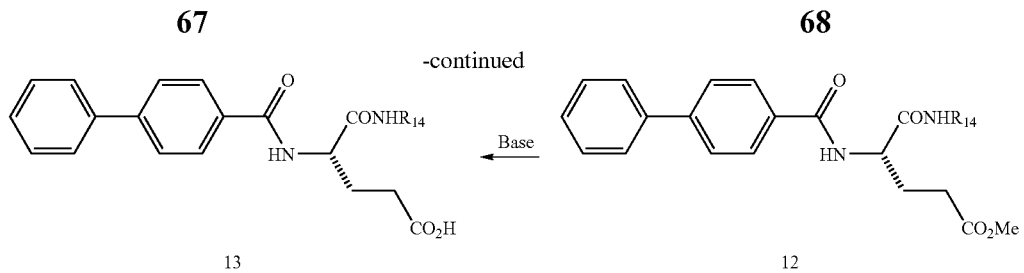

-continued

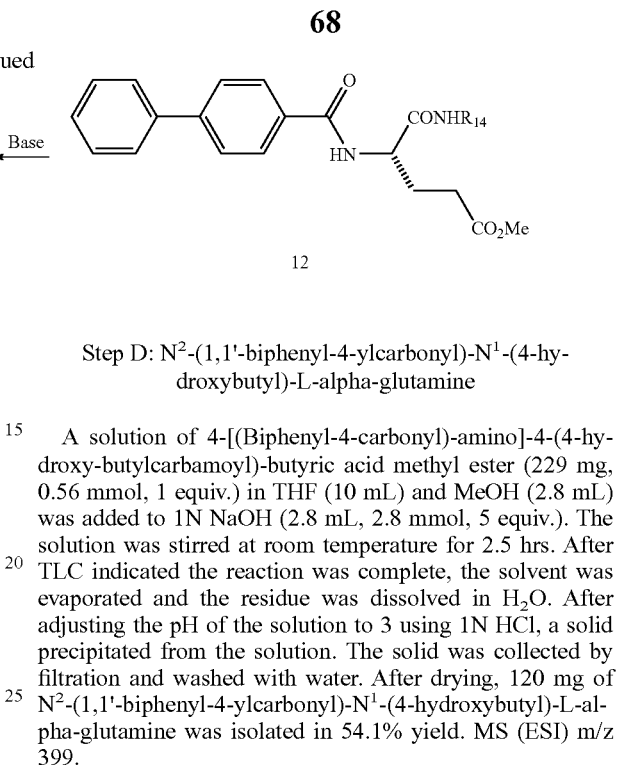

Example 5

N²-(1,1'-biphenyl-4-ylcarbonyl)-N¹-(4-hydroxybutyl)-L-alpha-glutamine

Step A:
2-[(Biphenyl-4-carbonyl)-amino]-pentanedioic acid 1-tert-butyl ester 5-methyl ester A solution of 4-diphenyl carboxylic acid (3.57 g, 18 mmol, 1.0 equiv.) in DMF (40 mL) was added to EDCI (4.28 g, 22.3 mmol, 1.24 equiv.) and stirred at room temperature for 0.5 hrs. H-Glu(OMe)Ot-Bu (5.02 g, 19.8 mmol, 1.1 equiv.) was added, followed by the addition of Et$_3$N (6.77 mL, 48.6 mmol, 2.7 equiv.) and DMAP (330 mg, 2.7 mmol, 15%). The mixture was stirred overnight under N$_2$. Reaction was complete as determined by TLC. The reaction mixture was diluted with EtOAc, washed with H$_2$O, then brine solution. The organic layer was separated and then dried over MgSO$_4$. After concentration, crude was purified by column chromatography (Silica gel, 20% EtOAc/Hexane) to afford 3.2 g of 2-[(Biphenyl-4-carbonyl)-amino]-pentanedioic acid 1-tert-butyl ester 5-methyl ester in 44.7% yield. MS (ESI) m/z 396.

Step B:
2-[(Biphenyl-4-carbonyl)-amino]-pentanedioic acid 5-methyl ester

A solution of 2-[(Biphenyl-4-carbonyl)-amino]-pentanedioic acid 1-tert-butyl ester 5-methyl ester (1.5 g, 3.8 mmol) in dichloroethane (26 mL) was added to TFA (13 mL) at room temperature. The mixture was stirred for 4 hrs. and TLC indicated the reaction was complete. Solvent was removed by rotovap. The solid thus obtained was dried under vacuum to provide 1.128 g of 2-[(Biphenyl-4-carbonyl)-amino]-pentanedioic acid 5-methyl ester [G9591-161-1] in 87% yield. MS (ESI) m/z 342.

Step C: 4-[(Biphenyl-4-carbonyl)-amino]-4-(4-hydroxy-butylcarbamoyl)-butyric acid methyl ester A solution of 2-[(Biphenyl-4-carbonyl)-amino]-pentanedioic acid 5-methyl ester (400 mg, 1.2 mmol, 1 equiv.) in DMF (10 mL) was added to EDCI (337 mg, 1.8 mmol, 1.5 equiv.). The solution was stirred at room temperature under N$_2$ for 40 min. 4-Amino-1-butanol (0.11 mL, 1.2 mmol, 1 equiv.) was added, followed by addition of Et$_3$N (0.41 mL, 2.9 mmol, 2.5 equiv.) and DMAP (72 mg, 0.59 mmol, 0.5 equiv.). The mixture was stirred overnight under N$_2$. The reaction mixture was then poured into cold water and a solid precipitated from the solution. The solid was collected by filtration and dried under vacuum to give 229 mg of 4-[(Biphenyl-4-carbonyl)-amino]-4-(4-hydroxy-butylcarbamoyl)-butyric acid methyl ester in 47% yield. MS (ESI) m/z 413.

Step D: N²-(1,1'-biphenyl-4-ylcarbonyl)-N¹-(4-hydroxybutyl)-L-alpha-glutamine A solution of 4-[(Biphenyl-4-carbonyl)-amino]-4-(4-hydroxy-butylcarbamoyl)-butyric acid methyl ester (229 mg, 0.56 mmol, 1 equiv.) in THF (10 mL) and MeOH (2.8 mL) was added to 1N NaOH (2.8 mL, 2.8 mmol, 5 equiv.). The solution was stirred at room temperature for 2.5 hrs. After TLC indicated the reaction was complete, the solvent was evaporated and the residue was dissolved in H$_2$O. After adjusting the pH of the solution to 3 using 1N HCl, a solid precipitated from the solution. The solid was collected by filtration and washed with water. After drying, 120 mg of N²-(1,1'-biphenyl-4-ylcarbonyl)-N¹-(4-hydroxybutyl)-L-alpha-glutamine was isolated in 54.1% yield. MS (ESI) m/z 399.

Example 6

The following compounds were prepared according to the procedures similar to those described in Example 5.

Example 6A

N²-(1,1'-biphenyl-4-ylcarbonyl)-N¹-2,3-dihydro-1H-inden-2-yl-L-α-glutamine

Step C: methyl N²-(1,1'-biphenyl-4-ylcarbonyl)-N¹-2,3-dihydro-1H-inden-2-yl-L-α-glutaminate Described as above according to the procedure in Example 5, except PyBop/DIEA (or Bop/DIEA) was used. MS (ESI) m/z 457.2; MS (ESI) m/z 913.4; HRMS: calcd for C$_{28}$H$_{28}$N$_2$O$_4$+H+, 457.21218. found (ESI-FTMS, [M+H]$^{1+}$), 457.21403.

Step D: N²-(1,1'-biphenyl-4-ylcarbonyl)-N¹-2,3-dihydro-1H-inden-2-yl-L-α-glutamine MS (ESI) m/z 441.2; MS (ESI) m/z 883.3; HRMS: calcd for C$_{27}$H$_{26}$N$_2$O$_4$+H+, 443.19653. found (ESI-FTMS, [M+H]$^{1+}$), 443.19699.

Example 6B

N²-(biphenyl-4-ylcarbonyl)-N¹-(2-hydroxy-1,1-dimethylethyl)-L-α-glutamine

Step C: methyl N²-(biphenyl-4-ylcarbonyl)-N¹-(2-hydroxy-1,1-dimethylethyl)-L-α-glutaminate Described as above according to the procedure in Example 5, except PyBop/DIEA (or Bop/DIEA) was used. MS (ESI) m/z 413.1; MS (ESI) m/z 825.2; HRMS: calcd for C$_{23}$H$_{28}$N$_2$O$_5$+H+, 413.20710. found (ESI-FTMS, [M+H]$^{1+}$), 413.20705.

Step D: $N^2$-(biphenyl-4-ylcarbonyl)-$N^1$-(2-hydroxy-1,1-dimethylethyl)-L-α-glutamine MS (ESI) m/z 399.1; MS (ESI) m/z 797.3; HRMS: calcd for $C_{22}H_{26}N_2O_5$+H+, 399.19145. found (ESI-FTMS, [M+H]$^{1+}$), 399.19217.

Example 6C $N^2$-(biphenyl-4-ylcarbonyl)-$N^1$-(1,1,3,3-tetramethylbutyl)-L-α-glutamine Step C: methyl $N^2$-(biphenyl-4-ylcarbonyl)-$N^1$-(1,1,3,3-tetramethylbutyl)-L-α-glutaminate Described as above according to the procedure in Example 5, except PyBop/DIEA (or Bop/DIEA) was used. MS (ESI) m/z 453.2; MS (ESI) m/z 905.4; HRMS: calcd for $C_{27}H_{36}N_2O_4$+H+, 453.27478. found (ESI-FTMS, [M+H]$^{1+}$), 453.27588.

Step D: $N^2$— (biphenyl-4-ylcarbonyl)-$N^1$-(1,1,3,3-tetramethylbutyl)-L-α-glutamine MS (ESI) m/z 439.2; MS (ESI) m/z 877.4; HRMS: calcd for $C_{26}H_{34}N_2O_4$+H+, 439.25913. found (ESI-FTMS, [M+H]$^{1+}$), 439.25974.

Example 6D $N^1$-(1,1-dimethyl-2-phenylethyl)-$N^2$-(9H-fluoren-2-ylcarbonyl)-L-α-glutamine Step A: 1-tert-butyl 5-methyl-N-(9H-fluoren-2-ylcarbonyl)-L-glutamate Described as above according to the procedure in Example 5, except 2-fluorenecarboxylic acid was used. MS (ESI) m/z 410.2; MS (ESI) m/z 819.4; HRMS: calcd for $C_{24}H_{27}NO_5$+Na+, 432.17814. found (ESI-FTMS, [M+Na]$^{1+}$), 432.17902.

Step B: (2S)-2-[(9H-fluoren-2-ylcarbonyl)amino]-5-methoxy-5-oxopentanoic acid

MS (ESI) m/z 354.1; MS (ESI) m/z 707.3; HRMS: calcd for $C_{20}H_{19}NO_5$+H+, 354.13360. found (ESI-FTMS, [M+H]$^{1+}$), 354.13428.

Step C: methyl $N^1$-(1,1-dimethyl-2-phenylethyl)-$N^2$-(9H-fluoren-2-ylcarbonyl)-L-α-glutaminate MS (ESI) m/z 485.3; MS (ESI) m/z 969.5; MS (ESI) m/z 507.3; HRMS: calcd for $C_{30}H_{32}N_2O_4$+Na+, 507.22543. found (ESI-FTMS, [M+Na]$^{1+}$), 507.22863.

Step D: $N^1$-(1,1-dimethyl-2-phenylethyl)-$N^2$-(9H-fluoren-2-ylcarbonyl)-L-α-glutamine MS (ESI) m/z 471.3; MS (ESI) m/z 941.5.

Example 6E $N^1$-[2-(4-chlorophenyl)-1,1-dimethylethyl]-$N^2$-(9H-fluoren-2-ylcarbonyl)-L-α-glutamine Step A: described as above according to the procedure in Example 5, except 2-fluorenecarboxylic acid was used.

Step C: methyl $N^1$-[2-(4-chlorophenyl)-1,1-dimethylethyl]-$N^2$-(9H-fluoren-2-ylcarbonyl)-L-α-glutaminate MS (ESI) m/z 519.2; MS (ESI) m/z 1037.5; HRMS: calcd for $C_{30}H_{31}ClN_2O_4$+H+, 519.20451. found (ESI-FTMS, [M+H]$^{1+}$), 519.20406.

Step D: $N^1$-[2-(4-chlorophenyl)-1,1-dimethylethyl]-$N^2$-(9H-fluoren-2-ylcarbonyl)-L-α-glutamine MS (ESI) m/z 505.2; MS (ESI) m/z 1009.5.

Scheme 7

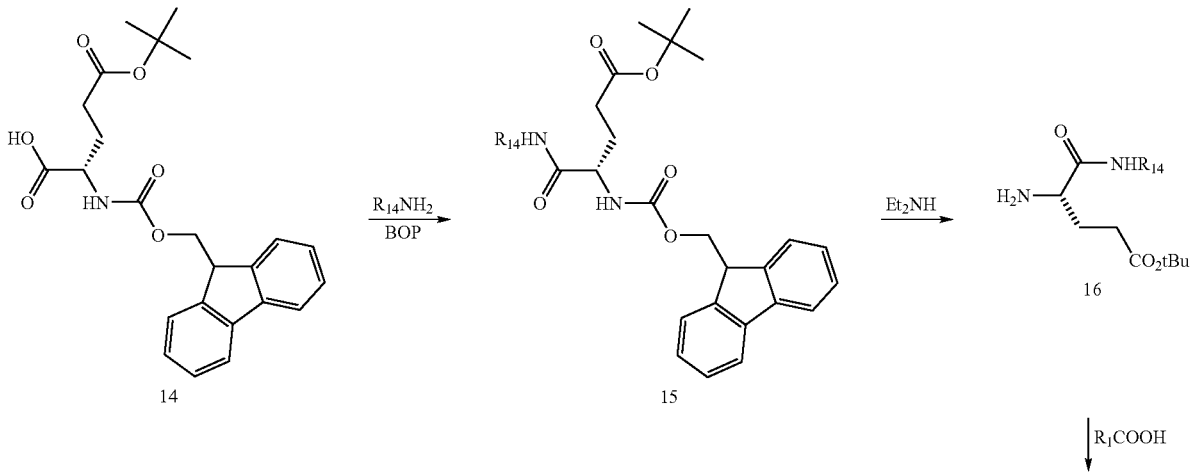

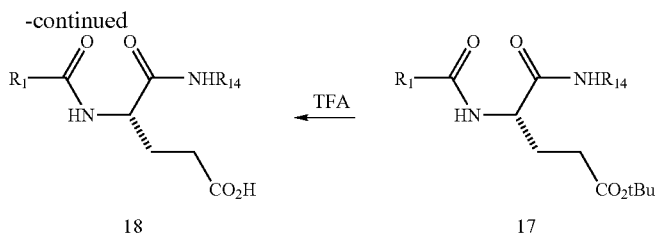

Example 7

N[1]-(1,3-benzodioxol-5-ylmethyl)-N[2]-(1,1'-biphenyl-4-ylcarbonyl)-L-α-glutamine Step A: tert-butyl N[1]-(1,3-benzodioxol-5-ylmethyl)-N[2]-[(9H-fluoren-9-ylmethoxy)carbonyl]-L-α-glutaminate In a 50 mL round bottom flask, Fmoc-L-Glu-(OtBu)—OH (2.127 g, 5 mmol) was dissolved in DMF (10 mL) and stirred at room temperature under nitrogen. PyBOP (2.6 g, 5 mmol) was added to the stirring mixture followed by piperonylamine (0.755 g, 5 mmol), and DIEA (1.2 equivalent) added dropwise. The mixture was stirred overnight (18-24 hr) at room temperature under nitrogen. The reaction mixture was then poured into 150 mL of water and the solid was collected and washed with water. The wet solid was then dissolved in ethyl acetate (ca. 500 mL), and washed consecutively with 10% HCl (aq.), NaHCO$_3$ (satd.), and NaCl (satd.). The organic phase was dried over MgSO$_4$ (anh.) and concentrated. The crude product was redissolved in acetone and hexanes were added. The precipitated solid was filtered, washed with hexanes and dried in a vacuum desiccator overnight to give 1.56 g of tert-butyl N[1]-(1,3-benzodioxol-5-ylmethyl)-N[2]-[(9H-fluoren-9-ylmethoxy)carbonyl]-L-α-glutaminate as fine white solid. MS (ESI) m/z 559.1; HRMS: calcd for C$_{32}$H$_{34}$N$_2$O$_7$+H+, 559.24388. found (ESI_FT, [M+H]$^{1+}$), 559.24348.

Step B: tert-butyl N[1]-(1,3-benzodioxol-5-ylmethyl)-L-α-glutaminate

The Fmoc-ester product (1.5 g, 2.7 mmol) was (partially) dissolved in acetonitrile (17 mL) and stirred at room temperature under nitrogen. The mixture was fully dissolved about 30 min after addition of diethylamine (4.2 mL) and was stirred for two hours. After reaction completion, the mixture is carefully concentrated (<30° C.) under reduced pressure by rotary evaporator. The crude product (clear oil) was then filtered through a short flash column. The column was gradient eluted starting with 5% Acetone/CH$_2$Cl$_2$ until the Fmoc byproduct was removed and ramped to 50% Acetone/CH$_2$Cl$_2$ while the product eluted. The desired fractions were collected and concentrated giving 0.8 g clear oil. MS (ESI) m/z 337.1; HRMS: calcd for C$_{17}$H$_{24}$N$_2$O$_5$+H+, 337.17580. found (ESI_FT, [M+H]$^{1+}$), 337.17605.

Step C: tert-butyl N[1]-(1,3-benzodioxol-5-ylmethyl)-N[2]-(1,1'-biphenyl-4-ylcarbonyl)-L-α-glutaminate The free amine (0.36 g, 1.07 mmol) was dissolved in DMF (5 mL) and stirred at rt under nitrogen. 4-Biphenyl carboxylic acid (0.557 g, 1.07 mmol) was added followed by PyBOP reagent (0.21 g, 1.07 mmol) with vigorous stirring. The reaction mixture was cooled to 0° C. and DIEA (1.2 equiv.) was added dropwise. The reaction was complete in 14-24 hours. The reaction mixture was then poured into 100 mL water and the solid collected. The solid was redissolved in ethyl acetate and washed with 10% HCl (aq.), NaHCO$_3$ (satd.), and NaCl (satd.). The organic phase was dried over Na$_2$SO$_4$ (anh.) and concentrated. Acetone was added to the residue and diluted with hexanes. The precipitate was collected and dried in a vacuum desiccator overnight to give 0.4 g of desired product. MS (ESI) m/z 517.2; HRMS: calcd for C$_{30}$H$_{32}$N$_2$O$_6$+H+, 517.23331. found (ESI_FT, [M+H]$^{1+}$), 517.23311.

Step D: N[1]-(1,3-benzodioxol-5-ylmethyl)-N[2]-(1,1'-biphenyl-4-ylcarbonyl)-L-α-glutamine The t-butyl ester (0.31 g, 0.6 mmol) was dissolved in CH$_2$Cl$_2$ (4 mL) and stirred at rt under nitrogen. Trifluoroacetic acid (4 mL) dissolved in CH$_2$Cl$_2$ (4 mL) is added to the solution and the light yellow solution is stirred at rt for 2 hours. The mixture is evaporated and diluted toluene (10 mL), evaporated to fully remove the TFA. A solid is obtained and dissolved in minimum acetone (ca. 25-50 mL) warmed slightly and hexanes added. The white solid was collected and dried in a vacuum desiccator to yield 0.214 g product. MS (ESI) m/z 461.1; HRMS: calcd for C$_{26}$H$_{24}$N$_2$O$_6$+H+, 461.17071. found (ESI_FT, [M+H]$^{1+}$), 461.1704.

Example 8

The following compounds were prepared according to the procedures similar to those of Example 7.

Example 8A

N[2]-(1,1'-biphenyl-4-ylcarbonyl)-N[1]-cyclohexyl-L-α-glutamine

Step A: tert-butyl N[1]-cyclohexyl-N[2]-[(9H-fluoren-9-ylmethoxy)carbonyl]-L-α-glutaminate MS (ESI) m/z 507.2; HRMS: calcd for C$_{30}$H$_{38}$N$_2$O$_5$+H+, 507.28535. found (ESI_FT, [M+H]$^{1+}$), 507.28583.

Step B: tert-butyl N[1]-cyclohexyl-L-α-glutaminate

MS (ESI) m/z 285.2; HRMS: calcd for C$_{15}$H$_{28}$N$_2$O$_3$+H+, 285.21727. found (ESI_FT, [M+H]$^{1+}$), 285.21644.

Step C: tert-butyl N[2]-(1,1'-biphenyl-4-ylcarbonyl)-N[1]-cyclohexyl-L-α-glutaminate MS (ESI) m/z 465.2; HRMS: calcd for C$_{28}$H$_{36}$N$_2$O$_4$+H+, 465.27478. found (ESI_FT, [M+H]$^{1+}$), 465.27386.

Step D: N²-(1,1'-biphenyl-4-ylcarbonyl)-N¹-cyclo-hexyl-L-α-glutamine

HRMS: calcd for C$_{24}$H$_{28}$N$_2$O$_4$+H+, 409.21218. found (ESI_FT, [M+H]$^{1+}$), 409.21163.

Example 8B

N²-(1,1'-biphenyl-4-ylcarbonyl)-N¹-cyclopropyl-L-α-glutamine

Step A: tert-butyl N¹-cyclopropyl-N²-[(9H-fluoren-9-ylmethoxy)carbonyl]-L-α-glutaminate MS (ESI) m/z 465.1; HRMS: calcd for C$_{27}$H$_{32}$N$_2$O$_5$+H+, 465.23840. found (ESI_FT, [M+H]$^{1+}$), 465.23816.

Step C: tert-butyl N²-(1,1'-biphenyl-4-ylcarbonyl)-N¹-cyclopropyl-L-α-glutaminate MS (ESI) m/z 423.2; HRMS: calcd for C$_{25}$H$_{30}$N$_2$O$_4$+H+, 423.22783. found (ESI_FT, [M+H]$^{1+}$), 423.22725.

Step D: N²-(1,1'-biphenyl-4-ylcarbonyl)-N¹-cyclopropyl-L-α-glutamine

MS (ESI) m/z 367.1; MS (ESI) m/z 733.2; HRMS: calcd for C$_{21}$H$_{22}$N$_2$O$_4$+H+, 367.16523. found (ESI_FT, [M+H]$^{1+}$), 367.16454.

Example 8C

N²-(1,1'-biphenyl-4-ylcarbonyl)-N¹-butyl-L-α-glutamine

Step A: tert-butyl N¹-butyl-N²-[(9H-fluoren-9-ylmethoxy)carbonyl]-L-α-glutaminate MS (ESI) m/z 481.2; MS (ESI) m/z 503.2; HRMS: calcd for C$_{28}$H$_{36}$N$_2$O$_5$+H+, 481.26970. found (ESI_FT, [M+H]$^{1+}$), 481.26789.

Step C: tert-butyl N²-(1,1'-biphenyl-4-ylcarbonyl)-N¹-butyl-L-α-glutaminate

MS (ESI) m/z 439.1; MS (ESI) m/z 877.3; HRMS: calcd for C$_{26}$H$_{34}$N$_2$O$_4$+H+, 439.25913. found (ESI_FT, [M+H]$^{1+}$), 439.25884.

Step D: N²-(1,1'-biphenyl-4-ylcarbonyl)-N¹-butyl-L-α-glutamine

MS (ESI) m/z 381.2; MS (ESI) m/z 763.3; HRMS: calcd for C$_{22}$H$_{26}$N$_2$O$_4$+H+, 383.19653. found (ESI_FT, [M+H]$^{1+}$), 383.19514.

Example 8D

N²-(1,1'-biphenyl-4-ylcarbonyl)-N¹-(4-fluorobenzyl)-L-α-glutamine

Step A: tert-butyl N²-[(9H-fluoren-9-ylmethoxy)carbonyl]-N¹-(4-fluorobenzyl)-L-α-glutaminate MS (ESI) m/z 533.2; HRMS: calcd for C$_{31}$H$_{33}$FN$_2$O$_5$+H+, 533.24463. found (ESI_FT, [M+H]$^{1+}$), 533.24546.

Step B: tert-butyl N¹-(4-fluorobenzyl)-L-α-glutaminate

MS (ESI) m/z 311.1; HRMS: calcd for C$_{16}$H$_{23}$FN$_2$O$_3$+H+, 311.17655. found (ESI_FT, [M+H]$^{1+}$), 311.17696.

Step C: tert-butyl N²-(1,1'-biphenyl-4-ylcarbonyl)-N¹-(4-fluorobenzyl)-L-α-glutaminate MS (ESI) m/z 491.2; HRMS: calcd for C$_{29}$H$_{31}$FN$_2$O$_4$+H+, 491.23406. found (ESI_FT, [M+H]$^{1+}$), 491.23339.

Step D: N²-(1,1'-biphenyl-4-ylcarbonyl)-N¹-(4-fluorobenzyl)-L-α-glutamine

MS (ESI) m/z 435.1; HRMS: calcd for C$_{25}$H$_{23}$FN$_2$O$_4$+H+, 435.17146. found (ESI_FT, [M+H]$^{1+}$), 435.17056.

Example 8E

N²-(1,1'-biphenyl-4-ylcarbonyl)-N¹-cyclooctyl-L-α-glutamine

Step A: tert-butyl N¹-cyclooctyl-N²-[(9H-fluoren-9-ylmethoxy)carbonyl]-L-α-glutaminate MS (ESI) m/z 535.2; HRMS: calcd for C$_{32}$H$_{42}$N$_2$O$_5$+H+, 535.31665. found (ESI_FT, [M+H]$^{1+}$), 535.31782.

Step B: tert-butyl N¹-cyclooctyl-L-α-glutaminate

MS (ESI_FT) m/z 313.24821; MS (ESI_FT) m/z 313.24857; HRMS: calcd for C$_{17}$H$_{32}$N$_2$O$_3$+H+, 313.24857. found (ESI_FT, [M+H]$^{1+}$), 313.24821.

Step C: tert-butyl N²-(1,1'-biphenyl-4-ylcarbonyl)-N¹-cyclooctyl-L-α-glutaminate MS (ESI) m/z 493.4; MS (ESI) m/z 985.6; HRMS: calcd for C$_{30}$H$_{40}$N$_2$O$_4$+H+, 493.30608. found (ESI_FTMS, [M+H]$^{1+}$), 493.30412.

Step D: N²-(1,1'-biphenyl-4-ylcarbonyl)-N¹-cyclooctyl-L-α-glutamine

MS (ESI) m/z 437.3; MS (ESI) m/z 873.6; HRMS: calcd for C$_{26}$H$_{32}$N$_2$O$_4$+H+, 437.24348. found (ESI_FT, [M+H]$^{1+}$), 437.24272.

Example 8F

N²-(1,1'-biphenyl-4-ylcarbonyl)-N¹-(3,4-dimethoxybenzyl)-L-α-glutamine

Step A: tert-butyl N¹-(3,4-dimethoxybenzyl)-N²-[(9H-fluoren-9-ylmethoxy)carbonyl]-L-α-glutaminate MS (ESI) m/z 575.3; MS (ESI) m/z 1149.6; HRMS: calcd for C$_{33}$H$_{38}$N$_2$O$_7$+H+, 575.27518. found (ESI_FT, [M+H]$^{1+}$), 575.27609.

Step B: tert-butyl $N^1$-(3,4-dimethoxybenzyl)-L-α-glutaminate

MS (ESI+) m/z 353.2; MS (ESI+) m/z 297.1; HRMS: calcd for $C_{18}H_{28}N_2O_5$+H+, 353.20710. found (ESI_FT, [M+H]$^{1+}$), 353.20629.

Step C: tert-butyl $N^2$-(1,1'-biphenyl-4-ylcarbonyl)-$N^1$-(3,4-dimethoxybenzyl)-L-α-glutaminate MS (ESI+) m/z 533.3; HRMS: calcd for $C_{31}H_{36}N_2O_6$+H+, 533.26461. found (ESI_FT, [M+H]$^{1+}$), 533.26323.

Step D: $N^2$-(1,1'-biphenyl-4-ylcarbonyl)-$N^1$-(3,4-dimethoxybenzyl)-L-α-glutamine MS (ESI−) m/z 475.3; HRMS: calcd for $C_{27}H_{28}N_2O_6$+H+, 477.20201. found (ESI_FT, [M+H]$^{1+}$), 477.20053.

Example 8G $N^2$-(1,1'-biphenyl-4-ylcarbonyl)-$N^1$-cyclopentyl-L-α-glutamine

Step A: tert-butyl $N^1$-cyclopentyl-$N^2$-[(9H-fluoren-9-ylmethoxy)carbonyl]-L-α-glutaminate MS (ESI+) m/z 493.3; MS (ESI+) m/z 437.2; HRMS: calcd for $C_{29}H_{36}N_2O_5$+H+, 493.26970. found (ESI_FT, [M+H]$^{1+}$), 493.26812.

Step B: tert-butyl $N^1$-cyclopentyl-L-α-glutaminate

MS (ESI) m/z 271.2; HRMS: calcd for $C_{14}H_{26}N_2O_3$+H+, 271.20162. found (ESI_FT, [M+H]$^{1+}$), 271.202.

Step C: tert-butyl $N^2$-(1,1'-biphenyl-4-ylcarbonyl)-$N^1$-cyclopentyl-L-α-glutaminate MS (ESI) m/z 451.3; MS (ESI) m/z 901.6; HRMS: calcd for $C_{27}H_{34}N_2O_4$+H+, 451.25913. found (ESI_FT, [M+H]$^{1+}$), 451.25803.

Step D: $N^2$-(1,1'-biphenyl-4-ylcarbonyl)-$N^1$-cyclopentyl-L-α-glutamine

MS (ESI) m/z 395.2; MS (ESI) m/z 789.4; HRMS: calcd for $C_{23}H_{26}N_2O_4$+H+, 395.19653. found (ESI_FT, [M+H]$^{1+}$), 395.19564.

Example 8H $N^1$-2-adamantyl-$N^2$-(1,1'-biphenyl-4-ylcarbonyl)-L-α-glutamine

Step A: tert-butyl $N^1$-2-adamantyl-$N^2$-[(9H-fluoren-9-ylmethoxy)carbonyl]-L-α-glutaminate MS (ESI) m/z 559.4; MS (ESI) m/z 1117.7; HRMS: calcd for $C_{34}H_{42}N_2O_5$+H+, 559.31665. found (ESI_FT, [M+H]$^{1+}$), 559.31524.

Step B: tert-butyl $N^1$-2-adamantyl-L-α-glutaminate

MS (ESI) m/z 337.2; MS (ESI) m/z 673.5; HRMS: calcd for $C_{19}H_{32}N_2O_3$+H+, 337.24857. found (ESI_FT, [M+H]$^{1+}$), 337.2475.

Step C: tert-butyl $N^1$-2-adamantyl-$N^2$-(1,1'-biphenyl-4-ylcarbonyl)-L-α-glutaminate MS (ESI) m/z 517.3; MS (ESI) m/z 1033.6; HRMS: calcd for $C_{32}H_{40}N_2O_4$+H+, 517.30608. found (ESI_FT, [M+H]$^{1+}$), 517.30505.

Step D: $N^1$-2-adamantyl-$N^2$-(1,1'-biphenyl-4-ylcarbonyl)-L-α-glutamine

MS (ESI) m/z 461.3; MS (ESI) m/z 921.5; HRMS: calcd for $C_{28}H_{32}N_2O_4$+H+, 461.24348. found (ESI_FT, [M+H]$^{1+}$), 461.24227.

Example 8I $N^1$-(2-adamantylmethyl)-$N^2$-(1,1'-biphenyl-4-ylcarbonyl)-L-α-glutamine Step A: tert-butyl $N^1$-(2-adamantylmethyl)-$N^2$-[(9H-fluoren-9-ylmethoxy)carbonyl]-L-α-glutaminate MS (ESI) m/z 573.3; MS (ESI) m/z 1145.5; HRMS: calcd for $C_{35}H_{44}N_2O_5$+H+, 573.33230. found (ESI_FT, [M+H]$^{1+}$), 573.33089.

Step B: tert-butyl $N^1$-(2-adamantylmethyl)-L-α-glutaminate

MS (ESI) m/z 351.2; HRMS: calcd for $C_{20}H_{34}N_2O_3$+H+, 351.26422. found (ESI_FT, [M+H]$^{1+}$), 351.26491.

Step C: tert-butyl $N^1$-(2-adamantylmethyl)-$N^2$-(1,1'-biphenyl-4-ylcarbonyl)-L-α-glutaminate MS (ESI) m/z 531.3; MS (ESI) m/z 1061.4; HRMS: calcd for $C_{33}H_{42}N_2O_4$+H+, 531.32173. found (ESI_FT, [M+H]$^{1+}$), 531.32031.

Step D: $N^1$-(2-adamantylmethyl)-$N^2$-(1,1'-biphenyl-4-ylcarbonyl)-L-α-glutamine MS (ESI) m/z 475.2; MS (ESI) m/z 949.3; HRMS: calcd for $C_{29}H_{34}N_2O_4$+H+, 475.25913. found (ESI_FT, [M+H]$^{1+}$), 475.25734.

Example 8J $N^2$-(1,1'-biphenyl-4-ylcarbonyl)-$N^1$-(2-methoxyethyl)-L-α-glutamine Step A: tert-butyl $N^2$-[(9H-fluoren-9-ylmethoxy)carbonyl]-$N^1$-(2-methoxyethyl)-L-α-glutaminate MS (ESI) m/z 483.2; MS (ESI) m/z 965.3; HRMS: calcd for $C_{27}H_{34}N_2O_6$+H+, 483.24896. found (ESI_FT, [M+H]$^{1+}$), 483.24851.

Step B: tert-butyl $N^1$-(2-methoxyethyl)-L-α-glutaminate

MS (ESI) m/z 261.1; HRMS: calcd for $C_{12}H_{24}N_2O_4$+H+, 261.18088. found (ESI_FT, [M+H]$^{1+}$), 261.18071.

Step C: tert-butyl $N^2$-(1,1'-biphenyl-4-ylcarbonyl)-$N^1$-(2-methoxyethyl)-L-α-glutaminate MS (ESI) m/z 441.2; MS (ESI) m/z 881.3; HRMS: calcd for $C_{25}H_{32}N_2O_5$+H+, 441.23840. found (ESI_FT, [M+H]$^{1+}$), 441.23803.

Step D: $N^2$-(1,1'-biphenyl-4-ylcarbonyl)-$N^1$-(2-methoxyethyl)-L-α-glutamine

MS (ESI) m/z 385.1; MS (ESI) m/z 769.2; HRMS: calcd for $C_{21}H_{24}N_2O_5$+H+, 385.17580. found (ESI_FT, [M+H]$^{1+}$), 385.17538.

Example 8K $N^2$-(1,1'-biphenyl-4-ylcarbonyl)-$N^1$-(4-methoxybenzyl)-L-α-glutamine Step A: tert-butyl $N^2$-[(9H-fluoren-9-ylmethoxy)carbonyl]-$N^1$-(4-methoxybenzyl)-L-α-glutaminate MS (ESI) m/z 545.2; MS (ESI) m/z 1089.3; HRMS: calcd for $C_{32}H_{36}N_2O_6$+H+, 545.26461. found (ESI_FT, [M+H]$^{1+}$), 545.26277.

Step B: tert-butyl $N^1$-(4-methoxybenzyl)-L-α-glutaminate

MS (ESI) m/z 323.2; HRMS: calcd for $C_{17}H_{26}N_2O_4$+H+, 323.19653. found (ESI_FT, [M+H]$^{1+}$), 323.19702.

Step C: tert-butyl $N^2$-(1,1'-biphenyl-4-ylcarbonyl)-$N^1$-(4-methoxybenzyl)-L-α-glutaminate MS (ESI) m/z 503.2; MS (ESI) m/z 1005.4; HRMS: calcd for $C_{30}H_{34}N_2O_5$+H+, 503.25405. found (ESI_FT, [M+H]$^{1+}$), 503.25435.

Step D: $N^2$-(1,1'-biphenyl-4-ylcarbonyl)-$N^1$-(4-methoxybenzyl)-L-α-glutamine MS (ESI) m/z 445.2; MS (ESI) m/z 891.5; HRMS: calcd for $C_{26}H_{26}N_2O_5$+H+, 447.19145. found (ESI_FT, [M+H]$^{1+}$), 447.19235.

Example 8L $N^2$-(1,1'-biphenyl-4-ylcarbonyl)-$N^1$-[2-(3,4-dimethoxyphenyl)ethyl]-L-α-glutamine Step A: tert-butyl $N^1$-[2-(3,4-dimethoxyphenyl)ethyl]-$N^2$-[(9H-fluoren-9-ylmethoxy)carbonyl]-L-α-glutaminate MS (ESI) m/z 589.2; MS (ESI) m/z 1177.3; HRMS: calcd for $C_{34}H_{40}N_2O_7$+H+, 589.29083. found (ESI_FT, [M+H]$^{1+}$), 589.28932.

Step B: tert-butyl $N^1$-[2-(3,4-dimethoxyphenyl)ethyl]-L-α-glutaminate

MS (ESI) m/z 367.2; HRMS: calcd for $C_{19}H_{30}N_2O_5$+H+, 367.22275. found (ESI_FT, [M+H]$^{1+}$), 367.22308.

Step C: tert-butyl $N^2$-(1,1'-biphenyl-4-ylcarbonyl)-$N^1$-[2-(3,4-dimethoxyphenyl)ethyl]-L-α-glutaminate MS (ESI) m/z 547.3; MS (ESI) m/z 1093.4; HRMS: calcd for $C_{32}H_{38}N_2O_6$+H+, 547.28026. found (ESI_FT, [M+H]$^{1+}$), 547.280241.

Step D: $N^2$-(1,1'-biphenyl-4-ylcarbonyl)-$N^1$-[2-(3,4-dimethoxyphenyl)ethyl]-L-α-glutamine MS (ESI) m/z 491.2; MS (ESI) m/z 981.2; HRMS: calcd for $C_{28}H_{30}N_2O_6$+H+, 491.21766. found (ESI_FT, [M+H]$^{1+}$), 491.21697.

Example 8M $N^2$-(1,1'-biphenyl-4-ylcarbonyl)-$N^1$-[2-(4-methoxyphenyl)ethyl]-L-α-glutamine Step A: tert-butyl $N^2$-[(9H-fluoren-9-ylmethoxy)carbonyl]-$N^1$-[2-(4-methoxyphenyl)ethyl]-L-α-glutaminate MS (ESI) m/z 559.2; MS (ESI) m/z 1117.3; HRMS: calcd for $C_{33}H_{38}N_2O_6$+H+, 559.28026. found (ESI_FT, [M+H]$^{1+}$), 559.27899.

Step B: tert-butyl $N^1$-[2-(4-methoxyphenyl)ethyl]-L-α-glutaminate

MS (ESI) m/z 337.1; MS (ESI) m/z 673.3; HRMS: calcd for $C_{18}H_{28}N_2O_4$+H+, 337.21218. found (ESI_FT, [M+H]$^{1+}$), 337.21196.

Step C: tert-butyl $N^2$-(1,1'-biphenyl-4-ylcarbonyl)-$N^1$-[2-(4-methoxyphenyl)ethyl]-L-α-glutaminate MS (ESI) m/z 517.2; MS (ESI) m/z 1033.4; HRMS: calcd for $C_{31}H_{36}N_2O_5$+H+, 517.26970. found (ESI_FT, [M+H]$^{1+}$), 517.26875.

Step D: $N^2$-(1,1'-biphenyl-4-ylcarbonyl)-$N^1$-[2-(4-methoxyphenyl)ethyl]-L-α-glutamine MS (ESI) m/z 461.2; MS (ESI) m/z 921.3; HRMS: calcd for $C_{27}H_{28}N_2O_5$+H+, 461.20710. found (ESI_FT, [M+H]$^{1+}$), 461.2062.

Example 8N $N^2$-(1,1'-biphenyl-4-ylcarbonyl)-$N^1$-(1-naphthylmethyl)-L-α-glutamine Step A: tert-butyl $N^2$-[(9H-fluoren-9-ylmethoxy)carbonyl]-$N^1$-(1-naphthylmethyl)-L-α-glutaminate MS (ESI) m/z 565.2; MS (ESI) m/z 1129.4; HRMS: calcd for $C_{35}H_{36}N_2O_5$+H+, 565.26970. found (ESI_FT, [M+H]$^{1+}$), 565.26849.

Step B: tert-butyl $N^1$-(1-naphthylmethyl)-L-α-glutaminate

MS (ESI) m/z 343.1; MS (ESI) m/z 685.3; HRMS: calcd for $C_{20}H_{26}N_2O_3$+H+, 343.20162. found (ESI_FT, [M+H]$^{1+}$), 343.2014.

Step C: tert-butyl $N^2$-(1,1'-biphenyl-4-ylcarbonyl)-$N^1$-(1-naphthylmethyl)-L-α-glutaminate MS (ESI) m/z 523.2; MS (ESI) m/z 1045.4; HRMS: calcd for $C_{33}H_{34}N_2O_4$+H+, 523.25913. found (ESI_FT, [M+H]$^{1+}$), 523.2583.

Step D: $N^2$-(1,1'-biphenyl-4-ylcarbonyl)-$N^1$-(1-naphthylmethyl)-L-α-glutamine MS (ESI) m/z 467.2; MS (ESI) m/z 933.3; HRMS: calcd for $C_{29}H_{26}N_2O_4$+H+, 467.19653. found (ESI_FT, [M+H]$^{1+}$), 467.19528.

Example 8O $N^2$-(1,1'-biphenyl-4-ylcarbonyl)-$N^1$-(3-methylbenzyl)-L-α-glutamine Step A: tert-butyl $N^2$-[(9H-fluoren-9-ylmethoxy)carbonyl]-$N^1$-(3-methylbenzyl)-L-α-glutaminate MS (ESI) m/z 529.1; MS (ESI) m/z 1057.4; HRMS: calcd for $C_{32}H_{36}N_2O_5$+H+, 529.26970. found (ESI_FT, [M+H]$^{1+}$), 529.26804.

Step B: tert-butyl $N^1$-(3-methylbenzyl)-L-α-glutaminate

MS (ESI) m/z 307.1; MS (ESI) m/z 613.3; HRMS: calcd for $C_{17}H_{26}N_2O_3$+H+, 307.20162. found (ESI_FT, [M+H]$^{1+}$), 307.20079.

Step C: tert-butyl $N^2$-(1,1'-biphenyl-4-ylcarbonyl)-$N^1$-(3-methylbenzyl)-L-α-glutaminate HRMS: calcd for $C_{30}H_{34}N_2O_4$+H+, 487.25913. found (ESI_FT, [M+H]$^{1+}$), 487.25842.

Step D: $N^2$-(1,1'-biphenyl-4-ylcarbonyl)-$N^1$-(3-methylbenzyl)-L-α-glutamine

HRMS: calcd for $C_{26}H_{26}N_2O_4$+H+, 431.19653. found (ESI_FT, [M+H]$^{1+}$), 431.19568.

Example 8P $N^2$-(1,1'-biphenyl-4-ylcarbonyl)-$N^1$-(2-furylmethyl)-L-α-glutamine Step A: tert-butyl $N^2$-[(9H-fluoren-9-ylmethoxy)carbonyl]-$N^1$-(2-furylmethyl)-L-α-glutaminate MS (ESI) m/z 505.2; HRMS: calcd for $C_{29}H_{32}N_2O_6$+H+, 505.23331. found (ESI_FT, [M+H]$^{1+}$), 505.23263.

Step B: tert-butyl $N^1$-(2-furylmethyl)-L-α-glutaminate

HRMS: calcd for $C_{14}H_{22}N_2O_4$+H+, 283.16523. found (ESI_FT, [M+H]$^{1+}$), 283.16497.

Step C: tert-butyl $N^2$-(1,1'-biphenyl-4-ylcarbonyl)-$N^1$-(2-furylmethyl)-L-α-glutaminate HRMS: calcd for $C_{27}H_{30}N_2O_5$+H+, 463.22275. found (ESI_FT, [M+H]$^{1+}$), 463.22212.

Step D: $N^2$-(1,1'-biphenyl-4-ylcarbonyl)-$N^1$-(2-furylmethyl)-L-α-glutamine

HRMS: calcd for $C_{23}H_{22}N_2O_5$+H+, 407.16015. found (ESI_FT, [M+H]$^{1+}$), 407.15957.

Example 8Q $N^2$-(1,1'-biphenyl-4-ylcarbonyl)-$N^1$-(3-methoxybenzyl)-L-α-glutamine Step A: tert-butyl $N^2$-[(9H-fluoren-9-ylmethoxy)carbonyl]-$N^1$-(3-methoxybenzyl)-L-α-glutaminate MS (ESI) m/z 545.3; MS (ESI) m/z 1089.5; HRMS: calcd for $C_{32}H_{36}N_2O_6$+H+, 545.26461; found (ESI_FT, [M+H]$^{1+}$), 545.26286.

Step B: tert-butyl $N^1$-(3-methoxybenzyl)-L-α-glutaminate

MS (ESI) m/z 323.3; MS (ESI) m/z 645.7; HRMS: calcd for $C_{17}H_{26}N_2O_4$+H+, 323.19653. found (ESI_FT, [M+H]$^{1+}$), 323.19687.

Step C: tert-butyl $N^2$-(1,1'-biphenyl-4-ylcarbonyl)-$N^1$-(3-methoxybenzyl)-L-α-glutaminate MS (ESI) m/z 503.2; MS (ESI) m/z 1005.5; HRMS: calcd for $C_{30}H_{34}N_2O_5$+H+, 503.25405. found (ESI_FT, [M+H]$^{1+}$), 503.25322.

Step D: $N^2$-(1,1'-biphenyl-4-ylcarbonyl)-$N^1$-(3-methoxybenzyl)-L-α-glutamine MS (ESI) m/z 447.2; MS (ESI) m/z 893.3; HRMS: calcd for $C_{26}H_{26}N_2O_5$+H+, 447.19145. found (ESI_FT, [M+H]$^{1+}$), 447.19079.

Example 8R $N^2$-(1,1'-biphenyl-4-ylcarbonyl)-$N^1$-(3,4,5-trimethoxybenzyl)-L-α-glutamine Step A: tert-butyl $N^2$-[(9H-fluoren-9-ylmethoxy)carbonyl]-$N^1$-(3,4,5-trimethoxybenzyl)-L-α-glutaminate MS (ESI) m/z 605.2; MS (ESI) m/z 1209.4; HRMS: calcd for $C_{34}H_{40}N_2O_8$+H+, 605.28574. found (ESI_FT, [M+H]$^{1+}$), 605.28453.

Step B: tert-butyl $N^1$-(3,4,5-trimethoxybenzyl)-L-α-glutaminate

MS (ESI) m/z 383.1; MS (ESI) m/z 765.3; HRMS: calcd for $C_{19}H_{30}N_2O_6$+H+, 383.21766. found (ESI_FT, [M+H]$^{1+}$), 383.21755.

Step C: tert-butyl $N^2$-(1,1'-biphenyl-4-ylcarbonyl)-$N^1$-(3,4,5-trimethoxybenzyl)-L-α-glutaminate MS (ESI) m/z 563.3; MS (ESI) m/z 1125.5; HRMS: calcd for $C_{32}H_{38}N_2O_7$+H+, 563.27518. found (ESI_FT, [M+H]$^{1+}$), 563.2744.

Step D: $N^2$-(1,1'-biphenyl-4-ylcarbonyl)-$N^1$-(3,4,5-trimethoxybenzyl)-L-α-glutamine MS (ESI) m/z 507.2; MS (ESI) m/z 1013.4; HRMS: calcd for $C_{28}H_{30}N_2O_7$+H+, 507.21258. found (ESI_FT, [M+H]$^{1+}$), 507.21179.

Example 8S $N^2$-(1,1'-biphenyl-4-ylcarbonyl)-$N^1$-(2,4-dichlorobenzyl)-L-α-glutamine Step A: tert-butyl $N^1$-(2,4-dichlorobenzyl)-$N^2$-[(9H-fluoren-9-ylmethoxy)carbonyl]-L-α-glutaminate MS (ESI) m/z 583.1; HRMS: calcd for $C_{31}H_{32}Cl_2N_2O_5$+H+, 583.17610. found (ESI_FT, [M+H]$^{1+}$), 583.1742.

Step B: tert-butyl $N^1$-(2,4-dichlorobenzyl)-L-α-glutaminate

MS (ESI) m/z 361.1; MS (ESI) m/z 721.2; HRMS: calcd for $C_{16}H_{22}Cl_2N_2O_3$+H+, 361.10802. found (ESI_FT, [M+H]$^{1+}$), 361.10891.

Step C: tert-butyl $N^2$-(1,1'-biphenyl-4-ylcarbonyl)-$N^1$-(2,4-dichlorobenzyl)-L-α-glutaminate MS (ESI) m/z 541.2; MS (ESI) m/z 1081.3; HRMS: calcd for $C_{29}H_{30}Cl_2N_2O_4$+H+, 541.16554. found (ESI_FT, [M+H]$^{1+}$), 541.16693.

Step D: $N^2$-(1,1'-biphenyl-4-ylcarbonyl)-$N^1$-(2,4-dichlorobenzyl)-L-α-glutamine MS (ESI) m/z 483.1; MS (ESI) m/z 967.2; HRMS: calcd for $C_{25}H_{22}Cl_2N_2O_4$+H+, 485.10294. found (ESI_FT, [M+H]$^{1+}$), 485.10231.

Example 8T $N^2$-(1,1'-biphenyl-4-ylcarbonyl)-$N^1$-[4-(trifluoromethoxy)benzyl]-L-α-glutamine Step A: tert-butyl $N^2$-[(9H-fluoren-9-ylmethoxy)carbonyl]-$N^1$-[4-(trifluoromethoxy)benzyl]-L-α-glutaminate MS (ESI) m/z 599.1; MS (ESI) m/z 1197.3; HRMS: calcd for $C_{32}H_{33}F_3N_2O_6$+H+, 599.23635. found (ESI_FT, [M+H]$^{1+}$), 599.23521.

Step B: tert-butyl $N^1$-[4-(trifluoromethoxy)benzyl]-L-α-glutaminate

MS (ESI) m/z 377.1; HRMS: calcd for $C_{17}H_{23}F_3N_2O_4$+H+, 377.16827. found (ESI_FT, [M+H]$^{1+}$), 377.16901.

Step C: tert-butyl $N^2$-(1,1'-biphenyl-4-ylcarbonyl)-$N^1$-[4-(trifluoromethoxy)benzyl]-L-α-glutaminate MS (ESI) m/z 557.2; MS (ESI) m/z 1113.4; HRMS: calcd for $C_{30}H_{31}F_3N_2O_5$+H+, 557.22578. found (ESI_FT, [M+H]$^{1+}$), 557.22537.

Step D: $N^2$-(1,1'-biphenyl-4-ylcarbonyl)-$N^1$-[4-(trifluoromethoxy)benzyl]-L-α-glutamine MS (ESI) m/z 501.2; MS (ESI) m/z 1001.3; HRMS: calcd for $C_{26}H_{23}F_3N_2O_5$+H+, 501.16318. found (ESI_FT, [M+H]$^{1+}$), 501.16263.

Example 8U $N^2$-(1,1'-biphenyl-4-ylcarbonyl)-$N^1$-[3-(trifluoromethoxy)benzyl]-L-α-glutamine Step A: tert-butyl $N^2$-[(9H-fluoren-9-ylmethoxy)carbonyl]-$N^1$-[3-(trifluoromethoxy)benzyl]-L-α-glutaminate MS (ESI) m/z 599.2; MS (ESI) m/z 1197.4; HRMS: calcd for $C_{32}H_{33}F_3N_2O_6$+H+, 599.23635. found (ESI_FT, [M+H]$^{1+}$), 599.23596.

Step B: tert-butyl $N^1$-[3-(trifluoromethoxy)benzyl]-L-α-glutaminate

MS (ESI) m/z 377.1; MS (ESI) m/z 753.3; HRMS: calcd for $C_{17}H_{23}F_3N_2O_4$+H+, 377.16827. found (ESI_FT, [M+H]$^{1+}$), 377.1691.

Step C: tert-butyl $N^2$-(1,1'-biphenyl-4-ylcarbonyl)-$N^1$-[3-(trifluoromethoxy)benzyl]-L-α-glutaminate MS (ESI) m/z 557.2; MS (ESI) m/z 1113.4; HRMS: calcd for $C_{30}H_{31}F_3N_2O_5$+H+, 557.22578. found (ESI_FT, [M+H]$^{1+}$), 557.22558.

Step D: $N^2$-(1,1'-biphenyl-4-ylcarbonyl)-$N^1$-[3-(trifluoromethoxy)benzyl]-L-α-glutamine MS (ESI) m/z 499.1; MS (ESI) m/z 999.3; HRMS: calcd for $C_{26}H_{23}F_3N_2O_5$+H+, 501.16318. found (ESI_FT, [M+H]$^{1+}$), 501.16265.

Example 8V $N^2$-(1,1'-biphenyl-4-ylcarbonyl)-$N^1$-[4-(methylthio)benzyl]-L-α-glutamine Step A: tert-butyl $N^2$-[(9H-fluoren-9-ylmethoxy)carbonyl]-$N^1$-[4-(methylthio)benzyl]-L-α-glutaminate MS (ESI) m/z 561.2; MS (ESI) m/z 1121.4; HRMS: calcd for $C_{32}H_{36}N_2O_5S$+H+, 561.24177. found (ESI_FT, [M+H]$^{1+}$), 561.24183.

Step B: tert-butyl $N^1$-[4-(methylthio)benzyl]-L-α-glutaminate

MS (ESI) m/z 339.2; MS (ESI) m/z 677.3; HRMS: calcd for $C_{17}H_{26}N_2O_3S$+H+, 339.17369. found (ESI_FT, [M+H]$^{1+}$), 339.1748.

Step C: tert-butyl $N^2$-(1,1'-biphenyl-4-ylcarbonyl)-$N^1$-[4-(methylthio)benzyl]-L-α-glutaminate MS (ESI) m/z 519.2; MS (ESI) m/z 1037.4; HRMS: calcd for $C_{30}H_{34}N_2O_4S$+H+, 519.23120. found (ESI_FT, [M+H]$^{1+}$), 519.23078.

Step D: $N^2$-(1,1'-biphenyl-4-ylcarbonyl)-$N^1$-[4-(methylthio)benzyl]-L-α-glutamine MS (ESI) m/z 461.1; MS (ESI) m/z 923.3; HRMS: calcd for $C_{26}H_{26}N_2O_4S$+H+, 463.16860. found (ESI_FT, [M+H]$^{1+}$), 463.16807.

Example 8W $N^2$-(1,1'-biphenyl-4-ylcarbonyl)-$N^1$-(4-phenoxybenzyl)-L-α-glutamine Step A: tert-butyl $N^2$-[(9H-fluoren-9-ylmethoxy)carbonyl]-$N^1$-(4-phenoxybenzyl)-L-α-glutaminate MS (ESI) m/z 607.3; MS (ESI) m/z 1213.5; HRMS: calcd for $C_{37}H_{38}N_2O_6$+H+, 607.28026. found (ESI_FT, [M+H]$^{1+}$), 607.27904.

Step B: tert-butyl $N^1$-(4-phenoxybenzyl)-L-α-glutaminate

MS (ESI) m/z 385.2; MS (ESI) m/z 769.4; HRMS: calcd for $C_{22}H_{28}N_2O_4$+H+, 385.21218. found (ESI_FT, [M+H]$^{1+}$), 385.21141.

Step C: tert-butyl $N^2$-(1,1'-biphenyl-4-ylcarbonyl)-$N^1$-(4-phenoxybenzyl)-L-α-glutaminate MS (ESI) m/z 565.3; MS (ESI) m/z 1129.5; HRMS: calcd for $C_{35}H_{36}N_2O_5$+H+, 565.26970. found (ESI_FT, [M+H]$^{1+}$), 565.27062.

Step D: $N^2$-(1,1'-biphenyl-4-ylcarbonyl)-$N^1$-(4-phenoxybenzyl)-L-α-glutamine MS (ESI) m/z 507.2; MS (ESI) m/z 1015.4; HRMS: calcd for $C_{31}H_{28}N_2O_5$+H+, 509.20710. found (ESI_FT, [M+H]$^{1+}$), 509.20657.

Example 8X $N^2$-(1,1'-biphenyl-4-ylcarbonyl)-$N^1$-[2-(3-methoxyphenyl)ethyl]-L-α-glutamine Step A: tert-butyl $N^2$-[(9H-fluoren-9-ylmethoxy)carbonyl]-$N^1$-[2-(3-methoxyphenyl)ethyl]-L-α-glutaminate MS (ESI) m/z 559.3; MS (ESI) m/z 1117.6; HRMS: calcd for $C_{33}H_{38}N_2O_6$+H+, 559.28026. found (ESI_FT, [M+H]$^{1+}$), 559.28074.

Step B: tert-butyl $N^1$-[2-(3-methoxyphenyl)ethyl]-L-α-glutaminate

MS (ESI) m/z 337.2; HRMS: calcd for $C_{18}H_{28}N_2O_4$+H+, 337.21218. found (ESI_FT, [M+H]$^{1+}$), 337.21275.

Step C: tert-butyl $N^2$-(1,1'-biphenyl-4-ylcarbonyl)-$N^1$-[2-(3-methoxyphenyl)ethyl]-L-α-glutaminate MS (ESI) m/z 517.3; MS (ESI) m/z 1033.6; HRMS: calcd for $C_{31}H_{36}N_2O_5$+H+, 517.26970. found (ESI_FT, [M+H]$^{1+}$), 517.27068.

Step D: $N^2$-(1,1'-biphenyl-4-ylcarbonyl)-$N^1$-[2-(3-methoxyphenyl)ethyl]-L-α-glutamine MS (ESI) m/z 461.2; MS (ESI) m/z 921.4; HRMS: calcd for $C_{27}H_{28}N_2O_5$+H+, 461.20710. found (ESI_FT, [M+H]$^{1+}$), 461.20723.

Example 8Y $N^2$-(1,1'-biphenyl-4-ylcarbonyl)-$N^1$-(2,4-dimethoxybenzyl)-L-α-glutamine Step A: tert-butyl $N^1$-(2,4-dimethoxybenzyl)-$N^2$-[(9H-fluoren-9-ylmethoxy)carbonyl]-L-α-glutaminate MS (ESI) m/z 575.3; MS (ESI) m/z 1149.5; HRMS: calcd for $C_{33}H_{38}N_2O_7$+H+, 575.27518. found (ESI_FT, [M+H]$^{1+}$), 575.275181.

Step B: tert-butyl $N^1$-(2,4-dimethoxybenzyl)-L-α-glutaminate

MS (ESI) m/z 353.2; MS (ESI) m/z 705.4; HRMS: calcd for $C_{18}H_{28}N_2O_5$+H+, 353.20710. found (ESI_FT, [M+H]$^{1+}$), 353.20767.

Step C: tert-butyl $N^2$-(1,1'-biphenyl-4-ylcarbonyl)-$N^1$-(2,4-dimethoxybenzyl)-L-α-glutaminate MS (ESI) m/z 533.3; MS (ESI) m/z 1065.6; HRMS: calcd for $C_{31}H_{36}N_2O_6$+H+, 533.26461. found (ESI_FT, [M+H]$^{1+}$), 533.26569.

Step D: $N^2$-(1,1'-biphenyl-4-ylcarbonyl)-$N^1$-(2,4-dimethoxybenzyl)-L-α-glutamine MS (ESI) m/z 477.2; MS (ESI) m/z 953.4; HRMS: calcd for $C_{27}H_{28}N_2O_6$+H+, 477.20201. found (ESI_FT, [M+H]$^{1+}$), 477.2019.

Example 8Z $N^2$-(1,1'-biphenyl-4-ylcarbonyl)-$N^1$-(2-methoxybenzyl)-L-α-glutamine Step A: tert-butyl $N^2$-[(9H-fluoren-9-ylmethoxy)carbonyl]-$N^1$-(2-methoxybenzyl)-L-α-glutaminate MS (ESI) m/z 545.2; HRMS: calcd for $C_{32}H_{36}N_2O_6$+H+, 545.26461. found (ESI_FT, [M+H]$^{1+}$), 545.26356.

Step B: tert-butyl $N^1$-(2-methoxybenzyl)-L-α-glutaminate

MS (ESI) m/z 323.2; MS (ESI) m/z 645.4; HRMS: calcd for $C_{17}H_{26}N_2O_4$+H+, 323.19653. found (ESI_FT, [M+H]$^{1+}$), 323.19657.

Step C: tert-butyl $N^2$-(1,1'-biphenyl-4-ylcarbonyl)-$N^1$-(2-methoxybenzyl)-L-α-glutaminate MS (ESI) m/z 503.2; MS (ESI) m/z 1005.5; HRMS: calcd for $C_{30}H_{34}N_2O_5$+H+, 503.25405. found (ESI_FT, [M+H]$^{1+}$), 503.2546.

Step D: N²-(1,1'-biphenyl-4-ylcarbonyl)-N¹-(2-methoxybenzyl)-L-α-glutamine

MS (ESI) m/z 447.2; MS (ESI) m/z 893.4; HRMS: calcd for $C_{26}H_{26}N_2O_5$+H+, 447.19145. found (ESI_FT, [M+H]$^{1+}$), 447.19143.

Example 8AA

N²-(1,1'-biphenyl-4-ylcarbonyl)-N¹-(3,5-difluorobenzyl)-L-α-glutamine

Step A: tert-butyl N¹-(3,5-difluorobenzyl)-N²-[(9H-fluoren-9-ylmethoxy)carbonyl]-L-α-glutaminate MS (ESI) m/z 551.2; MS (ESI) m/z 1101.4; HRMS: calcd for $C_{31}H_{32}F_2N_2O_5$+H+, 551.23521. found (ESI_FT, [M+H]$^{1+}$), 551.23338.

Step B: tert-butyl N¹-(3,5-difluorobenzyl)-L-α-glutaminate

MS (ESI) m/z 329.1; MS (ESI) m/z 657.3; HRMS: calcd for $C_{16}H_{22}F_2N_2O_3$+H+, 329.16712. found (ESI_FT, [M+H]$^{1+}$), 329.16762.

Step C: tert-butyl N²-(1,1'-biphenyl-4-ylcarbonyl)-N¹-(3,5-difluorobenzyl)-L-α-glutaminate MS (ESI) m/z 509.2; MS (ESI) m/z 1017.3; HRMS: calcd for $C_{29}H_{30}F_2N_2O_4$+H+, 509.22464. found (ESI_FTMS, [M+H]$^{1+}$), 509.22463.

Step D: N²-(1,1'-biphenyl-4-ylcarbonyl)-N¹-(3,5-difluorobenzyl)-L-α-glutamine

MS (ESI) m/z 451.1; MS (ESI) m/z 903.3; HRMS: calcd for $C_{25}H_{22}F_2N_2O_4$+H+, 453.16204. found (ESI_FTMS, [M+H]$^{1+}$), 453.16222.

Example 8BB

N²-(1,1'-biphenyl-4-ylcarbonyl)-N¹-(3,4-dichlorobenzyl)-L-α-glutamine

Step A: tert-butyl N¹-(3,4-dichlorobenzyl)-N²-[(9H-fluoren-9-ylmethoxy)carbonyl]-L-α-glutaminate MS (ESI) m/z 583.1; MS (ESI) m/z 1165.2; HRMS: calcd for $C_{31}H_{32}Cl_2N_2O_5$+H+, 583.17610. found (ESI_FT, [M+H]$^{1+}$), 583.17528.

Step B: tert-butyl N¹-(3,4-dichlorobenzyl)-L-α-glutaminate

MS (ESI) m/z 361.1; MS (ESI) m/z 721.2; HRMS: calcd for $C_{16}H_{22}Cl_2N_2O_3$+H+, 361.10802. found (ESI_FT, [M+H]$^{1+}$), 361.10861.

Step C: tert-butyl N²-(1,1'-biphenyl-4-ylcarbonyl)-N¹-(3,4-dichlorobenzyl)-L-α-glutaminate MS (ESI) m/z 541.2; MS (ESI) m/z 1081.3; HRMS: calcd for $C_{29}H_{30}Cl_2N_2O_4$+H+, 541.16554. found (ESI_FT, [M+H]$^{1+}$), 541.16685.

Step D: N²-(1,1'-biphenyl-4-ylcarbonyl)-N¹-(3,4-dichlorobenzyl)-L-α-glutamine

MS (ESI) m/z 483.1; MS (ESI) m/z 967.2; HRMS: calcd for $C_{25}H_{22}Cl_2N_2O_4$+H+, 485.10294. found (ESI_FTMS, [M+H]$^{1+}$), 485.10288.

Example 8CC

N²-(1,1'-biphenyl-4-ylcarbonyl)-N¹-(3,5-dimethoxybenzyl)-L-α-glutamine

Step A: tert-butyl N¹-(3,5-dimethoxybenzyl)-N²-[(9H-fluoren-9-ylmethoxy)carbonyl]-L-α-glutaminate MS (ESI) m/z 575.3; HRMS: calcd for $C_{33}H_{38}N_2O_7$+H+, 575.27518. found (ESI_FTMS, [M+H]$^{1+}$), 575.27468.

Step B: tert-butyl N¹-(3,5-dimethoxybenzyl)-L-α-glutaminate

MS (ESI) m/z 353.2; HRMS: calcd for $C_{18}H_{28}N_2O_5$+H+, 353.20710. found (ESI_FTMS, [M+H]$^{1+}$), 353.20732.

Step C: tert-butyl N²-(1,1'-biphenyl-4-ylcarbonyl)-N¹-(3,5-dimethoxybenzyl)-L-α-glutaminate MS (ESI) m/z 533.3; MS (ESI) m/z 1065.5; HRMS: calcd for $C_{31}H_{36}N_2O_6$+H+, 533.26461. found (ESI_FTMS, [M+H]$^{1+}$), 533.26474.

Step D: N²-(1,1'-biphenyl-4-ylcarbonyl)-N¹-(3,5-dimethoxybenzyl)-L-α-glutamine

MS (ESI) m/z 477.2; MS (ESI) m/z 953.4; HRMS: calcd for $C_{27}H_{28}N_2O_6$+H+, 477.20201. found (ESI-FTMS, [M+H]$^{1+}$), 477.202.

Example 8DD

N²-(1,1'-biphenyl-4-ylcarbonyl)-N¹-(3,4-dimethylbenzyl)-L-α-glutamine

Step A: tert-butyl N¹-(3,4-dimethylbenzyl)-N²-[(9H-fluoren-9-ylmethoxy)carbonyl]-L-α-glutaminate MS (ESI) m/z 543.3; MS (ESI) m/z 1085.4; HRMS: calcd for $C_{33}H_{38}N_2O_5$+H+, 543.28535. found (ESI_FTMS, [M+H]$^{1+}$), 543.28604.

Step B: tert-butyl N¹-(3,4-dimethylbenzyl)-L-α-glutaminate

MS (ESI) m/z 321.2; HRMS: calcd for $C_{18}H_{28}N_2O_3$+H+, 321.21727. found (ESI_FTMS, [M+H]$^{1+}$), 321.21716.

Step C: tert-butyl N²-(1,1'-biphenyl-4-ylcarbonyl)-N¹-(3,4-dimethylbenzyl)-L-α-glutaminate MS (ESI) m/z 501.3; MS (ESI) m/z 1001.4; HRMS: calcd for $C_{31}H_{36}N_2O_4$+H+, 501.27478. found (ESI_FTMS, [M+H]$^{1+}$), 501.2735.

Step D: $N^2$-(1,1'-biphenyl-4-ylcarbonyl)-$N^1$-(3,4-dimethylbenzyl)-L-α-glutamine MS (ESI) m/z 445.2; MS (ESI) m/z 889.3; HRMS: calcd for $C_{27}H_{28}N_2O_4$+H+, 445.21218. found (ESI_FTMS, [M+H]$^{1+}$), 445.21199.

Example 8EE $N^2$-(1,1'-biphenyl-4-ylcarbonyl)-$N^1$-(2-methylbenzyl)-L-α-glutamine Step A: tert-butyl $N^2$-[(9H-fluoren-9-ylmethoxy)carbonyl]-$N^1$-(2-methylbenzyl)-L-α-glutaminate MS (ESI) m/z 529.2; MS (ESI) m/z 1057.4; HRMS: calcd for $C_{32}H_{36}N_2O_5$+H+, 529.26970. found (ESI_FTMS, [M+H]$^{1+}$), 529.27003.

Step B: tert-butyl $N^1$-(2-methylbenzyl)-L-α-glutaminate

MS (ESI) m/z 307.2; MS (ESI) m/z 613.4; HRMS: calcd for $C_{17}H_{26}N_2O_3$+H+, 307.20162. found (ESI_FTMS, [M+H]$^{1+}$), 307.20094.

Step C: tert-butyl $N^2$-(1,1'-biphenyl-4-ylcarbonyl)-$N^1$-(2-methylbenzyl)-L-α-glutaminate MS (ESI) m/z 487.2; MS (ESI) m/z 973.3; HRMS: calcd for $C_{30}H_{34}N_2O_4$+H+, 487.25913. found (ESI_FTMS, [M+H]$^{1+}$), 487.2588.

Step D: $N^2$-(1,1'-biphenyl-4-ylcarbonyl)-$N^1$-(2-methylbenzyl)-L-α-glutamine

MS (ESI) m/z 431.2; MS (ESI) m/z 861.3; HRMS: calcd for $C_{26}H_{26}N_2O_4$+H+, 431.19653. found (ESI_FTMS, [M+H]$^{1+}$), 431.1966.

Example 8FF $N^2$-(1,1'-biphenyl-4-ylcarbonyl)-$N^1$-(3-phenylpropyl)-L-α-glutamine Step A: tert-butyl $N^2$-[(9H-fluoren-9-ylmethoxy)carbonyl]-$N^1$-(3-phenylpropyl)-L-α-glutaminate MS (ESI) m/z 543.3; HRMS: calcd for $C_{33}H_{38}N_2O_5$+H+, 543.28535. found (ESI_FTMS, [M+H]$^{1+}$), 543.2847.

Step B: tert-butyl $N^1$-(3-phenylpropyl)-L-α-glutaminate

MS (ESI) m/z 321.2; MS (ESI) m/z 641.4; HRMS: calcd for $C_{18}H_{28}N_2O_3$+H+, 321.21727. found (ESI_FTMS, [M+H]$^{1+}$), 321.2167.

Step C: tert-butyl $N^2$-(1,1'-biphenyl-4-ylcarbonyl)-$N^1$-(3-phenylpropyl)-L-α-glutaminate MS (ESI) m/z 501.3; HRMS: calcd for $C_{31}H_{36}N_2O_4$+H+, 501.27478. found (ESI_FTMS, [M+H]$^{1+}$), 501.2742.

Step D: $N^2$-(1,1'-biphenyl-4-ylcarbonyl)-$N^1$-(3-phenylpropyl)-L-α-glutamine

MS (ESI) m/z 445.2; HRMS: calcd for $C_{27}H_{28}N_2O_4$+H+, 445.21218. found (ESI_FTMS, [M+H]$^{1+}$), 445.2121.

Example 8GG $N^2$-(1,1'-biphenyl-4-ylcarbonyl)-$N^1$-2,3-dihydro-1H-inden-2-yl-L-α-glutamine Step A: tert-butyl $N^1$-2,3-dihydro-1H-inden-2-yl-$N^2$-[(9H-fluoren-9-ylmethoxy)carbonyl]-L-α-glutaminate MS (ESI) m/z 541.2; MS (ESI) m/z 1081.4; HRMS: calcd for $C_{33}H_{36}N_2O_5$+H+, 541.26970. found (ESI-FTMS, [M+H]$^{1+}$), 541.27088.

Step B: tert-butyl $N^1$-2,3-dihydro-1H-inden-2-yl-L-α-glutaminate

MS (ESI) m/z 319.1; MS (ESI) m/z 637.3; HRMS: calcd for $C_{18}H_{26}N_2O_3$+H+, 319.20162. found (ESI-FTMS, [M+H]$^{1+}$), 319.20275.

Step C: tert-butyl $N^2$-(1,1'-biphenyl-4-ylcarbonyl)-$N^1$-2,3-dihydro-1H-inden-2-yl-L-α-glutaminate MS (ESI) m/z 499.2; MS (ESI) m/z 997.4; HRMS: calcd for $C_{31}H_{34}N_2O_4$+H+, 499.25913. found (ESI-FTMS, [M+H]$^{1+}$), 499.258.

Step D: $N^2$-(1,1'-biphenyl-4-ylcarbonyl)-$N^1$-2,3-dihydro-1H-inden-2-yl-L-α-glutamine MS (ESI) m/z 441.2; MS (ESI) m/z 883.3; HRMS: calcd for $C_{27}H_{26}N_2O_4$+H+, 443.19653. found (ESI-FTMS, [M+H]$^{1+}$), 443.19699.

Example 8HH $N^2$-(1,1'-biphenyl-4-ylcarbonyl)-$N^1$-(2,3-dimethylbenzyl)-L-α-glutamine Step A: tert-butyl $N^1$-(2,3-dimethylbenzyl)-$N^2$-[(9H-fluoren-9-ylmethoxy)carbonyl]-L-α-glutaminate MS (ESI) m/z 543.2; MS (ESI) m/z 1085.4; HRMS: calcd for $C_{33}H_{38}N_2O_5$+H+, 543.28535. found (ESI-FTMS, [M+H]$^{1+}$), 543.28623.

Step B: tert-butyl $N^1$-(2,3-dimethylbenzyl)-L-α-glutaminate

MS (ESI) m/z 321.2; MS (ESI) m/z 641.4; HRMS: calcd for $C_{18}H_{28}N_2O_3$+H+, 321.21727. found (ESI-FTMS, [M+H]$^{1+}$), 321.2186.

Step C: tert-butyl $N^2$-(1,1'-biphenyl-4-ylcarbonyl)-$N^1$-(2,3-dimethylbenzyl)-L-α-glutaminate MS (ESI) m/z 501.2; MS (ESI) m/z 1001.4; HRMS: calcd for $C_{31}H_{36}N_2O_4$+H+, 501.27478. found (ESI-FTMS, [M+H]$^{1+}$), 501.27629.

Step D: $N^2$-(1,1'-biphenyl-4-ylcarbonyl)-$N^1$-(2,3-dimethylbenzyl)-L-α-glutamine MS (ESI) m/z 443.2; HRMS: calcd for $C_{27}H_{28}N_2O_4$+H+, 445.21218. found (ESI-FTMS, [M+H]$^{1+}$), 445.21354.

Example 8II $N^2$-(1,1'-biphenyl-4-ylcarbonyl)-$N^1$-(4-phenylbutyl)-L-α-glutamine Step A: tert-butyl $N^2$-[(9H-fluoren-9-ylmethoxy)carbonyl]-$N^1$-(4-phenylbutyl)-L-α-glutaminate MS (ESI) m/z 557.2; MS (ESI) m/z 1113.4; HRMS: calcd for $C_{34}H_{40}N_2O_5$+H+, 557.30100. found (ESI-FTMS, [M+H]$^{1+}$), 557.30162.

Step B: tert-butyl $N^1$-(4-phenylbutyl)-L-α-glutaminate

MS (ESI) m/z 335.2; HRMS: calcd for $C_{19}H_{30}N_2O_3$+H+, 335.23292. found (ESI-FTMS, [M+H]$^{1+}$), 335.23453;

Step C: tert-butyl $N^2$-(1,1'-biphenyl-4-ylcarbonyl)-$N^1$-(4-phenylbutyl)-L-α-glutaminate MS (ESI) m/z 515.3; MS (ESI) m/z 1029.5; HRMS: calcd for $C_{32}H_{38}N_2O_4$+H+, 515.29043. found (ESI-FTMS, [M+H]$^{1+}$), 515.29152.

Step D: $N^2$-(1,1'-biphenyl-4-ylcarbonyl)-$N^1$-(4-phenylbutyl)-L-α-glutamine

MS (ESI) m/z 459.2; MS (ESI) m/z 917.4; HRMS: calcd for $C_{28}H_{30}N_2O_4$+H+, 459.22783. found (ESI-FTMS, [M+H]$^{1+}$), 459.22972.

Example 8JJ $N^2$-(1,1'-biphenyl-4-ylcarbonyl)-$N^1$-(3-iodobenzyl)-L-α-glutamine Step A: tert-butyl $N^2$-[(9H-fluoren-9-ylmethoxy)carbonyl]-$N^1$-(3-iodobenzyl)-L-α-glutaminate MS (ESI) m/z 641.1; MS (ESI) m/z 1281.1; HRMS: calcd for $C_{31}H_{33}IN_2O_5$+H+, 641.15070. found (ESI-FTMS, [M+H]$^{1+}$), 641.15111.

Step B: tert-butyl $N^1$-(3-iodobenzyl)-L-α-glutaminate

MS (ESI) m/z 419.1; MS (ESI) m/z 837.1; HRMS: calcd for $C_{16}H_{23}IN_2O_3$+H+, 419.08262. found (ESI-FTMS, [M+H]$^{1+}$), 419.08459.

Step C: tert-butyl $N^2$-(1,1'-biphenyl-4-ylcarbonyl)-$N^1$-(3-iodobenzyl)-L-α-glutaminate MS (ESI) m/z 599.1; MS (ESI) m/z 1197.1; HRMS: calcd for $C_{29}H_{31}IN_2O_4$+H+, 599.14013. found (ESI-FTMS, [M+H]$^{1+}$), 599.1414.

Step D: $N^2$-(1,1'-biphenyl-4-ylcarbonyl)-$N^1$-(3-iodobenzyl)-L-α-glutamine

MS (ESI) m/z 543.1; MS (ESI) m/z 1085.1; MS (ESI) m/z 601.1; HRMS: calcd for $C_{25}H_{23}IN_2O_4$+H+, 543.07753. found (ESI-FTMS, [M+H]$^{1+}$), 543.07723.

Example 8KK $N^2$-(1,1'-biphenyl-4-ylcarbonyl)-$N^1$-(4-tert-butylbenzyl)-L-α-glutamine Step A: tert-butyl $N^1$-(4-tert-butylbenzyl)-$N^2$-[(9H-fluoren-9-ylmethoxy)carbonyl]-L-α-glutaminate MS (ESI) m/z 571.3; MS (ESI) m/z 1141.6; HRMS: calcd for $C_{35}H_{42}N_2O_5$+H+, 571.31665. found (ESI_FT, [M+H]$^{1+}$), 571.31581.

Step B: tert-butyl $N^1$-(4-tert-butylbenzyl)-L-α-glutaminate

MS (ESI) m/z 349.2; HRMS: calcd for $C_{20}H_{32}N_2O_3$+H+, 349.24857. found (ESI-FTMS, [M+H]$^{1+}$), 349.2489.

Step C: tert-butyl $N^2$-(1,1'-biphenyl-4-ylcarbonyl)-$N^1$-(4-tert-butylbenzyl)-L-α-glutaminate MS (ESI) m/z 529.2; MS (ESI) m/z 1057.4; HRMS: calcd for $C_{33}H_{40}N_2O_4$+H+, 529.30608. found (ESI-FTMS, [M+H]$^{1+}$), 529.30622.

Step D: $N^2$-(1,1'-biphenyl-4-ylcarbonyl)-$N^1$-(4-tert-butylbenzyl)-L-α-glutamine MS (ESI) m/z 473.2; MS (ESI) m/z 945.3; MS (ESI) m/z 531.2; HRMS: calcd for $C_{29}H_{32}N_2O_4$+H+, 473.24348. found (ESI-FTMS, [M+H]$^{1+}$), 473.24348.

Example 8LL $N^2$-(1,1'-biphenyl-4-ylcarbonyl)-$N^1$-(4-iodobenzyl)-L-α-glutamine Step A: tert-butyl $N^2$-[(9H-fluoren-9-ylmethoxy)carbonyl]-$N^1$-(4-iodobenzyl)-L-α-glutaminate MS (ESI) m/z 641.1; MS (ESI) m/z 1281.1; HRMS: calcd for $C_{31}H_{33}IN_2O_5$+H+, 641.15070. found (ESI-FTMS, [M+H]$^{1+}$), 641.15129.

Step B: tert-butyl $N^1$-(4-iodobenzyl)-L-α-glutaminate

MS (ESI) m/z 419; HRMS: calcd for $C_{16}H_{23}IN_2O_3$+H+, 419.08262. found (ESI-FTMS, [M+H]$^{1+}$), 419.08332.

Step C: tert-butyl $N^2$-(1,1'-biphenyl-4-ylcarbonyl)-$N^1$-(4-iodobenzyl)-L-α-glutaminate MS (ESI) m/z 599; MS (ESI) m/z 1197; HRMS: calcd for $C_{29}H_{31}IN_2O_4$+H+, 599.14013. found (ESI-FTMS, [M+H]$^{1+}$), 599.1407.

Step D: $N^2$-(1,1'-biphenyl-4-ylcarbonyl)-$N^1$-(4-iodobenzyl)-L-α-glutamine

MS (ESI) m/z 543; MS (ESI) m/z 1085; HRMS: calcd for $C_{25}H_{23}IN_2O_4$+H+, 543.07753. found (ESI-FTMS, [M+H]$^{1+}$), 543.07755.

Example 8MM $N^2$-(biphenyl-4-ylcarbonyl)-$N^1$-(1,1-dimethylpropyl)-L-α-glutamine Step A: tert-butyl $N^1$-(1,1-dimethylpropyl)-$N^2$-[(9H-fluoren-9-ylmethoxy)carbonyl]-L-α-glutaminate MS (ESI) m/z 495.3; HRMS: calcd for $C_{29}H_{38}N_2O_5$+H+, 495.28535. found (ESI_FT, [M+H]$^{1+}$), 495.28577.

Step B: tert-butyl $N^1$-(1,1-dimethylpropyl)-L-α-glutaminate

MS (ESI) m/z 273.2; HRMS: calcd for $C_{14}H_{28}N_2O_3$+H+, 273.21727. found (ESI-FTMS, [M+H]$^{1+}$), 273.21738.

Step C: tert-butyl $N^2$-(biphenyl-4-ylcarbonyl)-$N^1$-(1,1-dimethylpropyl)-L-α-glutaminate MS (ESI) m/z 453.2; MS (ESI) m/z 905.5; HRMS: calcd for $C_{27}H_{36}N_2O_4$+H+, 453.27478. found (ESI-FTMS, [M+H]$^{1+}$), 453.27627.

Step D: $N^2$-(biphenyl-4-ylcarbonyl)-$N^1$-(1,1-dimethylpropyl)-L-α-glutamine

MS (ESI) m/z 397.2; MS (ESI) m/z 793.4; HRMS: calcd for $C_{23}H_{28}N_2O_4$+H+, 397.21218. found (ESI-FTMS, [M+H]$^{1+}$), 397.2139.

Example 8NN $N^2$-(biphenyl-4-ylcarbonyl)-$N^1$-[2-(4-chlorophenyl)-1,1-dimethylethyl]-L-α-glutamine Step A: tert-butyl $N^1$-[2-(4-chlorophenyl)-1,1-dimethylethyl]-$N^2$-[(9H-fluoren-9-ylmethoxy)carbonyl]-L-α-glutaminate MS (ESI) m/z 591.1; MS (ESI) m/z 1181.2; HRMS: calcd for $C_{34}H_{39}ClN_2O_5$+H+, 591.26203. found (ESI-FTMS, [M+H]$^{1+}$), 591.26263.

Step B: tert-butyl $N^1$-[2-(4-chlorophenyl)-1,1-dimethylethyl]-L-α-glutaminate

MS (ESI) m/z 369.1; MS (ESI) m/z 737.2; HRMS: calcd for $C_{19}H_{29}ClN_2O_3$+H+, 369.19395. found (ESI-FTMS, [M+H]$^{1+}$), 369.19351.

Step C: tert-butyl $N^2$-(biphenyl-4-ylcarbonyl)-$N^1$-[2-(4-chlorophenyl)-1,1-dimethylethyl]-L-α-glutaminate MS (ESI) m/z 549.1; MS (ESI) m/z 1097.2; RMS: calcd for $C_{32}H_{37}ClN_2O_4$+H+, 549.25146. found (ESI-FTMS, [M+H]$^{1+}$), 549.25189.

Step D: $^2$-(biphenyl-4-ylcarbonyl)-$N^1$-[2-(4-chlorophenyl)-1,1-dimethylethyl]-L-α-glutamine MS (ESI) m/z 493.1; HRMS: calcd for $C_{28}H_{29}ClN_2O_4$+H+, 493.18886. found (ESI-FTMS, [M+H]$^{1+}$), 493.1895.

Example 8OO $N^2$-(1,1'-biphenyl-4-ylcarbonyl)-$N^1$-[2-(4-fluorophenyl)-1,1-dimethylethyl]-L-α-glutamine Step A: tert-butyl $N^2$-[(9H-fluoren-9-ylmethoxy)carbonyl]-$N^1$-[2-(4-fluorophenyl)-1,1-dimethylethyl]-L-α-glutaminate MS (ESI) m/z 575.3; MS (ESI) m/z 1149.4; HRMS: calcd for $C_{34}H_{39}FN_2O_5$+H+, 575.29158. found (ESI-FTMS, [M+H]$^{1+}$), 575.29261.

Step B: tert-butyl $N^1$-[2-(4-fluorophenyl)-1,1-dimethylethyl]-L-α-glutaminate

MS (ESI) m/z 353.2; HRMS: calcd for $C_{19}H_{29}FN_2O_3$+H+, 353.22350. found (ESI-FTMS, [M+H]$^{1+}$), 353.22526.

Step C: tert-butyl $N^2$-(1,1'-biphenyl-4-ylcarbonyl)-$N^1$-[2-(4-fluorophenyl)-1,1-dimethylethyl]-L-α-glutaminate MS (ESI) m/z 533.2; MS (ESI) m/z 1065.4; HRMS: calcd for $C_{32}H_{37}FN_2O_4$+H+, 533.28101. found (ESI-FTMS, [M+H]$^{1+}$), 533.28063.

Step D: $N^2$-(1,1'-biphenyl-4-ylcarbonyl)-$N^1$-[2-(4-fluorophenyl)-1,1-dimethylethyl]-L-α-glutamine MS (ESI) m/z 477.2; MS (ESI) m/z 953.3; HRMS: calcd for $C_{28}H_{29}FN_2O_4$+H+, 477.21841. found (ESI-FTMS, [M+H]$^{1+}$), 477.21783.

Example 8PP $N^2$-(biphenyl-4-ylcarbonyl)-$N^1$-(1,1-dimethyl-2-phenylethyl)-L-α-glutamine Step A: tert-butyl $N^1$-(1,1-dimethyl-2-phenylethyl)-$N^2$-[(9H-fluoren-9-ylmethoxy)carbonyl]-L-α-glutaminate MS (ESI) m/z 557.2; HRMS: calcd for $C_{34}H_{40}N_2O_5$+H+, 557.30100. found (ESI-FTMS, [M+H]$^{1+}$), 557.2994.

Step B: tert-butyl $N^1$-(1,1-dimethyl-2-phenylethyl)-L-α-glutaminate

MS (ESI) m/z 335.1; MS (ESI) m/z 669.3; HRMS: calcd for $C_{19}H_{30}N_2O_3$+H+, 335.23292. found (ESI-FTMS, [M+H]$^{1+}$), 335.23259.

Step C: tert-butyl $N^2$-(biphenyl-4-ylcarbonyl)-$N^1$-(1,1-dimethyl-2-phenylethyl)-L-α-glutaminate MS (ESI) m/z 515.2; MS (ESI) m/z 1029.3; HRMS: calcd for $C_{32}H_{38}N_2O_4$+H+, 515.29043. found (ESI-FTMS, [M+H]$^{1+}$), 515.29018.

Step D: N²-(biphenyl-4-ylcarbonyl)-N¹-(1,1-dimethyl-2-phenylethyl)-L-α-glutamine MS (ESI) m/z 459.1; MS (ESI) m/z 917.3; HRMS: calcd for $C_{28}H_{30}N_2O_4$+H+, 459.22783. found (ESI-FTMS, [M+H]$^{1+}$), 459.22858.

Example 8QQ

N²-(biphenyl-4-ylcarbonyl)-N¹-(3-isopropoxypropyl)-L-α-glutamine

Step A: tert-butyl N²-[(9H-fluoren-9-ylmethoxy)carbonyl]-N¹-(3-isopropoxypropyl)-L-α-glutaminate MS (ESI) m/z 525.3; MS (ESI) m/z 1049.5; HRMS: calcd for $C_{30}H_{40}N_2O_6$+H+, 525.29591. found (ESI-FTMS, [M+H]$^{1+}$), 525.29528.

Step B: tert-butyl N¹-(3-isopropoxypropyl)-L-α-glutaminate

MS (ESI) m/z 303.2; HRMS: calcd for $C_{15}H_{30}N_2O_4$+H+, 303.22783. found (ESI-FTMS, [M+H]$^{1+}$), 303.22747.

Step C: tert-butyl N²-(biphenyl-4-ylcarbonyl)-N¹-(3-isopropoxypropyl)-L-α-glutaminate MS (ESI) m/z 483.3; MS (ESI) m/z 965.5; HRMS: calcd for $C_{28}H_{38}N_2O_5$+H+, 483.28535. found (ESI-FTMS, [M+H]$^{1+}$), 483.28364.

Step D: N²-(biphenyl-4-ylcarbonyl)-N¹-(3-isopropoxypropyl)-L-α-glutamine

MS (ESI) m/z 427.2; MS (ESI) m/z 853.4; MS (ESI) m/z 449.2; HRMS: calcd for $C_{24}H_{30}N_2O_5$+H+, 427.22275. found (ESI-FTMS, [M+H]$^{1+}$), 427.22227.

Example 8RR

N²-(biphenyl-4-ylcarbonyl)-N¹-(3-methylbutyl)-L-α-glutamine

Step A: tert-butyl N²-[(9H-fluoren-9-ylmethoxy)carbonyl]-N¹-(3-methylbutyl)-L-α-glutaminate MS (ESI) m/z 495.2; MS (ESI) m/z 989.5; HRMS: calcd for $C_{29}H_{38}N_2O_5$+H+, 495.28535. found (ESI-FTMS, [M+H]$^{1+}$), 495.28729.

Step B: tert-butyl N¹-(3-methylbutyl)-L-α-glutaminate

MS (ESI) m/z 273.2; HRMS: calcd for $C_{14}H_{28}N_2O_3$+H+, 273.21727. found (ESI-FTMS, [M+H]$^{1+}$), 273.21718.

Step C: tert-butyl N²-(biphenyl-4-ylcarbonyl)-N¹-(3-methylbutyl)-L-α-glutaminate MS (ESI) m/z 453.3; MS (ESI) m/z 905.5; MS (ESI) m/z 475.2; HRMS: calcd for $C_{27}H_{36}N_2O_4$+H+, 453.27478. found (ESI-FTMS, [M+H]$^{1+}$), 453.27427.

Step D: N²-(biphenyl-4-ylcarbonyl)-N¹-(3-methylbutyl)-L-α-glutamine

MS (ESI) m/z 397.2; MS (ESI) m/z 793.3; HRMS: calcd for $C_{23}H_{28}N_2O_4$+H+, 397.21218. found (ESI-FTMS, [M+H]$^{1+}$), 397.21129.

Example 8SS

N²-(biphenyl-4-ylcarbonyl)-N¹-[2-(4-fluorophenyl)ethyl]-L-α-glutamine

Step A: tert-butyl N²-[(9H-fluoren-9-ylmethoxy)carbonyl]-N¹-[2-(4-fluorophenyl)ethyl]-L-α-glutaminate MS (ESI) m/z 547.2; MS (ESI) m/z 1093.3; HRMS: calcd for $C_{32}H_{35}FN_2O_5$+H+, 547.26028. found (ESI-FTMS, [M+H]$^{1+}$), 547.26067.

Step B: tert-butyl N¹-[2-(4-fluorophenyl)ethyl]-L-α-glutaminate

MS (ESI) m/z 325.1; HRMS: calcd for $C_{17}H_{25}FN_2O_3$+H+, 325.19220. found (ESI-FTMS, [M+H]$^{1+}$), 325.19212.

Step C: tert-butyl N²-(biphenyl-4-ylcarbonyl)-N¹-[2-(4-fluorophenyl)ethyl]-L-α-glutaminate MS (ESI) m/z 505.2; MS (ESI) m/z 1009.3; HRMS: calcd for $C_{30}H_{33}FN_2O_4$+H+, 505.24971. found (ESI-FTMS, [M+H]$^{1+}$), 505.25021.

Step D: N²-(biphenyl-4-ylcarbonyl)-N¹-[2-(4-fluorophenyl)ethyl]-L-α-glutamine

MS (ESI) m/z 449.1; MS (ESI) m/z 897.2; HRMS: calcd for $C_{26}H_{25}FN_2O_4$+H+, 449.18711. found (ESI-FTMS, [M+H]$^{1+}$), 449.18705.

Example 8TT

N²-(biphenyl-4-ylcarbonyl)-N¹-[2-(2-fluorophenyl)ethyl]-L-α-glutamine

Step A: tert-butyl N²-[(9H-fluoren-9-ylmethoxy)carbonyl]-N¹-[2-(2-fluorophenyl)ethyl]-L-α-glutaminate MS (ESI) m/z 547.2; MS (ESI) m/z 1093.3; HRMS: calcd for $C_{32}H_{35}FN_2O_5$+H+, 547.26028. found (ESI-FTMS, [M+H]$^{1+}$), 547.26138.

Step B: tert-butyl N¹-[2-(2-fluorophenyl)ethyl]-L-α-glutaminate

MS (ESI) m/z 325.1; MS (ESI) m/z 649.3; HRMS: calcd for $C_{17}H_{25}FN_2O_3$+H+, 325.19220. found (ESI-FTMS, [M+H]$^{1+}$), 325.19217.

Step C: tert-butyl N²-(biphenyl-4-ylcarbonyl)-N¹-[2-(2-fluorophenyl)ethyl]-L-α-glutaminate MS (ESI) m/z 505.2; MS (ESI) m/z 1009.3; HRMS: calcd for $C_{30}H_{33}FN_2O_4$+H+, 505.24971. found (ESI-FTMS, [M+H]$^{1+}$), 505.2497.

Step D: N²-(biphenyl-4-ylcarbonyl)-N¹-[2-(2-fluorophenyl)ethyl]-L-α-glutamine

MS (ESI) m/z 449.1; MS (ESI) m/z 897.2; HRMS: calcd for $C_{26}H_{25}FN_2O_4$+H+, 449.18711. found (ESI-FTMS, [M+H]$^{1+}$), 449.18744.

Example 8UU

N²-(biphenyl-4-ylcarbonyl)-N¹-[2-(4-chlorophenyl)ethyl]-L-α-glutamine

Step A: tert-butyl N¹-[2-(4-chlorophenyl)ethyl]-N²-[(9H-fluoren-9-ylmethoxy)carbonyl]-L-α-glutaminate MS (ESI) m/z 563.1; MS (ESI) m/z 1125.2; HRMS: calcd for $C_{32}H_{35}ClN_2O_5$+Na+, 585.21267. found (ESI-FTMS, [M+Na]$^{1+}$), 585.21454.

Step B: tert-butyl N¹-[2-(4-chlorophenyl)ethyl]-L-α-glutaminate

MS (ESI) m/z 341.1; MS (ESI) m/z 681.2; HRMS: calcd for $C_{17}H_{25}ClN_2O_3$+H+, 341.16265. found (ESI-FTMS, [M+H]$^{1+}$), 341.16311.

Step C: tert-butyl N²-(biphenyl-4-ylcarbonyl)-N¹-[2-(4-chlorophenyl)ethyl]-L-α-glutaminate MS (ESI) m/z 521.2; MS (ESI) m/z 1041.3; HRMS: calcd for $C_{30}H_{33}ClN_2O_4$+Na+, 543.20210. found (ESI-FTMS, [M+Na]$^{1+}$), 543.20393.

Step D: N²-(biphenyl-4-ylcarbonyl)-N¹-[2-(4-chlorophenyl)ethyl]-L-α-glutamine

MS (ESI) m/z 463.1; MS (ESI) m/z 927.1; HRMS: calcd for $C_{26}H_{25}ClN_2O_4$+H+, 465.15756. found (ESI-FTMS, [M+H]$^{1+}$), 465.15776.

Example 8VV

N²-(biphenyl-4-ylcarbonyl)-N¹-[2-(2-chlorophenyl)ethyl]-L-α-glutamine

Step A: tert-butyl N¹-[2-(2-chlorophenyl)ethyl]-N²-[(9H-fluoren-9-ylmethoxy)carbonyl]-L-α-glutaminate MS (ESI) m/z 563.1; MS (ESI) m/z 1125.2; HRMS: calcd for $C_{32}H_{35}ClN_2O_5$+H+, 563.23073. found (ESI-FTMS, [M+H]$^{1+}$), 563.23042.

Step B: tert-butyl N¹-[2-(2-chlorophenyl)ethyl]-L-α-glutaminate

MS (ESI) m/z 341.2; MS (ESI) m/z 681.3; MS (ESI) m/z 703.3; HRMS: calcd for $C_{17}H_{25}ClN_2O_3$+H+, 341.16265. found (ESI-FTMS, [M+H]$^{1+}$), 341.16301.

Step C: tert-butyl N²-(biphenyl-4-ylcarbonyl)-N¹-[2-(2-chlorophenyl)ethyl]-L-α-glutaminate MS (ESI) m/z 521.2; MS (ESI) m/z 1041.4; HRMS: calcd for $C_{30}H_{33}ClN_2O_4$+H+, 521.22016. found (ESI-FTMS, [M+H]$^{1+}$), 521.22075.

Step D: N²-(biphenyl-4-ylcarbonyl)-N¹-[2-(2-chlorophenyl)ethyl]-L-α-glutamine

MS (ESI) m/z 465; MS (ESI) m/z 487; HRMS: calcd for $C_{26}H_{25}ClN_2O_4$+H+, 465.15756. found (ESI-FTMS, [M+H]$^{1+}$), 465.15834.

Example 8WW

N²-(biphenyl-4-ylcarbonyl)-N¹-[2-(2-thienyl)ethyl]-L-α-glutamine

Step A: tert-butyl N²-[(9H-fluoren-9-ylmethoxy)carbonyl]-N¹-[2-(2-thienyl)ethyl]-L-α-glutaminate MS (ESI) m/z 535.1; MS (ESI) m/z 1069.2; HRMS: calcd for $C_{30}H_{34}N_2O_5S$+H+, 535.22612. found (ESI-FTMS, [M+H]$^{1+}$), 535.22756.

Step B: tert-butyl N¹-[2-(2-thienyl)ethyl]-L-α-glutaminate

MS (ESI) m/z 313.1; MS (ESI) m/z 625.2; HRMS: calcd for $C_{15}H_{24}N_2O_3S$+H+, 313.15804. found (ESI-FTMS, [M+H]$^{1+}$), 313.15788.

Step C: tert-butyl N²-(biphenyl-4-ylcarbonyl)-N¹-[2-(2-thienyl)ethyl]-L-α-glutaminate MS (ESI) m/z 493.2; MS (ESI) m/z 985.4; HRMS: calcd for $C_{28}H_{32}N_2O_4S$+H+, 493.21555. found (ESI-FTMS, [M+H]$^{1+}$), 493.21561.

Step D: N²-(biphenyl-4-ylcarbonyl)-N¹-[2-(2-thienyl)ethyl]-L-α-glutamine

MS (ESI) m/z 437.1; MS (ESI) m/z 873.3; HRMS: calcd for $C_{24}H_{24}N_2O_4S$+H+, 437.15295. found (ESI-FTMS, [M+H]$^{1+}$), 437.15163.

Example 8XX

N²-(1,1'-biphenyl-4-ylcarbonyl)-N¹-(3-fluorobenzyl)-L-α-glutamine

Step A: tert-butyl N²-[(9H-fluoren-9-ylmethoxy)carbonyl]-N¹-(3-fluorobenzyl)-L-α-glutaminate MS (ESI) m/z 533.2; HRMS: calcd for $C_{31}H_{33}FN_2O_5$+H+, 533.24463. found (ESI_FTMS, [M+H]$^{1+}$), 533.2447.

Step B: tert-butyl N¹-(3-fluorobenzyl)-L-α-glutaminate

MS (ESI) m/z 311.2; HRMS: calcd for $C_{16}H_{23}FN_2O_3$+H+, 311.17655. found (ESI_FTMS, [M+H]$^{1+}$), 311.1764.

Step C: tert-butyl N²-(1,1'-biphenyl-4-ylcarbonyl)-N¹-(3-fluorobenzyl)-L-α-glutaminate MS (ESI) m/z 491.2; MS (ESI) m/z 981.4; HRMS: calcd for $C_{29}H_{31}FN_2O_4$+H+, 491.23406. found (ESI_FTMS, [M+H]$^{1+}$), 491.2339.

Step D: N²-(1,1'-biphenyl-4-ylcarbonyl)-N¹-(3-fluo-
robenzyl)-L-α-glutamine

MS (ESI) m/z 435.1; MS (ESI) m/z 869.2; HRMS: calcd for $C_{25}H_{23}FN_2O_4$+H+, 435.17146. found (ESI_FTMS, [M+H]$^{1+}$), 435.1712.

Example 8YY

N²-(1,1'-biphenyl-4-ylcarbonyl)-N¹-[2-(3-chlorophe-
nyl)ethyl]-L-α-glutamine

Step A: tert-butyl N¹-[2-(3-chlorophenyl)ethyl]-N²-
[(9H-fluoren-9-ylmethoxy)carbonyl]-L-α-glutami-
nate MS m/z 03-305496LMS; HRMS: calcd for $C_{32}H_{35}ClN_2O_5$+H+, 563.23073. found (ESI_FTMS, [M+H]$^{1+}$), 563.2309.

Step B: tert-butyl N¹-[2-(3-chlorophenyl)ethyl]-L-α-
glutaminate

MS (ESI) m/z 341.1; HRMS: calcd for $C_{17}H_{25}ClN_2O_3$+H+, 341.16265. found (ESI_FTMS, [M+H]$^{1+}$), 341.1611.

Step C: tert-butyl N²-(1,1'-biphenyl-4-ylcarbonyl)-
N¹-[2-(3-chlorophenyl)ethyl]-L-α-glutaminate MS (ESI) m/z 521.1; MS (ESI) m/z 1041.1; HRMS: calcd for $C_{30}H_{33}ClN_2O_4$+H+, 521.22016. found (ESI-FTMS, [M+H]$^{1+}$), 521.22136.

Step D: N²-(1,1'-biphenyl-4-ylcarbonyl)-N¹-[2-(3-
chlorophenyl)ethyl]-L-α-glutamine MS (ESI–) m/z 463.2; MS (ESI–) m/z 197; HRMS: calcd for $C_{26}H_{25}ClN_2O_4$+H+, 465.15756. found (ESI-FTMS, [M+H]$^{1+}$), 465.15709.

Example 8ZZ

N²-(1,1'-biphenyl-4-ylcarbonyl)-N¹-(2-fluoroben-
zyl)-L-α-glutamine

Step A: tert-butyl N²-[(9H-fluoren-9-ylmethoxy)
carbonyl]-N¹-(2-fluorobenzyl)-L-α-glutaminate MS (ESI) m/z 533.1; MS (ESI) m/z 1065.1; HRMS: calcd for $C_{31}H_{33}FN_2O_5$+H+, 533.24463. found (ESI_FTMS, [M+H]$^{1+}$), 533.24461.

Step B: tert-butyl N¹-(2-fluorobenzyl)-L-α-glutami-
nate

MS (ESI) m/z 311.1; MS (ESI) m/z 621.2; HRMS: calcd for $C_{16}H_{23}FN_2O_3$+H+, 311.17655. found (ESI_FTMS, [M+H]$^{1+}$), 311.1762.

Step C: tert-butyl N²-(1,1'-biphenyl-4-ylcarbonyl)-
N¹-(2-fluorobenzyl)-L-α-glutaminate MS (ESI) m/z 491.1; MS (ESI) m/z 981.2; HRMS: calcd for $C_{29}H_{31}FN_2O_4$+H+, 491.23406. found (ESI-FTMS, [M+H]$^{1+}$), 491.23526.

Step D: N²-(1,1'-biphenyl-4-ylcarbonyl)-N¹-(2-fluo-
robenzyl)-L-α-glutamine

MS (ESI–) m/z 433.1; HRMS: calcd for $C_{25}H_{23}FN_2O_4$+H+, 435.17146. found (ESI-FTMS, [M+H]$^{1+}$), 435.17161.

Example 8AAA

N²-(1,1'-biphenyl-4-ylcarbonyl)-N¹-(3,4-difluo-
robenzyl)-L-α-glutamine

Step A: tert-butyl N¹-(3,4-difluorobenzyl)-N²-[(9H-
fluoren-9-ylmethoxy)carbonyl]-L-α-glutaminate MS (ESI) m/z 551.2; MS (ESI) m/z 1101.4; HRMS: calcd for $C_{31}H_{32}F_2N_2O_5$+H+, 551.23521. found (ESI_FT, [M+H]$^{1+}$), 551.23407.

Step B: tert-butyl N¹-(3,4-difluorobenzyl)-L-α-
glutaminate

MS (ESI) m/z 329; MS (ESI) m/z 657.2; HRMS: calcd for $C_{16}H_{22}F_2N_2O_3$+H+, 329.16712. found (ESI_FTMS, [M+H]$^{1+}$), 329.1664.

Step C: tert-butyl N²-(1,1'-biphenyl-4-ylcarbonyl)-
N¹-(3,4-difluorobenzyl)-L-α-glutaminate MS (ESI) m/z 509.1; MS (ESI) m/z 1017.1; HRMS: calcd for $C_{29}H_{30}F_2N_2O_4$+H+, 509.22464. found (ESI-FTMS, [M+H]$^{1+}$), 509.22485.

Step D: N²-(1,1'-biphenyl-4-ylcarbonyl)-N¹-(3,4-
difluorobenzyl)-L-α-glutamine

MS (ESI–) m/z 451.1; HRMS: calcd for $C_{25}H_{22}F_2N_2O_4$+H+, 453.16204. found (ESI-FTMS, [M+H]$^{1+}$), 453.1614.

Example 8BBB

N²-(1,1'-biphenyl-4-ylcarbonyl)-N¹-(sec-butyl)-L-α-
glutamine

Step A: tert-butyl N¹-(sec-butyl)-N²-[(9H-fluoren-9-
ylmethoxy)carbonyl]-L-α-glutaminate MS (ESI) m/z 481.2; HRMS: calcd for $C_{28}H_{36}N_2O_5$+H+, 481.26970. found (ESI-FTMS, [M+H]$^{1+}$), 481.26966.

Step B: tert-butyl N¹-(sec-butyl)-L-α-glutaminate

MS (ESI) m/z 259.1; HRMS: calcd for $C_{13}H_{26}N_2O_3$+H+, 259.20162. found (ESI-FTMS, [M+H]$^{1+}$), 259.20164.

Step C: tert-butyl N²-(1,1'-biphenyl-4-ylcarbonyl)-
N¹-(sec-butyl)-L-α-glutaminate MS (ESI) m/z 439.2; MS (ESI) m/z 877.4; HRMS: calcd for $C_{26}H_{34}N_2O_4$+H+, 439.25913. found (ESI-FTMS, [M+H]$^{1+}$), 439.25972.

Step D: N²-(1,1'-biphenyl-4-ylcarbonyl)-N¹-(sec-
butyl)-L-α-glutamine

MS (ESI) m/z 383.1; MS (ESI) m/z 765.3; MS (ESI) m/z 441.2; HRMS: calcd for $C_{22}H_{26}N_2O_4$+H+, 383.19653. found (ESI-FTMS, [M+H]$^{1+}$), 383.19745.

Example 8CCC $N^2$-(1,1'-biphenyl-4-ylcarbonyl)-$N^1$-(cyclopropylmethyl)-L-α-glutamine Step A: tert-butyl $N^1$-(cyclopropylmethyl)-$N^2$-[(9H-fluoren-9-ylmethoxy)carbonyl]-L-α-glutaminate MS (ESI) m/z 479.2; MS (ESI) m/z 957.3; HRMS: calcd for $C_{28}H_{34}N_2O_5$+H+, 479.25405. found (ESI-FTMS, [M+H]$^{1+}$), 479.25563.

Step B: tert-butyl $N^1$-(cyclopropylmethyl)-L-α-glutaminate

MS (ESI) m/z 257.1; HRMS: calcd for $C_{13}H_{24}N_2O_3$+H+, 257.18597. found (ESI-FTMS, [M+H]$^{1+}$), 257.18608.

Step C: tert-butyl $N^2$-(1,1'-biphenyl-4-ylcarbonyl)-$N^1$-(cyclopropylmethyl)-L-α-glutaminate MS (ESI) m/z 437.2; MS (ESI) m/z 873.3; HRMS: calcd for $C_{26}H_{32}N_2O_4$+H+, 437.24348. found (ESI-FTMS, [M+H]$^{1+}$), 437.24446.

Step D: $N^2$-(1,1'-biphenyl-4-ylcarbonyl)-$N^1$-(cyclopropylmethyl)-L-α-glutamine MS (ESI) m/z 381.1; MS (ESI) m/z 761.2; HRMS: calcd for $C_{22}H_{24}N_2O_4$+H+, 381.18088. found (ESI-FTMS, [M+H]$^{1+}$), 381.18186.

Example 8DDD $N^2$-(biphenyl-4-ylcarbonyl)-$N^1$-(2-morpholin-4-ylethyl)-L-α-glutamine Step A: tert-butyl $N^2$-[(9H-fluoren-9-ylmethoxy)carbonyl]-$N^1$-(2-morpholin-4-ylethyl)-L-α-glutaminate MS (ESI) m/z 538.3; HRMS: calcd for $C_{30}H_{39}N_3O_6$+H+, 538.29116. found (ESI-FTMS, [M+H]$^{1+}$), 538.29233.

Step C: tert-butyl $N^2$-(biphenyl-4-ylcarbonyl)-$N^1$-(2-morpholin-4-ylethyl)-L-α-glutaminate MS (ESI) m/z 496.2; HRMS: calcd for $C_{28}H_{37}N_3O_5$+H+, 496.28060. found (ESI-FTMS, [M+H]$^{1+}$), 496.28079.

Step D: $N^2$-(biphenyl-4-ylcarbonyl)-$N^1$-(2-morpholin-4-ylethyl)-L-α-glutamine MS (ESI) m/z 440.2; HRMS: calcd for $C_{24}H_{29}N_3O_5$+H+, 440.21800. found (ESI-FTMS, [M+H]$^{1+}$), 440.21827.

Example 8EEE $N^2$-(biphenyl-4-ylcarbonyl)-$N^1$,$N^1$-diethyl-L-α-glutamine Step A: tert-butyl $N^1$,$N^1$-diethyl-$N^2$-[(9H-fluoren-9-ylmethoxy)carbonyl]-L-α-glutaminate MS (ESI) m/z 481.3; MS (ESI) m/z 961.5; HRMS: calcd for $C_{28}H_{36}N_2O_5$+Na+, 503.25164. found (ESI-FTMS, [M+Na]$^{1+}$), 503.25163.

Step B: tert-butyl $N^1$,$N^1$-diethyl-L-α-glutaminate

MS (ESI) m/z 259.2; HRMS: calcd for $C_{13}H_{26}N_2O_3$+H+, 259.20162. found (ESI-FTMS, [M+H]$^{1+}$), 259.20149.

Step C: tert-butyl $N^2$-(biphenyl-4-ylcarbonyl)-$N^1$,$N^1$-diethyl-L-α-glutaminate MS (ESI) m/z 439.2; MS (ESI) m/z 877.4; HRMS: calcd for $C_{26}H_{34}N_2O_4$+H+, 439.25913. found (ESI-FTMS, [M+H]$^{1+}$), 439.26093.

Step D: $N^2$-(biphenyl-4-ylcarbonyl)-$N^1$,$N^1$-diethyl-L-α-glutamine

MS (ESI) m/z 383.2; MS (ESI) m/z 765.4; HRMS: calcd for $C_{22}H_{26}N_2O_4$+H+, 383.19653. found (ESI-FTMS, [M+H]$^{1+}$), 383.19675.

Example 8FFF $N^2$-(1,1'-biphenyl-4-ylcarbonyl)-$N^1$-(2-phenylethyl)-L-α-glutamine Step A: tert-butyl $N^2$-[(9H-fluoren-9-ylmethoxy)carbonyl]-$N^1$-(2-phenylethyl)-L-α-glutaminate MS (ESI) m/z 529.2; HRMS: calcd for $C_{32}H_{36}N_2O_5$+H+, 529.26970. found (ESI_FTMS, [M+H]$^{1+}$), 529.2693.

Step B: tert-butyl $N^1$-(2-phenylethyl)-L-α-glutaminate

HRMS: calcd for $C_{17}H_{26}N_2O_3$+H+, 307.20162. found (ESI_FTMS, [M+H]$^{1+}$), 307.2011.

Step C: tert-butyl $N^2$-(1,1'-biphenyl-4-ylcarbonyl)-$N^1$-(2-phenylethyl)-L-α-glutaminate MS (ESI) m/z 487.2; MS (ESI) m/z 973.3; HRMS: calcd for $C_{30}H_{34}N_2O_4$+H+, 487.25913. found (ESI_FTMS, [M+H]$^{1+}$), 487.2588.

Step D: $N^2$-(1,1'-biphenyl-4-ylcarbonyl)-$N^1$-(2-phenylethyl)-L-α-glutamine

MS (ESI) m/z 431.2; MS (ESI) m/z 861.3; HRMS: calcd for $C_{26}H_{26}N_2O_4$+H+, 431.19653. found (ESI_FTMS, [M+H]$^{1+}$), 431.1963.

Example 8GGG $N^2$-(1,1'-biphenyl-4-ylcarbonyl)-$N^1$-[3-(trifluoromethyl)benzyl]-L-α-glutamine Step A: tert-butyl $N^2$-[(9H-fluoren-9-ylmethoxy)carbonyl]-$N^1$-[3-(trifluoromethyl)benzyl]-L-α-glutaminate MS (ESI) m/z 583.2; HRMS: calcd for $C_{32}H_{33}F_3N_2O_5$+H+, 583.24143. found (ESI_FTMS, [M+H]$^{1+}$), 583.2409.

Step B: tert-butyl $N^1$-[3-(trifluoromethyl)benzyl]-L-α-glutaminate

HRMS: calcd for $C_{17}H_{23}F_3N_2O_3$+H+, 361.17335. found (ESI_FTMS, [M+H]$^{1+}$), 361.173.

Step C: tert-butyl $N^2$-(1,1'-biphenyl-4-ylcarbonyl)-$N^1$-[3-(trifluoromethyl)benzyl]-L-α-glutaminate MS (ESI) m/z 541.2; MS (ESI) m/z 1081.3; HRMS: calcd for $C_{30}H_{31}F_3N_2O_4$+H+, 541.23087. found (ESI_FTMS, [M+H]$^{1+}$), 541.2301.

Step D: $N^2$-(1,1'-biphenyl-4-ylcarbonyl)-$N^1$-[3-(trifluoromethyl)benzyl]-L-α-glutamine MS (ESI) m/z 485.2; MS (ESI) m/z 969.3; HRMS: calcd for $C_{26}H_{23}F_3N_2O_4$+H+, 485.16827. found (ESI_FTMS, [M+H]$^{1+}$), 485.1682.

Example 8HHH $N^2$-(1,1'-biphenyl-4-ylcarbonyl)-$N^1$-[2-(trifluoromethyl)benzyl]-L-α-glutamine Step A: tert-butyl $N^2$-[(9H-fluoren-9-ylmethoxy)carbonyl]-$N^1$-[2-(trifluoromethyl)benzyl]-L-α-glutaminate MS (ESI) m/z 583.2; HRMS: calcd for $C_{32}H_{33}F_3N_2O_5$+H+, 583.24143. found (ESI_FT, [M+H]$^{1+}$), 583.24162.

Step B: tert-butyl $N^1$-[2-(trifluoromethyl)benzyl]-L-α-glutaminate

HRMS: calcd for $C_{17}H_{23}F_3N_2O_3$+H+, 361.17335. found (ESI_FTMS, [M+H]$^{1+}$), 361.1725.

Step C: tert-butyl $N^2$-(1,1'-biphenyl-4-ylcarbonyl)-$N^1$-[2-(trifluoromethyl)benzyl]-L-α-glutaminate MS (ESI) m/z 541.2; MS (ESI) m/z 1081.2; HRMS: calcd for $C_{30}H_{31}F_3N_2O_4$+H+, 541.23087. found (ESI_FTMS, [M+H]$^{1+}$), 541.23091.

Step D: $N^2$-(1,1'-biphenyl-4-ylcarbonyl)-$N^1$-[2-(trifluoromethyl)benzyl]-L-α-glutamine MS (ESI) m/z 485; MS (ESI) m/z 969; HRMS: calcd for $C_{26}H_{23}F_3N_2O_4$+H+, 485.16827. found (ESI_FTMS, [M+H]$^{1+}$), 485.168.

Example 8III $N^2$-(1,1'-biphenyl-4-ylcarbonyl)-$N^1$-(4-methylbenzyl)-L-α-glutamine Step A: tert-butyl $N^2$-[(9H-fluoren-9-ylmethoxy)carbonyl]-$N^1$-(4-methylbenzyl)-L-α-glutaminate MS (ESI) m/z 529.2; MS (ESI) m/z 1057.4; HRMS: calcd for $C_{32}H_{36}N_2O_5$+H+, 529.26970. found (ESI_FT, [M+H]$^{1+}$), 529.26796.

Step B: tert-butyl $N^1$-(4-methylbenzyl)-L-α-glutaminate

HRMS: calcd for $C_{17}H_{26}N_2O_3$+H+, 307.20162. found (ESI-FTMS, [M+H]$^{1+}$), 307.20274.

Step C: tert-butyl $N^2$-(1,1'-biphenyl-4-ylcarbonyl)-$N^1$-(4-methylbenzyl)-L-α-glutaminate HRMS: calcd for $C_{30}H_{34}N_2O_4$+H+, 487.25913. found (ESI-FTMS, [M+H]$^{1+}$), 487.25856.

Step D: $N^2$-(1,1'-biphenyl-4-ylcarbonyl)-$N^1$-(4-methylbenzyl)-L-α-glutamine

HRMS: calcd for $C_{26}H_{26}N_2O_4$+H+, 431.19653. found (ESI-FTMS, [M+H]$^{1+}$), 431.19627.

Example 8JJJ $N^2$-(1,1'-biphenyl-4-ylcarbonyl)-$N^1$-heptyl-L-α-glutamine

Step A: tert-butyl $N^2$-[(9H-fluoren-9-ylmethoxy)carbonyl]-$N^1$-heptyl-L-α-glutaminate MS (ESI) m/z 523.3; MS (ESI) m/z 1045.5; HRMS: calcd for $C_{31}H_{42}N_2O_5$+H+, 523.31665. found (ESI-FTMS, [M+H]$^{1+}$), 523.31783.

Step B: tert-butyl $N^1$-heptyl-L-α-glutaminate

HRMS: calcd for $C_{16}H_{32}N_2O_3$+H+, 301.24857. found (ESI-FTMS, [M+H]$^{1+}$), 301.2499.

Step C: tert-butyl $N^2$-(1,1'-biphenyl-4-ylcarbonyl)-$N^1$-heptyl-L-α-glutaminate HRMS: calcd for $C_{29}H_{40}N_2O_4$+H+, 481.30608. found (ESI-FTMS, [M+H]$^{1+}$), 481.30706.

Step D: $N^2$-(1,1'-biphenyl-4-ylcarbonyl)-$N^1$-heptyl-L-α-glutamine

HRMS: calcd for $C_{25}H_{32}N_2O_4$+H+, 425.24348. found (ESI-FTMS, [M+H]$^{1+}$), 425.24417.

Example 8KKK $N^2$-(biphenyl-4-ylcarbonyl)-$N^1$-[2-(4-bromophenyl)ethyl]-L-α-glutamine Step A: tert-butyl $N^1$-[2-(4-bromophenyl)ethyl]-$N^2$-[(9H-fluoren-9-ylmethoxy)carbonyl]-L-α-glutaminate MS (ESI) m/z 607.1; HRMS: calcd for $C_{32}H_{35}BrN_2O_5$+H+, 607.18021. found (ESI-FTMS, [M+H]$^{1+}$), 607.18182.

Step B: tert-butyl $N^1$-[2-(4-bromophenyl)ethyl]-L-α-glutaminate

MS (ESI) m/z 385; HRMS: calcd for $C_{17}H_{25}BrN_2O_3$+H+, 385.11213. found (ESI-FTMS, [M+H]$^{1+}$), 385.11309.

Step C: tert-butyl $N^2$-(biphenyl-4-ylcarbonyl)-$N^1$-[2-(4-bromophenyl)ethyl]-L-α-glutaminate MS (ESI) m/z 565.1; MS (ESI) m/z 1129.1; HRMS: calcd for $C_{30}H_{33}BrN_2O_4$+H+, 565.16965. found (ESI-FTMS, [M+H]$^{1+}$), 565.17.

Step D: $N^2$-(biphenyl-4-ylcarbonyl)-$N^1$-[2-(4-bromophenyl)ethyl]-L-α-glutamine MS (ESI) m/z 507.2; HRMS: calcd for $C_{26}H_{25}BrN_2O_4$+H+, 509.10705. found (ESI-FTMS, [M+H]$^{1+}$), 509.10906.

Example 8LLL $N^2$-(biphenyl-4-ylcarbonyl)-$N^1$-(3,3-dimethylbutyl)-L-α-glutamine Step A: tert-butyl $N^1$-(3,3-dimethylbutyl)-$N^2$-[(9H-fluoren-9-ylmethoxy)carbonyl]-L-α-glutaminate MS (ESI) m/z 509.3; MS (ESI) m/z 1017.5; HRMS: calcd for $C_{30}H_{40}N_2O_5$+H+, 509.30100. found (ESI-FTMS, [M+H]$^{1+}$), 509.30165.

Step C: tert-butyl $N^2$-(biphenyl-4-ylcarbonyl)-$N^1$-(3,3-dimethylbutyl)-L-α-glutaminate MS (ESI) m/z 467.3; MS (ESI) m/z 933.5; MS (ESI) m/z 489.3; HRMS: calcd for $C_{28}H_{38}N_2O_4$+H+, 467.29043. found (ESI-FTMS, [M+H]$^{1+}$), 467.29134.

Step D: $N^2$-(biphenyl-4-ylcarbonyl)-$N^1$-(3,3-dimethylbutyl)-L-α-glutamine

HRMS: calcd for $C_{24}H_{30}N_2O_4$+H+, 411.22783. found (ESI-FTMS, [M+H]$^{1+}$), 411.22929.

Example 8MMM $N^2$-(biphenyl-4-ylcarbonyl)-$N^1$-[2-(3-bromophenyl)ethyl]-L-α-glutamine Step A: tert-butyl $N^1$-[2-(3-bromophenyl)ethyl]-$N^2$-[(9H-fluoren-9-ylmethoxy)carbonyl]-L-α-glutaminate MS (ESI) m/z 607.1; MS (ESI) m/z 1213.3; HRMS: calcd for $C_{32}H_{35}BrN_2O_5$+H+, 607.18021. found (ESI-FTMS, [M+H]$^{1+}$), 607.18017.

Step B: tert-butyl $N^1$-[2-(3-bromophenyl)ethyl]-L-α-glutaminate

MS (ESI) m/z 385.1; MS (ESI) m/z 769.2; HRMS: calcd for $C_{17}H_{25}BrN_2O_3$+H+, 385.11213. found (ESI-FTMS, [M+H]$^{1+}$), 385.11175.

Step C: tert-butyl $N^2$-(biphenyl-4-ylcarbonyl)-$N^1$-[2-(3-bromophenyl)ethyl]-L-α-glutaminate HRMS: calcd for $C_{30}H_{33}BrN_2O_4$+H+, 565.16965. found (ESI-FTMS, [M+H]$^{1+}$), 565.16854.

Step D: $N^2$-(biphenyl-4-ylcarbonyl)-$N^1$-[2-(3-bromophenyl)ethyl]-L-α-glutamine HRMS: calcd for $C_{26}H_{25}BrN_2O_4$+H+, 509.10705. found (ESI-FTMS, [M+H]$^{1+}$), 509.10648.

Example 8NNN $N^2$-(1,1'-biphenyl-4-ylcarbonyl)-$N^1$-[4-fluoro-3-(trifluoromethyl)benzyl]-L-α-glutamine Step A: tert-butyl $N^2$-[(9H-fluoren-9-ylmethoxy)carbonyl]-$N^1$-[4-fluoro-3-(trifluoromethyl)benzyl]-L-α-glutaminate MS (ESI) m/z 601.2; MS (ESI) m/z 1201.3; HRMS: calcd for $C_{32}H_{32}F_4N_2O_5$+H+, 601.23201. found (ESI-FTMS, [M+H]$^{1+}$), 601.23172.

Step B: tert-butyl $N^1$-[4-fluoro-3-(trifluoromethyl)benzyl]-L-α-glutaminate

HRMS: calcd for $C_{17}H_{22}F_4N_2O_3$+H+, 379.16393. found (ESI-FTMS, [M+H]$^{1+}$), 379.16566.

Step C: tert-butyl $N^2$-(1,1'-biphenyl-4-ylcarbonyl)-$N^1$-[4-fluoro-3-(trifluoromethyl)benzyl]-L-α-glutaminate HRMS: calcd for $C_{30}H_{30}F_4N_2O_4$+H+, 559.22145. found (ESI-FTMS, [M+H]$^{1+}$), 559.22077.

Step D: $N^2$-(1,1'-biphenyl-4-ylcarbonyl)-$N^1$-[4-fluoro-3-(trifluoromethyl)benzyl]-L-α-glutamine HRMS: calcd for $C_{26}H_{22}F_4N_2O_4$+H+, 503.15885. found (ESI-FTMS, [M+H]$^{1+}$), 503.1582.

Example 8OOO $N^2$-(biphenyl-4-ylcarbonyl)-$N^1$-(3,3-diphenylpropyl)-L-α-glutamine Step A: tert-butyl $N^1$-(3,3-diphenylpropyl)-$N^2$-[(9H-fluoren-9-ylmethoxy)carbonyl]-L-α-glutaminate MS (ESI) m/z 619.3; MS (ESI) m/z 1237.6; HRMS: calcd for $C_{39}H_{42}N_2O_5$+H+, 619.31665. found (ESI-FTMS, [M+H]$^{1+}$), 619.31658.

Step C: tert-butyl $N^2$-(biphenyl-4-ylcarbonyl)-$N^1$-(3,3-diphenylpropyl)-L-α-glutaminate HRMS: calcd for $C_{37}H_{40}N_2O_4$+H+, 577.30608. found (ESI-FTMS, [M+H]$^{1+}$), 577.30483.

Step D: $N^2$-(biphenyl-4-ylcarbonyl)-$N^1$-(3,3-diphenylpropyl)-L-α-glutamine

HRMS: calcd for $C_{33}H_{32}N_2O_4$+H+, 521.24348. found (ESI-FTMS, [M+H]$^{1+}$), 521.24166.

Example 8PPP $N^2$-(biphenyl-4-ylcarbonyl)-$N^1$-isopropyl-L-α-glutamine

Step A: tert-butyl $N^2$-[(9H-fluoren-9-ylmethoxy)carbonyl]-$N^1$-isopropyl-L-α-glutaminate MS (ESI) m/z 467.2; MS (ESI) m/z 933.5; HRMS: calcd for $C_{27}H_{34}N_2O_5$+Na+, 489.23599. found (ESI-FTMS, [M+Na]$^{1+}$), 489.23577.

Step C: tert-butyl $N^2$-(biphenyl-4-ylcarbonyl)-$N^1$-isopropyl-L-α-glutaminate MS (ESI) m/z 425.2; MS (ESI) m/z 447.2; MS (ESI) m/z 871.4; HRMS: calcd for $C_{25}H_{32}N_2O_4$+Na+, 447.22543. found (ESI-FTMS, [M+Na]$^{1+}$), 447.22701.

Step D: $N^2$-(biphenyl-4-ylcarbonyl)-$N^1$-isopropyl-L-α-glutamine

MS (ESI) m/z 367.2; MS (ESI) m/z 735.3; MS (ESI) m/z 481.2; HRMS: calcd for $C_{21}H_{24}N_2O_4$+Na+, 391.16283. found (ESI-FTMS, [M+Na]$^{1+}$), 391.16451.

Example 8QQQ $N^2$-(biphenyl-4-ylcarbonyl)-$N^1$-(pyridin-4-ylmethyl)-L-α-glutamine Step A: tert-butyl $N^2$-[(9H-fluoren-9-ylmethoxy)carbonyl]-$N^1$-(pyridin-4-ylmethyl)-L-α-glutaminate MS (ESI) m/z 516.3; HRMS: calcd for $C_{30}H_{33}N_3O_5$+H+, 516.24930. found (ESI_FTMS, [M+H]$^{1+}$), 516.24875.

Step C: tert-butyl $N^2$-(biphenyl-4-ylcarbonyl)-$N^1$-(pyridin-4-ylmethyl)-L-α-glutaminate MS (ESI) m/z 474.2; HRMS: calcd for $C_{28}H_{31}N_3O_4$+H+, 474.23873. found (ESI-FTMS, [M+H]$^{1+}$), 474.24265.

Step D: $N^2$-(biphenyl-4-ylcarbonyl)-$N^1$-(pyridin-4-ylmethyl)-L-α-glutamine

HRMS: calcd for $C_{24}H_{23}N_3O_4$+H+, 418.17613. found (ESI-FTMS, [M+H]$^{1+}$), 418.17812.

Example 8RRR $N^2$-(biphenyl-4-ylcarbonyl)-$N^1$-pentyl-L-α-glutamine

Step A: tert-butyl $N^2$-[(9H-fluoren-9-ylmethoxy)carbonyl]-$N^1$-pentyl-L-α-glutaminate MS (ESI) m/z 495.2; MS (ESI) m/z 989.5; HRMS: calcd for $C_{29}H_{38}N_2O_5$+Na+, 517.26729. found (ESI-FTMS, [M+Na]$^{1+}$), 517.26785.

Step B: tert-butyl $N^1$-pentyl-L-α-glutaminate

MS (ESI) m/z 273.2; HRMS: calcd for $C_{14}H_{28}N_2O_3$+H+, 273.21727. found (ESI-FTMS, [M+H]$^{1+}$), 273.21761.

Step C: tert-butyl $N^2$-(biphenyl-4-ylcarbonyl)-$N^1$-pentyl-L-α-glutaminate

MS (ESI) m/z 453.2; MS (ESI) m/z 905.5; HRMS: calcd for $C_{27}H_{36}N_2O_4$+H+, 453.27478. found (ESI-FTMS, [M+H]$^{1+}$), 453.27694.

Step D: $N^2$-(biphenyl-4-ylcarbonyl)-$N^1$-pentyl-L-α-glutamine

MS (ESI) m/z 397.2; MS (ESI) m/z 793.4; HRMS: calcd for $C_{23}H_{28}N_2O_4$+H+, 397.21218. found (ESI-FTMS, [M+H]$^{1+}$), 397.2136.

Example 8SSS $N^2$-(biphenyl-4-ylcarbonyl)-$N^1$-(tert-butyl)-L-α-glutamine

Step A: tert-butyl $N^1$-(tert-butyl)-$N^2$-[(9H-fluoren-9-ylmethoxy)carbonyl]-L-α-glutaminate MS (ESI) m/z 481.2; MS (ESI) m/z 961.5; HRMS: calcd for $C_{28}H_{36}N_2O_5$+H+, 481.26970. found (ESI-FTMS, [M+H]$^{1+}$), 481.27074.

Step B: tert-butyl $N^1$-(tert-butyl)-L-α-glutaminate

MS (ESI) m/z 259.1; MS (ESI) m/z 517.3; HRMS: calcd for $C_{13}H_{26}N_2O_3$+H+, 259.20162. found (ESI-FTMS, [M+H]$^{1+}$), 259.20174.

Step C: tert-butyl $N^2$-(biphenyl-4-ylcarbonyl)-$N^1$-(tert-butyl)-L-α-glutaminate MS (ESI) m/z 439.2; MS (ESI) m/z 877.4; HRMS: calcd for $C_{26}H_{34}N_2O_4$+H+, 439.25913. found (ESI-FTMS, [M+H]$^{1+}$), 439.25922.

Step D: $N^2$-(biphenyl-4-ylcarbonyl)-$N^1$-(tert-butyl)-L-α-glutamine

MS (ESI) m/z 383.2; MS (ESI) m/z 765.3; HRMS: calcd for $C_{22}H_{26}N_2O_4$+H+, 383.19653. found (ESI-FTMS, [M+H]$^{1+}$), 383.19812.

Example 8TTT $N^2$-(biphenyl-4-ylcarbonyl)-$N^1$-(1-methyl-1-phenylethyl)-L-α-glutamine Step A: tert-butyl $N^2$-[(9H-fluoren-9-ylmethoxy)carbonyl]-$N^1$-(1-methyl-1-phenylethyl)-L-α-glutaminate MS (ESI) m/z 543.2; MS (ESI) m/z 1085.4; HRMS: calcd for $C_{33}H_{38}N_2O_5$+H+, 543.28535. found (ESI-FTMS, [M+H]$^{1+}$), 543.28707.

Step B: tert-butyl $N^1$-(1-methyl-1-phenylethyl)-L-α-glutaminate

MS (ESI) m/z 321.1; MS (ESI) m/z 641.3; HRMS: calcd for $C_{18}H_{28}N_2O_3$+H+, 321.21727. found (ESI-FTMS, [M+H]$^{1+}$), 321.21716.

Step C: tert-butyl $N^2$-(biphenyl-4-ylcarbonyl)-$N^1$-(1-methyl-1-phenylethyl)-L-α-glutaminate MS (ESI) m/z 501.2; MS (ESI) m/z 1001.4; HRMS: calcd for $C_{31}H_{36}N_2O_4$+H+, 501.27478. found (ESI-FTMS, [M+H]$^{1+}$), 501.27462.

Step D: $N^2$-(biphenyl-4-ylcarbonyl)-$N^1$-(1-methyl-1-phenylethyl)-L-α-glutamine HRMS: calcd for $C_{27}H_{28}N_2O_4$+H+, 445.21218. found (ESI-FTMS, [M+H]$^{1+}$), 445.21311.

Example 8UUU $N^2$-(biphenyl-4-ylcarbonyl)-$N^1$-(2,2-dimethylpropyl)-L-α-glutamine Step A: tert-butyl $N^1$-(2,2-dimethylpropyl)-$N^2$-[(9H-fluoren-9-ylmethoxy)carbonyl]-L-α-glutaminate MS (ESI) m/z 495.2; MS (ESI) m/z 989.4; HRMS: calcd for $C_{29}H_{38}N_2O_5$+H+, 495.28535. found (ESI-FTMS, [M+H]$^{1+}$), 495.2859.

Step C: tert-butyl $N^2$-(biphenyl-4-ylcarbonyl)-$N^1$-(2,2-dimethylpropyl)-L-α-glutaminate MS (ESI) m/z 453.2; MS (ESI) m/z 905.4; HRMS: calcd for $C_{27}H_{36}N_2O_4$+H+, 453.27478. found (ESI-FTMS, [M+H]$^{1+}$), 453.2764.

Step D: $N^2$-(biphenyl-4-ylcarbonyl)-$N^1$-(2,2-dimethylpropyl)-L-α-glutamine

MS (ESI) m/z 397.1; MS (ESI) m/z 793.3; HRMS: calcd for $C_{23}H_{28}N_2O_4$+H+, 397.21218. found (ESI-FTMS, [M+H]$^{1+}$), 397.21242.

Example 8VVV $N^2$-(biphenyl-4-ylcarbonyl)-$N^1$-hexyl-L-α-glutamine

Step A: tert-butyl $N^2$-[(9H-fluoren-9-ylmethoxy)carbonyl]-$N^1$-hexyl-L-α-glutaminate MS (ESI) m/z 509.3; MS (ESI) m/z 1017.5; HRMS: calcd for $C_{30}H_{40}N_2O_5$+H+, 509.30100. found (ESI-FTMS, [M+H]$^{1+}$), 509.30265.

Step B: tert-butyl $N^1$-hexyl-L-α-glutaminate

HRMS: calcd for $C_{15}H_{30}N_2O_3$+H+, 287.23292. found (ESI-FTMS, [M+H]$^{1+}$), 287.23282.

Step C: tert-butyl $N^2$-(biphenyl-4-ylcarbonyl)-$N^1$-hexyl-L-α-glutaminate

MS (ESI) m/z 467.2; MS (ESI) m/z 933.4; HRMS: calcd for $C_{28}H_{38}N_2O_4$+H+, 467.29043. found (ESI-FTMS, [M+H]$^{1+}$), 467.29169.

Step D: $N^2$-(biphenyl-4-ylcarbonyl)-$N^1$-hexyl-L-α-glutamine

MS (ESI) m/z 411.1; MS (ESI) m/z 821.3; HRMS: calcd for $C_{24}H_{30}N_2O_4$+H+, 411.22783. found (ESI-FTMS, [M+H]$^{1+}$), 411.22833.

Example 8WWW $N^2$-(biphenyl-4-ylcarbonyl)-$N^1$-(5-hydroxypentyl)-L-α-glutamine Step A: tert-butyl $N^2$-[(9H-fluoren-9-ylmethoxy)carbonyl]-$N^1$-(5-hydroxypentyl)-L-α-glutaminate MS (ESI) m/z 511.2; MS (ESI) m/z 1021.4; HRMS: calcd for $C_{29}H_{38}N_2O_6$+H+, 511.28026. found (ESI-FTMS, [M+H]$^{1+}$), 511.28078.

Step B: tert-butyl $N^1$-(5-hydroxypentyl)-L-α-glutaminate

HRMS: calcd for $C_{14}H_{28}N_2O_4$+H+, 289.21218. found (ESI-FTMS, [M+H]$^{1+}$), 289.21245.

Step C: tert-butyl $N^2$-(biphenyl-4-ylcarbonyl)-$N^1$-(5-hydroxypentyl)-L-α-glutaminate HRMS: calcd for $C_{27}H_{36}N_2O_5$+H+, 469.26970. found (ESI-FTMS, [M+H]$^{1+}$), 469.27133.

Step D: $N^2$-(biphenyl-4-ylcarbonyl)-$N^1$-(5-hydroxypentyl)-L-α-glutamine

HRMS: calcd for $C_{23}H_{28}N_2O_5$+H+, 413.20710. found (ESI-FTMS, [M+H]$^{1+}$), 413.20657.

Example 8XXX $N^2$-(biphenyl-4-ylcarbonyl)-$N^1$-(6-hydroxyhexyl)-L-α-glutamine Step A: tert-butyl $N^2$-[(9H-fluoren-9-ylmethoxy)carbonyl]-$N^1$-(6-hydroxyhexyl)-L-α-glutaminate MS (ESI) m/z 525.2; MS (ESI) m/z 1049.4; HRMS: calcd for $C_{30}H_{40}N_2O_6$+Na+, 547.27786. found (ESI-FTMS, [M+Na]$^{1+}$), 547.27869.

Step B: tert-butyl $N^1$-(6-hydroxyhexyl)-L-α-glutaminate

HRMS: calcd for $C_{15}H_{30}N_2O_4$+H+, 303.22783. found (ESI-FTMS, [M+H]$^{1+}$), 303.22841.

Step C: tert-butyl $N^2$-(biphenyl-4-ylcarbonyl)-$N^1$-(6-hydroxyhexyl)-L-α-glutaminate HRMS: calcd for $C_{28}H_{38}N_2O_5$+H+, 483.28535. found (ESI-FTMS, [M+H]$^{1+}$), 483.28725.

Step D: $N^2$-(biphenyl-4-ylcarbonyl)-$N^1$-(6-hydroxyhexyl)-L-α-glutamine

HRMS: calcd for $C_{24}H_{30}N_2O_5$+H+, 427.22275. found (ESI-FTMS, [M+H]$^{1+}$), 427.22304.

Example 8YYY $N^2$-(biphenyl-4-ylcarbonyl)-$N^1$-propyl-L-α-glutamine

Step A: tert-butyl $N^2$-[(9H-fluoren-9-ylmethoxy)carbonyl]-$N^1$-propyl-L-α-glutaminate MS (ESI) m/z 467.1; MS (ESI) m/z 933.1; MS (ESI) m/z 955.1; HRMS: calcd for $C_{27}H_{34}N_2O_5$+H+, 467.25405. found (ESI-FTMS, [M+H]$^{1+}$), 467.25527.

Step B: tert-butyl $N^1$-propyl-L-α-glutaminate

MS (ESI) m/z 245.1; MS (ESI) m/z 489.2; HRMS: calcd for $C_{12}H_{24}N_2O_3$+H+, 245.18597. found (ESI-FTMS, [M+H]$^{1+}$), 245.1861.

Step C: tert-butyl $N^2$-(biphenyl-4-ylcarbonyl)-$N^1$-propyl-L-α-glutaminate

HRMS: calcd for $C_{25}H_{32}N_2O_4$+H+, 425.24348. found (ESI-FTMS, [M+H]$^{1+}$), 425.24455.

Step D: $N^2$-(biphenyl-4-ylcarbonyl)-$N^1$-propyl-L-α-glutamine

HRMS: calcd for $C_{21}H_{24}N_2O_4$+H+, 369.18088. found (ESI-FTMS, [M+H]$^{1+}$), 369.18091.

Example 8ZZZ $N^2$-(biphenyl-4-ylcarbonyl)-$N^1$-[4-(dimethylamino)benzyl]-L-α-glutamine Step A: tert-butyl $N^1$-[4-(dimethylamino)benzyl]-$N^2$-[(9H-fluoren-9-ylmethoxy)carbonyl]-L-α-glutaminate MS (ESI) m/z 558.2; HRMS: calcd for $C_{33}H_{39}N_3O_5$+H+, 558.29625. found (ESI-FTMS, [M+H]$^{1+}$), 558.29668.

Step B: tert-butyl $N^1$-[4-(dimethylamino)benzyl]-L-α-glutaminate

MS (ESI) m/z 336.2; MS (ESI) m/z 671.3; HRMS: calcd for $C_{18}H_{29}N_3O_3$+H+, 336.22817. found (ESI-FTMS, [M+H]$^{1+}$), 336.22836.

Step C: tert-butyl $N^2$-(biphenyl-4-ylcarbonyl)-$N^1$-[4-(dimethylamino)benzyl]-L-α-glutaminate MS (ESI) m/z 516.2; HRMS: calcd for $C_{31}H_{37}N_3O_4$+H+, 516.28568. found (ESI-FTMS, [M+H]$^{1+}$), 516.28631.

Step D: $N^2$-(biphenyl-4-ylcarbonyl)-$N^1$-[4-(dimethylamino)benzyl]-L-α-glutamine MS (ESI) m/z 460.1; HRMS: calcd for $C_{27}H_{29}N_3O_4$+H+, 460.22308. found (ESI-FTMS, [M+H]$^{1+}$), 460.22347.

Example 8AAAA $N^1$-(4-aminobenzyl)-$N^2$-(1,1'-biphenyl-4-ylcarbonyl)-L-α-glutamine Step A: tert-butyl $N^2$-[(9H-fluoren-9-ylmethoxy)carbonyl]-$N^1$-(4-nitrobenzyl)-L-α-glutaminate MS (ESI) m/z 560.3; MS (ESI) m/z 1119.5; HRMS: calcd for $C_{31}H_{33}N_3O_7$+H+, 560.23913. found (ESI_FTMS, [M+H]$^{1+}$), 560.23944.

Step B: tert-butyl $N^1$-(4-nitrobenzyl)-L-α-glutaminate

MS (ESI) m/z 338.2; HRMS: calcd for $C_{16}H_{23}N_3O_5$+H+, 338.17105. found (ESI-FTMS, [M+H]$^{1+}$), 338.17116.

Step C: tert-butyl $N^2$-(1,1'-biphenyl-4-ylcarbonyl)-$N^1$-(4-nitrobenzyl)-L-α-glutaminate MS (ESI) m/z 518.2; MS (ESI) m/z 1035.5; HRMS: calcd for $C_{29}H_{31}N_3O_6$+H+, 518.22856. found (ESI-FTMS, [M+H]$^{1+}$), 518.22861.

Step C': Reductive alkylation of tert-butyl $N^2$-(1,1'-biphenyl-4-ylcarbonyl)-$N^1$-(4-nitrobenzyl)-L-α-glutaminate with 30% formalin in water and 10% Pd/C gave tert-butyl $N^1$-(4-aminobenzyl)-$N^2$-(1,1'-biphenyl-4-ylcarbonyl)-L-α-glutaminate MS (ESI) m/z 488.2; MS (ESI) m/z 975.4; HRMS: calcd for $C_{29}H_{33}N_3O_4$+H+, 488.25438. found (ESI_FTMS, [M+H]$^{1+}$), 488.2542.

Step D: $N^1$-(4-aminobenzyl)-$N^2$-(1,1'-biphenyl-4-ylcarbonyl)-L-α-glutamine

MS (ESI) m/z 432.2; HRMS: calcd for $C_{25}H_{25}N_3O_4$+H+, 432.19178. found (ESI_FTMS, [M+H]$^{1+}$), 432.1915.

Example 8BBBB $N^2$-(biphenyl-4-ylcarbonyl)-$N^1$-[3-(dimethylamino)benzyl]-L-α-glutamine Step A: tert-butyl $N^2$-[(9H-fluoren-9-ylmethoxy)carbonyl]-$N^1$-(3-nitrobenzyl)-L-α-glutaminate MS (ESI) m/z 560.3; MS (ESI) m/z 1119.4; HRMS: calcd for $C_{31}H_{33}N_3O_7$+H+, 560.23913. found (ESI_FTMS, [M+H]$^{1+}$), 560.23892.

Step B: tert-butyl $N^1$-(3-nitrobenzyl)-L-α-glutaminate

MS (ESI) m/z 338.1; MS (ESI) m/z 675.3; HRMS: calcd for $C_{16}H_{23}N_3O_5$+H+, 338.17105. found (ESI-FTMS, [M+H]$^{1+}$), 338.17102.

Step C: tert-butyl $N^2$-(1,1'-biphenyl-4-ylcarbonyl)-$N^1$-(3-nitrobenzyl)-L-α-glutaminate MS (ESI) m/z 518.2; MS (ESI) m/z 1035.4; HRMS: calcd for $C_{29}H_{31}N_3O_6$+H+, 518.22856. found (ESI-FTMS, [M+H]$^{1+}$), 518.22868.

Step C': Reductive alkylation of tert-butyl $N^2$-(1,1'-biphenyl-4-ylcarbonyl)-$N^1$-(3-nitrobenzyl)-L-α-glutaminate 30% formalin and 10% Pd/C gave tert-butyl $N^2$-(biphenyl-4-ylcarbonyl)-$N^1$-[3-(dimethylamino)benzyl]-L-α-glutaminate MS (ESI) m/z 516.2; HRMS: calcd for $C_{31}H_{37}N_3O_4$+H+, 516.28568. found (ESI-FTMS, [M+H]$^{1+}$), 516.28548.

Step D: $N^2$-(biphenyl-4-ylcarbonyl)-$N^1$-[3-(dimethylamino)benzyl]-L-α-glutamine MS (ESI) m/z 460.3; HRMS: calcd for $C_{27}H_{29}N_3O_4$+H+, 460.22308. found (ESI-FTMS, [M+H]$^{1+}$), 460.22304.

Example 8CCCC $N^2$-(1,1'-biphenyl-4-ylcarbonyl)-$N^1$-(3-nitrobenzyl)-L-α-glutamine MS (ESI) m/z 462.2; MS (ESI) m/z 923.2; HRMS: calcd for $C_{25}H_{23}N_3O_6$+H+, 462.16596. found (ESI_FTMS, [M+H]$^{1+}$), 462.16599.

Example 8DDDD $N^1$-(3-aminobenzyl)-$N^2$-(1,1'-biphenyl-4-ylcarbonyl)-L-α-glutamine HRMS: calcd for $C_{25}H_{25}N_3O_4$+H+, 432.19178. found (ESI_FTMS, [M+H]$^{1+}$), 432.1917.

Example 8EEEE $N^1$-benzyl-$N^2$-(1,1-biphenyl-4-ylcarbonyl)-L-α-glutamine

Step A: tert-butyl $N^1$-benzyl-$N^2$-[(9H-fluoren-9-ylmethoxy)carbonyl]-L-α-glutaminate MS (ESI) m/z 458 (M-tBut).

Step B: tert-butyl $N^1$-benzyl-L-α-glutaminate

MS (ESI) m/z 293.

Step C: tert-butyl $N^1$-benzyl-$N^2$-(1,1'-biphenyl-4-ylcarbonyl)-L-α-glutaminate MS (ESI) m/z 473.

Step D: $N^1$-benzyl-$N^2$-(1,1'-biphenyl-4-ylcarbonyl)-L-α-glutamine

MS (ESI) m/z 417.

Example 8FFFF $N^2$-(biphenyl-4-ylcarbonyl)-$N^1$-[2-(4-fluorophenyl)-1,1-dimethylethyl]-D-α-glutamine Step A: tert-butyl $N^2$-[(9H-fluoren-9-ylmethoxy)carbonyl]-$N^1$-[2-(4-fluorophenyl)-1,1-dimethylethyl]-D-α-glutaminate Described as above according to the procedure of Example 7, except Fmoc-D-Glu-(OtBu)—OH was used as starting material for the first step. HRMS: calcd for $C_{34}H_{39}FN_2O_5$+H+, 575.29158. found (ESI-FTMS, [M+H]$^{1+}$), 575.2927.

Step B: tert-butyl $N^1$-[2-(4-fluorophenyl)-1,1-dimethylethyl]-D-α-glutaminate

HRMS: calcd for $C_{19}H_{29}FN_2O_3$+H+, 353.22350. found (ESI-FTMS, [M+H]$^{1+}$), 353.22483.

Step C: tert-butyl $N^2$-(biphenyl-4-ylcarbonyl)-$N^1$-[2-(4-fluorophenyl)-1,1-dimethylethyl]-D-α-glutaminate HRMS: calcd for $C_{32}H_{37}FN_2O_4$+H+, 533.28101. found (ESI-FTMS, [M+H]$^{1+}$), 533.28347.

Step D: $N^2$-(biphenyl-4-ylcarbonyl)-$N^1$-[2-(4-fluorophenyl)-1,1-dimethylethyl]-D-α-glutamine MS (ESI) m/z 477.1; MS (ESI) m/z 499; MS (ESI) m/z 953.1; HRMS: calcd for $C_{28}H_{29}FN_2O_4$+H+, 477.21841. found (ESI-FTMS, [M+H]$^{1+}$), 477.21815.

Example 8GGGG $N^2$-(biphenyl-4-ylcarbonyl)-$N^1$-[2-(4-fluorophenyl)-1,1-dimethylethyl]-α-glutamine Step A: tert-butyl $N^2$-[(9H-fluoren-9-ylmethoxy)carbonyl]-$N^1$-[2-(4-fluorophenyl)-1,1-dimethylethyl]-α-glutaminate Described as above according to the procedure of Example 7, except Fmoc-DL-Glu-(OtBu)—OH (racemic mixture) was used as starting material for the first step. HRMS: calcd for $C_{34}H_{39}FN_2O_5$+H+, 575.29158. found (ESI-FTMS, [M+H]$^{1+}$), 575.29217.

Step B: tert-butyl $N^1$-[2-(4-fluorophenyl)-1,1-dimethylethyl]-α-glutaminate

HRMS: calcd for $C_{19}H_{29}FN_2O_3$+H+, 353.22350. found (ESI-FTMS, [M+H]$^{1+}$), 353.22429.

Step C: tert-butyl $N^2$-(biphenyl-4-ylcarbonyl)-$N^1$-[2-(4-fluorophenyl)-1,1-dimethylethyl]-α-glutaminate HRMS: calcd for $C_{32}H_{37}FN_2O_4$+H+, 533.28101. found (ESI-FTMS, [M+H]$^{1+}$), 533.28268.

Step D: $N^2$-(biphenyl-4-ylcarbonyl)-$N^1$-[2-(4-fluorophenyl)-1,1-dimethylethyl]-α-glutamine MS (ESI) m/z 477.1; MS (ESI) m/z 953.1; HRMS: calcd for $C_{28}H_{29}FN_2O_4$+H+, 477.21841. found (ESI-FTMS, [M+H]$^{1+}$), 477.21805.

Example 8HHHH

4-Benzylcarbamoyl-4-[4-(pyrimidin-2-ylamino)-benzoylamino-butyric acid tert-butyric acid Step C: 4-Benzylcarbamoyl-4-[4-(pyrimidin-2-ylamino)-benzoylamino-butyric acid tert-butyl ester MS (ESI) m/z 488.

Step D: 4-Benzylcarbamoyl-4-[4-(pyrimidin-2-ylamino)-benzoylamino-butyric acid tert-butyric acid MS (ESI) m/z 432.

Example 8IIII $N^2$-(9H-fluoren-2-ylcarbonyl)-$N^1$-(3-phenylpropyl)-L-α-glutamine Step A: tert-butyl $N^2$-[(9H-fluoren-9-ylmethoxy)carbonyl]-$N^1$-(3-phenylpropyl)-L-α-glutaminate 1,9 (Fmoc)L-glutamic acid-tert-butylester monohydrate (1.33 g, 3.00 mmol) was dissolved in DMF (8 mL) under nitrogen. BOP (1.33 g, 3.00 mmol) was added as a solid, followed by 3-phenyl-1-propylamine (427 mL, 3 mmol). Finally DIEA (627 mL, 3.6 mmol) was added dropwise. The reaction was monitored by TLC, and stirred for 24 hrs. The reaction mixture was then added to stirring $H_2O$ (400 mL). After stirring for 1 hour, clumps of white solid were formed. The clumps were broken up with a spatula and stirred for an additional 30 minutes. The solid was filtered and washed with H₂O. The solid was then dissolved in CH₂Cl₂ and dried with Na₂SO₄. The solution was filtered and concentrated, leaving a white solid. The solid was dissolved in minimal acetone and hexanes were added. The solvents were then removed and the white solid was dried under vacuum. Yield 1.58 g of tert-butyl N²-[(9H-fluoren-9-ylmethoxy)carbonyl]-N¹-(3-phenylpropyl)-L-α-glutaminate at 97% yield.

MS (ESI) m/z 543.3; HRMS: calcd for $C_{33}H_{38}N_2O_5$+H+, 543.2853. found (ESI-FTMS, [M+H]$^{1+}$), 543.2847.

Step B: tert-butyl N¹-(3-phenylpropyl)-L-α-glutaminate

Tert-butyl N²-[(9H-fluoren-9-ylmethoxy)carbonyl]-N¹-(3-phenylpropyl)-L-α-glutaminate (1.5 g, 2.76 mmol) was partially dissolved in CH₃CN (15 mL). DEA (2.9 mL, 27.6 mmol) was added, which was fully dissolved within 10 minutes. The reaction was monitored by TLC and was complete at 2 hrs. The solvent was removed and the remaining material dried under vacuum. The material was purified on a short silica column using 5% Acetone/CH₂Cl₂ to elute the Fmoc by-product and then 50% Acetone/CH₂Cl₂ to elute the product. The clear oil present at the end was dried shortly under vacuum, and then taken to the next step immediately. It was never fully solvent free so the yield of tert-butyl N¹-(3-phenylpropyl)-L-α-glutaminate was 1.65 g, and was assumed to be quantitative. MS (ESI) m/z 321.2; MS (ESI) m/z 641.4; HRMS: calcd for $C_{18}H_{28}N_2O_3$+H+, 321.2173. found (ESI-FTMS, [M+H]$^{1+}$), 321.2167.

Step C: tert-butyl N²-(9H-fluoren-2-ylcarbonyl)-N¹-(3-phenylpropyl)-L-α-glutaminate Tert-butyl N¹-(3-phenylpropyl)-L-α-glutaminate (350 mg, 1.09 mmol) was dissolved in DMF (5 mL), in a 20 mL vial under nitrogen. 2-Fluorenecarboxylic acid (229 mg, 1.09 mmol) and BOP (530 mg, 1.20 mmol) were added as solids and dissolved. Finally DIEA (228 mL, 1.31 mmol) was added, and the reaction stirred overnight. Monitored by TLC, the reaction was complete after stirring overnight. The reaction mixture was added to H₂O (100 mL), precipitating a pale yellow solid. The solid was filtered and dried in a dessicator overnight. Once dry, the solid was taken up in a small amount of acetone, and hexanes were added to precipitate a pale yellow solid. The solid was filtered, washed with hexanes and dried in a dessicator. Yield 293 mg of tert-butyl N²-(9H-fluoren-2-ylcarbonyl)-N¹-(3-phenylpropyl)-L-α-glutaminate at 52% yield. MS (ESI) m/z 513.3; MS (ESI) m/z 1025.6; MS (ESI) m/z 535.3; HRMS: calcd for $C_{32}H_{36}N_2O_4$+H+, 513.27478. found (ESI-FTMS, [M+H]$^{1+}$), 513.2766.

Step D: N²-(9H-fluoren-2-ylcarbonyl)-N¹-(3-phenylpropyl)-L-α-glutamine

Tert-butyl N²-(9H-fluoren-2-ylcarbonyl)-N¹-(3-phenylpropyl)-L-α-glutaminate (273 mg, 0.533 mmol) was dissolved in CH₂Cl₂ (1.5 mL). TFA (1.23 mL, 16.0 mmol) was diluted in CH₂Cl₂ (2 mL) and was then slowly added to the first solution. The reaction was monitored by TLC and complete at 2 hrs. The solvent was removed with a nitrogen blower and the remaining yellow oil dried under vacuum. The yellow oil was then dissolved in minimal acetone and hexanes was added precipitating a white solid. The solid was filtered, washed with hexanes and then dried under vacuum. The reaction yielded 194 mg of N²-(9H-fluoren-2-ylcarbonyl)-N¹-(3-phenylpropyl)-L-α-glutamine at an 80% yield. MS (ESI) m/z 457.3; MS (ESI) m/z 913.5.

Example 8JJJJ

N²-(9H-fluoren-1-ylcarbonyl)-N¹-(3-phenylpropyl)-L-α-glutamine

Step C: tert-butyl N²-(9H-fluoren-1-ylcarbonyl)-N¹-(3-phenylpropyl)-L-α-glutaminate MS (ESI) m/z 513.3; MS (ESI) m/z 1025.6; HRMS: calcd for $C_{32}H_{36}N_2O_4$+H+, 513.27478. found (ESI-FTMS, [M+H]$^{1+}$), 513.27653.

Step D: N²-(9H-fluoren-1-ylcarbonyl)-N¹-(3-phenylpropyl)-L-α-glutamine

MS (ESI) m/z 457.3; MS (ESI) m/z 913.5; MS (ESI) m/z 479.3.

Example 8KKKK

N²-(9H-fluoren-2-ylcarbonyl)-N¹-(3,4,5-trimethoxybenzyl)-L-α-glutamine

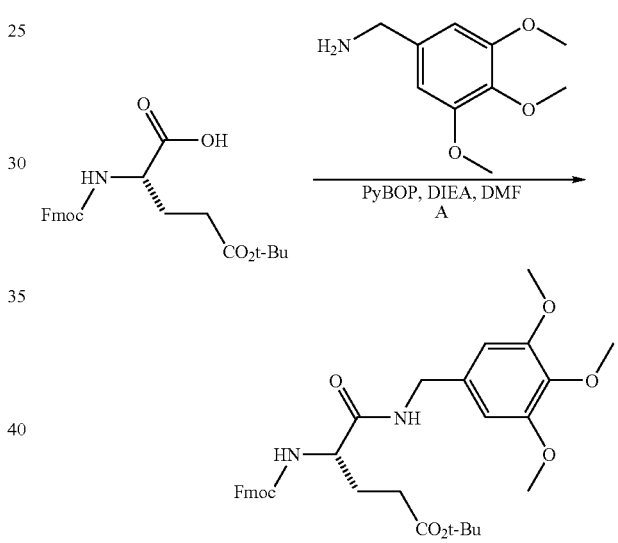

Step A: tert-butyl N²-[(9H-fluoren-9-ylmethoxy)carbonyl]-N¹-(3,4,5-trimethoxybenzyl)-L-α-glutaminate MS (ESI) m/z 605.2; MS (ESI) m/z 1209.4; HRMS: calcd for $C_{34}H_{40}N_2O_8$+H+, 605.28574. found (ESI_FT, [M+H]$^{1+}$), 605.28453.

Step B: tert-butyl N¹-(3,4,5-trimethoxybenzyl)-L-α-glutaminate

MS (ESI) m/z 383.1; MS (ESI) m/z 765.3; HRMS: calcd for $C_{19}H_{30}N_2O_6$+H+, 383.21766. found (ESI_FT, [M+H]$^{1+}$), 383.21755.

Step C: tert-butyl N²-(9H-fluoren-2-ylcarbonyl)-N¹-(3,4,5-trimethoxybenzyl)-L-α-glutaminate MS (ESI) m/z 575.4; MS (ESI) m/z 1149.7; HRMS: calcd for $C_{33}H_{38}N_2O_7$+H+, 575.27518. found (ESI-FTMS, [M+H]$^{1+}$), 575.27604.

Step D: N²-(9H-fluoren-2-ylcarbonyl)-N¹-(3,4,5-trimethoxybenzyl)-L-α-glutamine

MS (ESI) m/z 519.3; MS (ESI) m/z 1037.6; HRMS: calcd for $C_{29}H_{30}N_2O_7$+H+, 519.21258. found (ESI-FTMS, [M+H]$^{1+}$), 519.2133.

Example 8LLLL

N²-(9H-fluoren-1-ylcarbonyl)-N¹-(3,4,5-trimethoxybenzyl)-L-α-glutamine

Step C: tert-butyl N²-(9H-fluoren-1-ylcarbonyl)-N¹-(3,4,5-trimethoxybenzyl)-L-α-glutaminate MS (ESI) m/z 575.4; MS (ESI) m/z 1149.7; HRMS: calcd for $C_{33}H_{38}N_2O_7$+H+, 575.27518. found (ESI-FTMS, [M+H]$^{1+}$), 575.2761.

Step D: N²-(9H-fluoren-1-ylcarbonyl)-N¹-(3,4,5-trimethoxybenzyl)-L-α-glutamine

MS (ESI) m/z 519.3; MS (ESI) m/z 1037.6; MS (ESI) m/z 541.3; HRMS: calcd for $C_{29}H_{30}N_2O_7$+H+, 519.21258. found (ESI-FTMS, [M+H]$^{1+}$), 519.21329.

Example 8MMMM

N²-[(9-oxo-9H-fluoren-2-yl)carbonyl]-N¹-(3,4,5-trimethoxybenzyl)-L-α-glutamine

Step C: tert-butyl N²-[(9-oxo-9H-fluoren-2-yl)carbonyl]-N¹-(3,4,5-trimethoxybenzyl)-L-α-glutaminate MS (ESI) m/z 589.4; MS (ESI) m/z 1177.7; MS (ESI) m/z 606.4; HRMS: calcd for $C_{33}H_{36}N_2O_8$+H+, 589.25444. found (ESI-FTMS, [M+H]$^{1+}$), 589.25507.

Step D: N²-[(9-oxo-9H-fluoren-2-yl)carbonyl]-N¹-(3,4,5-trimethoxybenzyl)-L-α-glutamine MS (ESI) m/z 531.3; MS (ESI) m/z 1063.5; HRMS: calcd for $C_{29}H_{28}N_2O_8$+H+, 533.19184. found (ESI-FTMS, [M+H]$^{1+}$), 533.19236.

Example 8NNNN

N²-(4-phenoxybenzoyl)-N¹-(3,4,5-trimethoxybenzyl)-L-α-glutamine

Step C: tert-butyl N²-(4-phenoxybenzoyl)-N¹-(3,4,5-trimethoxybenzyl)-L-α-glutaminate MS (ESI) m/z 579.3; MS (ESI) m/z 1157.7; HRMS: calcd for $C_{32}H_{38}N_2O_8$+H+, 579.27009. found (ESI-FTMS, [M+H]$^{1+}$), 579.2719.

Step D: N²-(4-phenoxybenzoyl)-N¹-(3,4,5-trimethoxybenzyl)-L-α-glutamine

MS (ESI) m/z 523.3; MS (ESI) m/z 1045.5.

Example 8OOOO

N²-(9H-fluoren-2-ylcarbonyl)-N¹-hexyl-L-α-glutamine

Step A: tert-butyl N²-[(9H-fluoren-9-ylmethoxy)carbonyl]-N¹-hexyl-L-α-glutaminate MS (ESI) m/z 509.3; MS (ESI) m/z 1017.5; HRMS: calcd for $C_{30}H_{40}N_2O_5$+H+, 509.30100. found (ESI-FTMS, [M+H]$^{1+}$), 509.30265.

Step B: tert-butyl N¹-hexyl-L-α-glutaminate

HRMS: calcd for $C_{15}H_{30}N_2O_3$+H+, 287.23292. found (ESI-FTMS, [M+H]$^{1+}$), 287.23282.

Step C: tert-butyl N²-(9H-fluoren-2-ylcarbonyl)-N¹-hexyl-L-α-glutaminate

MS (ESI) m/z 479.1; MS (ESI) m/z 979.2; MS (ESI) m/z 501.1; HRMS: calcd for $C_{29}H_{38}N_2O_4$+H+, 479.29043. found (ESI-FTMS, [M+H]$^{1+}$), 479.29145.

Step D: N²-(9H-fluoren-2-ylcarbonyl)-N¹-hexyl-L-α-glutamine

MS (ESI) m/z 423.3; MS (ESI) m/z 845.6; MS (ESI) m/z 445.3.

Example 8PPPP

N²-(9H-fluoren-1-ylcarbonyl)-N¹-hexyl-L-α-glutamine

Step C: tert-butyl N²-(9H-fluoren-1-ylcarbonyl)-N¹-hexyl-L-α-glutaminate

MS (ESI) m/z 479.1; MS (ESI) m/z 957.3; MS (ESI) m/z 979.2; HRMS: calcd for $C_{29}H_{38}N_2O_4$+H+, 479.29043. found (ESI-FTMS, [M+H]$^{1+}$), 479.29145.

Step D: N²-(9H-fluoren-1-ylcarbonyl)-N¹-hexyl-L-α-glutamine

MS (ESI) m/z 423.3; MS (ESI) m/z 845.5; MS (ESI) m/z 445.3.

Example 8QQQQ

N$^1$-hexyl-N$^2$-(4-phenoxybenzoyl)-L-α-glutamine

Step C: tert-butyl N$^1$-hexyl-N$^2$-(4-phenoxybenzoyl)-L-α-glutaminate

MS (ESI) m/z 483.1; MS (ESI) m/z 965.3; MS (ESI) m/z 987.3; HRMS: calcd for C$_{28}$H$_{38}$N$_2$O$_5$+H+, 483.28535. found (ESI-FTMS, [M+H]$^{1+}$), 483.28715.

Step D: N$^1$-hexyl-N$^2$-(4-phenoxybenzoyl)-L-α-glutamine

MS (ESI) m/z 427.3; MS (ESI) m/z 853.5; MS (ESI) m/z 449.3.

Example 8RRRR

N$^1$-hexyl-N$^2$-[(9-oxo-9H-fluoren-2-yl)carbonyl]-L-α-glutamine

Step C: tert-butyl N$^1$-hexyl-N$^2$-[(9-oxo-9H-fluoren-2-yl)carbonyl]-L-α-glutaminate MS (ESI) m/z 493.1; MS (ESI) m/z 985.3; HRMS: calcd for C$_{29}$H$_{36}$N$_2$O$_5$+H+, 493.26970. found (ESI-FTMS, [M+H]$^{1+}$), 493.27119.

Step D: N$^1$-hexyl-N$^2$-[(9-oxo-9H-fluoren-2-yl)carbonyl]-L-α-glutamine

MS (ESI) m/z 437.3; MS (ESI) m/z 873.5; MS (ESI) m/z 1309.8.

Example 8SSSS

N$^2$-(4-benzoylbenzoyl)-N$^1$-benzyl-L-α-glutamine

Step C: tert-butyl N$^2$-(4-benzoylbenzoyl)-N$^1$-benzyl-L-α-glutaminate

MS (ESI) m/z 501.2; MS (ESI) m/z 523.2; HRMS: calcd for C$_{30}$H$_{32}$N$_2$O$_5$+H+, 501.23840. found (ESI+, [M+H]$^{1+}$), 501.23859.

Step: D N$^2$-(4-benzoylbenzoyl)-N$^1$-benzyl-L-α-glutamine

MS (ESI) m/z 445.2; HRMS: calcd for C$_{26}$H$_{24}$N$_2$O$_5$+H+, 445.17580. found (ESI+, [M+H]$^{1+}$), 445.17619.

Example 8TTTT

N$^1$-(6-hydroxyhexyl)-N$^2$-(4-phenoxybenzoyl)-L-α-glutamine

MS (ESI) m/z 443.2; MS (ESI) m/z 885.5; HRMS: calcd for C$_{24}$H$_{30}$N$_2$O$_6$+H+, 443.21766. found (ESI-FTMS, [M+H]$^{1+}$), 443.21905.

Example 8UUUU

N$^2$-(9H-fluoren-9-ylcarbonyl)-N$^1$-(6-hydroxyhexyl)-L-α-glutamine

MS (ESI) m/z 437.3; MS (ESI) m/z 551.3; HRMS: calcd for C$_{25}$H$_{30}$N$_2$O$_5$+H+, 439.22275. found (ESI-FTMS, [M+H]$^{1+}$), 439.22374.

Example 8VVVV

N$^2$-(9H-fluoren-9-ylcarbonyl)-N$^1$-(3,4,5-trimethoxybenzyl)-L-α-glutamine

MS (ESI) m/z 519.1; MS (ESI) m/z 1037.2; MS (ESI) m/z 536.1; HRMS: calcd for C$_{29}$H$_{30}$N$_2$O$_7$+H+, 519.21258. found (ESI-FTMS, [M+H]$^{1+}$), 519.213.

Example 8WWWW

N$^2$-(3-phenoxybenzoyl)-N$^1$-(3,4,5-trimethoxybenzyl)-L-α-glutamine

MS (ESI) m/z 523.1; MS (ESI) m/z 1045.2; MS (ESI) m/z 545.1; HRMS: calcd for C$_{28}$H$_{30}$N$_2$O$_8$+H+, 523.20749. found (ESI-FTMS, [M+H]$^{1+}$), 523.20712.

Example 8XXXX

N$^2$-(9H-fluoren-4-ylcarbonyl)-N$^1$-(3,4,5-trimethoxybenzyl)-L-α-glutamine

MS (ESI) m/z 519.1; MS (ESI) m/z 1037.2; HRMS: calcd for C$_{29}$H$_{30}$N$_2$O$_7$+H+, 519.21258. found (ESI-FTMS, [M+H]$^{1+}$), 519.21308.

Example 8YYYY

N$^1$-1-adamantyl-N$^2$-[(9-oxo-9H-fluoren-2-yl)carbonyl]-L-α-glutamine

MS (ESI) m/z 485.3; MS (ESI) m/z 971.6; MS (ESI) m/z 521.3; HRMS: calcd for C$_{29}$H$_{30}$N$_2$O$_5$+H+, 487.22275. found (ESI-FTMS, [M+H]$^{1+}$), 487.22272.

Example 8ZZZZ

N$^1$-1-adamantyl-N$^2$-(4-phenoxybenzoyl)-L-α-glutamine

MS (ESI) m/z 477.1; MS (ESI) m/z 953.3; MS (ESI) m/z 499.1; HRMS: calcd for C$_{28}$H$_{32}$N$_2$O$_5$+H+, 477.23840. found (ESI-FTMS, [M+H]$^{1+}$), 477.23857.

Example 8AAAAA

N$^1$-1-adamantyl-N$^2$-(9H-fluoren-2-ylcarbonyl)-L-α-glutamine

MS (ESI) m/z 473.3; MS (ESI) m/z 945.5; HRMS: calcd for C$_{29}$H$_{32}$N$_2$O$_4$+H+, 473.24348. found (ESI-FTMS, [M+H]$^{1+}$), 473.24374.

Example 8BBBBB $N^1$-1-adamantyl-$N^2$-(9H-fluoren-9-ylcarbonyl)-L-α-glutamine MS (ESI) m/z 471.3; MS (ESI) m/z 585.3; MS (ESI) m/z 943.6; HRMS: calcd for $C_{29}H_{32}N_2O_4$+H+, 473.24348. found (ESI-FTMS, [M+H]$^{1+}$), 473.2437.

Example 8CCCCC $N^2$-(9H-fluoren-2-ylcarbonyl)-$N^1$-(3-methylbenzyl)-L-α-glutamine HRMS: calcd for $C_{27}H_{26}N_2O_4$+H+, 443.19653. found (ESI-FTMS, [M+H]$^{1+}$), 443.1974.

Example 8DDDDD $N^1$-(3-methylbenzyl)-$N^2$-[(9-oxo-9H-fluoren-2-yl)carbonyl]-L-α-glutamine HRMS: calcd for $C_{27}H_{24}N_2O_5$+H+, 457.17580. found (ESI-FTMS, [M+H]$^{1+}$), 457.17616.

Example 8EEEEE $N^2$-(9H-fluoren-9-ylcarbonyl)-$N^1$-(3-methylbenzyl)-L-α-glutamine HRMS: calcd for $C_{27}H_{26}N_2O_4$+H+, 443.19653. found (ESI-FTMS, [M+H]$^{1+}$), 443.19709.

Example 8FFFFF $N^2$-(9H-fluoren-2-ylcarbonyl)-$N^1$-propyl-L-α-glutamine

HRMS: calcd for $C_{22}H_{24}N_2O_4$+H+, 381.18088. found (ESI-FTMS, [M+H]$^{1+}$), 381.18117.

Example 8GGGGG

4-[(9H-fluoren-9-carbonyl)-amino]-4-propylcarbamoyl-butyric acid

MS (ESI) m/z 395.1; MS (ESI) m/z 789.2; MS (ESI) m/z 811.2; HRMS: calcd for $C_{22}H_{24}N_2O_4$+H+, 381.18088. found (ESI-FTMS, [M+H]$^{1+}$), 395.16097.

Example 8HHHHH

4-[(9-Oxo-9H-fluorene-2-carbonyl)-amino]-4-propylcarbamoyl-butyric acid

MS (ESI) m/z 381.1; MS (ESI) m/z 403.1; MS (ESI) m/z 761.2; HRMS: calcd for $C_{22}H_{22}N_2O_5$+H+, 395.16015. found (ESI-FTMS, [M+H]$^{1+}$), 381.18165.

Example 8IIIII $N^1$-benzyl-$N^2$-[(9-oxo-9H-fluoren-2-yl)carbonyl]-L-α-glutamine MS (ESI) m/z 441.2; MS (ESI) m/z 883.3; HRMS: calcd for $C_{26}H_{22}N_2O_5$+H+, 443.16015. found (ESI-FTMS, [M+H]$^{1+}$), 443.16063.

Example 8JJJJJ $N^1$-benzyl-$N^2$-(9H-fluoren-2-ylcarbonyl)-L-α-glutamine

MS (ESI) m/z 427.2; MS (ESI) m/z 855.3; HRMS: calcd for $C_{26}H_{24}N_2O_4$+H+, 429.18088. found (ESI-FTMS, [M+H]$^{1+}$), 429.18148.

Example 8KKKKK $N^1$-benzyl-$N^2$-(9H-fluoren-9-ylcarbonyl)-L-α-glutamine

MS (ESI) m/z 429; MS (ESI) m/z 857; MS (ESI) m/z 451; HRMS: calcd for $C_{26}H_{24}N_2O_4$+H+, 429.18088. found (ESI-FTMS, [M+H]$^{1+}$), 429.1815.

Example 8LLLLL $N^1$-benzyl-$N^2$-(3-phenoxybenzoyl)-L-α-glutamine

MS (ESI) m/z 433; MS (ESI) m/z 455; MS (ESI) m/z 865; HRMS: calcd for $C_{25}H_{24}N_2O_5$+H+, 433.17580. found (ESI-FTMS, [M+H]$^{1+}$), 433.17696.

Example 8MMMMM $N^1$-(1-methyl-1-phenylethyl)-$N^2$-[(9-oxo-9H-fluoren-2-yl)carbonyl]-L-α-glutamine MS (ESI) m/z 471.2; MS (ESI) m/z 941.5; MS (ESI) m/z 493.2; HRMS: calcd for $C_{28}H_{26}N_2O_5$+H+, 471.19145. found (ESI-FTMS, [M+H]$^{1+}$), 471.19271.

Example 8NNNNN $N^2$-(9H-fluoren-9-ylcarbonyl)-$N^1$-(1-methyl-1-phenylethyl)-L-α-glutamine MS (ESI) m/z 455.1; MS (ESI) m/z 911.3; HRMS: calcd for $C_{28}H_{28}N_2O_4$+H+, 457.21218. found (ESI-FTMS, [M+H]$^{1+}$), 457.214.

Example 8OOOOO $N^1$-(1-methyl-1-phenylethyl)-$N^2$-(3-phenoxybenzoyl)-L-α-glutamine MS (ESI) m/z 461.2; MS (ESI) m/z 921.5; MS (ESI) m/z 483.2; HRMS: calcd for $C_{27}H_{28}N_2O_5$+H+, 461.20710. found (ESI-FTMS, [M+H]$^{1+}$), 461.20882.

Example 8PPPPP $N^2$-(biphenyl-4-ylcarbonyl)-$N^1$-[(1S)-1-phenylethyl]-L-α-glutamine MS (ESI) m/z 431.2; MS (ESI) m/z 861.4; MS (ESI) m/z 453.2; HRMS: calcd for $C_{26}H_{26}N_2O_4$+H+, 431.19653. found (ESI-FTMS, [M+H]$^{1+}$), 431.19802.

Example 8QQQQQ

N²-(9H-fluoren-2-ylcarbonyl)-N¹-[(1S)-1-phenyl-ethyl]-L-α-glutamine

MS (ESI) m/z 443.2; MS (ESI) m/z 885.4; MS (ESI) m/z 465.2; HRMS: calcd for $C_{27}H_{26}N_2O_4$+H+, 443.19653. found (ESI-FTMS, [M+H]$^{1+}$), 443.19772.

Example 8RRRRR

N²-(biphenyl-4-ylcarbonyl)-N1-[(1S)-1-(4-fluorophenyl)ethyl]-L-α-glutamine

MS (ESI) m/z 449.2; MS (ESI) m/z 897.4; HRMS: calcd for $C_{26}H_{25}FN_2O_4$+H+, 449.18711. found (ESI-FTMS, [M+H]$^{1+}$), 449.18839.

Example 8SSSSS tert-butyl N²-(biphenyl-4-ylcarbonyl)-N¹-(1-Phenylethyl)-L-α-glutaminate MS (ESI) m/z 505.3.

Example 8TTTTT

N²-(biphenyl-4-ylcarbonyl)-N¹-[(1R)-1-(4-fluorophenyl)ethyl]-L-α-glutamine

MS (ESI) m/z 449.2; MS (ESI) m/z 897.5; MS (ESI) m/z 471.2; HRMS: calcd for $C_{26}H_{25}FN_2O_4$+H+, 449.18711. found (ESI-FTMS, [M+H]$^{1+}$), 449.18679.

Example 8UUUUU

N²-(biphenyl-4-ylcarbonyl)-N¹-[(1R)-1-phenyl-ethyl]-L-α-glutamine

MS (ESI) m/z 431.2; MS (ESI) m/z 861.5; MS (ESI) m/z 453.2; HRMS: calcd for $C_{26}H_{26}N_2O_4$+H+, 431.19653. found (ESI-FTMS, [M+H]$^{1+}$), 431.19828.

Example 8VVVVV

N²-(9H-fluoren-2-ylcarbonyl)-N¹-[(1R)-1-phenyl-ethyl]-L-α-glutamine

MS (ESI) m/z 443.2; MS (ESI) m/z 885.5; MS (ESI) m/z 465.2; HRMS: calcd for $C_{27}H_{26}N_2O_4$+H+, 443.19653. found (ESI-FTMS, [M+H]$^{1+}$), 443.19676.

Example 8WWWWW

N²-(9H-fluoren-1-ylcarbonyl)-N¹-(6-hydroxyhexyl)-L-α-glutamine

MS (ESI) m/z 437.3; MS (ESI) m/z 875.5; HRMS: calcd for $C_{25}H_{30}N_2O_5$+H+, 439.22275. found (ESI-FTMS, [M+H]$^{1+}$), 439.22313.

Example 8XXXXX

N¹-(6-hydroxyhexyl)-N²-[(9-oxo-9H-fluoren-2-yl)carbonyl]-L-α-glutamine

MS (ESI) m/z 453.2; HRMS: calcd for $C_{25}H_{28}N_2O_6$+H+, 453.20201. found (ESI-FTMS, [M+H]$^{1+}$), 453.2027.

Example 8YYYYY

N²-(biphenyl-4-ylcarbonyl)-N¹-9H-fluoren-9-yl-L-α-glutamine

MS (ESI) m/z 489.1; MS (ESI) m/z 979.2; HRMS: calcd for $C_{31}H_{26}N_2O_4$+H+, 491.19653. found (ESI-FTMS, [M+H]$^{1+}$), 491.19778.

Example 8ZZZZZ

N²-(9H-fluoren-2-ylcarbonyl)-N¹-[2-(4-fluorophenyl)-1,1-dimethylethyl]-L-α-glutamine MS (ESI) m/z 489.2; MS (ESI) m/z 977.4; HRMS: calcd for $C_{29}H_{29}FN_2O_4$+H+, 489.21841. found (ESI-FTMS, [M+H]$^{1+}$), 489.21827.

Example 8AAAAAA

N-(1-adamantylmethyl)-N²-(biphenyl-4-ylcarbonyl)-L-α-glutamine

MS (ESI) m/z 475.2; MS (ESI) m/z 949.5; HRMS: calcd for $C_{29}H_{34}N_2O_4$+H+, 475.25913. found (ESI-FTMS, [M+H]$^{1+}$), 475.25916.

Example 8BBBBBB

N-[(1S)-1-benzyl-2-hydroxyethyl]-N²-(9H-fluoren-2-ylcarbonyl)-L-α-glutamine

MS (ESI) m/z 473.2; MS (ESI) m/z 945.4; HRMS: calcd for $C_{28}H_{28}N_2O_5$+H+, 473.20710. found (ESI-FTMS, [M+H]$^{1+}$), 473.2073.

Example 8CCCCCC

N²-(biphenyl-4-ylcarbonyl)-N-methyl-N-(2-phenylethyl)-L-α-glutamine

MS (ESI) m/z 445.4; MS (ESI) m/z 889.7; HRMS: calcd for $C_{27}H_{28}N_2O_4$+H+, 445.21218. found (ESI-FTMS, [M+H]$^{1+}$), 445.21312.

Example 8DDDDDD

N²-(9H-fluoren-2-ylcarbonyl)-N-methyl-N-(2-phenylethyl)-L-α-glutamine

MS (ESI) m/z 457.4; MS (ESI) m/z 913.7; HRMS: calcd for $C_{28}H_{28}N_2O_4$+H+, 457.21218. found (ESI-FTMS, [M+H]$^{1+}$), 457.21146.

Example 8EEEEEE $N^2$-(biphenyl-4-ylcarbonyl)-N-butyl-N-methyl-L-α-glutamine MS (ESI) m/z 397.2; MS (ESI) m/z 793.4; MS (ESI) m/z 419.2; HRMS: calcd for $C_{23}H_{28}N_2O_4$+H+, 397.21218. found (ESI-FTMS, [M+H]$^{1+}$), 397.21249.

Example 8FFFFFF

N-butyl-$N^2$-(9H-fluoren-2-ylcarbonyl)-N-methyl-L-α-glutamine

MS (ESI) m/z 409.3; MS (ESI) m/z 817.5; HRMS: calcd for $C_{24}H_{28}N_2O_4$+H+, 409.21218. found (ESI-FTMS, [M+H]$^{1+}$), 409.21227.

Example 8GGGGGG $N^2$-(biphenyl-4-ylcarbonyl)-N-[2-(3,4-dimethoxyphenyl)ethyl]-N-methyl-L-α-glutamine MS (ESI) m/z 505.3; MS (ESI) m/z 527.3; MS (ESI) m/z 1009.6; HRMS: calcd for $C_{29}H_{32}N_2O_6$+H+, 505.23331. found (ESI-FTMS, [M+H]$^{1+}$), 505.23512.

Example 8HHHHHH $N^2$-[4-(1,3-benzodioxol-5-yl)benzoyl]-N-[2-(4-fluorophenyl)-1,1-dimethylethyl]-L-α-glutamine MS (ESI) m/z 521.1; MS (ESI) m/z 1041.3; HRMS: calcd for $C_{29}H_{29}FN_2O_6$+H+, 521.20824. found (ESI-FTMS, [M+H]$^{1+}$), 521.20872.

Example 8IIIIII

N-[2-(3,4-dimethoxyphenyl)ethyl]-$N^2$-(9H-fluoren-2-ylcarbonyl)-N-methyl-L-α-glutamine MS (ESI) m/z 517.2; MS (ESI) m/z 1033.3; HRMS: calcd for $C_{30}H_{32}N_2O_6$+H+, 517.23331. found (ESI-FTMS, [M+H]$^{1+}$), 517.23342.

Example 8JJJJJJ $N^2$-(9H-fluoren-2-ylcarbonyl)-N-[(2R)-2-phenylpropyl]-L-α-glutamine MS (ESI) m/z 457.2; MS (ESI) m/z 913.3; MS (ESI) m/z 479.1; HRMS: calcd for $C_{28}H_{28}N_2O_4$+H+, 457.21218. found (ESI-FTMS, [M+H]$^{1+}$), 457.21246.

Example 8KKKKKK $N^2$-(biphenyl-4-ylcarbonyl)-N-[(2R)-2-phenylpropyl]-L-α-glutamine MS (ESI) m/z 445.2; MS (ESI) m/z 889.3; HRMS: calcd for $C_{27}H_{28}N_2O_4$+H+, 445.21218. found (ESI-FTMS, [M+H]$^{1+}$), 445.21285.

Example 8LLLLLL $N^2$-(biphenyl-4-ylcarbonyl)-$N^1$-[2-(4-fluorophenyl)-1,1-dimethylethyl]-L-α-glutamamide MS (ESI) m/z 476.2; MS (ESI) m/z 951.5; HRMS: calcd for $C_{28}H_{30}FN_3O_3$+H+, 476.23440. found (ESI-FTMS, [M+H]$^{1+}$), 476.23543.

Example 8MMMMMM

N-[(1S)-1-benzyl-2-hydroxyethyl]-$N^2$-(biphenyl-4-ylcarbonyl)-L-α-glutamine

MS (ESI) m/z 461.2; MS (ESI) m/z 921.4; MS (ESI) m/z 943.4; HRMS: calcd for $C_{27}H_{28}N_2O_5$+H+, 461.20710. found (ESI-FTMS, [M+H]$^{1+}$), 461.20748.

Example 8NNNNNN $N^1$-benzyl-$N^2$-(4-bromobenzoyl)-L-α-glutamine

MS (ESI) m/z 419.1; MS (ESI) m/z 837.2; HRMS: calcd for $C_{19}H_{19}BrN_2O_4$+H+, 419.06009. found (ESI_FT, [M+H]$^{1+}$), 419.05998.

Example 8OOOOOO $N^1$-[2-(acetylamino)ethyl]-$N^2$-(1,1'-biphenyl-4-ylcarbonyl)-L-α-glutamine MS (ESI) m/z 410.2; MS (ESI) m/z 821.5; HRMS: calcd for $C_{22}H_{25}N_3O_5$+H+, 412.18670. found (ESI_FT, [M+H]$^{1+}$), 412.18628.

Example 8PPPPPP $N^2$-(1,1'-biphenyl-4-ylacetyl)-$N^1$-(3-methoxybenzyl)-L-α-glutamine The title compound was prepared according to procedures similar to those described in Example 7, except biphenylacetic acid was used. MS (ESI) m/z 461.2; MS (ESI) m/z 921.4; HRMS: calcd for $C_{27}H_{28}N_2O_5$+H+, 461.20710. found (ESI_FTMS, [M+H]$^{1+}$), 461.20514.

Example 8QQQQQQ $N^1$-(2-benzylphenyl)-$N^2$-(1,1'-biphenyl-4-ylcarbonyl)-L-α-glutamine MS (ESI−) m/z 491.3; HRMS: calcd for $C_{31}H_{28}N_2O_4$+H+, 493.21218. found (ESI-FTMS, [M+H]$^{1+}$), 493.21319.

Example 8RRRRRR $N^2$-2-naphthoyl-$N^1$-(3-phenylpropyl)-L-α-glutamine

MS (ESI) m/z 419.1; MS (ESI) m/z 837.1; MS (ESI) m/z 441.1; HRMS: calcd for $C_{25}H_{26}N_2O_4$+H+, 419.19653. found (ESI-FTMS, [M+H]$^{1+}$), 419.19678.

Example 8SSSSSS

N²-[(9-oxo-9H-fluoren-2-yl)carbonyl]-N¹-(3-phenyl-propyl)-L-α-glutamine

MS (ESI) m/z 471.3; MS (ESI) m/z 941.5; HRMS: calcd for $C_{28}H_{26}N_2O_5$+H+, 471.19145. found (ESI-FTMS, [M+H]$^{1+}$), 471.19142.

Example 8TTTTTT

N²-(4-phenoxybenzoyl)-N¹-(3-phenylpropyl)-L-α-glutamine

HRMS: calcd for $C_{27}H_{28}N_2O_5$+H+, 461.20710. found (ESI-FTMS, [M+H]$^{1+}$), 461.20673.

Example 8UUUUUU

N¹-benzyl-N²-[4-(pyrimidin-2-ylamino)benzoyl]-L-α-glutamine

MS m/z 02-101699GMS.

Example 8VVVVVV

N²-(9H-fluoren-2-ylcarbonyl)-N¹-(6-hydroxyhexyl)-L-α-glutamine

MS (ESI) m/z 439.2; HRMS: calcd for $C_{25}H_{30}N_2O_5$+H+, 439.22275. found (ESI-FTMS, [M+H]$^{1+}$), 439.22379.

Example 8WWWWWW

N²-[4-(5-bromo-2-thienyl)benzoyl]-N-[2-(4-fluorophenyl)-1,1-dimethylethyl]-L-α-glutamine MS (ESI) m/z 561.3; MS (ESI) m/z 1121.5; HRMS: calcd for $C_{26}H_{26}BrFN_2O_4S$+H+, 561.08534. found (ESI-FTMS, [M+H]$^{1+}$), 561.08472.

Example 8XXXXXX

N-[2-(5-chloro-2-thienyl)-1,1-dimethylethyl]-N²-[(3'-fluorobiphenyl-4-yl)carbonyl]-L-α-glutamine MS (ESI) m/z 517.3; MS (ESI) m/z 1033.5; MS (ESI) m/z 539.3; HRMS: calcd for $C_{26}H_{26}ClFN_2O_4S$+H+, 517.13586. found (ESI-FTMS, [M+H]$^{1+}$), 517.13517.

MS (ESI) m/z 517.3; MS (ESI) m/z 1033.6; MS (ESI) m/z 539.3; HRMS: calcd for $C_{26}H_{26}ClFN_2O_4S$+H+, 517.13586. found (ESI-FTMS, [M+H]$^{1+}$), 517.13686.

Example 8YYYYYY

N²-[(3',4'-difluorobiphenyl-4-yl)carbonyl]-N-[2-(4-fluorophenyl)-1,1-dimethylethyl]-L-α-glutamine MS (ESI) m/z 513.4; MS (ESI) m/z 1025.7; MS (ESI) m/z 535.3; HRMS: calcd for $C_{28}H_{27}F_3N_2O_4$+H+, 513.19957. found (ESI-FTMS, [M+H]$^{1+}$), 513.19837.

MS (ESI) m/z 513.4; MS (ESI) m/z 1025.8; MS (ESI) m/z 535.4; HRMS: calcd for $C_{28}H_{27}F_3N_2O_4$+H+, 513.19957. found (ESI-FTMS, [M+H]$^{1+}$), 513.20152.

Example 8ZZZZZZ

N-[2-(4-chlorophenyl)-1,1-dimethylethyl]-N²-[(3',4'-difluorobiphenyl-4-yl)carbonyl]-L-α-glutamine MS (ESI) m/z 529.2; MS (ESI) m/z 1057.5; HRMS: calcd for $C_{28}H_{27}ClF_2N_2O_4$+H+, 529.17002. found (ESI-FTMS, [M+H]$^{1+}$), 529.16931.

Example 8AAAAAAA

N-[2-(4-chlorophenyl)-1,1-dimethylethyl]-N²-[(2',4'-difluorobiphenyl-4-yl)carbonyl]-L-α-glutamine MS (ESI) m/z 529.2; MS (ESI) m/z 1057.5; HRMS: calcd for $C_{28}H_{27}ClF_2N_2O_4$+H+, 529.17002. found (ESI-FTMS, [M+H]$^{1+}$), 529.16951.

Example 8BBBBBBB

N-[2-(4-chlorophenyl)-1,1-dimethylethyl]-N²-[(2',5'-difluorobiphenyl-4-yl)carbonyl]-L-α-glutamine MS (ESI) m/z 529.3; MS (ESI) m/z 1057.5; MS (ESI) m/z 551.2; HRMS: calcd for $C_{28}H_{27}ClF_2N_2O_4$+H+, 529.17002. found (ESI-FTMS, [M+H]$^{1+}$), 529.16954.

Example 8CCCCCCC

N-[2-(4-chlorophenyl)-1,1-dimethylethyl]-N²-[(2',6'-difluorobiphenyl-4-yl)carbonyl]-L-α-glutamine MS (ESI) m/z 529.2; MS (ESI) m/z 1057.4; HRMS: calcd for $C_{28}H_{27}ClF_2N_2O_4$+H+, 529.17002. found (ESI-FTMS, [M+H]$^{1+}$), 529.16943.

Example 8DDDDDDD

N-[2-(4-chlorophenyl)-1,1-dimethylethyl]-N²-[(3',5'-difluorobiphenyl-4-yl)carbonyl]-L-α-glutamine MS (ESI) m/z 529.3; MS (ESI) m/z 1057.5; MS (ESI) m/z 551.3; HRMS: calcd for $C_{28}H_{27}ClF_2N_2O_4$+H+, 529.17002. found (ESI-FTMS, [M+H]$^{1+}$), 529.17191.

Example 8EEEEEEE

N-[2-(4-chlorophenyl)-1,1-dimethylethyl]-N²-[(2',3'-difluorobiphenyl-4-yl)carbonyl]-L-α-glutamine HRMS: calcd for $C_{28}H_{27}ClF_2N_2O_4$+H+, 529.17002. found (ESI-FTMS, [M+H]$^{1+}$), 529.17167.

Example 8FFFFFFF

N-(1,1-dimethyl-2-phenylethyl)-N²-(4-pyrimidin-5-ylbenzoyl)-L-α-glutamine

MS (ESI) m/z 461.2; MS (ESI) m/z 921.4; HRMS: calcd for $C_{26}H_{28}N_4O_4$+H+, 461.21833. found (ESI-FTMS, [M+H]$^{1+}$), 461.21863.

Example 8GGGGGGG $N^2$-[(3',4'-difluorobiphenyl-4-yl)carbonyl]-N-(1,1-dimethyl-2-phenylethyl)-L-α-glutamine MS (ESI) m/z 495.2; MS (ESI) m/z 989.4; HRMS: calcd for $C_{28}H_{28}F_2N_2O_4$+H+, 495.20899. found (ESI-FTMS, [M+H]$^{1+}$), 495.21035.

Example 8HHHHHHH $N^2$-[(3',5'-difluorobiphenyl-4-yl)carbonyl]-N-(1,1-dimethyl-2-phenylethyl)-L-α-glutamine MS (ESI) m/z 495.2; MS (ESI) m/z 989.4; MS (ESI) m/z 517.2; HRMS: calcd for $C_{28}H_{28}F_2N_2O_4$+H+, 495.20899. found (ESI-FTMS, [M+H]$^{1+}$), 495.21017.

Example 8IIIIIII

N-[2-(5-chloro-2-thienyl)-1,1-dimethylethyl]-$N^2$-[(3',4'-difluorobiphenyl-4-yl)carbonyl]-L-α-glutamine MS (ESI) m/z 533.3; MS (ESI) m/z 1067.7; HRMS: calcd for $C_{26}H_{25}ClF_2N_2O_4S$+H+, 535.12644. found (ESI-FTMS, [M+H]$^{1+}$), 535.1267.

Example 8JJJJJJJ $N^2$-(biphenyl-4-ylcarbonyl)-N-[2-(5-chloro-2-thienyl)-1,1-dimethylethyl]-L-α-glutamine MS (ESI) m/z 499.4; MS (ESI) m/z 997.7; MS (ESI) m/z 521.4; HRMS: calcd for $C_{26}H_{27}ClN_2O_4S$+H+, 499.14528. found (ESI-FTMS, [M+H]$^{1+}$), 499.14616.

Example 8KKKKKKK $N^2$-{[5-(3-chloro-4-fluorophenyl)-2-thienyl]carbonyl}-N-[2-(5-chloro-2-thienyl)-1,1-dimethylethyl]-L-α-glutamine MS (ESI) m/z 557.3; MS (ESI) m/z 1113.6; HRMS: calcd for $C_{24}H_{23}Cl_2FN_2O_4S_2$+H+, 557.05331. found (ESI-FTMS, [M+H]$^{1+}$), 557.05439.

Example 8LLLLLLL $N^2$-{[4'-(hydroxymethyl)biphenyl-4-yl]carbonyl}-N-(3,4,5-trimethoxybenzyl)-L-α-glutamine MS (ESI) m/z 537.1; MS (ESI) m/z 1073.3; HRMS: calcd for $C_{29}H_{32}N_2O_8$+H+, 537.22314. found (ESI-FTMS, [M+H]$^{1+}$), 537.22326.

Example 8MMMMMMM $N^2$-{[4'-(bromomethyl)biphenyl-4-yl]carbonyl}-N-(3,4,5-trimethoxybenzyl)-L-α-glutamine MS (ESI) m/z 599.1; MS (ESI) m/z 1197.1; HRMS: calcd for $C_{29}H_{31}BrN_2O_7$+H+, 599.13874. found (ESI-FTMS, [M+H]$^{1+}$), 599.13934.

Example 8NNNNNNN

N-[2-(4-fluorophenyl)-1,1-dimethylethyl]-$N^2$-[4-(2-thienyl)benzoyl]-L-α-glutamine MS (ESI) m/z 483.3; MS (ESI) m/z 965.5; HRMS: calcd for $C_{26}H_{27}FN_2O_4S$+H+, 483.17483. found (ESI-FTMS, [M+H]$^{1+}$), 483.1743.

Example 8OOOOOOO

N-[2-(4-fluorophenyl)-1,1-dimethylethyl]-$N^2$-[4-(2-furyl)benzoyl]-L-α-glutamine MS (ESI) m/z 467.3; MS (ESI) m/z 933.6; HRMS: calcd for $C_{26}H_{27}FN_2O_5$+H+, 467.19768. found (ESI-FTMS, [M+H]$^{1+}$), 467.19704.

Example 8PPPPPPP $N^2$-{[4'-(hydroxymethyl)biphenyl-4-yl]carbonyl}-N-(3-methylbenzyl)-L-α-glutamine MS (ESI) m/z 459.1; MS (ESI) m/z 919.5; HRMS: calcd for $C_{27}H_{28}N_2O_5$+H+, 461.20710. found (ESI-FTMS, [M+H]$^{1+}$), 461.20822.

Example 8QQQQQQQ $N^2$-{[3'-(hydroxymethyl)biphenyl-4-yl]carbonyl}-N-(3-methylbenzyl)-L-α-glutamine MS (ESI) m/z 459.2; HRMS: calcd for $C_{27}H_{28}N_2O_5$+H+, 461.20710. found (ESI-FTMS, [M+H]$^{1+}$), 461.20807.

Example 8RRRRRRR $N^2$-[4-(2,3-dihydro-1-benzofuran-5-yl)benzoyl]-N-[2-(4-fluorophenyl)-1,1-dimethylethyl]-L-α-glutamine MS (ESI) m/z 517.3; MS (ESI) m/z 1035.7; HRMS: calcd for $C_{30}H_{31}FN_2O_5$+H+, 519.22898. found (ESI-FTMS, [M+H]$^{1+}$), 519.22989.

Example 8SSSSSSS $N^2$-[(3'-chloro-4'-fluorobiphenyl-4-yl)carbonyl]-N-[2-(4-fluorophenyl)-1,1-dimethylethyl]-L-α-glutamine MS (ESI) m/z 529.3; MS (ESI) m/z 1057.6; HRMS: calcd for $C_{28}H_{27}ClF_2N_2O_4$+H+, 529.17002. found (ESI-FTMS, [M+H]$^{1+}$), 529.17061.

Example 8TTTTTTT $N^2$-{[3'-(bromomethyl)biphenyl-4-yl]carbonyl}-N-(3-methylbenzyl)-L-α-glutamine MS (ESI) m/z 521.1; HRMS: calcd for $C_{27}H_{27}BrN_2O_4$+H+, 523.12270. found (ESI-FTMS, [M+H]$^{1+}$), 523.12235.

Example 8UUUUUUU

N-[2-(4-fluorophenyl)-1,1-dimethylethyl]-N$^2$-[4-(3-thienyl)benzoyl]-L-α-glutamine MS (ESI) m/z 483.1; MS (ESI) m/z 965.3; HRMS: calcd for C$_{26}$H$_{27}$FN$_2$O$_4$S+H+, 483.17483. found (ESI-FTMS, [M+H]$^{1+}$), 483.17572.

Example 8VVVVVVV

N-[2-(4-fluorophenyl)-1,1-dimethylethyl]-N$^2$-[4-(5-methyl-2-thienyl)benzoyl]-L-α-glutamine MS (ESI) m/z 495.4; MS (ESI) m/z 991.7; HRMS: calcd for C$_{27}$H$_{29}$FN$_2$O$_4$S+H+, 497.19048. found (ESI-FTMS, [M+H]$^{1+}$), 497.19118.

Example 8WWWWWWW

N$^2$-[4-(5-chloro-2-thienyl)benzoyl]-N-[2-(4-fluorophenyl)-1,1-dimethylethyl]-L-α-glutamine MS (ESI) m/z 515.3; MS (ESI) m/z 1031.7; HRMS: calcd for C$_{26}$H$_{26}$ClFN$_2$O$_4$S+H+, 517.13586. found (ESI-FTMS, [M+H]$^{1+}$), 517.13644.

MS (ESI) m/z 515.3; MS (ESI) m/z 1031.6; HRMS: calcd for C$_{26}$H$_{26}$ClFN$_2$O$_4$S+H+, 517.13586. found (ESI-FTMS, [M+H]$^{1+}$), 517.13658.

Example 8XXXXXXX

N-[2-(4-chlorophenyl)-1,1-dimethylethyl]-N$^2$-[4-(2-thienyl)benzoyl]-L-α-glutamine MS (ESI) m/z 497.3; MS (ESI) m/z 995.6; HRMS: calcd for C$_{26}$H$_{27}$ClN$_2$O$_4$S+H+, 499.14528. found (ESI-FTMS, [M+H]$^{1+}$), 499.14509.

Example 8YYYYYYY

N-[2-(4-chlorophenyl)-1,1-dimethylethyl]-N$^2$-{[5-(3-methoxyphenyl)-2-thienyl]carbonyl}-L-α-glutamine MS (ESI) m/z 529.3; MS (ESI) m/z 1057.5; HRMS: calcd for C$_{27}$H$_{29}$ClN$_2$O$_5$S+H+, 529.15585. found (ESI-FTMS, [M+H]$^{1+}$), 529.15608.

Example 8ZZZZZZZ

N-[2-(4-chlorophenyl)-1,1-dimethylethyl]-N$^2$-[(5-phenyl-2-thienyl)carbonyl]-L-α-glutamine MS (ESI) m/z 499.2; MS (ESI) m/z 997.5; HRMS: calcd for C$_{26}$H$_{27}$ClN$_2$O$_4$S+H+, 499.14528. found (ESI-FTMS, [M+H]$^{1+}$), 499.14644.

Example 8AAAAAAAA

N$^2$-(2,2'-bithien-5-ylcarbonyl)-N-[2-(4-chlorophenyl)-1,1-dimethylethyl]-L-α-glutamine MS (ESI) m/z 505.1; MS (ESI) m/z 1009.1; HRMS: calcd for C$_{24}$H$_{25}$ClN$_2$O$_4$S$_2$+H+, 505.10170. found (ESI-FTMS, [M+H]$^{1+}$), 505.10282.

Example 8BBBBBBBB

N$^2$-[4-(2,3-dihydro-1-benzofuran-6-yl)benzoyl]-N-[2-(4-fluorophenyl)-1,1-dimethylethyl]-L-α-glutamine MS (ESI) m/z 517.5; MS (ESI) m/z 1035.9; HRMS: calcd for C$_{30}$H$_{31}$FN$_2$O$_5$+H+, 519.22898. found (ESI-FTMS, [M+H]$^{1+}$), 519.22971.

Example 8CCCCCCCC

N-[2-(4-fluorophenyl)-1,1-dimethylethyl]-N$^2$-{[6-(3-methoxyphenyl)pyridin-3-yl]carbonyl}-L-α-glutamine MS (ESI) m/z 508.4; HRMS: calcd for C$_{28}$H$_{30}$FN$_3$O$_5$+H+, 508.22423. found (ESI-FTMS, [M+H]$^{1+}$), 508.22472.

Example 8DDDDDDDD

N-[2-(4-fluorophenyl)-1,1-dimethylethyl]-N$^2$-[(6-phenylpyridin-3-yl)carbonyl]-L-α-glutamine MS (ESI) m/z 478.4; HRMS: calcd for C$_{27}$H$_{28}$FN$_3$O$_4$+H+, 478.21366. found (ESI-FTMS, [M+H]$^{1+}$), 478.21435.

Example 8EEEEEEEE

N-[2-(4-fluorophenyl)-1,1-dimethylethyl]-N$^2$-[(5-phenyl-2-thienyl)carbonyl]-L-α-glutamine MS (ESI) m/z 483.2; MS (ESI) m/z 965.4; HRMS: calcd for C$_{26}$H$_{27}$FN$_2$O$_4$S+H+, 483.17483. found (ESI-FTMS, [M+H]$^{1+}$), 483.17576.

Example 8FFFFFFFF

N$^2$-[(3-fluorobiphenyl-4-yl)carbonyl]-N-[2-(4-fluorophenyl)-1,1-dimethylethyl]-L-α-glutamine MS (ESI) m/z 495.3; MS (ESI) m/z 989.6; HRMS: calcd for C$_{28}$H$_{28}$F$_2$N$_2$O$_4$+H+, 495.20899. found (ESI-FTMS, [M+H]$^{1+}$), 495.20963.

Example 8GGGGGGGG

N-[2-(4-chlorophenyl)-1,1-dimethylethyl]-N$^2$-[(5-pyridin-4-yl-2-thienyl)carbonyl]-L-α-glutamine MS (ESI) m/z 500.3; HRMS: calcd for C$_{25}$H$_{26}$ClN$_3$O$_4$S+H+, 500.14053. found (ESI-FTMS, [M+H]$^{1+}$), 500.13984.

Example 8HHHHHHHH

N$^2$-{[5-(3-chloro-4-fluorophenyl)-2-thienyl]carbonyl}-N-[2-(4-chlorophenyl)-1,1-dimethylethyl]-L-α-glutamine MS (ESI) m/z 549.3; HRMS: calcd for C$_{26}$H$_{25}$Cl$_2$FN$_2$O$_4$S+H+, 551.09689. found (ESI-FTMS, [M+H]$^{1+}$), 551.09834.

Example 8IIIIIIII

N-[2-(4-chlorophenyl)-1,1-dimethylethyl]-$N^2$-[4-(2,3-dihydro-1-benzofuran-6-yl)benzoyl]-L-α-glutamine MS (ESI) m/z 535.4; MS (ESI) m/z 1069.8; HRMS: calcd for $C_{30}H_{31}ClN_2O_5$+H+, 535.19943. found (ESI-FTMS, [M+H]$^{1+}$), 535.20047.

Example 8JJJJJJJJ

N-[2-(4-chlorophenyl)-1,1-dimethylethyl]-$N^2$-[(5-pyridin-3-yl-2-thienyl)carbonyl]-L-α-glutamine MS (ESI) m/z 500.3; HRMS: calcd for $C_{25}H_{26}ClN_3O_4S$+H+, 500.14053. found (ESI-FTMS, [M+H]$^{1+}$), 500.1423.

Example 8KKKKKKKK $N^2$-[4-(2,3-dihydro-1-benzofuran-6-yl)benzoyl]-N-(1,1-dimethyl-2-phenylethyl)-L-α-glutamine MS (ESI) m/z 501.4; MS (ESI) m/z 1001.8; HRMS: calcd for $C_{30}H_{32}N_2O_5$+H+, 501.23840. found (ESI-FTMS, [M+H]$^{1+}$), 501.23954.

Example 8LLLLLLLL $N^2$-{[5-(3-chloro-4-fluorophenyl)-2-thienyl]carbonyl}-N-(1,1-dimethyl-2-phenylethyl)-L-α-glutamine MS (ESI) m/z 515.3; MS (ESI) m/z 1031.7; HRMS: calcd for $C_{26}H_{26}ClFN_2O_4S$+H+, 517.13586. found (ESI-FTMS, [M+H]$^{1+}$), 517.13443.

Example 8MMMMMMMM

N-(1,1-dimethyl-2-phenylethyl)-$N^2$-[4-(2-thienyl)benzoyl]-L-α-glutamine

MS (ESI) m/z 465.2; MS (ESI) m/z 929.4; HRMS: calcd for $C_{26}H_{28}N_2O_4S$+H+, 465.18425. found (ESI-FTMS, [M+H]$^{1+}$), 465.18402.

Example 8NNNNNNNN

N-(1,1-dimethyl-2-phenylethyl)-$N^2$-{[5-(3-methoxyphenyl)-2-thienyl]carbonyl}-L-α-glutamine MS (ESI) m/z 495.2; MS (ESI) m/z 989.4; HRMS: calcd for $C_{27}H_{30}N_2O_5S$+H+, 495.19482. found (ESI-FTMS, [M+H]$^{1+}$), 495.1942.

Example 8OOOOOOOO

N-(1,1-dimethyl-2-phenylethyl)-$N^2$-[(5-phenyl-2-thienyl)carbonyl]-L-α-glutamine MS (ESI) m/z 465.2; MS (ESI) m/z 929.4; HRMS: calcd for $C_{26}H_{28}N_2O_4S$+H+, 465.18425. found (ESI-FTMS, [M+H]$^{1+}$), 465.18359.

Example 8PPPPPPPP $N^2$-(2,2'-bithien-5-ylcarbonyl)-N-(1,1-dimethyl-2-phenylethyl)-L-α-glutamine MS (ESI) m/z 469.3; MS (ESI) m/z 939.6; HRMS: calcd for $C_{24}H_{26}N_2O_4S_2$+H+, 471.14067. found (ESI-FTMS, [M+H]$^{1+}$), 471.1403.

Example 8QQQQQQQQ

N-(1,1-dimethyl-2-phenylethyl)-$N^2$-[(5-pyridin-4-yl-2-thienyl)carbonyl]-L-α-glutamine MS (ESI) m/z 466.4; HRMS: calcd for $C_{25}H_{27}N_3O_4S$+H+, 466.17950. found (ESI-FTMS, [M+H]$^{1+}$), 466.17836.

Example 8RRRRRRRR

N-(1,1-dimethyl-2-phenylethyl)-$N^2$-[(5-pyridin-3-yl-2-thienyl)carbonyl]-L-α-glutamine MS (ESI) m/z 466.3; HRMS: calcd for $C_{25}H_{27}N_3O_4S$+H+, 466.17950. found (ESI-FTMS, [M+H]$^{1+}$), 466.17912.

Example 8SSSSSSSS

N-[2-(4-chlorophenyl)-1,1-dimethylethyl]-$N^2$-[4-(5-chloro-2-thienyl)benzoyl]-L-α-glutamine HRMS: calcd for $C_{26}H_{26}Cl_2N_2O_4S$+H+, 533.10631. found (ESI-FTMS, [M+H]$^{1+}$), 533.10629.

Example 8TTTTTTTT $N^2$-{[6-(5-chloro-2-thienyl)pyridin-3-yl]carbonyl}-N-(1,1-dimethyl-2-phenylethyl)-L-α-glutamine MS (ESI) m/z 500.3; MS (ESI) m/z 999.6; HRMS: calcd for $C_{25}H_{26}ClN_3O_4S$+H+, 500.14053. found (ESI-FTMS, [M+H]$^{1+}$), 500.14123.

Example 8UUUUUUUU

N-(1,1-dimethyl-2-phenylethyl)-$N^2$-[(6-phenylpyridin-3-yl)carbonyl]-L-α-glutamine MS (ESI) m/z 460.4; HRMS: calcd for $C_{27}H_{29}N_3O_4$+H+, 460.22308. found (ESI-FTMS, [M+H]$^{1+}$), 460.22319.

Example 8VVVVVVVV

N-[2-(4-chlorophenyl)-1,1-dimethylethyl]-$N^2$-(5-phenyl-2-furoyl)-L-α-glutamine MS (ESI) m/z 483.3; MS (ESI) m/z 965.6; MS (ESI) m/z 987.6; HRMS: calcd for $C_{26}H_{27}ClN_2O_5$+H+, 483.16813. found (ESI-FTMS, [M+H]$^{1+}$), 483.16818.

Example 8WWWWWWWW

N-[2-(4-chlorophenyl)-1,1-dimethylethyl]-$N^2$-{[6-(5-chloro-2-thienyl)pyridin-3-yl]carbonyl}-L-α-glutamine MS (ESI) m/z 534.3; HRMS: calcd for $C_{25}H_{25}Cl_2N_3O_4S$+H+, 534.10156. found (ESI-FTMS, [M+H]$^{1+}$), 534.10123.

Example 8XXXXXXXX

N-[2-(4-chlorophenyl)-1,1-dimethylethyl]-N²-[(6-phenylpyridin-3-yl)carbonyl]-L-α-glutamine MS (ESI) m/z 494.4; HRMS: calcd for $C_{27}H_{28}ClN_3O_4$+H+, 494.18411. found (ESI-FTMS, [M+H]$^{1+}$), 494.18423.

Example 8YYYYYYYY

N-[2-(4-fluorophenyl)-1,1-dimethylethyl]-N²-{[5-(3-methoxyphenyl)-2-thienyl]carbonyl}-L-α-glutamine MS (ESI) m/z 513.3; MS (ESI) m/z 1025.7; HRMS: calcd for $C_{27}H_{29}FN_2O_5S$+H+, 513.18540. found (ESI-FTMS, [M+H]$^{1+}$), 513.18635.

Example 8ZZZZZZZZ

N-[2-(4-fluorophenyl)-1,1-dimethylethyl]-N²-[(5-pyridin-3-yl-2-thienyl)carbonyl]-L-α-glutamine MS (ESI) m/z 484.3; HRMS: calcd for $C_{25}H_{26}FN_3O_4S$+H+, 484.17008. found (ESI-FTMS, [M+H]$^{1+}$), 484.17109.

Example 8AAAAAAAAA

N²-{[5-(3-chloro-4-fluorophenyl)-2-thienyl]carbonyl}-N-[2-(4-fluorophenyl)-1,1-dimethylethyl]-L-α-glutamine MS (ESI) m/z 535.2; MS (ESI) m/z 557.2; MS (ESI) m/z 1069.5; HRMS: calcd for $C_{26}H_{25}ClF_2N_2O_4S$+H+, 535.12644. found (ESI-FTMS, [M+H]$^{1+}$), 535.12696.
MS (ESI) m/z 533.3; MS (ESI) m/z 1067.6; HRMS: calcd for $C_{26}H_{25}ClF_2N_2O_4S$+H+, 535.12644. found (ESI-FTMS, [M+H]$^{1+}$), 535.12796.

Example 8BBBBBBBBB

N²-(2,2'-bithien-5-ylcarbonyl)-N-[2-(4-fluorophenyl)-1,1-dimethylethyl]-L-α-glutamine MS (ESI) m/z 489.3; MS (ESI) m/z 977.5; HRMS: calcd for $C_{24}H_{25}FN_2O_4S_2$+H+, 489.13125. found (ESI-FTMS, [M+H]$^{1+}$), 489.13208.

Example 8CCCCCCCCC

N-[2-(4-chlorophenyl)-1,1-dimethylethyl]-N²-[4-(5-formyl-2-thienyl)benzoyl]-L-α-glutamine MS (ESI) m/z 527.1; MS (ESI) m/z 1053.1; MS (ESI) m/z 549; HRMS: calcd for $C_{27}H_{27}ClN_2O_5S$+H+, 527.14020. found (ESI-FTMS, [M+H]$^{1+}$), 527.14185.

Example 8DDDDDDDDD

N²-[4-(5-acetyl-2-thienyl)benzoyl]-N-[2-(4-chlorophenyl)-1,1-dimethylethyl]-L-α-glutamine MS (ESI) m/z 541.1; MS (ESI) m/z 1081.2; MS (ESI) m/z 563.1; HRMS: calcd for $C_{28}H_{29}ClN_2O_5S$+H+, 541.15585. found (ESI-FTMS, [M+H]$^{1+}$), 541.15471.

Example 8EEEEEEEEE

N-[2-(4-chlorophenyl)-1,1-dimethylethyl]-N²-[4-(1,3-thiazol-2-yl)benzoyl]-L-α-glutamine MS (ESI) m/z 500.3; HRMS: calcd for $C_{25}H_{26}ClN_3O_4S$+H+, 500.14053. found (ESI-FTMS, [M+H]$^{1+}$), 500.14163.

Example 8FFFFFFFFF

N-(1,1-dimethyl-2-phenylethyl)-N²-[4-(1,3-thiazol-2-yl)benzoyl]-L-α-glutamine

MS (ESI) m/z 466.3; HRMS: calcd for $C_{25}H_{27}N_3O_4S$+H+, 466.17950. found (ESI-FTMS, [M+H]$^{1+}$), 466.18052.

Example 8GGGGGGGGG

N-(1,1-dimethyl-2-phenylethyl)-N²-(5-phenyl-2-furoyl)-L-α-glutamine

MS (ESI) m/z 449.3; MS (ESI) m/z 897.6; MS (ESI) m/z 471.3; HRMS: calcd for $C_{26}H_{28}N_2O_5$+H+, 449.20710. found (ESI-FTMS, [M+H]$^{1+}$), 449.20772.

Example 8HHHHHHHHH

N-(1,1-dimethyl-2-phenylethyl)-N²-[4-(5-formyl-2-thienyl)benzoyl]-L-α-glutamine

MS (ESI) m/z 493.3; MS (ESI) m/z 985.6; MS (ESI) m/z 515.3; HRMS: calcd for $C_{27}H_{28}N_2O_5S$+H+, 493.17917. found (ESI-FTMS, [M+H]$^{1+}$), 493.18011.

Example 8IIIIIIIII

N²-[4-(5-acetyl-2-thienyl)benzoyl]-N-(1,1-dimethyl-2-phenylethyl)-L-α-glutamine

MS (ESI) m/z 507.3; MS (ESI) m/z 1013.7; MS (ESI) m/z 529.3; HRMS: calcd for $C_{28}H_{30}N_2O_5S$+H+, 507.19482. found (ESI-FTMS, [M+H]$^{1+}$), 507.19518.

Example 8JJJJJJJJJ

N-[2-(4-chlorophenyl)-1,1-dimethylethyl]-N²-[3-(5-chloro-2-thienyl)benzoyl]-L-α-glutamine MS (ESI) m/z 533.3; MS (ESI) m/z 1065.5; MS (ESI) m/z 555.3; HRMS: calcd for $C_{26}H_{26}Cl_2N_2O_4S$+H+, 533.10631. found (ESI-FTMS, [M+H]$^{1+}$), 533.10835.

Example 8KKKKKKKKK

N-[2-(4-chlorophenyl)-1,1-dimethylethyl]-N²-[3-(2-thienyl)benzoyl]-L-α-glutamine MS (ESI) m/z 499.3; MS (ESI) m/z 997.6; MS (ESI) m/z 521.3; HRMS: calcd for $C_{26}H_{27}ClN_2O_4S$+H+, 499.14528. found (ESI-FTMS, [M+H]$^{1+}$), 499.14679.

Example 8LLLLLLLLL

N-[2-(4-chlorophenyl)-1,1-dimethylethyl]-N²-{[5-(4-chlorophenyl)-2-thienyl]carbonyl}-L-α-glutamine MS (ESI) m/z 533.3; MS (ESI) m/z 1065.5; MS (ESI) m/z 555.3; HRMS: calcd for $C_{26}H_{26}Cl_2N_2O_4S+H+$, 533.10631. found (ESI-FTMS, $[M+H]^{1+}$), 533.10784.

Example 8MMMMMMMMM

N-[2-(4-chlorophenyl)-1,1-dimethylethyl]-N²-{[5-(4-fluorophenyl)-2-thienyl]carbonyl}-L-α-glutamine MS (ESI) m/z 517.3; MS (ESI) m/z 539.3; MS (ESI) m/z 1033.6; HRMS: calcd for $C_{26}H_{26}ClFN_2O_4S+H+$, 517.13586. found (ESI-FTMS, $[M+H]^{1+}$), 517.13691.

Example 8NNNNNNNNN

N²-[4-(5-bromo-2-thienyl)benzoyl]-N-[2-(4-chlorophenyl)-1,1-dimethylethyl]-L-α-glutamine MS (ESI) m/z 577.2; MS (ESI) m/z 1153.4; HRMS: calcd for $C_{26}H_{26}BrClN_2O_4S+H+$, 577.05579. found (ESI-FTMS, $[M+H]^{1+}$), 577.05597.

Example 8OOOOOOOOO

N²-[4-(5-bromo-2-thienyl)benzoyl]-N-(1,1-dimethyl-2-phenylethyl)-L-α-glutamine

MS (ESI) m/z 543.1; MS (ESI) m/z 1085.2; HRMS: calcd for $C_{26}H_{27}BrN_2O_4S+H+$, 543.09477. found (ESI-FTMS, $[M+H]^{1+}$), 543.0965; HRMS: calcd for $C_{26}H_{27}BrN_2O_4S+H+$, 543.09477. found (ESI-FTMS, $[M+H]^{1+}$), 543.09494.

Example 8PPPPPPPPP

N-(1,1-dimethyl-2-phenylethyl)-N²-{[5-(4-fluorophenyl)-2-thienyl]carbonyl}-L-α-glutamine MS (ESI) m/z 483.2; MS (ESI) m/z 965.4; MS (ESI) m/z 505.2; HRMS: calcd for $C_{26}H_{27}FN_2O_4S+H+$, 483.17483. found (ESI-FTMS, $[M+H]^{1+}$), 483.17634.

Example 8QQQQQQQQQ

N²-[3-(5-chloro-2-thienyl)benzoyl]-N-(1,1-dimethyl-2-phenylethyl)-L-α-glutamine

MS (ESI) m/z 499.2; MS (ESI) m/z 997.3; MS (ESI) m/z 521.1; HRMS: calcd for $C_{26}H_{27}ClN_2O_4S+H+$, 499.14528. found (ESI-FTMS, $[M+H]^{1+}$), 499.14544.

Example 8RRRRRRRRR

N-(1,1-dimethyl-2-phenylethyl)-N²-[3-(2-thienyl)benzoyl]-L-α-glutamine

MS (ESI) m/z 465.2; MS (ESI) m/z 929.4; MS (ESI) m/z 487.2; HRMS: calcd for $C_{26}H_{28}N_2O_4S+H+$, 465.18425. found (ESI-FTMS, $[M+H]^{1+}$), 465.18439.

Example 8SSSSSSSSS

N²-[(3'-chlorobiphenyl-4-yl)carbonyl]-N-[2-(4-fluorophenyl)-1,1-dimethylethyl]-L-α-glutamine HRMS: calcd for $C_{28}H_{28}ClFN_2O_4+H+$, 511.17944. found (ESI-FTMS, $[M+H]^{1+}$), 511.17974.

Example 8TTTTTTTTT

N²-[(4'-chlorobiphenyl-4-yl)carbonyl]-N-[2-(4-fluorophenyl)-1,1-dimethylethyl]-L-α-glutamine HRMS: calcd for $C_{28}H_{28}ClFN_2O_4+H+$, 511.17944. found (ESI-FTMS, $[M+H]^{1+}$), 511.17972.

Example 8UUUUUUUUU

N²-[(4'-fluorobiphenyl-4-yl)carbonyl]-N-[2-(4-fluorophenyl)-1,1-dimethylethyl]-L-α-glutamine HRMS: calcd for $C_{28}H_{28}F_2N_2O_4+H+$, 495.20899. found (ESI-FTMS, $[M+H]^{1+}$), 495.20933.

Example 8VVVVVVVVV

N²-[(3'-fluorobiphenyl-4-yl)carbonyl]-N-[2-(4-fluorophenyl)-1,1-dimethylethyl]-L-α-glutamine HRMS: calcd for $C_{28}H_{28}F_2N_2O_4+H+$, 495.20899. found (ESI-FTMS, $[M+H]^{1+}$), 495.20937.

Example 8WWWWWWWWW

N-[2-(4-chloro phenyl)-1,1-dimethylethyl]-N²-[(3-phenyl-2-thienyl)carbonyl]-L-α-glutamine HRMS: calcd for $C_{26}H_{27}ClN_2O_4S+H+$, 499.14528. found (ESI-FTMS, $[M+H]^{1+}$), 499.14664.

Example 8XXXXXXXXX

N²-[(4'-chlorobiphenyl-4-yl)carbonyl]-N-[2-(4-chlorophenyl)-1,1-dimethylethyl]-L-α-glutamine MS (ESI) m/z 527.3; MS (ESI) m/z 1053.7; MS (ESI) m/z 549.3; HRMS: calcd for $C_{28}H_{28}Cl_2N_2O_4+H+$, 527.14989. found (ESI-FTMS, $[M+H]^{1+}$), 527.15049.
HRMS: calcd for $C_{28}H_{28}Cl_2N_2O_4+H+$, 527.14989. found (ESI-FTMS, $[M+H]^{1+}$), 527.14931.

Example 8YYYYYYYYY

N²-[(3'-chlorobiphenyl-4-yl)carbonyl]-N-[2-(4-chlorophenyl)-1,1-dimethylethyl]-L-α-glutamine MS (ESI) m/z 527.3; MS (ESI) m/z 1053.7; MS (ESI) m/z 549.3; HRMS: calcd for $C_{28}H_{28}Cl_2N_2O_4+H+$, 527.14989. found (ESI-FTMS, $[M+H]^{1+}$), 527.15048.

Example 8ZZZZZZZZZ

N-[2-(4-fluorophenyl)-1,1-dimethylethyl]-N²-{[5-(4-fluorophenyl)-2-thienyl]carbonyl}-L-α-glutamine MS (ESI) m/z 501.3; MS (ESI) m/z 1001.6; MS (ESI) m/z 523.3; HRMS: calcd for $C_{26}H_{26}F_2N_2O_4S+H+$, 501.16541. found (ESI-FTMS, $[M+H]^{1+}$), 501.16642.

MS (ESI) m/z 501.3; MS (ESI) m/z 1001.6; MS (ESI) m/z 523.3; HRMS: calcd for $C_{26}H_{26}F_2N_2O_4S+H+$, 501.16541. found (ESI-FTMS, $[M+H]^{1+}$), 501.16709.

Example 8AAAAAAAAAA $N^2$-{[5-(4-chlorophenyl)-2-thienyl]carbonyl}-N-(1,1-dimethyl-2-phenylethyl)-L-α-glutamine MS (ESI) m/z 499.1; MS (ESI) m/z 997.2; HRMS: calcd for $C_{26}H_{27}ClN_2O_4S+H+$, 499.14528. found (ESI-FTMS, $[M+H]^{1+}$), 499.14552.

Example 8BBBBBBBBBB

N-(1,1-dimethyl-2-phenylethyl)-$N^2$-[(3-phenyl-2-thienyl)carbonyl]-L-α-glutamine MS (ESI) m/z 465.2; MS (ESI) m/z 929.4; MS (ESI) m/z 951.4; HRMS: calcd for $C_{26}H_{28}N_2O_4S+H+$, 465.18425. found (ESI-FTMS, $[M+H]^{1+}$), 465.18455.

Example 8CCCCCCCCCC $N^2$-(4-bromobenzoyl)-N-[2-(4-fluorophenyl)-1,1-dimethylethyl]-L-α-glutamine MS (ESI) m/z 479.3; MS (ESI) m/z 957.5; MS (ESI) m/z 501.2; HRMS: calcd for $C_{22}H_{24}BrFN_2O_4+H+$, 479.09762. found (ESI-FTMS, $[M+H]^{1+}$), 479.0983.

Example 8DDDDDDDDDD

N-(1,1-dimethyl-2-phenylethyl)-$N^2$-[(4'-fluorobiphenyl-4-yl)carbonyl]-L-α-glutamine MS (ESI) m/z 477.3; MS (ESI) m/z 499.3; MS (ESI) m/z 953.7; HRMS: calcd for $C_{28}H_{29}FN_2O_4+H+$, 477.21841. found (ESI-FTMS, $[M+H]^{1+}$), 477.21891.

Example 8EEEEEEEEEE

N-(1,1-dimethyl-2-phenylethyl)-$N^2$-[(3'-fluorobiphenyl-4-yl)carbonyl]-L-α-glutamine MS (ESI) m/z 477.3; MS (ESI) m/z 499.3; MS (ESI) m/z 953.7; HRMS: calcd for $C_{28}H_{29}FN_2O_4+H+$, 477.21841. found (ESI-FTMS, $[M+H]^{1+}$), 477.21875.

Example 8FFFFFFFFFF $N^2$-[4-(5-chloro-2-thienyl)benzoyl]-N-[2-(4-fluorophenyl)-1,1-dimethylethyl]-D-α-glutamine MS (ESI) m/z 517.2; MS (ESI) m/z 539.2; MS (ESI) m/z 1033.5; HRMS: calcd for $C_{26}H_{26}ClFN_2O_4S+H+$, 517.13586. found (ESI-FTMS, $[M+H]^{1+}$), 517.1365.

Example 8GGGGGGGGGG $N^2$-{[6-(5-chloro-2-thienyl)pyridin-3-yl]carbonyl}-N-[2-(4-fluorophenyl)-1,1-dimethylethyl]-L-α-glutamine MS (ESI) m/z 518.2; HRMS: calcd for $C_{25}H_{25}ClFN_3O_4S+$H+, 518.13111. found (ESI-FTMS, $[M+H]^{1+}$), 518.13169.

Example 8HHHHHHHHHH $N^2$-{[5-(4-chlorophenyl)-2-thienyl]carbonyl}-N-[2-(4-fluorophenyl)-1,1-dimethylethyl]-L-α-glutamine MS (ESI) m/z 517.3; MS (ESI) m/z 539.3; MS (ESI) m/z 1033.6; HRMS: calcd for $C_{26}H_{26}ClFN_2O_4S+H+$, 517.13586. found (ESI-FTMS, $[M+H]^{1+}$), 517.1363.

Example 8IIIIIIIII $N^2$-{[5-(3,4-difluorophenyl)-2-thienyl]carbonyl}-N-[2-(4-fluorophenyl)-1,1-dimethylethyl]-L-α-glutamine MS (ESI) m/z 519.3; MS (ESI) m/z 1037.7; MS (ESI) m/z 541.3; HRMS: calcd for $C_{26}H_{25}F_3N_2O_4S+H+$, 519.15599. found (ESI-FTMS, $[M+H]^{1+}$), 519.1568.

The following intermediates ($R_1$COOH in scheme 7) were prepared and used in the preparation of some of the compounds of Example 8:

Example 8JJJJJJJJJJ 4-(2-thienyl)benzoic acid

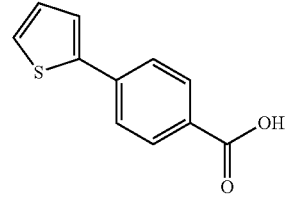

4-iodobenzoic acid (3 g, 12.1 mmol), 2-thiopheneboronic acid (3.10 g, 24.2 mmol), and $Pd(PPh_3)_4$ (1.4 g, 1.21 mmol) were dissolved in DMF (75 mL) in a 350 mL screw-cap pressure vessel. In a separate flask, $K_2CO_3$ (5.02 g, 36.3 mmol) was dissolved in $H_2O$ (12 mL) and was then added to the reaction. The flask was sealed, heated to 100° C. and stirred overnight (17 h).

The reaction was then diluted with $H_2O$ (150 mL), placed in a sep. funnel, and 1N NaOH was added to raise the pH to 10. The aqueous layer was washed with EtOAc (2×250 mL). The aqueous layer was kept, activated charcoal was added, and the mixture heated and stirred. Celite was added, followed by the mixture being filtered through celite. The filtrate was then acidified with concentrated HCl. At pH 7 a tan solid starts to precipitate. The pH was lowered to 5 and the solid formed is filtered out. The solid was partially dissolved in a small amount of toluene, which was then removed to remove some of the water still present. This step was repeated, then the solid was dried under vacuum. Yield—2.01 g tan solid, 81%. MS (ESI) m/z 202.9; HRMS: calcd for $C_{11}H_8O_2S+H+$, 205.03178. found (ESI-FTMS, $[M+H]^{1+}$), 205.03127.

The following compounds were prepared according to the procedure similar to the one described in Example 8JJJJJJJJJJ, from appropriate commercially available reagents:

i: 5-(3-methoxyphenyl)thiophene-2-carboxylic acid

MS (ESI) m/z 233.1; HRMS: calcd for $C_{12}H_{10}O_3S+H+$, 235.04234. found (ESI-FTMS, $[M+H]^{1+}$), 235.04226;

ii. 2,2'-bithiophene-5-carboxylic acid

MS (ESI) m/z 209.1; HRMS: calcd for $C_9H_6O_2S_2$+H+, 210.98820. found (ESI-FTMS, $[M+H]^{1+}$), 210.98816;

iii. 5-pyridin-4-ylthiophene-2-carboxylic acid

MS (ESI) m/z 206.1; HRMS: calcd for $C_{10}H_7NO_2S$+H+, 206.02703. found (ESI-FTMS, $[M+H]^{1+}$), 206.02691;

iv. 4-(5-chloro-2-thienyl)benzoic acid

HRMS: calcd for $C_{11}H_7ClO_2S$–H+, 236.97825. found (ESI-FTMS, $[M-H]^{1-}$), 236.97751;

v. 5-phenyl-2-furoic acid

HRMS: calcd for $C_{11}H_8O_3$+H+, 189.05462. found (ESI-FTMS, $[M+H]^{1+}$), 189.05445;

vi. 4-(5-acetyl-2-thienyl)benzoic acid

MS (ESI) m/z 245.1; HRMS: calcd for $C_{13}H_{10}O_3S$+H+, 247.04234. found (ESI-FTMS, $[M+H]^{1+}$), 247.04223;

vii. 3-(5-chloro-2-thienyl)benzoic acid

MS (ESI) m/z 237; HRMS: calcd for $C_{11}H_7ClO_2S$–H+, 236.97825. found (ESI-FTMS, $[M-H]^{1-}$), 236.97757;

viii. 3-(2-thienyl)benzoic acid

MS (ESI) m/z 203.1; HRMS: calcd for $C_{11}H_8O_2S$+H+, 205.03178. found (ESI-FTMS, $[M+H]^{1+}$), 205.03194;

ix. 5-(4-chlorophenyl)thiophene-2-carboxylic acid

MS (ESI) m/z 237; MS (ESI) m/z 283; MS (ESI) m/z 475.1; HRMS: calcd for $C_{11}H_7ClO_2S$–H+, 236.97825. found (ESI-FTMS, $[M-H]^{1-}$), 236.97825;

x. 3-phenylthiophene-2-carboxylic acid

MS (ESI) m/z 203.1; MS (ESI) m/z 249.1; HRMS: calcd for $C_{11}H_8O_2S$+H+, 205.03178. found (ESI-FTMS, $[M+H]^{1+}$), 205.03177;

xi. 4'-chlorobiphenyl-4-carboxylic acid

MS (ESI) m/z 231.1; HRMS: calcd for $C_{13}H_9ClO_2$–H+, 231.02183. found (ESI-FTMS, $[M-H]^{1-}$), 231.02129;

xii. 3'-chlorobiphenyl-4-carboxylic acid

MS (ESI) m/z 231.1; HRMS: calcd for $C_{13}H_9ClO_2$–H+, 231.02183. found (ESI-FTMS, $[M-H]^{1-}$), 231.02128;

xiii. 5-(3,4-difluorophenyl)thiophene-2-carboxylic acid

MS (ESI) m/z 239; MS (ESI) m/z 285.1; MS (ESI) m/z 479.1; HRMS: calcd for $C_{11}H_6F_2O_2S$+H+, 241.01293. found (ESI-FTMS, $[M+H]^{1+}$), 241.01183;

xiv. 5-(2,4-difluorophenyl)thiophene-2-carboxylic acid

MS (ESI) m/z 239; MS (ESI) m/z 285; HRMS: calcd for $C_{11}H_6F_2O_2S$+H+, 241.01293; found (ESI-FTMS, $[M+H]^{1+}$), 241.01187;

xv. 4-phenoxybenzoic acid

MS (ESI) m/z 213.1; HRMS: calcd for $C_{13}H_{10}O_3$+H+, 215.07027. found (ESI-FTMS, $[M+H]^{1+}$), 215.07029;

xvi. 4-(2,3-dihydro-1-benzofuran-6-yl)benzoic acid

MS (ESI) m/z 239.1; HRMS: calcd for $C_{15}H_{12}O_3$–H+, 239.07137. found (ESI-FTMS, $[M-H]^{1-}$), 239.07131;

xvii. 5-(3-chloro-4-fluorophenyl)thiophene-2-carboxylic acid

MS (ESI) m/z 255.1; MS (ESI) m/z 511.2; HRMS: calcd for $C_{11}H_6ClFO_2S$–H+, 254.96883. found (ESI-FTMS, $[M-H]^{1-}$), 254.96892;

xviii. 5-pyridin-3-ylthiophene-2-carboxylic acid

MS (ESI) m/z 206.1; HRMS: calcd for $C_{10}H_7NO_2S$+H+, 206.02703. found (ESI-FTMS, $[M+H]^{1+}$), 206.02708;

xix. 6-(5-chloro-2-thienyl)nicotinic acid

MS (ESI) m/z 238;

xx. 6-phenylnicotinic acid

MS (ESI) m/z 200.1; HRMS: calcd for $C_{12}H_9NO_2$+H+, 200.07061. found (ESI-FTMS, $[M+H]^{1+}$), 200.07052;

xxi. 4-(1,3-thiazol-2-yl)benzoic acid mp 235-237° C.; MS (ESI) m/z 206; MS (ESI) m/z 204;

xxii. 4-(5-bromo-2-thienyl)benzoic acid

MS (ESI) m/z 281; MS (ESI) m/z 394.8;

xxiii. 5-(4-fluorophenyl)thiophene-2-carboxylic acid

MS (ES) m/z 221.0; MS (ES) m/z 443.0;

xxiv. 4-[5-(aminosulfonyl)-2-thienyl]benzoic acid

MS (ESI) m/z 282.1; MS (ESI) m/z 565.2;

xxv. 4-(5-cyano-2-thienyl)benzoic acid

MS (ESI) m/z 228.1;

xxvi. 3'-fluorobiphenyl-4-carboxylic acid

MS (ESI) m/z 215.1;

xxvii. 3',4'-difluorobiphenyl-4-carboxylic acid

MS (ESI) m/z 233;

141 xxviii. 2',4'-difluorobiphenyl-4-carboxylic acid

MS (ESI) m/z 233.1;

xxix. 2',5'-difluorobiphenyl-4-carboxylic acid

MS (ESI) m/z 233.1;

xxx. 3',5'-difluorobiphenyl-4-carboxylic acid

MS (ESI) m/z 233.1;

xxxi. 2',6'-difluorobiphenyl-4-carboxylic acid

MS (ESI) m/z 233.1;

xxxii. 2',3'-difluorobiphenyl-4-carboxylic acid

MS (ESI) m/z 233;

xxxiii. 4-(5-methyl-2-thienyl)benzoic acid

MS (ESI) m/z 217.1; HRMS: calcd for $C_{12}H_{10}O_2S+H+$, 219.04743. found (ESI-FTMS, $[M+H]^{1+}$), 219.04744;

xxxiv. 6-(3-methoxyphenyl)nicotinic acid

MS (ESI) m/z 230.1;

xxxv. 3-fluorobiphenyl-4-carboxylic acid

MS (ESI) m/z 215.1; HRMS: calcd for $C_{13}H_9FO_2+H+$, 217.06593. found (ESI-FTMS, $[M+H]^{1+}$), 217.06598.

142

Example 9

$N^2$-(biphenyl-4-ylcarbonyl)-$N^1$-[2-(4'-formylbiphenyl-4-yl)ethyl]-L-α-glutamine Step A: tert-butyl $N^2$-(biphenyl-4-ylcarbonyl)-$N^1$-[2-(4'-formylbiphenyl-4-yl)ethyl]-L-α-glutaminate tert-butyl $N^2$-(biphenyl-4-ylcarbonyl)-$N^1$-[2-(4-bromophenyl)ethyl]-L-α-glutaminate (333 mg, 0.59 mmol, 1 equiv.) was dissolved in DME (5 mL) and the mixture was added to 4-formylphenyl boronic acid (0.97 g, 0.65 mmol, 1.1 equiv.) and Pd(PPh$_3$)$_4$ (68 mg, 0.059 mmol, 0.1 equiv.) and stirred for 30 minutes prior to the addition of aq. K$_2$CO$_3$ (163 mg, 1.18 mmol, 2 equiv.) in 1 mL H$_2$O. The mixture was capped in a sealed vessel and stirred overnight at 80° C. The reaction was complete as determined by TLC. The mixture was filtered over celite, the solvent was removed, and the resulting tan solid was diluted with EtOAc (20 mL) and washed consecutively with H$_2$O, 10% HCl, brine, and dried over Na$_2$SO$_4$. The solid was purified by column chromatography (silica gel, 41% Acetone/Hexanes) to give 38 mg of tert-butyl $N^2$-(biphenyl-4-ylcarbonyl)-$N^1$-[2-(4'-formylbiphenyl-4-yl)ethyl]-L-α-glutaminate in 11% yield. MS (ESI) m/z 591.3; MS (ESI) m/z 1181.5; HRMS: calcd for $C_{37}H_{38}N_2O_5$+H+, 591.28535. found (ESI-FTMS, $[M+H]^{1+}$), 591.28473.

Step B: $N^2$-(biphenyl-4-ylcarbonyl)-$N^1$-[2-(4'-formylbiphenyl-4-yl)ethyl]-L-α-glutamine tert-butyl $N^2$-(biphenyl-4-ylcarbonyl)-$N^1$-[2-(4'-formylbiphenyl-4-yl)ethyl]-L-α-glutaminate (100 mg, 0.17 mmol, 1

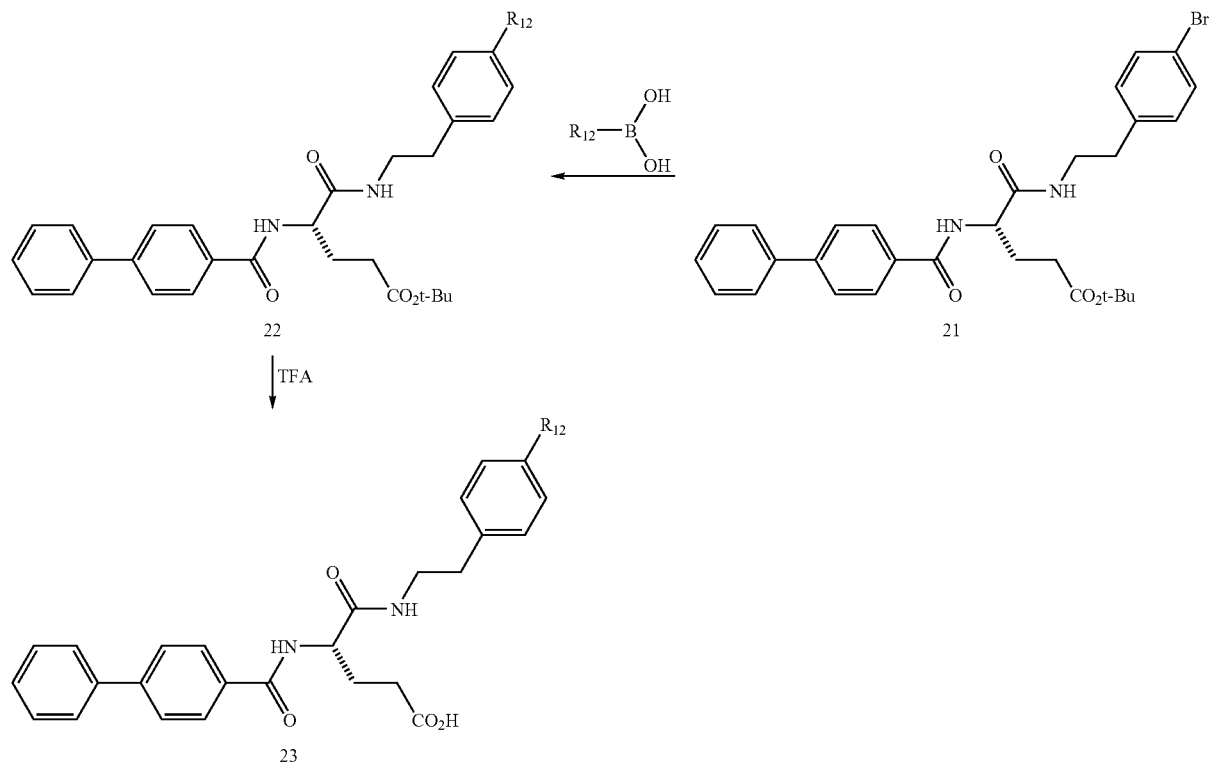

Scheme 8 equiv.) was dissolved in $CH_2Cl_2$ (5 mL) and added to TFA (2 mL). The mixture was stirred at room temperature for 3 hrs. The reaction was complete as determined by TLC. Solvent was removed and the resulting solid was purified by preparative HPLC to give $N^2$-(biphenyl-4-ylcarbonyl)-$N^1$-[2-(4'-formylbiphenyl-4-yl)ethyl]-L-α-glutamine in 89% yield (80 mg). MS (ESI) m/z 533.1; HRMS: calcd for $C_{33}H_{30}N_2O_5$+H+, 535.22275. found (ESI-FTMS, [M+H]$^{1+}$), 535.22464.

Example 10

The following compounds were prepared according to procedures similar to those described in Example 9.

Example 10A $N^2$-(biphenyl-4-ylcarbonyl)-$N^1$-{2-[4'-(trifluoromethyl)biphenyl-4-yl]ethyl}-L-α-glutamine Step A: tert-butyl $N^2$-(biphenyl-4-ylcarbonyl)-$N^1$-{2-[4'-(trifluoromethyl)biphenyl-4-yl]ethyl}-L-α-glutaminate MS (ESI) m/z 631.2; MS (ESI) m/z 1261.4; MS (ESI) m/z 653.2; HRMS: calcd for $C_{37}H_{37}F_3N_2O_4$+H+, 631.27782. found (ESI-FTMS, [M+H]$^{1+}$), 631.27719.

Step B: $N^2$-(biphenyl-4-ylcarbonyl)-$N^1$-{2-[4'-(trifluoromethyl)biphenyl-4-yl]ethyl}-L-α-glutamine HRMS: calcd for $C_{33}H_{29}F_3N_2O_4$+H+, 575.21522. found (ESI-FTMS, [M+H]$^{1+}$), 575.21548.

Example 10B $N^2$-(biphenyl-4-ylcarbonyl)-$N^1$-[2-(4'-methoxybiphenyl-4-yl)ethyl]-L-α-glutamine Step A: tert-butyl $N^2$-(biphenyl-4-ylcarbonyl)-$N^1$-[2-(4'-methoxybiphenyl-4-yl)ethyl]-L-α-glutaminate MS (ESI) m/z 593.3; MS (ESI) m/z 1185.5; HRMS: calcd for $C_{37}H_{40}N_2O_5$+H+, 593.30100. found (ESI-FTMS, [M+H]$^{1+}$), 593.29946.

Step B: $N^2$-(biphenyl-4-ylcarbonyl)-$N^1$-[2-(4'-methoxybiphenyl-4-yl)ethyl]-L-α-glutamine HRMS: calcd for $C_{33}H_{32}N_2O_5$+H+, 537.23840. found (ESI-FTMS, [M+H]$^{1+}$), 537.23906.

Example 10C $N^2$-(biphenyl-4-ylcarbonyl)-$N^1$-(2-biphenyl-4-ylethyl)-L-α-glutamine Step A: tert-butyl $N^2$-(biphenyl-4-ylcarbonyl)-$N^1$-(2-biphenyl-4-ylethyl)-L-α-glutaminate MS (ESI) m/z 563.3; MS (ESI) m/z 1125.5; HRMS: calcd for $C_{36}H_{38}N_2O_4$+H+, 563.29043. found (ESI-FTMS, [M+H]$^{1+}$), 563.28977.

Step B: $N^2$-(biphenyl-4-ylcarbonyl)-$N^1$-(2-biphenyl-4-ylethyl)-L-α-glutamine HRMS: calcd for $C_{32}H_{30}N_2O_4$+H+, 507.22783. found (ESI-FTMS, [M+H]$^{1+}$), 507.22688.

Example 10D $N^2$-(biphenyl-4-ylcarbonyl)-$N^1$-{2-[4-(2-thienyl)phenyl]ethyl}-L-α-glutamine Step A: tert-butyl $N^2$-(biphenyl-4-ylcarbonyl)-$N^1$-{2-[4-(2-thienyl)phenyl]ethyl}-L-α-glutaminate MS (ESI) m/z 569.2; MS (ESI) m/z 1137.4; HRMS: calcd for $C_{34}H_{36}N_2O_4S$+H+, 569.24685. found (ESI-FTMS, [M+H]$^{1+}$), 569.24702.

Step B: $N^2$-(biphenyl-4-ylcarbonyl)-$N^1$-{2-[4-(2-thienyl)phenyl]ethyl}-L-α-glutamine MS (ESI) m/z 511.1; HRMS: calcd for $C_{30}H_{28}N_2O_4S$+H+, 513.18425. found (ESI-FTMS, [M+H]$^{1+}$), 513.18417.

Example 10E $N^2$-(biphenyl-4-ylcarbonyl)-$N^1$-[2-(2'-ethoxybiphenyl-4-yl)ethyl]-L-α-glutamine MS (ESI) m/z 551.1; MS (ESI) m/z 1101.4; MS (ESI) m/z 573.1; HRMS: calcd for $C_{34}H_{34}N_2O_5$+H+, 551.25405. found (ESI-FTMS, [M+H]$^{1+}$), 551.2538.

Example 10F $N^2$-(biphenyl-4-ylcarbonyl)-$N^1$-[2-(4'-ethynylbiphenyl-4-yl)ethyl]-L-α-glutamine Step A: tert-butyl $N^2$-(biphenyl-4-ylcarbonyl)-$N^1$-[2-(4'-ethynylbiphenyl-4-yl)ethyl]-L-α-glutaminate MS (ESI) m/z 587.3; MS (ESI) m/z 1173.5; HRMS: calcd for $C_{38}H_{38}N_2O_4$+H+, 587.29043. found (ESI-FTMS, [M+H]$^{1+}$), 587.29016.

Step B: $N^2$-(biphenyl-4-ylcarbonyl)-$N^1$-[2-(4'-ethynylbiphenyl-4-yl)ethyl]-L-α-glutamine MS (ESI) m/z 529.2; HRMS: calcd for $C_{34}H_{30}N_2O_4$+H+, 531.22783. found (ESI-FTMS, [M+H]$^{1+}$), 531.22669.

Example 10G $N^2$-(biphenyl-4-ylcarbonyl)-$N^1$-[2-(4-pyridin-2-ylphenyl)ethyl]-L-α-glutamine Step A: tert-butyl $N^2$-(biphenyl-4-ylcarbonyl)-$N^1$-[2-(4-pyridin-2-ylphenyl)ethyl]-L-α-glutaminate MS (ESI) m/z 564.3; HRMS: calcd for $C_{35}H_{37}N_3O_4$+H+, 564.28568. found (ESI-FTMS, [M+H]$^{1+}$), 564.28472.

Step B: $N^2$-(biphenyl-4-ylcarbonyl)-$N^1$-[2-(4-pyridin-2-ylphenyl)ethyl]-L-α-glutamine MS (ESI) m/z 508.2.

Example 10H

N²-(biphenyl-4-ylcarbonyl)-N¹-[2-(4-pyridin-4-ylphenyl)ethyl]-L-α-glutamine

Step A: tert-butyl N²-(biphenyl-4-ylcarbonyl)-N¹-[2-(4-pyridin-4-ylphenyl)ethyl]-L-α-glutaminate MS (ESI) m/z 564.2; HRMS: calcd for $C_{35}H_{37}N_3O_4$+H+, 564.28568. found (ESI-FTMS, [M+H]$^{1+}$), 564.28648.

Step B: N²-(biphenyl-4-ylcarbonyl)-N¹-[2-(4-pyridin-4-ylphenyl)ethyl]-L-α-glutamine MS (ESI) m/z 508.1; MS (ESI) m/z 275.1; HRMS: calcd for $C_{31}H_{29}N_3O_4$+H+, 508.22308. found (ESI-FTMS, [M+H]$^{1+}$), 508.22403.

Example 10I

N²-(biphenyl-4-ylcarbonyl)-N¹-[2-(3-pyridin-2-ylphenyl)ethyl]-L-α-glutamine

Step A: tert-butyl N²-(biphenyl-4-ylcarbonyl)-N¹-[2-(3-pyridin-2-ylphenyl)ethyl]-L-α-glutaminate MS (ESI) m/z 564.3; HRMS: calcd for $C_{35}H_{37}N_3O_4$+H+, 564.28568. found (ESI-FTMS, [M+H]$^{1+}$), 564.28531.

Step B: N²-(biphenyl-4-ylcarbonyl)-N¹-[2-(3-pyridin-2-ylphenyl)ethyl]-L-α-glutamine MS (ESI) m/z 508.1; HRMS: calcd for $C_{31}H_{29}N_3O_4$+H+, 508.22308. found (ESI-FTMS, [M+H]$^{1+}$), 508.22432.

Example 10J

N²-(biphenyl-4-ylcarbonyl)-N¹-[2-(4'-formylbiphenyl-3-yl)ethyl]-L-α-glutamine

Step A: tert-butyl N²-(biphenyl-4-ylcarbonyl)-N¹-[2-(4'-formylbiphenyl-3-yl)ethyl]-L-α-glutaminate Step B: N²-(biphenyl-4-ylcarbonyl)-N¹-[2-(4'-formylbiphenyl-3-yl)ethyl]-L-α-glutamine MS (ESI) m/z 535.2; MS (ESI) m/z 1069.3; HRMS: calcd for $C_{33}H_{30}N_2O_5$+H+, 535.22275; found (ESI-FTMS, [M+H]$^{1+}$), 535.22147.

Example 10K

N²-(biphenyl-4-ylcarbonyl)-N¹-{2-[4'-(trifluoromethyl)biphenyl-3-yl]ethyl}-L-α-glutamine Step A: tert-butyl N²-(biphenyl-4-ylcarbonyl)-N¹-{2-[4'-(trifluoromethyl)biphenyl-3-yl]ethyl}-L-α-glutaminate HRMS: calcd for $C_{37}H_{37}F_3N_2O_4$+H+, 631.27782. found (ESI-FTMS, [M+H]$^{1+}$), 631.27639.

Step B: N²-(biphenyl-4-ylcarbonyl)-N¹-{2-[4'-(trifluoromethyl)biphenyl-3-yl]ethyl}-L-α-glutamine MS (ESI) m/z 575.2; HRMS: calcd for $C_{33}H_{29}F_3N_2O_4$+H+, 575.21522. found (ESI-FTMS, [M+H]$^{1+}$), 575.21382.

Example 10L

N²-(biphenyl-4-ylcarbonyl)-N¹-[2-(4'-methoxybiphenyl-3-yl)ethyl]-L-α-glutamine

Step A: tert-butyl N²-(biphenyl-4-ylcarbonyl)-N¹-[2-(4'-methoxybiphenyl-3-yl)ethyl]-L-α-glutaminate HRMS: calcd for $C_{37}H_{40}N_2O_5$+H+, 593.30100. found (ESI-FTMS, [M+H]$^{1+}$), 593.29993.

Step B: N²-(biphenyl-4-ylcarbonyl)-N¹-[2-(4'-methoxybiphenyl-3-yl)ethyl]-L-α-glutamine MS (ESI) m/z 537.2; HRMS: calcd for $C_{33}H_{32}N_2O_5$+H+, 537.23840. found (ESI-FTMS, [M+H]$^{1+}$), 537.23745.

Example 10M

N²-(1,1'-biphenyl-4-ylcarbonyl)-N¹-(3-vinylbenzyl)-L-α-glutamine

Step A: tert-butyl N²-(1,1'-biphenyl-4-ylcarbonyl)-N¹-(3-vinylbenzyl)-L-α-glutaminate Tert-butyl N²-(1,1'-biphenyl-4-ylcarbonyl)-N¹-(3-iodobenzyl)-L-α-glutaminate was used as the starting material, MS (ESI) m/z 499.2; MS (ESI) m/z 997.4; HRMS: calcd for $C_{31}H_{34}N_2O_4$+H+, 499.25913. found (ESI-FTMS, [M+H]$^{1+}$), 499.25906.

Step B: N²-(1,1'-biphenyl-4-ylcarbonyl)-N¹-(3-vinylbenzyl)-L-α-glutamine

MS (ESI) m/z 443.2; MS (ESI) m/z 885.3; HRMS: calcd for $C_{27}H_{26}N_2O_4$+H+, 443.19653. found (ESI-FTMS, [M+H]$^{1+}$), 443.19728.

Example 10N

N²-(1,1'-biphenyl-4-ylcarbonyl)-N¹-(3-thien-2-ylbenzyl)-L-α-glutamine

Step A: tert-butyl N²-(1,1'-biphenyl-4-ylcarbonyl)-N¹-(3-thien-2-ylbenzyl)-L-α-glutaminate Tert-butyl N²-(1,1'-biphenyl-4-ylcarbonyl)-N¹-(3-iodobenzyl)-L-α-glutaminate was used as the starting material. MS (ESI) m/z 555.2; MS (ESI) m/z 1109.3; HRMS: calcd for $C_{33}H_{34}N_2O_4S$+H+, 555.23120. found (ESI-FTMS, [M+H]$^{1+}$), 555.23173.

Step B: N²-(1,1'-biphenyl-4-ylcarbonyl)-N¹-(3-thien-2-ylbenzyl)-L-α-glutamine

MS (ESI) m/z 499.1; HRMS: calcd for $C_{29}H_{26}N_2O_4S$+H+, 499.16860. found (ESI-FTMS, [M+H]$^{1+}$), 499.16976.

Example 10O

N²-(biphenyl-4-ylcarbonyl)-N¹-{[4'-(trifluoromethyl)biphenyl-3-yl]methyl}-L-α-glutamine Step A: tert-butyl N²-(biphenyl-4-ylcarbonyl)-N¹-{[4'-(trifluoromethyl)biphenyl-3-yl]methyl}-L-α-glutaminate Tert-butyl N²-(1,1'-biphenyl-4-ylcarbonyl)-N¹-(3-iodobenzyl)-L-α-glutaminate was used as the starting material, MS (ESI) m/z 617.2; MS (ESI) m/z 1233.3; HRMS: calcd for $C_{36}H_{35}F_3N_2O_4$+H+, 617.26217. found (ESI-FTMS, [M+H]$^{1+}$), 617.26334.

Step B: $N^2$-(biphenyl-4-ylcarbonyl)-$N^1$-{[4'-(trifluoromethyl)biphenyl-3-yl]methyl}-L-α-glutamine MS (ESI) m/z 559.1; MS (ESI) m/z 1119.1; HRMS: calcd for $C_{32}H_{27}F_3N_2O_4$+H+, 561.19957. found (ESI-FTMS, [M+H]$^{1+}$), 561.2001.

Example 10P $N^2$-(biphenyl-4-ylcarbonyl)-$N^1$-[(4'-ethynylbiphenyl-3-yl)methyl]-L-α-glutamine Step A: tert-butyl $N^2$-(biphenyl-4-ylcarbonyl)-$N^1$-[(4'-ethynylbiphenyl-3-yl)methyl]-L-α-glutaminate Tert-butyl $N^2$-(1,1'-biphenyl-4-ylcarbonyl)-$N^1$-(3-iodobenzyl)-L-α-glutaminate was used as the starting material, MS (ESI) m/z 573.2; MS (ESI) m/z 1145.4; HRMS: calcd for $C_{37}H_{36}N_2O_4$+H+, 573.27478. found (ESI-FTMS, [M+H]$^{1+}$), 573.27518.

Step B: $N^2$-(biphenyl-4-ylcarbonyl)-$N^1$-[(4'-ethynylbiphenyl-3-yl)methyl]-L-α-glutamine MS (ESI) m/z 517.2; MS (ESI) m/z 1033.3; HRMS: calcd for $C_{33}H_{28}N_2O_4$+H+, 517.21218. found (ESI-FTMS, [M+H]$^{1+}$), 517.2125.

Example 10Q $N^2$-(biphenyl-4-ylcarbonyl)-$N^1$-(3-pyridin-2-ylbenzyl)-L-α-glutamine Step A: tert-butyl $N^2$-(biphenyl-4-ylcarbonyl)-$N^1$-(3-pyridin-2-ylbenzyl)-L-α-glutaminate Tert-butyl $N^2$-(1,1'-biphenyl-4-ylcarbonyl)-$N^1$-(3-iodobenzyl)-L-α-glutaminate was used as the starting material, MS (ESI) m/z 550.2; HRMS: calcd for $C_{34}H_{35}N_3O_4$+H+, 550.27003. found (ESI-FTMS, [M+H]$^{1+}$), 550.27066.

Step B: $N^2$-(biphenyl-4-ylcarbonyl)-$N^1$-(3-pyridin-2-ylbenzyl)-L-α-glutamine MS (ESI) m/z 494.1; HRMS: calcd for $C_{30}H_{27}N_3O_4$+H+, 494.20743. found (ESI-FTMS, [M+H]$^{1+}$), 494.20803.

Example 10R $N^2$-(1,1'-biphenyl-4-ylcarbonyl)-$N^1$-(4-vinylbenzyl)-L-α-glutamine Step A: tert-butyl $N^2$-(1,1'-biphenyl-4-ylcarbonyl)-$N^1$-(4-vinylbenzyl)-L-α-glutaminate Tert-butyl $N^2$-(1,1'-biphenyl-4-ylcarbonyl)-$N^1$-(4-iodobenzyl)-L-α-glutaminate was used as the starting material, MS (ESI) m/z 499.2; MS (ESI) m/z 997.3; HRMS: calcd for $C_{31}H_{34}N_2O_4$+H+, 499.25913. found (ESI-FTMS, [M+H]$^{1+}$), 499.25883.

Step B: $N^2$-(1,1'-biphenyl-4-ylcarbonyl)-$N^1$-(4-vinylbenzyl)-L-α-glutamine

MS (ESI) m/z 443.1; HRMS: calcd for $C_{27}H_{26}N_2O_4$+H+, 443.19653. found (ESI-FTMS, [M+H]$^{1+}$), 443.19697.

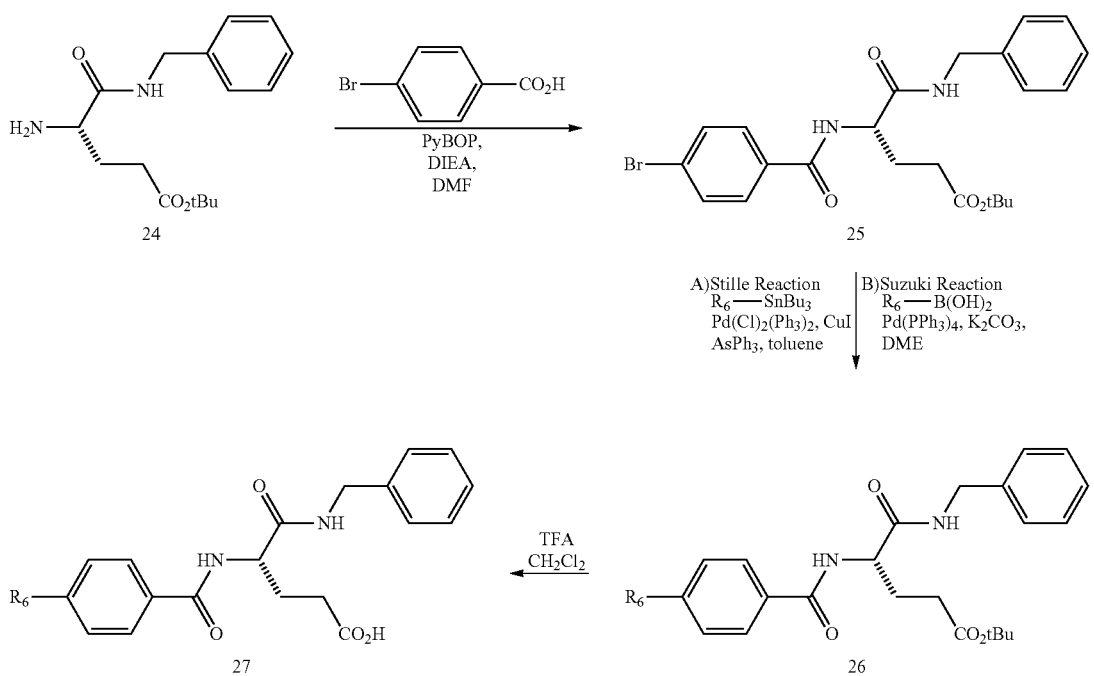

Scheme 9

Example 11

$N^1$-benzyl-$N^2$-(4-thien-2-ylbenzoyl)-L-α-glutamine

Step A: tert-butyl $N^1$-benzyl-$N^2$-(4-bromobenzoyl)-L-α-glutaminate

A solution of 4-Amino-4-benzylcarbamoyl-butyric acid tert-butyl ester (6.39 g, 21.9 mmol, 1 equiv.) in DMF (18 mL) was added to 4-Bromobenzoic acid (4.39 g, 21.9 mmol, 1 equiv.) and PyBOP (14.7 g, 28.2 mmol, 1.2 equiv.) and the solution was stirred at room temperature under nitrogen. DIEA (4.58 mL, 26.3 mmol, 1.2 equiv.) was then added dropwise and the solution was stirred for 2 hrs. The reaction was complete as determined by TLC. The solution was diluted with EtOAc (250 mL) and washed consecutively with $H_2O$, 10% HCl, satd. $NaHCO_3$, brine, and dried over $Na_2SO_4$. After the solvent was evaporated, the crude residue was dissolved in ether and washed with aq. LiBr (2×250 mL) and dried over $Na_2SO_4$. A light tan solid was obtained, 8.94 g of tert-butyl $N^1$-benzyl-$N^2$-(4-bromobenzoyl)-L-α-glutaminate in 86% yield.

MS (ESI) m/z 475.1; MS (ESI) m/z 949.2; HRMS: calcd for $C_{23}H_{27}BrN_2O_4$+Na+, 497.10464. found (ESI_FTMS, $[M+Na]^{1+}$), 497.10542.

Step B: tert-butyl $N^1$-benzyl-$N^2$-(4-thien-2-ylbenzoyl)-L-α-glutaminate

Tert-butyl $N^1$-benzyl-$N^2$-(4-bromobenzoyl)-L-α-glutaminate (200 mg, 0.421 mmol) was dissolved in toluene (4 mL) under nitrogen. Copper iodide (16.0 mg, 0.0841 mmol), triphenylarsine (26.0 mg, 0.0841 mmol), and $Pd(Cl)_2(PPh_3)_2$ (59 mg, 0.0841 mmol) were then added as solids. The reaction mixture was then fitted with a condenser and heated to reflux (115° C.), for 10 minutes. 2-(Tributylstannyl)-thiophene (267 mL, 0.841 mmol) was added and immediately the reaction went from orange to black. These are typical Stille reaction conditions. The reaction was monitored by TLC and was complete at 30 minutes. The reaction mixture was filtered through celite and the celite rinsed with MeOH (1 mL). Solvent was removed and the remaining yellow residue was dissolved in a minimal amount of $CH_2Cl_2$. Hexanes were added, precipitating a white solid that was filtered, washed with hexanes, and then dried at reduced pressure. 140 mg of tert-butyl $N^1$-benzyl-$N^2$-(4-thien-2-ylbenzoyl)-L-α-glutaminate, a white solid was obtained in 69% yield. MS (ESI) m/z 479.1; MS (ESI) m/z 957.3; HRMS: calcd for $C_{27}H_{30}N_2O_4S$+H+, 479.19990. found (ESI_FT, $[M+H]^{1+}$), 479.19826.

Step C: $N^1$-benzyl-$N^2$-(4-thien-2-ylbenzoyl)-L-α-glutamine

Tert-butyl $N^1$-benzyl-$N^2$-(4-thien-2-ylbenzoyl)-L-α-glutaminate (135 mg, 0.282 mmol) was dissolved in $CH_2Cl_2$ (1.5 mL) under nitrogen. TFA was diluted in $CH_2Cl_2$ (2 mL), and then added to the reaction. The reaction was monitored by TLC and was complete at 2 hrs. The solvent was removed and the remaining yellow residue was dissolved in toluene, which was then removed (2×) leaving an orange solid. The orange solid was taken up in acetone, and hexanes added, precipitating a pale orange solid. The solid was filtered, washed with hexanes, and dried at reduced pressure. The pale orange solid was run on a $SiO_2$ column, using 4% MeOH/$CH_2Cl_2$. The solvent was removed from the fractions yielding 79 mg of $N^1$-benzyl-$N^2$-(4-thien-2-ylbenzoyl)-L-α-glutamine, a white solid, at 66% yield. MS (ESI) m/z 421.1; MS (ESI) m/z 843.3; HRMS: calcd for $C_{23}H_{22}N_2O_4S$+H+, 423.13730. found (ESI_FTMS, $[M+H]^{1+}$), 423.13742.

Example 12

The following compounds were prepared according to procedures similar to those described in Example 11.

Example 12A $N^1$-benzyl-$N^2$-[4-(2-furyl)benzoyl]-L-α-glutamine

Step B: tert-butyl $N^1$-benzyl-$N^2$-[4-(2-furyl)benzoyl]-L-α-glutaminate

MS (ESI) m/z 463.2; MS (ESI) m/z 925.3; HRMS: calcd for $C_{27}H_{30}N_2O_5$+H+, 463.22275. found (ESI_FT, $[M+H]^{1+}$), 463.22159.

Step C: $N^1$-benzyl-$N^2$-[4-(2-furyl)benzoyl]-L-α-glutamine

MS (ESI) m/z 407.1; MS (ESI) m/z 813.2; HRMS: calcd for $C_{23}H_{22}N_2O_5$+H+, 407.16015. found (ESI_FTMS, $[M+H]^{1+}$), 407.16031.

Example 12B $N^1$-benzyl-$N^2$-[(4'-ethynyl-1,1'-biphenyl-4-yl)carbonyl]-L-α-glutamine Step B: tert-butyl $N^1$-benzyl-$N^2$-[(4'-ethynyl-1,1'-biphenyl-4-yl)carbonyl]-L-α-glutaminate MS (ESI) m/z 497.3; MS (ESI) m/z 993.5; HRMS: calcd for $C_{31}H_{32}N_2O_4$+H+, 497.24348. found (ESI_FTMS, $[M+H]^{1+}$), 497.24306.

Step C: $N^1$-benzyl-$N^2$-[(4'-ethynyl-1,1'-biphenyl-4-yl)carbonyl]-L-α-glutamine MS (ESI) m/z 439.2; MS (ESI) m/z 879.4; HRMS: calcd for $C_{27}H_{24}N_2O_4$+H+, 441.18088. found (ESI_FT, $[M+H]^{1+}$), 441.18056.

Example 12C $N^1$-benzyl-$N^2$-(4-pyridin-3-ylbenzoyl)-L-α-glutamine

Step B: tert-butyl $N^1$-benzyl-$N^2$-(4-pyridin-3-ylbenzoyl)-L-α-glutaminate

MS (ESI) m/z 474.2; HRMS: calcd for $C_{28}H_{31}N_3O_4$+H+, 474.23873. found (ESI_FT, $[M+H]^{1+}$), 474.238741.

Step C: $N^1$-benzyl-$N^2$-(4-pyridin-3-ylbenzoyl)-L-α-glutamine

MS (ESI) m/z 418.1; HRMS: calcd for $C_{24}H_{23}N_3O_4$+H+, 418.17613. found (ESI_FT, $[M+H]^{1+}$), 418.17555.

Example 12D $N^1$-benzyl-$N^2$-[4-(1,3-thiazol-2-yl)benzoyl]-L-α-glutamine

Step B: tert-butyl $N^1$-benzyl-$N^2$-[4-(1,3-thiazol-2-yl)benzoyl]-L-α-glutaminate MS (ESI) m/z 480.2; MS (ESI) m/z 959.2; HRMS: calcd for $C_{26}H_{29}N_3O_4S$+H+, 480.19515. found (ESI_FT, [M+H]$^{1+}$), 480.19659.

Step C: $N^1$-benzyl-$N^2$-[4-(1,3-thiazol-2-yl)benzoyl]-L-α-glutamine

MS (ESI) m/z 422.2; MS (ESI) m/z 845.3; HRMS: calcd for $C_{22}H_{21}N_3O_4S$+H+, 424.13255. found (ESI_FT, [M+H]$^{1+}$), 424.13204.

Example 12E $N^1$-benzyl-$N^2$-(4-pyridin-2-ylbenzoyl)-L-α-glutamine

Step B: tert-butyl $N^1$-benzyl-$N^2$-(4-pyridin-2-ylbenzoyl)-L-α-glutaminate

MS (ESI) m/z 474.2; HRMS: calcd for $C_{28}H_{31}N_3O_4$+H+, 474.23873. found (ESI_FT, [M+H]$^{1+}$), 474.2401.

Step C: $N^1$-benzyl-$N^2$-(4-pyridin-2-ylbenzoyl)-L-α-glutamine

MS (ESI) m/z 418.1; HRMS: calcd for $C_{24}H_{23}N_3O_4$+H+, 418.17613. found (ESI_FT, [M+H]$^{1+}$), 418.17517.

Example 12F

N-benzyl-$N^2$-[4-(2-naphthyl)benzoyl]-L-α-glutamine

MS (ESI) m/z 467.2; MS (ESI) m/z 933.4; HRMS: calcd for $C_{29}H_{26}N_2O_4$+H+, 467.19653. found (ESI-FTMS, [M+H]$^{1+}$), 467.19661.

Example 12G

N-benzyl-$N^2$-[4-(phenylethynyl)benzoyl]-L-α-glutamine

MS (ESI) m/z 441.2; MS (ESI) m/z 881.4.

Example 12H

N-benzyl-$N^2$-{4-[(9-hydroxy-9H-fluoren-9-yl)ethynyl]benzoyl}-L-α-glutamine

MS (ESI) m/z 543.1; MS (ESI) m/z 1087.2.

Example 12I

N-benzyl-$N^2$-{4-[(1E)-3-oxo-3-phenylprop-1-en-1-yl]benzoyl}-L-α-glutamine

MS (ESI) m/z 471.2; MS (ESI) m/z 941.4.

Example 12J $N^2$-{4-[(3-aminophenyl)ethynyl]benzoyl}-N-benzyl-L-α-glutamine MS (ESI) m/z 456.1; MS (ESI) m/z 249.1.

Example 12K

N-benzyl-$N^2$-[4-(3-hydroxy-3,3-diphenylprop-1-yn-1-yl)benzoyl]-L-α-glutamine

MS (ESI) m/z 545.1; MS (ESI) m/z 1091.2; MS (ESI) m/z 659.1.

Example 12L

N-benzyl-$N^2$-{4-[(3-methoxyphenyl)ethynyl]benzoyl}-L-α-glutamine

MS (ESI) m/z 471.1; MS (ESI) m/z 941.2.

Example 13

The following compounds were prepared according to procedures similar to those described in Example 11, except a Suzuki reaction was used at step B in place of a Stille reaction. Hydrolysis of the ester to the final product followed the same procedure as previously described.

Example 13A $N^1$-benzyl-$N^2$-[(3',5'-dimethyl-1,1'-biphenyl-4-yl)carbonyl]-L-α-glutamine Step B: tert-butyl $N^1$-benzyl-$N^2$-[(3',5'-dimethyl-1,1'-biphenyl-4-yl)carbonyl]-L-α-glutaminate Tert-butyl $N^1$-benzyl-$N^2$-(4-bromobenzoyl)-L-α-glutaminate (350 mg, 0.736 mmol) was dissolved in DME, under nitrogen in a sealed vial. 3,5-Dimethylboronic acid (110 mg, 0.736 mmol), and Pd(PPh$_3$)$_4$ (43 mg, 0.037 mmol) were added as solids, and the reaction heated to reflux for 10 minutes. At this point 2M K$_2$CO$_3$ (735 mL, 1.47 mmol) was added, the reaction vial was sealed, and the reaction heated to reflux and monitored by TLC. The reaction was complete at 2 hrs. The aqueous part of the reaction was removed via pipette. The reaction solution was then filtered through celite and the celite rinsed with MeOH. The solvent was removed, leaving a brown solid. The product was purified using a SiO$_2$ column and 33% EtOAc/Hex as the solvent. The product was obtained as a white solid, yielding 222 mg at 60% yield. MS (ESI) m/z 501.3; MS (ESI) m/z 1001.6; HRMS: calcd for $C_{31}H_{36}N_2O_4$+H+, 501.27478. found (ESI_FT, [M+H]$^{1+}$), 501.27332.

Step C: $N^1$-benzyl-$N^2$-[(3',5'-dimethyl-1,1'-biphenyl-4-yl)carbonyl]-L-α-glutamine MS (ESI_FT) m/z 445.21151; MS (ESI_FT) m/z 445.21219; HRMS: calcd for $C_{27}H_{28}N_2O_4$+H+, 445.21218. found (ESI_FT, [M+H]$^{1+}$), 445.21151.

Example 13B

N$^1$-benzyl-N$^2$-[(2',5'-dimethyl-1,1'-biphenyl-4-yl)carbonyl]-L-α-glutamine

Step B: tert-butyl N$^1$-benzyl-N$^2$-[(2',5'-dimethyl-1,1'-biphenyl-4-yl)carbonyl]-L-α-glutaminate MS (ESI) m/z 501.3; MS (ESI) m/z 1001.6; HRMS: calcd for C$_{31}$H$_{36}$N$_2$O$_4$+H+, 501.27478. found (ESI_FT, [M+H]$^{1+}$), 501.27441.

Step C: N$^1$-benzyl-N$^2$-[(2',5'-dimethyl-1,1'-biphenyl-4-yl)carbonyl]-L-α-glutamine MS (ESI) m/z 445.3; MS (ESI) m/z 889.5; HRMS: calcd for C$_{27}$H$_{28}$N$_2$O$_4$+H+, 445.21218. found (ESI_FT, [M+H]$^{1+}$), 445.21172.

Example 13C

N$^1$-benzyl-N$^2$-[(4'-ethyl-1,1'-biphenyl-4-yl)carbonyl]-L-α-glutamine

Step B: tert-butyl N$^1$-benzyl-N$^2$-[(4'-ethyl-1,1'-biphenyl-4-yl)carbonyl]-L-α-glutaminate MS (ESI) m/z 501.3; MS (ESI) m/z 1001.6; HRMS: calcd for C$_{31}$H$_{36}$N$_2$O$_4$+H+, 501.27478. found (ESI_FT, [M+H]$^{1+}$), 501.27326.

Step C: N$^1$-benzyl-N$^2$-[(4'-ethyl-1,1'-biphenyl-4-yl)carbonyl]-L-α-glutamine MS (ESI_FT) m/z 445.2115; MS (ESI_FT) m/z 445.21219; HRMS: calcd for C$_{27}$H$_{28}$N$_2$O$_4$+H+, 445.21218. found (ESI_FT, [M+H]$^{1+}$), 445.2115.

Example 13D

N$^1$-benzyl-N$^2$-[(3'-ethoxy-1,1'-biphenyl-4-yl)carbonyl]-L-α-glutamine

Step B: tert-butyl N$^1$-benzyl-N$^2$-[(3'-ethoxy-1,1'-biphenyl-4-yl)carbonyl]-L-α-glutaminate MS (ESI) m/z 517.3; MS (ESI) m/z 1033.6; HRMS: calcd for C$_{31}$H$_{36}$N$_2$O$_5$+H+, 517.26970. found (ESI_FT, [M+H]$^{1+}$), 517.26837.

Step C: N$^1$-benzyl-N$^2$-[(3'-ethoxy-1,1'-biphenyl-4-yl)carbonyl]-L-α-glutamine MS (ESI_FT) m/z 461.20568; MS (ESI_FT) m/z 461.2071; HRMS: calcd for C$_{27}$H$_{28}$N$_2$O$_5$+H+, 461.20710. found (ESI_FT, [M+H]$^{1+}$), 461.20568.

Example 13E

N$^1$-benzyl-N$^2$-[(2'-ethoxy-1,1'-biphenyl-4-yl)carbonyl]-L-α-glutamine

Step B: tert-butyl N$^1$-benzyl-N$^2$-[(2'-ethoxy-1,1'-biphenyl-4-yl)carbonyl]-L-α-glutaminate MS (ESI) m/z 517.3; MS (ESI) m/z 1033.5; HRMS: calcd for C$_{31}$H$_{36}$N$_2$O$_5$+H+, 517.26970. found (ESI_FT, [M+H]$^{1+}$), 517.26833.

Step C: N$^1$-benzyl-N$^2$-[(2'-ethoxy-1,1'-biphenyl-4-yl)carbonyl]-L-α-glutamine MS (ESI_FT) m/z 461.20572; MS (ESI_FT) m/z 461.2071; HRMS: calcd for C$_{27}$H$_{28}$N$_2$O$_5$+H+, 461.20710. found (ESI_FT, [M+H]$^{1+}$), 461.20572.

Example 13F

N$^1$-benzyl-N$^2$-[(2',6'-dimethyl-1,1'-biphenyl-4-yl)carbonyl]-L-α-glutamine

Step B: tert-butyl N$^1$-benzyl-N$^2$-[(2',6'-dimethyl-1,1'-biphenyl-4-yl)carbonyl]-L-α-glutaminate MS (ESI_FT) m/z 501.27323; MS (ESI_FT) m/z 501.27479; HRMS: calcd for C$_{31}$H$_{36}$N$_2$O$_4$+H+, 501.27478. found (ESI_FT, [M+H]$^{1+}$), 501.27323.

Step C: N$^1$-benzyl-N$^2$-[(2',6'-dimethyl-1,1'-biphenyl-4-yl)carbonyl]-L-α-glutamine MS (ESI_FT) m/z 445.21145; MS (ESI_FT) m/z 445.21219; HRMS: calcd for C$_{27}$H$_{28}$N$_2$O$_4$+H+, 445.21218. found (ESI_FT, [M+H]$^{1+}$), 445.21145.

Example 13G

N$^1$-benzyl-N$^2$-[(4'-vinyl-1,1'-biphenyl-4-yl)carbonyl]-L-α-glutamine

Step B: tert-butyl N$^1$-benzyl-N$^2$-[(4'-vinyl-1,1'-biphenyl-4-yl)carbonyl]-L-α-glutaminate MS (ESI) m/z 499.3; MS (ESI) m/z 997.5; HRMS: calcd for C$_{31}$H$_{34}$N$_2$O$_4$+H+, 499.25913. found (ESI_FT, [M+H]$^{1+}$), 499.25855.

Step C: N$^1$-benzyl-N$^2$-[(4'-vinyl-1,1'-biphenyl-4-yl)carbonyl]-L-α-glutamine MS (ESI) m/z 443.2; MS (ESI) m/z 885.4; HRMS: calcd for C$_{27}$H$_{26}$N$_2$O$_4$+H+, 443.19653. found (ESI-FTMS, [M+H]$^{1+}$), 443.19675.

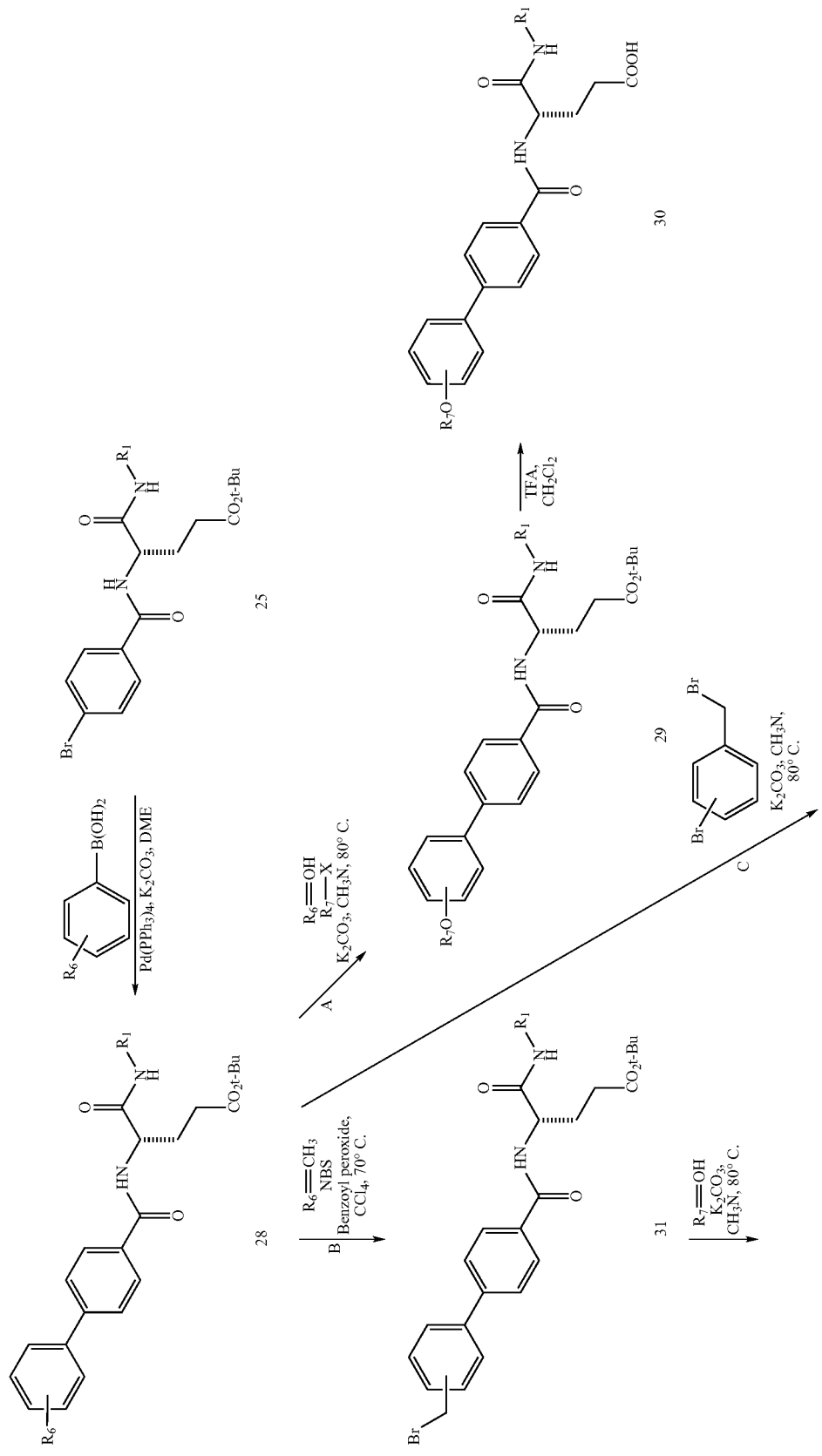

-continued
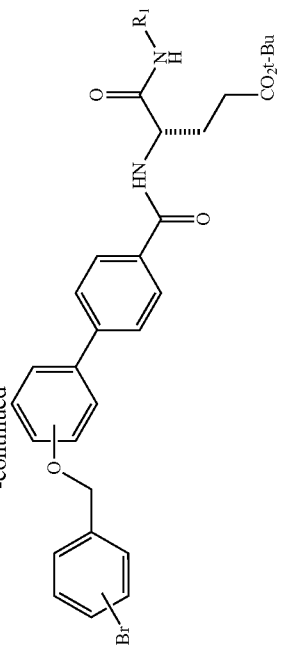 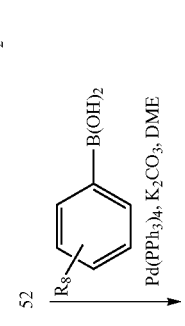 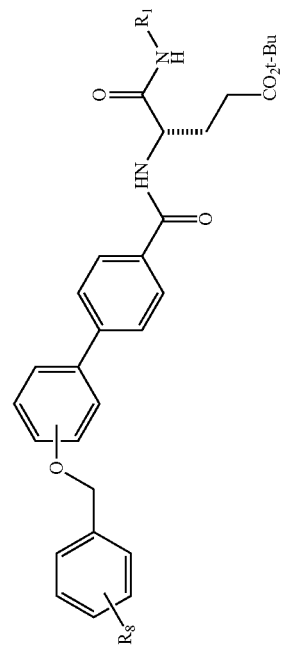 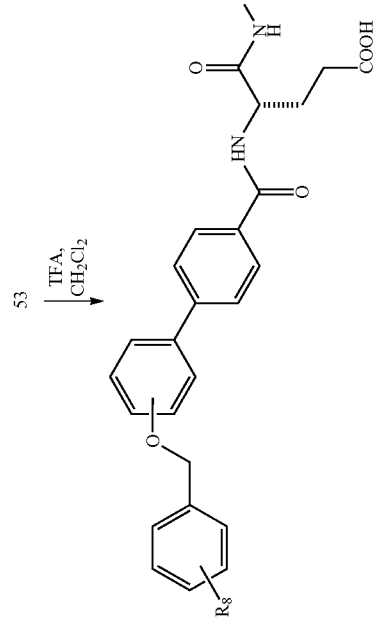
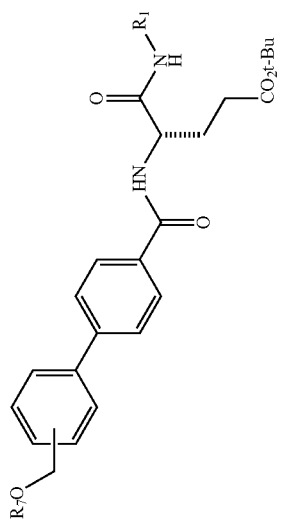 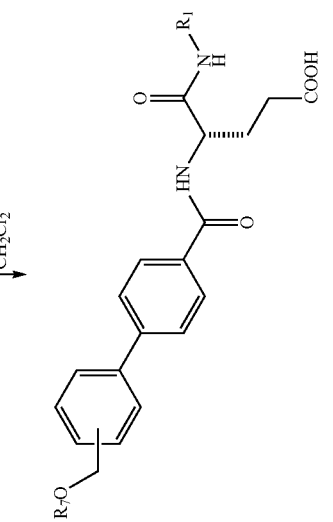

Example 14

$N^1$-benzyl-$N^2$-[(4'-ethoxy-1,1'-biphenyl-4-yl)carbonyl]-L-α-glutamine

Step A: tert-butyl $N^1$-benzyl-$N^2$-[(4'-hydroxy-1,1'-biphenyl-4-yl)carbonyl]-L-α-glutaminate Tert-butyl $N^1$-benzyl-$N^2$-(4-bromobenzoyl)-L-α-glutaminate (3.00 g, 6.31 mmol) was dissolved in DME (40 mL), under nitrogen in a 75 mL bomb flask. 4-Hydroxyphenylboronic acid (871 mg, 6.31 mmol), and Pd(PPh$_3$)$_4$ (729 mg, 0.631 mmol) were added as solids, and the reaction heated to reflux for 30 minutes. At this point K$_2$CO$_3$ (1.74 g, 12.6 mmol) was dissolved in H$_2$O (8 mL), and added to the reaction. The bomb flask was sealed and the reaction was heated to reflux, stirred overnight, and monitored by TLC. The reaction was complete after stirring overnight. The reaction mixture was filtered through celite and the celite rinsed with MeOH. The solvent was removed and the remaining solid was dissolved in EtOAc (200 mL) and then washed with 200 mL of 10% HCl (2×) and brine. The organic layer (top) was then dried (Na$_2$SO$_4$), filtered and concentrated, leaving a dark red oily solid. The product was purified using a SiO$_2$ column, and 40% Ace/Hex as the solvent. It would not dissolve in this solvent so it was dissolved in Acetone/MeOH (1:1) and dry mounted on the column. The product was obtained as the third spot of the column and as a yellow solid. Yield 1.9 g of tert-butyl $N^1$-benzyl-$N^2$-[(4'-hydroxy-1,1'-biphenyl-4-yl)carbonyl]-L-α-glutaminate at 62% yield. MS (ESI) m/z 487.4; MS (ESI) m/z 533.5; MS (ESI) m/z 975.8; HRMS: calcd for C$_{29}$H$_{32}$N$_2$O$_5$+H+, 489.23840. found (ESI_FTMS, [M+H]$^{1+}$), 489.23862.

Step B: tert-butyl $N^1$-benzyl-$N^2$-[(4'-ethoxy-1,1'-biphenyl-4-yl)carbonyl]-L-α-glutaminate Tert-butyl $N^1$-benzyl-$N^2$-[(4'-hydroxy-1,1'-biphenyl-4-yl)carbonyl]-L-α-glutaminate (300 mg, 0.614 mmol) was dissolved in CH$_3$CN (7 mL) in a sealed 20 mL vial. K$_2$CO$_3$ was added as a solid, the vial sealed and heated to 80° C. for 1 hour. Iodoethane (54 mL, 0.675 mmol) was added, the vial sealed and stirred at 80° C. overnight. The reaction was monitored by TLC and was complete after stirring overnight. The solvent was removed via nitrogen blower, and the remaining solid dissolved in CH$_2$Cl$_2$ (7 mL) and washed with 10% HCl (7 mL). The aqueous layer was decanted with a pipette, and the solvent was removed via nitrogen blower. The remaining solid was dissolved in DMSO (2 mL) and purified on a Gilson HPLC. Yield: 123 mg of tert-butyl $N^1$-benzyl-$N^2$-[(4'-ethoxy-1,1'-biphenyl-4-yl)carbonyl]-L-α-glutaminate, a white solid at 39% yield. MS (ESI) m/z 517.2; MS (ESI) m/z 1033.4; HRMS: calcd for C$_{31}$H$_{36}$N$_2$O$_5$+H+, 517.26970. found (ESI_FTMS, [M+H]$^{1+}$), 517.26801.

Step C: $N^1$-benzyl-$N^2$-[(4'-ethoxy-1,1'-biphenyl-4-yl)carbonyl]-L-α-glutamine The procedure used was similar to that described in Example 13. MS (ESI) m/z 461.2; MS (ESI) m/z 921.4; HRMS: calcd for C$_{27}$H$_{28}$N$_2$O$_5$+H+, 461.20710. found (ESI_FTMS, [M+H]$^{1+}$), 461.20542.

Example 15

The following compounds were prepared according to procedures similar to those described in Example 14.

Example 15A

$N^1$-benzyl-$N^2$-[(4'-propoxy-1,1'-biphenyl-4-yl)carbonyl]-L-α-glutamine

Step B: tert-butyl $N^1$-benzyl-$N^2$-[(4'-propoxy-1,1'-biphenyl-4-yl)carbonyl]-L-α-glutaminate MS (ESI) m/z 531.3; MS (ESI) m/z 1061.4; HRMS: calcd for C$_{32}$H$_{38}$N$_2$O$_5$+H+, 531.28535. found (ESI_FTMS, [M+H]$^{1+}$), 531.2844.

Step C: $N^1$-benzyl-$N^2$-[(4'-propoxy-1,1'-biphenyl-4-yl)carbonyl]-L-α-glutamine MS (ESI) m/z 475.2; MS (ESI) m/z 949.4; HRMS: calcd for C$_{28}$H$_{30}$N$_2$O$_5$+H+, 475.22275. found (ESI_FTMS, [M+H]$^{1+}$), 475.22333.

Example 15B

$N^1$-benzyl-$N^2$-[(4'-butoxy-1,1'-biphenyl-4-yl)carbonyl]-L-α-glutamine

Step B: tert-butyl $N^1$-benzyl-$N^2$-[(4'-butoxy-1,1'-biphenyl-4-yl)carbonyl]-L-α-glutaminate MS (ESI) m/z 545.3; MS (ESI) m/z 1089.5; HRMS: calcd for C$_{33}$H$_{40}$N$_2$O$_5$+H+, 545.30100. found (ESI_FTMS, [M+H]$^{1+}$), 545.30048.

Step C: $N^1$-benzyl-$N^2$-[(4'-butoxy-1,1'-biphenyl-4-yl)carbonyl]-L-α-glutamine MS (ESI) m/z 489.3; MS (ESI) m/z 977.4; HRMS: calcd for C$_{29}$H$_{32}$N$_2$O$_5$+H+, 489.23840. found (ESI_FTMS, [M+H]$^{1+}$), 489.23871.

Example 15C

$N^1$-benzyl-$N^2$-{[4'-(cyclobutylmethoxy)-1,1'-biphenyl-4-yl]carbonyl}-L-α-glutamine

Step B: tert-butyl $N^1$-benzyl-$N^2$-{[4'-(cyclobutylmethoxy)-1,1'-biphenyl-4-yl]carbonyl}-L-α-glutaminate MS (ESI) m/z 557.3; MS (ESI) m/z 1113.4; HRMS: calcd for C$_{34}$H$_{40}$N$_2$O$_5$+H+, 557.30100. found (ESI_FTMS, [M+H]$^{1+}$), 557.30064.

Step C: $N^1$-benzyl-$N^2$-{[4'-(cyclobutylmethoxy)-1,1'-biphenyl-4-yl]carbonyl}-L-α-glutamine MS (ESI) m/z 501.3; MS (ESI) m/z 1001.5; HRMS: calcd for C$_{30}$H$_{32}$N$_2$O$_5$+H+, 501.23840. found (ESI_FTMS, [M+H]$^{1+}$), 501.23937.

Example 15D

$N^1$-benzyl-$N^2$-{[4'-(cyclohexylmethoxy)-1,1'-biphenyl-4-yl]carbonyl}-L-α-glutamine

Step B: tert-butyl $N^1$-benzyl-$N^2$-{[4'-(cyclohexylmethoxy)-1,1'-biphenyl-4-yl]carbonyl}-L-α-glutaminate MS (ESI) m/z 585.3; MS (ESI) m/z 1169.5; HRMS: calcd for C$_{36}$H$_{44}$N$_2$O$_5$+H+, 585.33230. found (ESI_FTMS, [M+H]$^{1+}$), 585.33275.

Step C: N¹-benzyl-N²-{[4'-(cyclohexylmethoxy)-1,1'-biphenyl-4-yl]carbonyl}-L-α-glutamine MS (ESI) m/z 529.3; MS (ESI) m/z 1057.5; HRMS: calcd for $C_{32}H_{36}N_2O_5$+H+, 529.26970. found (ESI_FTMS, [M+H]$^{1+}$), 529.27022.

Example 15E

N²-{[4'-(allyloxy)-1,1'-biphenyl-4-yl]carbonyl}-N¹-benzyl-L-α-glutamine

Step B: tert-butyl N²-{[4'-(allyloxy)-1,1'-biphenyl-4-yl]carbonyl}-N¹-benzyl-L-α-glutaminate MS (ESI) m/z 529.2; MS (ESI) m/z 1057.4; HRMS: calcd for $C_{32}H_{36}N_2O_5$+H+, 529.26970. found (ESI_FTMS, [M+H]$^{1+}$), 529.26804.

Step C: N²-{[4'-(allyloxy)-1,1'-biphenyl-4-yl]carbonyl}-N¹-benzyl-L-α-glutamine

Example 15F

N¹-benzyl-N²-({4'-[(3-methoxybenzyl)oxy]-1,1'-biphenyl-4-yl}carbonyl)-L-α-glutamine Step B: tert-butyl N¹-benzyl-N²-({4'-[(3-methoxybenzyl)oxy]-1,1'-biphenyl-4-yl}carbonyl)-L-α-glutaminate MS (ESI) m/z 609.3; MS (ESI) m/z 1217.5; HRMS: calcd for $C_{37}H_{40}N_2O_6$+H+, 609.29591. found (ESI-FTMS, [M+H]$^{1+}$), 609.29669.

Step C: N¹-benzyl-N²-({4'-[(3-methoxybenzyl)oxy]-1,1'-biphenyl-4-yl}carbonyl)-L-α-glutamine MS (ESI) m/z 553.2; MS (ESI) m/z 1105.3; HRMS: calcd for $C_{33}H_{32}N_2O_6$+H+, 553.23331; found (ESI-FTMS, [M+H]$^{1+}$), 553.23235.

Example 15G

N¹-benzyl-N²-({4'-[(3,5-dimethoxybenzyl)oxy]-1,1'-biphenyl-4-yl}carbonyl)-L-α-glutamine Step B: tert-butyl N¹-benzyl-N²-({4'-[(3,5-dimethoxybenzyl)oxy]-1,1'-biphenyl-4-yl}carbonyl)-L-α-glutaminate MS (ESI) m/z 639.3; MS (ESI) m/z 1277.4; HRMS: calcd for $C_{38}H_{42}N_2O_7$+H+, 639.30648. found (ESI-FTMS, [M+H]$^{1+}$), 639.30698.

Step C: N¹-benzyl-N²-({4'-[(3,5-dimethoxybenzyl)oxy]-1,1'-biphenyl-4-yl}carbonyl)-L-α-glutamine MS (ESI) m/z 583.2; MS (ESI) m/z 1165.3; HRMS: calcd for $C_{34}H_{34}N_2O_7$+H+, 583.24388. found (ESI-FTMS, [M+H]$^{1+}$), 583.2433.

Example 15H

N¹-benzyl-N²-{[4'-(2-naphthylmethoxy)-1,1'-biphenyl-4-yl]carbonyl}-L-α-glutamine Step B: tert-butyl N¹-benzyl-N²-{[4'-(2-naphthylmethoxy)-1,1'-biphenyl-4-yl]carbonyl}-L-α-glutaminate MS (ESI) m/z 629.3; HRMS: calcd for $C_{40}H_{40}N_2O_5$+H+, 629.30100. found (ESI-FTMS, [M+H]$^{1+}$), 629.30277.

Step C: N¹-benzyl-N²-{[4'-(2-naphthylmethoxy)-1,1'-biphenyl-4-yl]carbonyl}-L-α-glutamine MS (ESI) m/z 571.3; HRMS: calcd for $C_{36}H_{32}N_2O_5$+H+, 573.23840. found (ESI-FTMS, [M+H]$^{1+}$), 573.23779.

Example 15I

N-benzyl-N²-({4'-[(3-fluorobenzyl)oxy]biphenyl-4-yl}carbonyl)-L-α-glutamine

MS (ESI) m/z 541.1; MS (ESI) m/z 1081.2.

Example 15J

N-benzyl-N²-{[4'-(benzyloxy)biphenyl-4-yl]carbonyl}-L-α-glutamine

MS (ESI) m/z 523.1; MS (ESI) m/z 1045.2.

The following compounds were prepared according to Scheme 10, Route A:

Example 15K

N²-{[3'-(benzyloxy)biphenyl-4-yl]carbonyl}-N-(3,4,5-trimethoxybenzyl)-L-α-glutamine MS (ESI) m/z 613.1; MS (ESI) m/z 1225.1; HRMS: calcd for $C_{35}H_{36}N_2O_8$+H+, 613.25444. found (ESI-FTMS, [M+H]$^{1+}$), 613.25451.

Example 15L

N²-({3'-[(3,5-dimethoxybenzyl)oxy]biphenyl-4-yl}carbonyl)-N-(3,4,5-trimethoxybenzyl)-L-α-glutamine MS (ESI) m/z 673.3; MS (ESI) m/z 1345.6; MS (ESI) m/z 690.4; HRMS: calcd for $C_{37}H_{40}N_2O_{10}$+H+, 673.27557. found (ESI-FTMS, [M+H]$^{1+}$), 673.27431.

Example 15M

N²-({3'-[(3-methoxybenzyl)oxy]biphenyl-4-yl}carbonyl)-N-(3,4,5-trimethoxybenzyl)-L-α-glutamine MS (ESI) m/z 643.3; MS (ESI) m/z 1285.6; HRMS: calcd for $C_{36}H_{38}N_2O_9$+H+, 643.26501. found (ESI-FTMS, [M+H]$^{1+}$), 643.26574.

Example 15N

N$^2$-({4'-[(3,5-dimethoxybenzyl)oxy]biphenyl-4-yl}carbonyl)-N-[2-(4-fluorophenyl)-1,1-dimethylethyl]-L-α-glutamine MS (ESI) m/z 643.3; MS (ESI) m/z 1285.6; HRMS: calcd for C$_{37}$H$_{39}$FN$_2$O$_7$+H+, 643.28141. found (ESI-FTMS, [M+H]$^{1+}$), 643.28187.

The following compounds were prepared according to Scheme 10, Route B:

Example 15O

N$^2$-[(4'-{[3,5-bis(trifluoromethyl)phenoxy]methyl}biphenyl-4-yl)carbonyl]-N-(1,1-dimethyl-2-phenylethyl)-L-α-glutamine Step A: tert-butyl N-(1,1-dimethyl-2-phenylethyl)-N$^2$-[(4'-methylbiphenyl-4-yl)carbonyl]-L-α-glutaminate tert-butyl N$^1$-benzyl-N$^2$-(4-bromobenzoyl)-L-α-glutaminate (1.00 g, 1.93 mmol) was dissolved in DME (10 mL) under nitrogen and placed in a microwave vial. 4-methylphenyl boronic acid (526 mg, 3.87.mmol), and Pd(PPh$_3$)$_4$ (334 mg, 0.290 mmol) were added as solids prior to the addition of K$_2$CO$_3$ (800 mg, 5.79 mmol) dissolved in H$_2$O (2.3 mL). The vial was sealed and heated to 80° C. in a microwave for 20 minutes. The solvent was removed and the remaining yellow oil was dissolved in diethyl ether (125 mL). The organics were washed consecutively with 10% HCl (125 mL), water (125 mL) and brine (125 mL). The organic layer was dried with MgSO$_4$, filtered through celite and the solvent was removed. The sticky solid was purified using on a 40 g Combi flash column using an increasing gradient of EtOAc/Hex as the solvent. The product was obtained as a light brown solid. Yield 792 mg of tert-butyl N-(1,1-dimethyl-2-phenylethyl)-N$^2$-[(4'-methylbiphenyl-4-yl)carbonyl]-L-α-glutaminate at 78% yield. MS (ESI) m/z 529.3; HRMS: calcd for C$_{33}$H$_{40}$N$_2$O$_4$+H+, 529.30608. found (ESI-FTMS, [M+H]$^{1+}$), 529.30594.

Step B: tert-butyl N$^2$-{[4'-(bromomethyl)biphenyl-4-yl]carbonyl}-N-(1,1-dimethyl-2-phenylethyl)-L-α-glutaminate tert-butyl N-(1,1-dimethyl-2-phenylethyl)-N$^2$-[(4'-methylbiphenyl-4-yl)carbonyl]-L-α-glutaminate (3.5 g, 6.62 mmol) was dissolved in CCl$_4$ (50 mL) along with N-Bromosuccinimide (2.36 g, 13.2 mmol) and benzoyl peroxide (321 mg, 1.32 mmol) in a 100 mL flask equipped with a reflux condenser. The reaction mixture stirred overnight at 70° C. The solvent was removed and the residue was purified using a SiO2 column and 20% EtOAc/Hex as the solvent giving a yellow solid. Yield 1.05 g tert-butyl N$^2$-{[4'-(bromomethyl)biphenyl-4-yl]carbonyl}-N-(1,1-dimethyl-2-phenylethyl)-L-α-glutaminate at 57% yield. MS (ESI) m/z 607.1; HRMS: calcd for C$_{33}$H$_{39}$BrN$_2$O$_4$+H+, 607.21660. found (ESI-FTMS, [M+H]$^{1+}$), 607.21591.

Step C: tert-butyl N$^2$-[(4'-{[3,5-bis(trifluoromethyl)phenoxy]methyl}biphenyl-4-yl)carbonyl]-N-(1,1-dimethyl-2-phenylethyl)-L-α-glutaminate tert-butyl N$^2$-{[4'-(bromomethyl)biphenyl-4-yl]carbonyl}-N-(1,1-dimethyl-2-phenylethyl)-L-α-glutaminate (253 mg, 0.41 mmol) 3,5-bis(trifluoromethyl)phenol (63 μL, 42 mmol) and K$_2$CO$_3$ (287 mg, 2.08 mmol) were all combined in a 10 mL vial. Acetonitrile (4 mL) was added dissolving some of the solids upon heating to 80° C. The reaction was monitored using TLC and MS. The reaction was stirred overnight (18 h). The reaction was filtered using a fritted funnel and the solvent was removed. The filtrate was collected and the solvent was removed. The residue was purified using a SiO$_2$ column and 20% EtOAc/Hex as the solvent giving a white solid. Yield 242 mg of tert-butyl N$^2$-[(4'-{[3,5-bis(trifluoromethyl)phenoxy]methyl}biphenyl-4-yl)carbonyl]-N-(1,1-dimethyl-2-phenylethyl)-L-α-glutaminate at 77% yield. MS (ESI) m/z 757.4; HRMS: calcd for C$_{41}$H$_{42}$F$_6$N$_2$O$_5$+H+, 757.30707. found (ESI-FTMS, [M+H]$^{1+}$), 757.30532.

Step D: N$^2$-[(4'-{[3,5-bis(trifluoromethyl)phenoxy]methyl}biphenyl-4-yl)carbonyl]-N-(1,1-dimethyl-2-phenylethyl)-L-α-glutamine tert-butyl N$^2$-[(4'-{[3,5-bis(trifluoromethyl)phenoxy]methyl}biphenyl-4-yl)carbonyl]-N-(1,1-dimethyl-2-phenylethyl)-L-α-glutaminate (215 mg, 0.284 mmol) was dissolved in CH$_2$Cl$_2$ (3 mL) and stirred in a 10 mL flask. Trifluoroacetic acid (1.09 mL, 14 mmol) was added and the solution was stirred for 2 hours. The solvent was removed and the dried under vacuum. The resulting residue was purified using preparative HPLC (ACN/H$_2$O, 0.02% TFA). The main peak fractions were collected and after removal of solvent gave the product as a white solid. Yield of 104 mg of N$^2$-[(4'-{[3,5-bis(trifluoromethyl)phenoxy]methyl}biphenyl-4-yl)carbonyl]-N-(1,1-dimethyl-2-phenylethyl)-L-α-glutamine was obtained in 52% yield. MS (ESI) m/z 699.3; HRMS: calcd for C$_{37}$H$_{34}$F$_6$N$_2$O$_5$+H+, 701.24447. found (ESI-FTMS, [M+H]$^{1+}$), 701.24429.

The following compounds were prepared according to the procedure described above for example 15O:

Example 15P

N$^2$-({4'-[(1,3-benzodioxol-5-yloxy)methyl]biphenyl-4-yl}carbonyl)-N-(1,1-dimethyl-2-phenylethyl)-L-α-glutamine MS (ESI) m/z 609.3; MS (ESI) m/z 1217.6; HRMS: calcd for C$_{36}$H$_{36}$N$_2$O$_7$+H+, 609.25953. found (ESI-FTMS, [M+H]$^{1+}$), 609.26109.

Example 15Q

N$^2$-({4'-[(3,5-dimethoxyphenoxy)methyl]biphenyl-4-yl}carbonyl)-N-(3-methylbenzyl)-L-α-glutamine MS (ESI) m/z 595.4; HRMS: calcd for C$_{35}$H$_{36}$N$_2$O$_7$+H+, 597.25953. found (ESI-FTMS, [M+H]$^{1+}$), 597.25901.

Example 15R

N$^2$-({3'-[(3,5-dimethoxyphenoxy)methyl]biphenyl-4-yl}carbonyl)-N-(3-methylbenzyl)-L-α-glutamine MS (ESI) m/z 595.2; HRMS: calcd for C$_{35}$H$_{36}$N$_2$O$_7$+H+, 597.25953. found (ESI-FTMS, [M+H]$^{1+}$), 597.2593.

Example 15S

N²-[(3'-{[3,5-bis(trifluoromethyl)phenoxy]methyl}biphenyl-4-yl)carbonyl]-N-(3-methylbenzyl)-L-α-glutamine MS (ESI) m/z 671.2; MS (ESI) m/z 1343.7; HRMS: calcd for $C_{35}H_{30}F_6N_2O_5$+H+, 673.21317. found (ESI-FTMS, [M+H]$^{1+}$), 673.21279.

Example 15T

N²-({3'-[(3-ethylphenoxy)methyl]biphenyl-4-yl}carbonyl)-N-(3-methylbenzyl)-L-α-glutamine MS (ESI) m/z 563.3; HRMS: calcd for $C_{35}H_{36}N_2O_5$+H+, 565.26970. found (ESI-FTMS, [M+H]$^{1+}$), 565.26999.

The following compounds were prepared according to Scheme 10, Route C:

Example 15U

N-benzyl-N²-{[4'-(biphenyl-3-ylmethoxy)biphenyl-4-yl]carbonyl}-L-α-glutamine

Step A: tert-butyl N¹-benzyl-N²-[(4'-hydroxy-1,1'-biphenyl-4-yl)carbonyl]-L-α-glutaminate tert-butyl N¹-benzyl-N²-(4-bromobenzoyl)-L-α-glutaminate (2.00 g, 4.21 mmol) was dissolved in DME (20 mL) under nitrogen and placed in a 75 mL flask. 4-Hydroxyphenyl boronic acid (638 mg, 4.63.mmol), and Pd(PPh₃)₄ (729 mg, 0.632 mmol) were added as solids prior to the addition of K₂CO₃ (1.75 g, 12.6 mmol) dissolved in H₂O (5 mL). The flask was sealed and the reaction was heated to reflux, stirred for two days and monitored by TLC. The reaction mixture was filtered through celite and then rinsed with MeOH. The solvent was removed and the resulting residue was purified using a SiO2 column and 33% EtOAc/Hex as the solvent. The product was obtained as a white solid. Yield: 514 mg of tert-butyl N¹-benzyl-N²-[(4'-hydroxy-1,1'-biphenyl-4-yl)carbonyl]-L-α-glutaminate at 25% yield. MS (ESI) m/z 487.4; HRMS: calcd for $C_{29}H_{32}N_2O_5$+H+, 489.23840. found (ESI_FTMS, [M+H]$^{1+}$), 489.23862.

Step B: tert-butyl N-benzyl-N²-({4'-[(3-bromobenzyl)oxy]biphenyl-4-yl}carbonyl)-L-α-glutaminate 3,3-bromobenzylbromide and K₂CO₃ were all combined in a 20 mL vial. CH₃CN (6 mL) was added, dissolving some of the solids upon heating to 80° C. The reaction was monitored using TLC and MS. After 2 hours the reaction was complete. The resulting product quickly precipitated upon cooling of the CH₃CN. The reaction was filtered using a fritted funnel and the filtrate was collected and redissolved in warm CH₃CN. The solution was allowed to crystallize overnight in the freezer. The white solid was collected and washed with cold CH₃CN. Yield: 357 mg of tert-butyl N-benzyl-N²-({4'-[(3-bromobenzyl)oxy]biphenyl-4-yl}carbonyl)-L-α-glutaminate at 57% yield. MS (ESI) m/z 657.2.

Step C: tert-butyl N-benzyl-N²-{[4'-(biphenyl-3-ylmethoxy)biphenyl-4-yl]carbonyl}-L-α-glutaminate tert-butyl N-benzyl-N²-({4'-[(3-bromobenzyl)oxy]biphenyl-4-yl}carbonyl)-L-α-glutaminate (250 mg, 0.38 mmol) was dissolved in DME (5 mL) under nitrogen in a 75 mL bomb flask. Phenylboronic acid (51 mg, 0.418 mmol), and Pd(PPh₃)₄ (66 mg, 0.057 mmol) were added as solids prior to the addition of K₂CO₃ (158 mg, 1.14 mmol) dissolved in H₂O (1.5 mL). The bomb flask was sealed and the reaction was heated to reflux, stirred two days and monitored by TLC. The reaction mixture was filtered through celite and the celite rinsed with MeOH. The solvent was removed and the resulting residue was purified using preparative HPLC. The product was obtained as a pale orange solid. Yield: 154 mg of tert-butyl N-benzyl-N²-{[4'-(biphenyl-3-ylmethoxy)biphenyl-4-yl]carbonyl}-L-α-glutaminate at 60% yield. MS (ESI) m/z 655.5; HRMS: calcd for $C_{42}H_{42}N_2O_5$+H+, 655.31665. found (ESI-FTMS, [M+H]$^{1+}$), 655.31636.

Step D: N-benzyl-N²-{[4'-(biphenyl-3-ylmethoxy)biphenyl-4-yl]carbonyl}-L-α-glutamine tert-butyl N-benzyl-N²-{[4'-(biphenyl-3-ylmethoxy)biphenyl-4-yl]carbonyl}-L-α-glutaminate (130 mg, 0.199 mmol) was dissolved in CH₂Cl₂ (3 mL) and stirred in a 10 mL flask. Trifluoroacetic acid (765 uL, 10 mmol) was added and the solution was stirred for 2 hours. The solvent was removed and the dried under vacuum. The orange residue was dissolved in minimum acetone and precipitated with hexanes. Yield of 109 mg of N-benzyl-N²-{[4'-(biphenyl-3-ylmethoxy)biphenyl-4-yl]carbonyl}-L-α-glutamine was obtained in 91% yield. MS (ESI) m/z 599.4; HRMS: calcd for $C_{38}H_{34}N_2O_5$+H+, 599.25405. found (ESI-FTMS, [M+H]$^{1+}$), 599.25511.

Example 15V

N-benzyl-N²-({4'-[(3'-methoxybiphenyl-3-yl)methoxy]biphenyl-4-yl}carbonyl)-L-α-glutamine MS (ESI) m/z 627.2; HRMS: calcd for $C_{39}H_{36}N_2O_6$+H+, 629.26461. found (ESI-FTMS, [M+H]$^{1+}$), 629.26493.

Example 15W

N-benzyl-N²-{[4'-(biphenyl-2-ylmethoxy)biphenyl-4-yl]carbonyl}-L-α-glutamine

MS (ESI) m/z 597.3; HRMS: calcd for $C_{38}H_{34}N_2O_5$+H+, 599.25405. found (ESI-FTMS, [M+H]$^{1+}$), 599.25523.

Example 15X

N-benzyl-N²-({4'-[(3'-methoxybiphenyl-2-yl)methoxy]biphenyl-4-yl}carbonyl)-L-α-glutamine MS (ESI) m/z 627.3; HRMS: calcd for $C_{39}H_{36}N_2O_6$+H+, 629.26461. found (ESI-FTMS, [M+H]$^{1+}$), 629.26484.

Example 15Y

N²-({4'-[(3-tert-butylphenoxy)methyl]biphenyl-4-yl}carbonyl)-N-(1,1-dimethyl-2-phenylethyl)-L-α-glutamine Tolyl-biphenylglutamate (1 g, 1.89 mmol) was dissolved in CCl₄ (20 mL), in a 40 mL sealed vial. N-Bromosuccinimide (NBS) (673 mg, 3.78 mmol) and Benzoyl peroxide (92 mg, 0.378 mmol) were added. The reaction was heated to 70° C., and stirred overnight. The reaction was cooled and the solvent removed. The remaining sticky orange solid was purified by silica column chromatography using 20% EtOAc/Hexanes.

400 mg of Bromo-tolyl-biphenylglutamate was obtained, as a pale yellow solid at 36% yield.

3-t-Butylphenol (56 mg, 0.374 mmol) was dissolved in $CH_3CN$ in a 20 ml sealed vial and $K_2CO_3$ (258 mg, 1.87 mmol) was added. The reaction was heated to 80° C. and stirred for 30 minutes. The Bromo-tolyl-biphenylglutamate (250 mg, 0.411 mmol) was added and the reaction stirred at 80° C. overnight. The reaction was filtered, the solvent was removed and the remainder of the reaction was purified by silica column chromatography to give the title compound as a white solid was obtained in 87% yield.

MS (ESI) m/z 621.2; MS (ESI) m/z 1241.4; HRMS: calcd for $C_{39}H_{44}N_2O_5$+H+, 621.33230. found (ESI-FTMS, [M+H]$^{1+}$), 621.33234.

The following compounds were prepared according to procedures similar to those described in Example 15Y:

Example 15Z $N^2$-({4'-[(3,5-di-tert-butylphenoxy)methyl]biphenyl-4-yl}carbonyl)-N-(1,1-dimethyl-2-phenylethyl)-L-α-glutamine MS (ESI) m/z 675.3; MS (ESI) m/z 1351.6; HRMS: calcd for $C_{43}H_{52}N_2O_5$+H+, 677.39490. found (ESI-FTMS, [M+H]$^{1+}$), 677.39504.

Example 15AA

N-(1,1-dimethyl-2-phenylethyl)-$N^2$-({4'-[(3-ethylphenoxy)methyl]biphenyl-4-yl}carbonyl)-L-α-glutamine MS (ESI) m/z 593.2; MS (ESI) m/z 1185.4; HRMS: calcd for $C_{37}H_{40}N_2O_5$+H+, 593.30100. found (ESI-FTMS, [M+H]$^{1+}$), 593.30054.

Example 15BB

N-(1,1-dimethyl-2-phenylethyl)-$N^2$-({4'-[(3-methoxyphenoxy)methyl]biphenyl-4-yl}carbonyl)-L-α-glutamine MS (ESI) m/z 595.3; MS (ESI) m/z 1189.6; HRMS: calcd for $C_{36}H_{38}N_2O_6$+H+, 595.28026. found (ESI-FTMS, [M+H]$^{1+}$), 595.28031.

Example 16

$N^2$-[(3'-ethoxybiphenyl-4-yl)carbonyl]-N-(3,4,5-trimethoxybenzyl)-L-α-glutamine The title compound was prepared according to procedures similar to those described in Examples 7 and 11. MS (ESI) m/z 551.2; MS (ESI) m/z 1101.4; MS (ESI) m/z 573.2; HRMS: calcd for $C_{30}H_{34}N_2O_8$+H+, 551.23879. found (ESI-FTMS, [M+H]$^{1+}$), 551.23735.

The following compounds were prepared according to procedures similar to those described in Example 16.

Example 17A $N^2$-[(2'-ethoxybiphenyl-4-yl)carbonyl]-N-(3,4,5-trimethoxybenzyl)-L-α-glutamine MS (ESI) m/z 551.2; MS (ESI) m/z 1101.4; MS (ESI) m/z 573.2; HRMS: calcd for $C_{30}H_{34}N_2O_8$+H+, 551.23879. found (ESI-FTMS, [M+H]$^{1+}$), 551.23739.

Example 17B $N^2$-[(4'-methoxybiphenyl-4-yl)carbonyl]-N-(3,4,5-trimethoxybenzyl)-L-α-glutamine MS (ESI) m/z 537.2; MS (ESI) m/z 1073.4; MS (ESI) m/z 559.2; HRMS: calcd for $C_{29}H_{32}N_2O_8$+H+, 537.22314. found (ESI-FTMS, [M+H]$^{1+}$), 537.22188.

Example 17C $N^2$-[(3'-methoxybiphenyl-4-yl)carbonyl]-N-(3,4,5-trimethoxybenzyl)-L-α-glutamine HRMS: calcd for $C_{29}H_{32}N_2O_8$+H+, 537.22314. found (ESI-FTMS, [M+H]$^{1+}$), 537.22188.

Example 17D

4'-{[((1S)-3-carboxy-1-{[(3,4,5-trimethoxybenzyl)amino]carbonyl}propyl)amino]carbonyl}biphenyl-3-carboxylic acid MS (ESI) m/z 551.1; MS (ESI) m/z 1101.3; MS (ESI) m/z 573.1; HRMS: calcd for $C_{29}H_{30}N_2O_9$+H+, 551.20241. found (ESI-FTMS, [M+H]$^{1+}$), 551.2008.

Example 17E $N^2$-[(4'-ethylbiphenyl-4-yl)carbonyl]-N-(3,4,5-trimethoxybenzyl)-L-α-glutamine MS (ESI) m/z 535.2; MS (ESI) m/z 1069.4; HRMS: calcd for $C_{30}H_{34}N_2O_7$+H+, 535.24388. found (ESI-FTMS, [M+H]$^{1+}$), 535.2425.

Example 17F $N^2$-[(3',4'-dimethoxybiphenyl-4-yl)carbonyl]-N-(3,4,5-trimethoxybenzyl)-L-α-glutamine MS (ESI) m/z 567.2; MS (ESI) m/z 1133.5; MS (ESI) m/z 589.2; HRMS: calcd for $C_{30}H_{34}N_2O_9$+H+, 567.23371. found (ESI-FTMS, [M+H]$^{1+}$), 567.23327.

Example 17G $N^2$-[(2',4'-dimethoxybiphenyl-4-yl)carbonyl]-N-(3,4,5-trimethoxybenzyl)-L-α-glutamine MS (ESI) m/z 567.2; MS (ESI) m/z 1133.5; HRMS: calcd for $C_{30}H_{34}N_2O_9$+H+, 567.23371. found (ESI-FTMS, [M+H]$^{1+}$), 567.23397.

Example 17H

N-(3,4,5-trimethoxybenzyl)-$N^2$-[(3',4',5'-trimethoxybiphenyl-4-yl)carbonyl]-L-α-glutamine MS (ESI) m/z 597.2; MS (ESI) m/z 1193.4; HRMS: calcd for $C_{31}H_{36}N_2O_{10}$+H+, 597.24427. found (ESI-FTMS, [M+H]$^{1+}$), 597.24385.

Example 17I

N-(1,1-dimethyl-2-phenylethyl)-$N^2$-[(3'-methoxybiphenyl-4-yl)carbonyl]-L-α-glutamine MS (ESI) m/z 489.2; MS (ESI) m/z 977.4; MS (ESI) m/z 511.2; HRMS: calcd for $C_{29}H_{32}N_2O_5$+H+, 489.23840. found (ESI-FTMS, [M+H]$^{1+}$), 489.2373.

Example 17J $N^2$-[(3',4'-dimethoxybiphenyl-4-yl)carbonyl]-N-(1,1-dimethyl-2-phenylethyl)-L-α-glutamine MS (ESI) m/z 519.2; MS (ESI) m/z 1037.5; HRMS: calcd for $C_{30}H_{34}N_2O_6$+H+, 519.24896. found (ESI-FTMS, [M+H]$^{1+}$), 519.248971.

Example 17K

N-(1,1-dimethyl-2-phenylethyl)-$N^2$-[(2'-ethoxybiphenyl-4-yl)carbonyl]-L-α-glutamine MS (ESI) m/z 503.2; MS (ESI) m/z 1005.5; HRMS: calcd for $C_{30}H_{34}N_2O_5$+H+, 503.25405. found (ESI-FTMS, [M+H]$^{1+}$), 503.25421.

Example 17L

N-(1,1-dimethyl-2-phenylethyl)-$N^2$-[(3'-fluoro-4'-methylbiphenyl-4-yl)carbonyl]-L-α-glutamine MS (ESI) m/z 491.2; MS (ESI) m/z 981.5; HRMS: calcd for $C_{29}H_{31}FN_2O_4$+H+, 491.23406. found (ESI-FTMS, [M+H]$^{1+}$), 491.23402.

Example 17M

4-[(4'-Methoxy-3'-methyl-biphenyl-4-carbonyl)-amino]-4-(3,4,5-trimethoxy-benzylcarbamoyl)-butyric acid MS (ESI) m/z 551.2; MS (ESI) m/z 1101.5; MS (ESI) m/z 1123.5.

Example 17N 4-(4-Benzo[1,3]dioxol-5-yl-benzoylamino)-4-(3,4,5-trimethoxy-benzylcarbamoyl)-butyric acid MS (ESI) m/z 551.2; MS (ESI) m/z 1101.4.

Example 17O

N-(1-adamantylmethyl)-$N^2$-[(4'-hydroxybiphenyl-4-yl)carbonyl]-L-α-glutamine

MS (ESI) m/z 491.4; MS (ESI) m/z 981.7; HRMS: calcd for $C_{29}H_{34}N_2O_5$+H+, 491.25405. found (ESI-FTMS, [M+H]$^{1+}$), 491.25465.

Example 17P $N^2$-[4-(1,3-benzodioxol-5-yl)benzoyl]-N-(1,1-dimethyl-2-phenylethyl)-L-α-glutamine MS (ESI) m/z 503.2; MS (ESI) m/z 1005.4; MS (ESI) m/z 525.2; HRMS: calcd for $C_{29}H_{30}N_2O_6$+H+, 503.21766. found (ESI-FTMS, [M+H]$^{1+}$), 503.21771.

Example 17Q $N^2$-[(2',4'-dimethoxybiphenyl-4-yl)carbonyl]-N-(1,1-dimethyl-2-phenylethyl)-L-α-glutamine MS (ESI) m/z 519.2; MS (ESI) m/z 1037.5; MS (ESI) m/z 541.2; HRMS: calcd for $C_{30}H_{34}N_2O_6$+H+, 519.24896. found (ESI-FTMS, [M+H]$^{1+}$), 519.24917.

Example 17R $N^2$-[(3'-fluoro-4'-methylbiphenyl-4-yl)carbonyl]-N-(3,4,5-trimethoxybenzyl)-L-α-glutamine MS (ESI) m/z 539.3; MS (ESI) m/z 1077.6; MS (ESI) m/z 561.3; HRMS: calcd for $C_{29}H_{31}FN_2O_7$+H+, 539.21881. found (ESI-FTMS, [M+H]$^{1+}$), 539.2182.

Example 17S $N^2$-[(4'-sec-butylbiphenyl-4-yl)carbonyl]-N-(1,1-dimethyl-2-phenylethyl)-L-α-glutamine MS (ESI) m/z 515.4; MS (ESI) m/z 1029.9; HRMS: calcd for $C_{32}H_{38}N_2O_4$+H+, 515.29043. found (ESI-FTMS, [M+H]$^{1+}$), 515.29203.

Example 17T

N-(1,1-dimethyl-2-phenylethyl)-$N^2$-[(4'-isopropylbiphenyl-4-yl)carbonyl]-L-α-glutamine MS (ESI) m/z 501.4; MS (ESI) m/z 1001.8; HRMS: calcd for $C_{31}H_{36}N_2O_4$+H+, 501.27478. found (ESI-FTMS, [M+H]$^{1+}$), 501.27468.

Example 17U

N-(1,1-dimethyl-2-phenylethyl)-$N^2$-(1,1':4',1''-terphenyl-4-ylcarbonyl)-L-α-glutamine MS (ESI) m/z 535.4; MS (ESI) m/z 1069.8; HRMS: calcd for $C_{34}H_{34}N_2O_4$+H+, 535.25913. found (ESI-FTMS, [M+H]$^{1+}$), 535.26044.

Example 17V $N^2$-[(4'-hydroxybiphenyl-4-yl)carbonyl]-N-(3,4,5-trimethoxybenzyl)-L-α-glutamine MS (ESI) m/z 521.3; MS (ESI) m/z 1043.7; HRMS: calcd for $C_{28}H_{30}N_2O_8$+H+, 523.20749. found (ESI-FTMS, [M+H]$^{1+}$), 523.20878.

Example 17W

N-(1-adamantylmethyl)-$N^2$-({3'-[(dimethylamino)carbonyl]biphenyl-4-yl}carbonyl)-L-α-glutamine MS (ESI) m/z 546.4; MS (ESI) m/z 1091.9; HRMS: calcd for $C_{32}H_{39}N_3O_5$+H+, 546.29625. found (ESI-FTMS, [M+H]$^{1+}$), 546.29678.

Example 17X

N-(1-adamantylmethyl)-$N^2$-[(3',5'-dimethylbiphenyl-4-yl)carbonyl]-L-α-glutamine MS (ESI) m/z 503.4; MS (ESI) m/z 1005.8; HRMS: calcd for $C_{31}H_{38}N_2O_4$+H+, 503.29043. found (ESI-FTMS, [M+H]$^{1+}$), 503.29107.

Example 17Y

N-[2-(4-fluorophenyl)-1,1-dimethylethyl]-$N^2$-[(3'-methylbiphenyl-4-yl)carbonyl]-L-α-glutamine MS (ESI) m/z 491.4; MS (ESI) m/z 981.7; MS (ESI) m/z 513.3; HRMS: calcd for $C_{29}H_{31}FN_2O_4$+H+, 491.23406. found (ESI-FTMS, [M+H]$^{1+}$), 491.23228.

Example 17Z $N^2$-[(3'-isopropylbiphenyl-4-yl)carbonyl]-N-(3,4,5-trimethoxybenzyl)-L-α-glutamine MS (ESI) m/z 549.4; MS (ESI) m/z 1097.9; HRMS: calcd for $C_{31}H_{36}N_2O_7$+H+, 549.25953. found (ESI-FTMS, [M+H]$^{1+}$), 549.26013.

Example 17AA $N^2$-[(4'-isopropylbiphenyl-4-yl)carbonyl]-N-(3,4,5-trimethoxybenzyl)-L-α-glutamine MS (ESI) m/z 549.4; MS (ESI) m/z 1097.9; HRMS: calcd for $C_{31}H_{36}N_2O_7$+H+, 549.25953. found (ESI-FTMS, [M+H]$^{1+}$), 549.26066.

Example 17BB

N-(1-adamantylmethyl)-$N^2$-[4-(1-benzofuran-5-yl)benzoyl]-L-α-glutamine

MS (ESI) m/z 515.4; MS (ESI) m/z 1029.9; HRMS: calcd for $C_{31}H_{34}N_2O_5$+H+, 515.25405. found (ESI-FTMS, [M+H]$^{1+}$), 515.25447.

Example 17CC

N-(1-adamantylmethyl)-$N^2$-[4-(1H-indol-5-yl)benzoyl]-L-α-glutamine

MS (ESI) m/z 514.4; MS (ESI) m/z 1027.7; HRMS: calcd for $C_{31}H_{35}N_3O_4$+H+, 514.27003. found (ESI-FTMS, [M+H]$^{1+}$), 514.27038.

Example 17DD $N^2$-[(3'-ethoxybiphenyl-4-yl)carbonyl]-N-[2-(4-fluorophenyl)-1,1-dimethylethyl]-L-α-glutamine MS (ESI) m/z 521.4; MS (ESI) m/z 1041.7; HRMS: calcd for $C_{30}H_{33}FN_2O_5$+H+, 521.24463. found (ESI-FTMS, [M+H]$^{1+}$), 521.24248.

Example 17EE

N-[2-(4-fluorophenyl)-1,1-dimethylethyl]-$N^2$-[(3'-methoxybiphenyl-4-yl)carbonyl]-L-α-glutamine MS (ESI) m/z 507.3; MS (ESI) m/z 1013.7; HRMS: calcd for $C_{29}H_{31}FN_2O_5$+H+, 507.22898. found (ESI-FTMS, [M+H]$^{1+}$), 507.22717.

Example 17FF

N-[2-(4-fluorophenyl)-1,1-dimethylethyl]-$N^2$-[(3'-isopropylbiphenyl-4-yl)carbonyl]-L-α-glutamine MS (ESI) m/z 519.4; MS (ESI) m/z 1037.7; HRMS: calcd for $C_{31}H_{35}FN_2O_4$+H+, 519.26536. found (ESI-FTMS, [M+H]$^{1+}$), 519.26474.

Example 17GG $N^2$-[(3'-fluoro-4'-methylbiphenyl-4-yl)carbonyl]-N-[2-(4-fluorophenyl)-1,1-dimethylethyl]-L-α-glutamine MS (ESI) m/z 509.3; MS (ESI) m/z 1017.7; HRMS: calcd for $C_{29}H_{30}F_2N_2O_4$+H+, 509.22464. found (ESI-FTMS, [M+H]$^{1+}$), 509.22537.

Example 17HH

N-[2-(4-fluorophenyl)-1,1-dimethylethyl]-$N^2$-[(4'-isobutylbiphenyl-4-yl)carbonyl]-L-α-glutamine MS (ESI) m/z 533.4; MS (ESI) m/z 1065.8; HRMS: calcd for $C_{32}H_{37}FN_2O_4$+H+, 533.28101. found (ESI-FTMS, [M+H]$^{1+}$), 533.28214.

Example 17II $N^2$-(1,1':4',1''-terphenyl-4-ylcarbonyl)-N-(3,4,5-trimethoxybenzyl)-L-α-glutamine MS (ESI) m/z 581.2; MS (ESI) m/z 1163.4; HRMS: calcd for $C_{34}H_{34}N_2O_7$+H+, 583.24388. found (ESI-FTMS, [M+H]$^{1+}$), 583.24414.

Example 17JJ

N-benzyl-$N^2$-{[3'-(hydroxymethyl)biphenyl-4-yl]carbonyl}-L-α-glutamine

MS (ESI) m/z 445.1; MS (ESI) m/z 891.2.

Example 17KK

N-(3,4,5-trimethoxybenzyl)-$N^2$-[(2',4',6'-trimethylbiphenyl-4-yl)carbonyl]-L-α-glutamine HRMS: calcd for $C_{31}H_{36}N_2O_7$+H+, 549.25953. found (ESI-FTMS, [M+H]$^{1+}$), 549.25817.

Example 17LL

N-(1,1-dimethyl-2-phenylethyl)-$N^2$-[(4'-hydroxybiphenyl-4-yl)carbonyl]-L-α-glutamine MS (ESI) m/z 475.2; MS (ESI) m/z 949.4; HRMS: calcd for $C_{28}H_{30}N_2O_5$+H+, 475.22275. found (ESI-FTMS, [M+H]$^{1+}$), 475.22358.

Example 17MM

N-(1,1-dimethyl-2-phenylethyl)-$N^2$-[(3'-ethoxybiphenyl-4-yl)carbonyl]-L-α-glutamine MS (ESI) m/z 503.2; MS (ESI) m/z 1005.3; MS (ESI) m/z 525.1; HRMS: calcd for $C_{30}H_{34}N_2O_5$+H+, 503.25405. found (ESI-FTMS, [M+H]$^{1+}$), 503.25252.

Example 17NN $N^2$-[4-(1,3-benzodioxol-5-yl)benzoyl]-N-(3-methylbenzyl)-L-α-glutamine MS (ESI) m/z 475.1; MS (ESI) m/z 949.2; HRMS: calcd for $C_{27}H_{26}N_2O_6$+H+, 475.18636. found (ESI-FTMS, [M+H]$^{1+}$), 475.1872.

Example 17OO

N-[2-(4-fluorophenyl)-1,1-dimethylethyl]-$N^2$-[(4'-hydroxybiphenyl-4-yl)carbonyl]-L-α-glutamine MS (ESI) m/z 493.2; MS (ESI) m/z 985.4; HRMS: calcd for $C_{28}H_{29}FN_2O_5$+H+, 493.21333. found (ESI-FTMS, [M+H]$^{1+}$), 493.21327.

Example 17PP $N^2$-[4-(1,3-benzodioxol-5-yl)benzoyl]-N-[2-(4-fluorophenyl)-1,1-dimethylethyl]-L-α-glutamine (1): MS (ESI) m/z 521.1; MS (ESI) m/z 1041.3; HRMS: calcd for $C_{29}H_{29}FN_2O_6$+H+, 521.20824. found (ESI-FTMS, [M+H]$^{1+}$), 521.20872; (2): MS (ESI) m/z 521.2; MS (ESI) m/z 1041.3.

Example 17QQ

N-benzyl-$N^2$-{4-[(4-hydroxycyclohexyl)ethynyl]benzoyl}-L-α-glutamine

MS (ESI) m/z 463.1; MS (ESI) m/z 925.3.

Example 17RR $N^2$-[(3'-hydroxybiphenyl-4-yl)carbonyl]-N-(3,4,5-trimethoxybenzyl)-L-α-glutamine HRMS: calcd for $C_{28}H_{30}N_2O_8$+H+, 523.20749. found (ESI-FTMS, [M+H]$^{1+}$), 523.20809.

Example 17SS

N-(1,1-dimethyl-2-phenylethyl)-$N^2$-{[4'-(hydroxymethyl)biphenyl-4-yl]carbonyl}-L-α-glutamine MS (ESI) m/z 487.1; MS (ESI) m/z 975.2; HRMS: calcd for $C_{29}H_{32}N_2O_5$+H+, 489.23840. found (ESI-FTMS, [M+H]$^{1+}$), 489.2389.

Example 17TT

N-(1,1-dimethyl-2-phenylethyl)-$N^2$-[(4'-methylbiphenyl-4-yl)carbonyl]-L-α-glutamine MS (ESI) m/z 473.1; MS (ESI) m/z 945.3; HRMS: calcd for $C_{29}H_{32}N_2O_4$+H+, 473.24348. found (ESI-FTMS, [M+H]$^{1+}$), 473.24409.

Example 17UU

N-[2-(4-fluorophenyl)-1,1-dimethylethyl]-$N^2$-[(3'-hydroxybiphenyl-4-yl)carbonyl]-L-α-glutamine MS (ESI) m/z 493.2; MS (ESI) m/z 985.4.

Example 17VV $N^1$-benzyl-$N^2$-(4-pyridin-4-ylbenzoyl)-L-α-glutamine

MS (ESI) m/z 418.2; HRMS: calcd for $C_{24}H_{23}N_3O_4$+H+, 418.17613. found (ESI_FT, [M+H]$^{1+}$), 418.17461.

Example 17WW $N^1$-benzyl-$N^2$-(1,1'-biphenyl-3-ylcarbonyl)-L-α-glutamine

MS (ESI) m/z 417.1; MS (ESI) m/z 833.1; HRMS: calcd for $C_{25}H_{24}N_2O_4$+H+, 417.18088. found (ESI-FTMS, [M+H]$^{1+}$), 417.18049.

Example 17XX $N^1$-benzyl-$N^2$-(3-thien-2-ylbenzoyl)-L-α-glutamine

MS (ESI) m/z 423.1; MS (ESI) m/z 845; HRMS: calcd for $C_{23}H_{22}N_2O_4S$+H+, 423.13730. found (ESI-FTMS, [M+H]$^{1+}$), 423.1383.

Example 17YY $N^1$-benzyl-$N^2$-[(3-chloro-1,1'-biphenyl-4-yl)carbonyl]-L-α-glutamine MS (ESI) m/z 451.1; MS (ESI) m/z 901; HRMS: calcd for $C_{25}H_{23}ClN_2O_4$+H+, 451.14191. found (ESI-FTMS, [M+H]$^{1+}$), 451.1417.

Example 17ZZ $N^1$-benzyl-$N^2$-[(3-fluoro-1,1'-biphenyl-4-yl)carbonyl]-L-α-glutamine HRMS: calcd for $C_{25}H_{23}FN_2O_4$+H+, 435.17146. found (ESI-FTMS, [M+H]$^{1+}$), 435.17091.

Example 17AAA $N^1$-benzyl-$N^2$-[(2,6-dimethoxy-1,1'-biphenyl-4-yl)carbonyl]-L-α-glutamine HRMS: calcd for $C_{27}H_{28}N_2O_6$+H+, 477.20201. found (ESI-FTMS, [M+H]$^{1+}$), 477.20098.

Example 17BBB $N^2$-(1,1'-biphenyl-4-ylcarbonyl)-$N^1$-(4-methoxy-1,1'-biphenyl-3-yl)-L-α-glutamine MS (ESI) m/z 509.2; MS (ESI) m/z 1017.2; HRMS: calcd for $C_{31}H_{28}N_2O_5$+H+, 509.20710. found (ESI-FTMS, [M+H]$^{1+}$), 509.20875.

Example 18

$N^2$-({4'-[(3,5-dimethoxybenzyl)oxy]biphenyl-4-yl}carbonyl)-N-(3,4,5-trimethoxybenzyl)-L-α-glutamine MS (ESI) m/z 673.4; MS (ESI) m/z 1345.9; HRMS: calcd for $C_{37}H_{40}N_2O_{10}$+H+, 673.27557. found (ESI-FTMS, [M+H]$^{1+}$), 673.27498.

Example 19

The following compounds were prepared according to procedures similar to those described in Example 18.

Example 19A

N-(1-adamantylmethyl)-$N^2$-({4'-[(3-methoxybenzyl)oxy]biphenyl-4-yl}carbonyl)-L-α-glutamine MS (ESI) m/z 611.5; MS (ESI) m/z 1222; HRMS: calcd for $C_{37}H_{42}N_2O_6$+H+, 611.31156. found (ESI-FTMS, [M+H]$^{1+}$), 611.31164.

Example 19B

N-(1-adamantylmethyl)-$N^2$-(4'-{[(3,5-dimethoxybenzyl)oxy]biphenyl-4-yl}carbonyl)-L-α-glutamine MS (ESI) m/z 641.5; MS (ESI) m/z 1282; HRMS: calcd for $C_{38}H_{44}N_2O_7$+H+, 641.32213. found (ESI-FTMS, [M+H]$^{1+}$), 641.32171.

Example 19C $N^2$-({4'-[(3,5-dimethoxybenzyl)oxy]biphenyl-4-yl}carbonyl)-N-(1,1-dimethyl-2-phenylethyl)-L-α-glutamine MS (ESI) m/z 625.5; MS (ESI) m/z 1249.9; HRMS: calcd for $C_{37}H_{40}N_2O_7$+H+, 625.29083. found (ESI-FTMS, [M+H]$^{1+}$), 625.2906.

Example 19D $N^2$-({4'-[(3,5-dimethylbenzyl)oxy]biphenyl-4-yl}carbonyl)-N-(3,4,5-trimethoxybenzyl)-L-α-glutamine MS (ESI) m/z 641.5; MS (ESI) m/z 1282.

Example 19E $N^2$-[(4'-{[3,5-bis(trifluoromethyl)benzyl]oxy}biphenyl-4-yl)carbonyl]-N-(3,4,5-trimethoxybenzyl)-L-α-glutamine MS (ESI) m/z 749.5; MS (ESI) m/z 771.5; HRMS: calcd for $C_{37}H_{34}F_6N_2O_8$+H+, 749.22921. found (ESI-FTMS, [M+H]$^{1+}$), 749.2297.

Example 19F

N-(1,1-dimethyl-2-phenylethyl)-$N^2$-({4'-[(3-methoxybenzyl)oxy]biphenyl-4-yl}carbonyl)-L-α-glutamine MS (ESI) m/z 595.3; MS (ESI) m/z 1189.5; HRMS: calcd for $C_{36}H_{38}N_2O_6$+H+, 595.28026. found (ESI-FTMS, [M+H]$^{1+}$), 595.28185.

Example 19G $N^2$-({4'-[(3,5-dimethoxybenzyl)oxy]biphenyl-4-yl}carbonyl)-N-(6-hydroxyhexyl)-L-α-glutamine MS (ESI) m/z 591.2; HRMS: calcd for $C_{33}H_{40}N_2O_8$+H+, 593.28574. found (ESI-FTMS, [M+H]$^{1+}$), 593.28726.

Example 19H $N^2$-({4'-[(3-methoxybenzyl)oxy]biphenyl-4-yl}carbonyl)-N-(3,4,5-trimethoxybenzyl)-L-α-glutamine MS (ESI-FTMS) m/z 643.26499; MS (ESI-FTMS) m/z 643.26501; HRMS: calcd for $C_{36}H_{38}N_2O_9$+H+, 643.26501. found (ESI-FTMS, [M+H]$^{1+}$), 643.26499.

Scheme 11

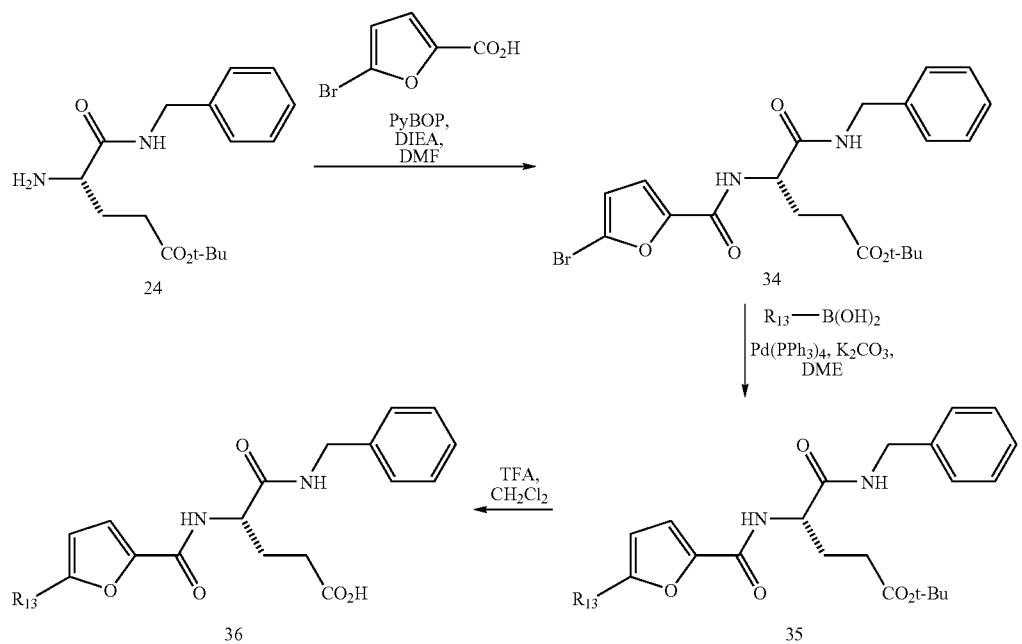

Example 20

N$^1$-benzyl-N$^2$-(5-phenyl-2-furoyl)-L-α-glutamine

Step A: tert-butyl N$^1$-benzyl-N$^2$-(5-bromo-2-furoyl)-L-α-glutaminate

Tert-butyl N$^1$-benzyl-L-α-glutaminate (2.33 g, 7.98 mmol) was dissolved in DMF (7 mL) under nitrogen. 5-Bromofuroic acid (1.52 g, 7.98 mmol) was added, followed by addition of PyBOP (5.00 g, 9.6 mmol). Finally, DIEA (1.67 mL, 9.6 mmol) was added dropwise over 5 minutes via addition funnel. The reaction was monitored by TLC and stirred overnight. The solution was diluted with EtOAc (250 mL), washed consecutively with H$_2$O, 10% HCl, saturated NaHCO$_3$, brine, and then dried over Na$_2$SO$_4$. After solvent was evaporated, the crude residue was dissolved in ether and washed with aq. LiBr (2×250 mL) and dried over Na$_2$SO$_4$. Ether was removed, leaving an oil which was further purified on a SiO$_2$ column using 33%-40% EtOAc/Hex as the solvent. The product was the third spot off the column and a sticky orange solid. Yield 1.60 g of tert-butyl N$^1$-benzyl-N$^2$-(5-bromo-2-furoyl)-L-α-glutaminate at 43% yield.

Step B: tert-butyl N$^1$-benzyl-N$^2$-(5-phenyl-2-furoyl)-L-α-glutaminate

HRMS: calcd for C$_{27}$H$_{30}$N$_2$O$_5$+Na+, 485.20469. found (ESI FTMS, [M+Na]$^{1+}$), 485.20466.

Step C: N$^1$-benzyl-N$^2$-(5-phenyl-2-furoyl)-L-α-glutamine

HRMS: calcd for C$_{23}$H$_{22}$N$_2$O$_5$+H+, 407.16015. found (ESI_FTMS, [M+H]$^{1+}$), 407.15841.

Example 21

The following compounds were prepared according to procedures similar to those described in Example 20.

Example 21A

N$^1$-benzyl-N$^2$-[5-(3-ethoxyphenyl)-2-furoyl]-L-α-glutamine

Step B: tert-butyl N$^1$-benzyl-N$^2$-[5-(3-ethoxyphenyl)-2-furoyl]-L-α-glutaminate HRMS: calcd for C$_{29}$H$_{34}$N$_2$O$_6$+H+, 507.24896. found (ESI_FTMS, [M+H]$^{1+}$), 507.24894.

Step C: N$^1$-benzyl-N$^2$-[5-(3-ethoxyphenyl)-2-furoyl]-L-α-glutamine

HRMS: calcd for C$_{25}$H$_{26}$N$_2$O$_6$+H+, 451.18636. found (ESI_FTMS, [M+H]$^{1+}$), 451.18545.

Example 21B

N$^1$-benzyl-N$^2$-[5-(3,5-dimethylphenyl)-2-furoyl]-L-α-glutamine

Step B: tert-butyl N$^1$-benzyl-N$^2$-[5-(3,5-dimethylphenyl)-2-furoyl]-L-α-glutaminate HRMS: calcd for C$_{29}$H$_{34}$N$_2$O$_5$+H+, 491.25405. found (ESI_FTMS, [M+H]$^{1+}$), 491.2538.

Step C: N$^1$-benzyl-N$^2$-[5-(3,5-dimethylphenyl)-2-furoyl]-L-α-glutamine

HRMS: calcd for C$_{25}$H$_{26}$N$_2$O$_5$+H+, 435.19145. found (ESI_FTMS, [M+H]$^{1+}$), 435.19034.

Example 21C $N^1$-benzyl-$N^2$-(2,2'-bifuran-5-ylcarbonyl)-L-α-glutamine

Step B: tert-butyl $N^1$-benzyl-$N^2$-(2,2'-bifuran-5-ylcarbonyl)-L-α-glutaminate HRMS: calcd for $C_{25}H_{28}N_2O_6$+H+, 453.20201. found (ESI_FTMS, [M+H]$^{1+}$), 453.20173.

Step C: $N^1$-benzyl-$N^2$-(2,2'-bifuran-5-ylcarbonyl)-L-α-glutamine

HRMS: calcd for $C_{21}H_{20}N_2O_6$+H+, 397.13941. found (ESI_FTMS, [M+H]$^{1+}$), 397.13777.

Example 21D $N^1$-benzyl-$N^2$-(5-thien-2-yl-2-furoyl)-L-α-glutamine

Step B: tert-butyl $N^1$-benzyl-$N^2$ (5-thien-2-yl-2-furoyl)-L-α-glutaminate

HRMS: calcd for $C_{25}H_{28}N_2O_5S$+H+, 469.17917. found (ESI_FTMS, [M+H]$^{1+}$), 469.1789.

Step C: $N^1$-benzyl-$N^2$-(5-thien-2-yl-2-furoyl)-L-α-glutamine

HRMS: calcd for $C_{21}H_{20}N_2O_5S$+H+, 413.11657. found (ESI_FTMS, [M+H]$^{1+}$), 413.11511.

Scheme 12

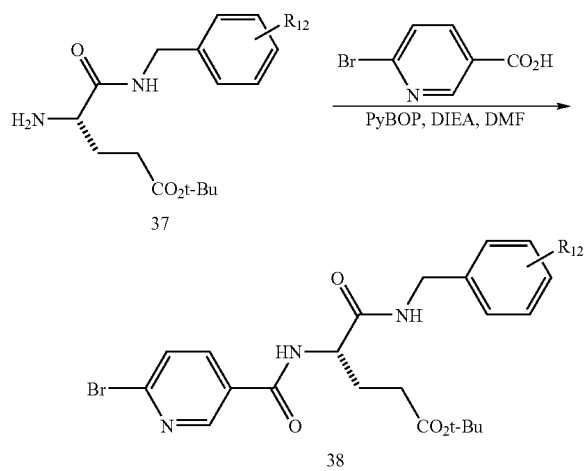

Example 22

The following compounds were prepared according to procedures similar to those described in Example 20.

Example 22A $N^1$-benzyl-$N^2$-[(6-phenylpyridin-3-yl)carbonyl]-L-α-glutamine Step A: tert-butyl $N^1$-benzyl-$N^2$-[(6-bromopyridin-3-yl)carbonyl]-L-α-glutaminate MS (ESI) m/z 476.1; MS (ESI) m/z 951.1; HRMS: calcd for $C_{22}H_{26}BrN_3O_4$+H+, 476.11794. found (ESI-FTMS, [M+H]$^{1+}$), 476.11935.

Step B: tert-butyl $N^1$-benzyl-$N^2$-[(6-phenylpyridin-3-yl)carbonyl]-L-α-glutaminate MS (ESI) m/z 474.2; HRMS: calcd for $C_{28}H_{31}N_3O_4$+H+, 474.23873. found (ESI-FTMS, [M+H]$^{1+}$), 474.23861.

Step C: $N^1$-benzyl-$N^2$-[(6-phenylpyridin-3-yl)carbonyl]-L-α-glutamine

MS (ESI) m/z 418.1; HRMS: calcd for $C_{24}H_{23}N_3O_4$+H+, 418.17613. found (ESI-FTMS, [M+H]$^{1+}$), 418.17674.

Example 22B $N^1$-(3-methoxybenzyl)-$N^2$-[(6-phenylpyridin-3-yl)carbonyl]-L-α-glutamine Step A: tert-butyl $N^2$-[(6-bromopyridin-3-yl)carbonyl]-$N^1$-(3-methoxybenzyl)-L-α-glutaminate MS (ESI) m/z 506.1; MS (ESI) m/z 1011.1; HRMS: calcd for $C_{23}H_{28}BrN_3O_5$+H+, 506.12851. found (ESI-FTMS, [M+H]$^{1+}$), 506.12839.

Step B: tert-butyl $N^1$-(3-methoxybenzyl)-$N^2$-[(6-phenylpyridin-3-yl)carbonyl]-L-α-glutaminate MS (ESI) m/z 504.2; HRMS: calcd for $C_{29}H_{33}N_3O_5$+H+, 504.24930. found (ESI-FTMS, [M+H]$^{1+}$), 504.24835.

Step C: $N^1$-(3-methoxybenzyl)-$N^2$-[(6-phenylpyridin-3-yl)carbonyl]-L-α-glutamine MS (ESI) m/z 448.1; HRMS: calcd for $C_{25}H_{25}N_3O_5$+H+, 448.18670. found (ESI-FTMS, [M+H]$^{1+}$), 448.18686.

Example 22C $N^2$-[(2,2'-dimethyl-1,1'-biphenyl-4-yl)carbonyl]-$N^1$-(3-methoxybenzyl)-L-α-glutamine Step B: tert-butyl $N^2$-[(2,2'-dimethyl-1,1'-biphenyl-4-yl)carbonyl]-$N^1$-(3-methoxybenzyl)-L-α-glutaminate MS (ESI) m/z 531.3; MS (ESI) m/z 1061.4; HRMS: calcd for $C_{32}H_{38}N_2O_5$+H+, 531.28535. found (ESI_FTMS, [M+H]$^{1+}$), 531.2855.

Step C: $N^2$-[(2,2'-dimethyl-1,1'-biphenyl-4-yl)carbonyl]-$N^1$-(3-methoxybenzyl)-L-α-glutamine HRMS: calcd for $C_{28}H_{30}N_2O_5$+H+, 475.22275. found (ESI_FTMS, [M+H]$^{1+}$), 475.22271.

Example 22D $N^2$-(4-bromobenzoyl)-N-(3,4,5-trimethoxybenzyl)-L-α-glutamine

MS (ESI) m/z 507; MS (ESI) m/z 1015.1; HRMS: calcd for $C_{22}H_{25}BrN_2O_7$+H+, 509.09179. found (ESI-FTMS, [M+H]$^{1+}$), 509.09078.

Example 22E $N^2$-(4-bromobenzoyl)-N-(1,1-dimethyl-2-phenylethyl)-L-α-glutamine

MS (ESI) m/z 461.1; MS (ESI) m/z 921.2; HRMS: calcd for $C_{22}H_{25}BrN_2O_4$+H+, 461.10705. found (ESI-FTMS, [M+H]$^{1+}$), 461.10805.

Example 22F

N-(1-adamantylmethyl)-$N^2$-(4-bromobenzoyl)-L-α-glutamine

MS (ESI) m/z 477.3; MS (ESI) m/z 953.5; HRMS: calcd for $C_{23}H_{29}BrN_2O_4$+H+, 477.13835. found (ESI-FTMS, [M+H]$^{1+}$), 477.13801.

Example 22G $N^2$-(4-bromobenzoyl)-N-(3-methylbenzyl)-L-α-glutamine

MS (ESI-FTMS) m/z 433.07562; MS (ESI-FTMS) m/z 433.07575; HRMS: calcd for $C_{20}H_{21}BrN_2O_4$+H+, 433.07575. found (ESI-FTMS, [M+H]$^{1+}$), 433.07562.

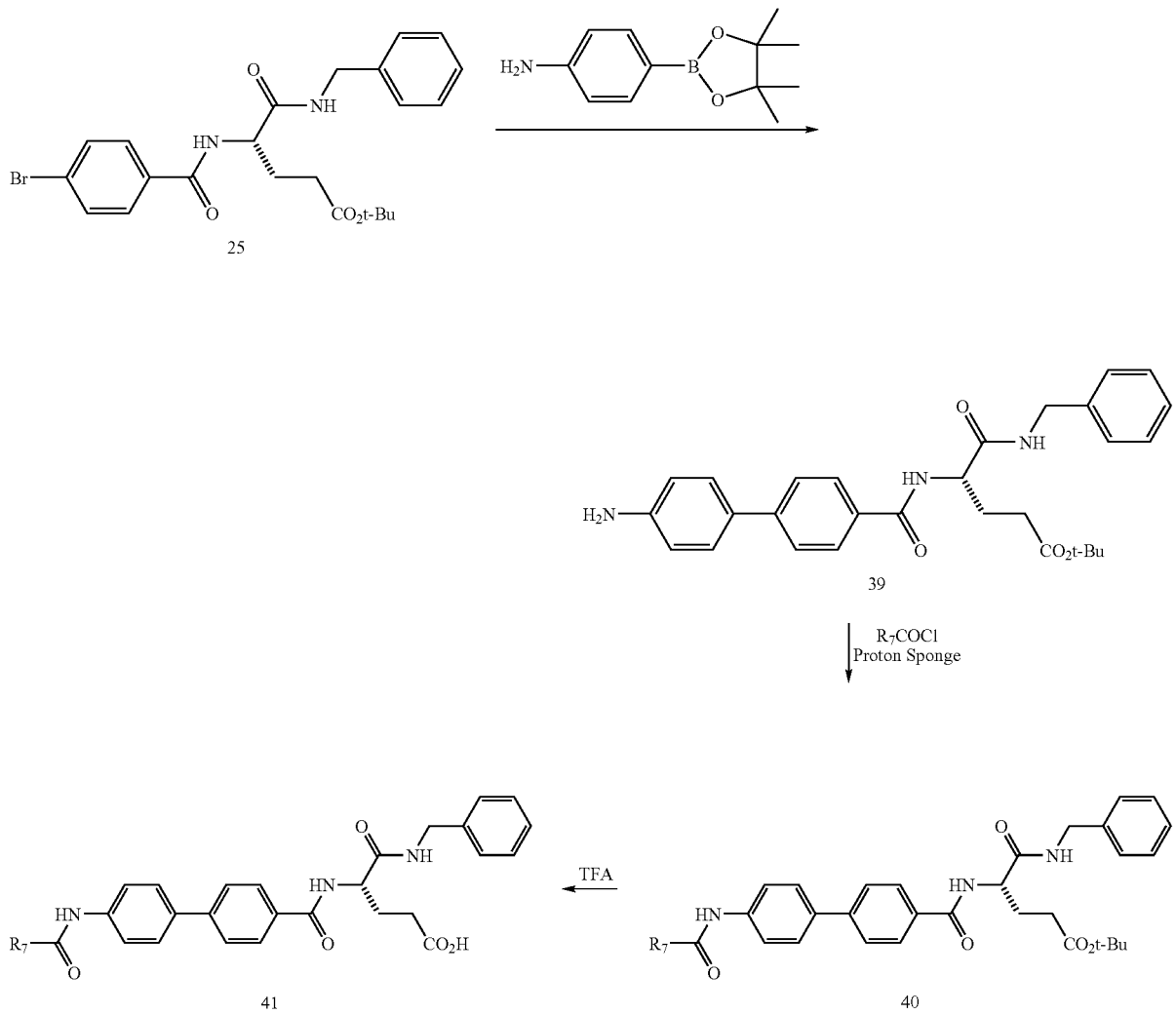

Scheme 13

Example 23

N²-{[4'-(acetylamino)-1,1'-biphenyl-4-yl]carbonyl}-N¹-benzyl-L-α-glutamine

Step A: tert-butyl N²-[(4'-amino-1,1'-biphenyl-4-yl)carbonyl]-N¹-benzyl-L-α-glutaminate 4-Benzylcarbamoyl-4-(4-bromo-benzoylamino)-butyric acid tert-butyl ester (3.0 g, 6.31 mmol, 1 equiv.) was dissolved in DME (60 mL) was added to 4-(4,4,5,5)-tetramethyl-1,3,2-dioxoborolan-2-yl)aniline (1.38 g, 6.31 mmol, 1 equiv.) and Pd(PPh$_3$)$_4$ (728 mg, 0.063 mmol, 0.1 equiv.). The mixture was stirred for 30 minutes prior to the addition of aq. K$_2$CO$_3$ (1.74 g, 12.6 mmol, 2 equiv.) in 12 mL H$_2$O. The mixture was capped in a sealed vessel and stirred overnight at 80° C. The reaction was complete as determined by TLC. The mixture was filtered over celite, the solvent was removed, and the resulting tan solid was diluted with EtOAc (200 mL) and washed consecutively with H$_2$O, 10% HCl, and brine, and then dried over Na$_2$SO$_4$. The solid was purified by column chromatography (silica gel, 41% Acetone/Hexanes) to give 1.89 g of tert-butyl N²-[(4'-amino-1,1'-biphenyl-4-yl)carbonyl]-N¹-benzyl-L-α-glutaminate in 61% yield. MS (ESI) m/z 488.2; HRMS: calcd for C$_{29}$H$_{33}$N$_3$O$_4$+H+, 488.25438. found (ESI_FTMS, [M+H]$^{1+}$), 488.25433.

Step B: isopropyl N²-{[4'-(acetylamino)-1,1'-biphenyl-4-yl]carbonyl}-N¹-benzyl-L-α-glutaminate 4-[(4'-Amino-biphenyl-4-carbonyl)-amino]-4-benzylcarbamoyl-butyric acid tert-butyl ester (300 mg, 0.62 mmol, 1 equiv.) was dissolved in CH$_2$Cl$_2$ (20 mL) and cooled to 0° C. followed by the addition of proton sponge (266 mg, 1.24 mmol, 2 equiv.). The mixture was stirred 30 minutes prior to the addition of acetyl chloride (48 µL, 0.68 mmol, 1.1 equiv.) The mixture was stirred at 0° C. for 1.5 hrs and allowed to warm to room temperature. Reaction was complete as determined by TLC. The mixture was washed consecutively with H$_2$O, NaHCO$_3$ satd., and brine, and then dried over Na$_2$SO$_4$. The tan solid was purified by preparative HPLC to give 85 mg of isopropyl N²-{[4'-(acetylamino)-1,1'-biphenyl-4-yl]carbonyl}-N¹-benzyl-L-α-glutaminate in 26% yield.
MS (ESI) m/z 557.2; MS (ESI) m/z 279.1.

Step C: N²-{[4'-(acetylamino)-1,1'-biphenyl-4-yl]carbonyl}-N¹-benzyl-L-α-glutamine 4-[(4'-Acetylamino-biphenyl-4-carbonyl)-amino]-4-benzylcarbamoyl-butyric acid tert-butyl ester (75 mg) was dissolved in dichloroethane (4 mL) and added to TFA (2 mL). The mixture was stirred at room temperature for 3 hrs. Reaction was complete as determined by TLC. The solvent was removed and the resulting solid was purified by preparative HPLC to give N²-{[4'-(acetylamino)-1,1'-biphenyl-4-yl]carbonyl}-N¹-benzyl-L-α-glutamine in 54% yield (37 mg). MS (ESI) m/z 474.2; MS (ESI) m/z 947.3; HRMS: calcd for C$_{27}$H$_{27}$N$_3$O$_5$+H+, 474.20235. found (ESI_FTMS, [M+H]$^{1+}$), 474.20274.

Example 24

The following compounds were prepared according to procedures similar to those described in Example 23.

Example 24A

N¹-benzyl-N²-{[4'-(2-furoylamino)-1,1'-biphenyl-4-yl]carbonyl}-L-α-glutamine

Step B: tert-butyl N¹-benzyl-N²-{[4'-(2-furoylamino)-1,1'-biphenyl-4-yl]carbonyl}-L-α-glutaminate MS (ESI) m/z 582.3; MS (ESI) m/z 1163.5; HRMS: calcd for C$_{34}$H$_{35}$N$_3$O$_6$+H+, 582.25986. found (ESI_FTMS, [M+H]$^{1+}$), 582.26058.

Step C: N¹-benzyl-N²-{[4'-(2-furoylamino)-1,1'-biphenyl-4-yl]carbonyl}-L-α-glutamine MS (ESI) m/z 526.2; MS (ESI) m/z 1051.3; HRMS: calcd for C$_{30}$H$_{27}$N$_3$O$_6$+H+, 526.19726. found (ESI FTMS, [M+H]$^{1+}$), 526.19773.

Example 24B

N¹-benzyl-N²-({4'-[(4-fluorobenzoyl)amino]1,1'-biphenyl-4-yl}carbonyl)-L-α-glutamine

Step B: tert-butyl N¹-benzyl-N²-({4'-[(4-fluorobenzoyl)amino]-1,1'-biphenyl-4-yl}carbonyl)-L-α-glutaminate

Step C: N¹-benzyl-N²-({4'-[(4-fluorobenzoyl)amino]-1,1'-biphenyl-4-yl}carbonyl)-L-α-glutamine

Example 24C

N²-{[4'-(benzoylamino)-1,1'-biphenyl-4-yl]carbonyl}-N¹-benzyl-L-α-glutamine HRMS: calcd for C$_{32}$H$_{29}$N$_3$O$_5$—H+, 534.20345. found (ESI-FTMS, [M–H]$^{1-}$), 534.2024.

Scheme 14

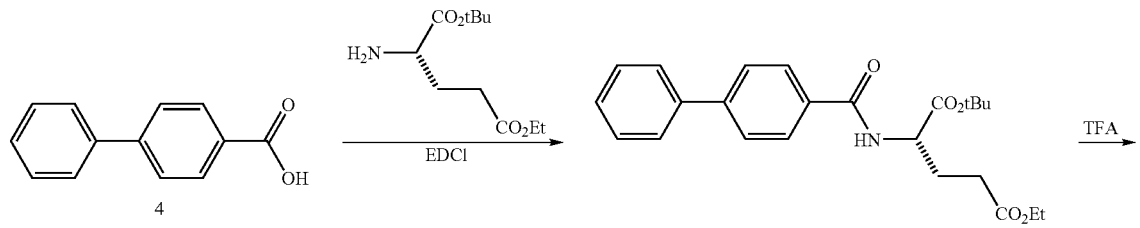

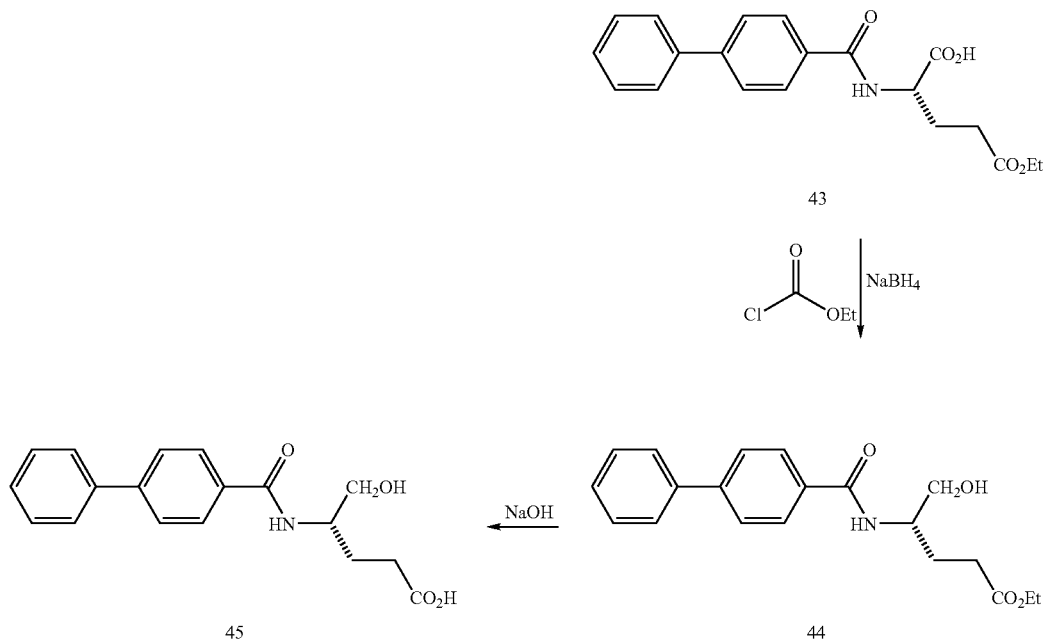

Example 25

4-[(Biphenyl-4-carbonyl)-amino]-5-hydroxy-pentanoic acid

Step A:
2-[(Biphenyl-4-carbonyl)-amino]-pentanedioic acid 1-tert-butyl ester 5-methyl ester 4-Diphenyl carboxylic acid (3.57 g, 18 mmol) and EDCI (4.28 g, 22.3 mmol, 1.2 equiv.) were dissolved in DMF (40 mL). The mixture was stirred at room temperature for 0.5 hrs. H-Glu(OMe)OtBu (5.02 g, 19.8 mmol, 1.1 equiv.) was added, followed by the addition of $Et_3N$ (6.77 mL, 48.6 mmol, 2.7 equiv.) and DMAP (330 mg, 2.7 mmol, 15%). The mixture was stirred overnight under $N_2$. The reaction mixture was then diluted with EtOAc and washed with $H_2O$ and brine. The organic layer was dried over $MgSO_4$, concentrated, and purified by column chromatography (20% EtOAc/Hexane) to afford 3.2 g of 2-[(Biphenyl-4-carbonyl)-amino]-pentanedioic acid 1-tert-butyl ester 5-methyl ester in 44.7% yield. MS (ESI) m/z 396.

Step B:
2-[(Biphenyl-4-carbonyl)-amino]-pentanedioic acid 5-methyl ester

2-[(Biphenyl-4-carbonyl)-amino]-pentanedioic acid 1-tert-butyl ester 5-methyl ester (1.5 g, 3.8 mmol) was dissolved in dichloroethane (26 mL) and the mixture was added to TFA (13 mL). The mixture was stirred at room temperature for 4 hrs. TLC indicated the reaction was complete. Solvent was evaporated by rotovap. The solid obtained was washed with EtOAc and water. After drying, 2-[(Biphenyl-4-carbonyl)-amino]-pentanedioic acid 5-methyl ester was obtained in 87% yield (1.128 g). MS (ESI) m/z 342.

Step C: 4-[(Biphenyl-4-carbonyl)-amino]-5-hydroxy-pentanoic acid methyl ester

2-[(Biphenyl-4-carbonyl)-amino]-pentanedioic acid 5-methyl ester (1.128 g, 3.30 mmol, 1.0 equiv.) was dissolved in THF (35 mL). The mixture was cooled to −20° C., followed by the addition of $Et_3N$ (343 mg, 3.3 mmol, 1.0 equiv.) and ethyl chloroformate (358 mg, 3.3 mmol, 1.0 equiv.). After stirring for 20 minutes, $NaBH_4$ (375 mg, 9.9 mmol, 3 equiv.) was added and the temperature was raised to −10° C. After stirring for 5 min, MeOH (30 mL) was introduced and the mixture was further stirred for 20 min at this temperature and then at 0° C. for 20 min. 1N HCl was then added slowly to quench the reaction. Solvent was evaporated and the residue partitioned between EtOAc and $H_2O$. The organic layer was washed with brine, dried over $MgSO_4$, and removed solvent by rotavap. The crude mixture was then purified by column chromatography (silica gel, 3% MeOH/$CH_2Cl_2$) to afford 333 mg of 4-[(Biphenyl-4-carbonyl)-amino]-5-hydroxy-pentanoic acid methyl ester in 31% yield. MS (ESI) m/z 328.

Step D: 4-[(Biphenyl-4-carbonyl)-amino]-5-hydroxy-pentanoic acid

A solution of 4-[(Biphenyl-4-carbonyl)-amino]-5-hydroxy-pentanoic acid methyl ester (333 mg, 1.06 mmol) in THF (10 mL) and MeOH (1.27 mL) was added to 1N NaOH (1.27 mL, 1.27 mmol, 1.2 equiv) at room temperature. The mixture was stirred for 2 hours and TLC indicated the reaction was complete. Solvent was removed and the residue was dissolved in water. After adjusting the pH to 4 with 1N HCl, solid precipitated from the solution. The solid was then collected by filtration, washed with water, and dried under vacuum overnight to afford 240 mg of 4-[(Biphenyl-4-carbonyl)-amino]-5-hydroxy-pentanoic acid in 76.7% yield. MS (ESI) m/z 314.

Scheme 15

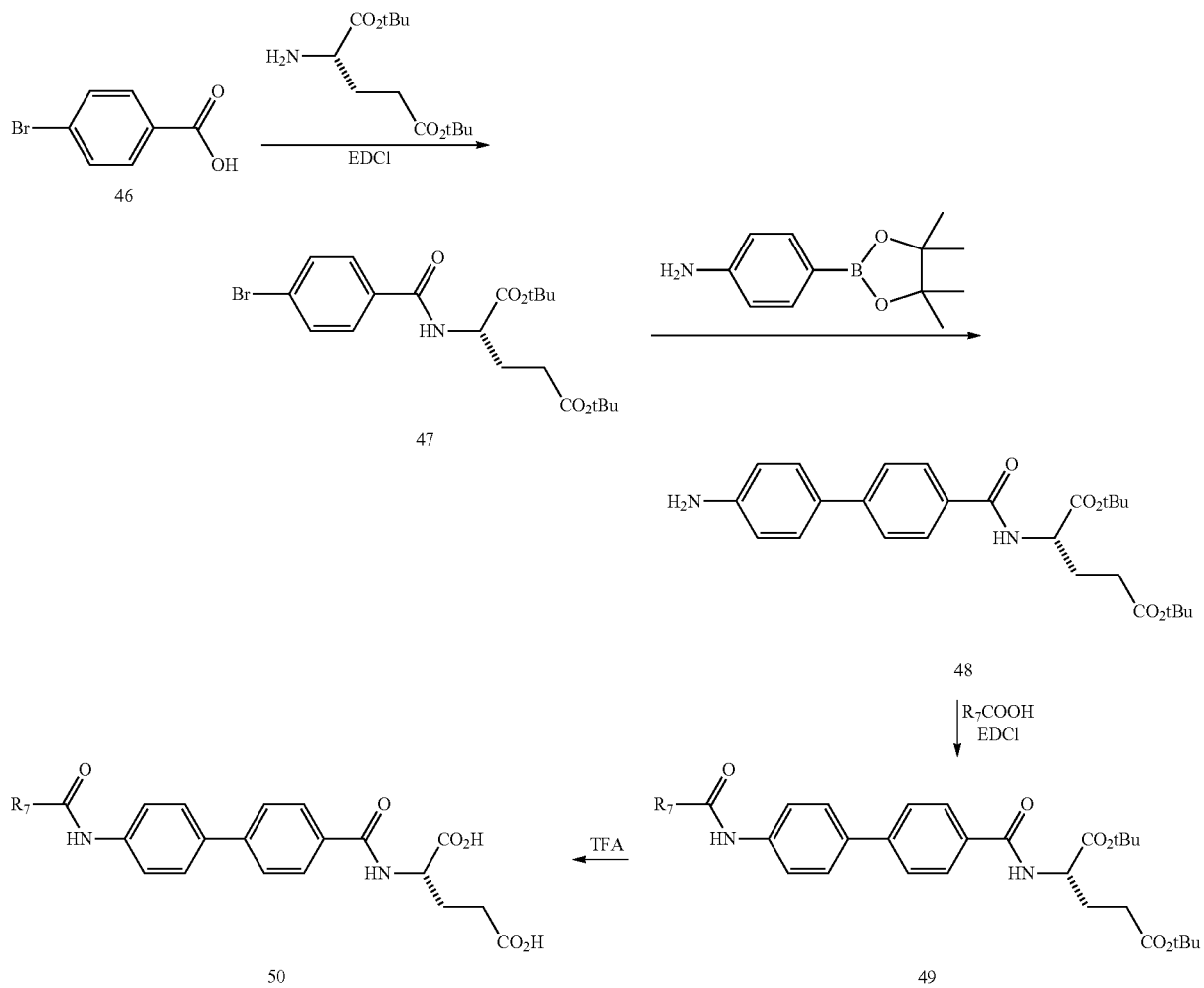

Example 26

N-({4'-[(Phenylacetyl)amino]1,1'-biphenyl-4-yl}carbonyl)-L-α-glutamic acid

Step A: 2-(4-Bromo-benzoylamino)-pentanedioic acid di-tert-butyl ester

A solution of 4-Bromobenzoic acid (4 g, 19.9 mmol, 1 equiv) in DMF (140 mL) was added to EDCI (5.72 g, 29.8 mmol, 1.5 equiv.) and the mixture was stirred at room temperature for 25 min. Et₃N (6.9 mL, 49.7 mmol, 2.5 equiv) was then added, followed by addition of DMAP (486 mg, 4.0 mmol, 20%). The reaction mixture was allowed to stir at room temperature overnight. Reaction was complete as determined by TLC. DMF was removed by rotavap and the residue partitioned between EtOAc and brine solution. The organic layer was separated, dried over MgSO₄ and concentrated. The crude mixture was purified by column chromatography (silica gel, 20% EtOAc/Hexane) to give 4.2 g of 2-(4-Bromo-benzoylamino)-pentanedioic acid di-tert-butyl ester in 47.7% yield. MS (ESI) m/z 441.

Step B: 2-[(4'-Amino-biphenyl-4-carbonyl)-amino]-pentanedioic acid di-tert-butyl ester 4-(4,4,5,5-Tetramethyl-[1,3,2]dioxaborolan-2-yl)-phenylamine (1.34 g, 6.104 mmol, 1 equiv.) and 2-(4-Bromo-benzoylamino)-pentanedioic acid di-tert-butyl ester (2.7 g, 6.104 mmol, 1 equiv.) were dissolved in DME (120 mL). A solution of K₂CO₃ (1.68 g, 12.21 mmol, 2 equiv.) in 30 mL of water was injected into the mixture, followed by the addition of Pd(PPh₃)₄ (352 mg, 0.31 mmol, 5%). The mixture was heated to reflux overnight. Reaction was complete as determined by TLC. Regular work-up and column chromatography (silica gel, 30-40% EtOAc/n-Hexane) afforded 2.3 g of 2-[(4'-Amino-biphenyl-4-carbonyl)-amino]-pentanedioic acid di-tert-butyl ester in 83% yield. MS (ESI) m/z 453.

Step C: Phenylacetylamino-biphenyl-4-carbonyl)-amino]-pentanedioic acid di-tert-butyl ester A solution of phenylacetic acid (89 mg, 0.65 mmol, 1 equiv) in DMF (10 mL) was added to EDCI (188 mg, 0.98 mmol, 1.5 equiv.). After stirring for 20 min, 2-[(4'-Amino-biphenyl-4-carbonyl)-amino]-pentanedioic acid di-tert-butyl ester (297 mg, 0.65 mmol, 1 equiv.) was added, followed by the addition of Et₃N (0.23 mL, 1.64 mmol, 2.5 equiv.) and DMAP (16 mg, 0.13 mmol, 20%). The reaction mixture was allowed to stir at room temperature overnight. Reaction was complete as determined by TLC. DMF was removed and the residue was dissolved in EtOAc. The organic layer was washed with H₂O and brine, and then dried over MgSO₄. After solvent was evaporated, the crude residue was purified by HPLC to give 45 mg of 2-[(4'-Phenylacetylamino-biphenyl-4-carbonyl)-amino]-pentanedioic acid di-tert-butyl ester in 12% yield. MS (ESI) m/z 573.

Step D: N-({4'-[(phenylacetyl)amino]-1,1'-biphenyl-4-yl}carbonyl)-L-glutamic acid 2-[(4'-Phenylacetylamino-biphenyl-4-carbonyl)-amino]-pentanedioic acid di-tert-butyl ester (45 mg) was dissolved in dichloroethane (3 mL) and added to TFA (1 mL). The mixture was stirred at room temperature for 3 hrs. Reaction was complete as determined by TLC. Solvent was removed and the resulting solid was dried under vacuum overnight. N-({4'[(phenylacetyl)amino]-1,1'-biphenyl-4-yl}carbonyl)-L-glutamic acid was obtained in 84.2% yield (30.3 mg). MS (ESI) m/z 461.

Example 27

N-[(4'-{[(3-Methyl-1-benzofuran-2-yl)carbonyl]-amino}-1,1'-biphenyl-4-yl)carbonyl]-L-α-glutamic acid

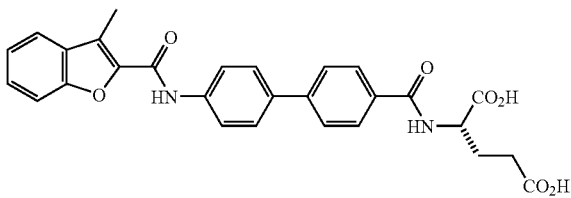

The title compound was prepared according to procedures similar to those described in Example 26.

Step C: 2-({4'-[(3-Methyl-benzofuran-2-carbonyl)-amino]-biphenyl-4-carbonyl}-amino)-pentanedioic acid di-tert-butyl ester EDCI coupling between 3-Methylbenzofuran 2 carboxylic acid (139 mg, 0.79 mmol) and 2-[(4'-Amino-biphenyl-4-carbonyl)-amino]-pentanedioic acid di-tert-butyl ester (358 mg, 0.79 mmol, 1 equiv.) was carried out according to the procedure in step C of Example 5 to give 2-({4'-[(3-Methyl-benzofuran-2-carbonyl)-amino]-biphenyl-4-carbonyl}-amino)-pentanedioic acid di-tert-butyl ester in 12.4% yield (60 mg). MS (ESI) m/z 611.

Step D: N-[(4'-{[(3-Methyl-1-benzofuran-2-yl)carbonyl]-amino}-1,1'-biphenyl-4-yl)carbonyl]-L-glutamic acid Hydrolysis of 2-({4'-[(3-Methyl-benzofuran-2-carbonyl)-amino]-biphenyl-4-carbonyl}-amino)-pentanedioic acid di-tert-butyl ester (60 mg) was carried out according to procedure in step D of Example 5 to give N-[(4'-{[(3-Methyl-1-benzofuran-2-yl)carbonyl]-amino}-1,1'-biphenyl-4-yl)carbonyl]-L-glutamic acid in 59% yield (28.9 mg). MS (ESI) m/z 499.

Example 28

N-{[4'-(2-furoylamino)-1,1'-biphenyl-4-yl]carbonyl}-L-α-glutamic acid

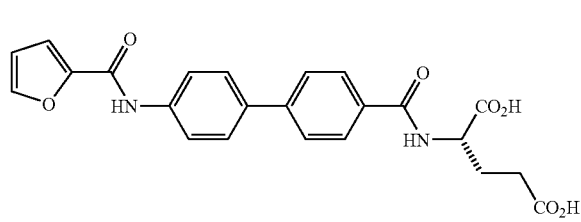

Step A: 2-({4'-[(Furan-2-carbonyl)-amino]-biphenyl-4-carbonyl}-amino)-pentanedioic acid di-tert-butyl ester To a solution of 2-[(4'-Amino-biphenyl-4-carbonyl)-amino]-pentanedioic acid di-tert-butyl ester (350 mg, 0.77 mmol) and 2-Furoic acid (87 mg, 0.77 mmol, 1 equiv.) in DMF (6 mL) was added BOP reagent (409 mg, 0.92 mmol, 1.2 equiv.) and Hunig base (0.16 mL, 0.92 mmol, 1.2 equiv.) under N₂. The mixture was stirred at room temperature overnight. Reaction was complete was determined by LC-MS. The reaction mixture was then poured onto cold water. Solid precipitated from the mixture was collected by filtration. The solid was then dissolved in EtOAc, washed with 1N HCl, saturated NaHCO₃, and brine, and then dried over MgSO₄. After removing the solvent, the solid was dried under vacuum overnight to provide 2-({4'-[(Furan-2-carbonyl)-amino]-biphenyl-4-carbonyl}-amino)-pentanedioic acid di-tert-butyl ester in 87% yield (369 mg). MS (ESI) m/z 549.

Step B: N-{[4'-(2-furoylamino)-1,1'-biphenyl-4-yl]carbonyl}-L-glutamic acid 2-({4'-[(Furan-2-carbonyl)-amino]-biphenyl-4-carbonyl}-amino)-pentanedioic acid di-tert-butyl ester (369 mg, 0.67 mmol) was dissolved in dichloroethane (10 mL) and added to TFA (5 mL) at 0° C. The cooling bath was removed after the addition was complete. The mixture was stirred at room temperature for 3 hrs. and the reaction was complete as determined by TLC. After removing solvent, the residue was washed 3 times with EtOAc. The solid was then dried under vacuum to give 2-({4'-[(Furan-2-carbonyl)-amino]-biphenyl-4-carbonyl}-amino)-pentanedioic acid in 85.6% yield (251 mg). MS (ESI) m/z 437.

Example 29

N-{[4'-(acetylamino)-1,1'-biphenyl-4-yl]carbonyl}-L-α-glutamic acid

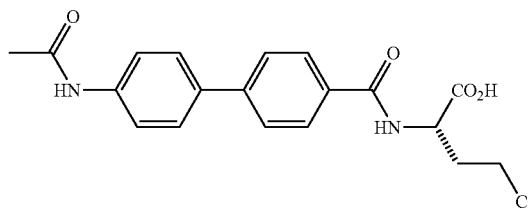

The title compound was prepared according to procedures similar to those described in Example 28.

Step A: 2-[(4'-Acetylamino-biphenyl-4-carbonyl)-amino]-pentanedioic acid di-tert-butyl ester BOP coupling of 2-[(4'-Amino-biphenyl-4-carbonyl)-amino]-pentanedioic acid di-tert-butyl ester (350 mg, 0.77 mmol) was carried out according to procedures in step A of Example 6B to give 344 mg of 2-[(4'-Acetylamino-4-carbonyl)-amino]-pentanedioic acid di-tert-butyl ester in 89% yield. MS (ESI) m/z 497.

Step B: N-{[4'-(acetylamino)-1,1'-biphenyl-4-yl] carbonyl}-L-glutamic acid

Hydrolysis of 2-[(4'-Acetylamino-biphenyl-4-carbonyl)-amino]-pentanedioic acid di-tert-butyl ester (344 mg, 0.69 mmol) was carried out according to procedures in step B for Example 6B to give 212 mg of 2-[(4'-Acetylamino-biphenyl-4-carbonyl)-amino]-pentanedioic acid in 79.7% yield. MS (ESI) m/z 383.

Example 30

N-{[4'-(benzoylamino)-1,1'-biphenyl-4-yl]carbonyl}-L-α-glutamic acid

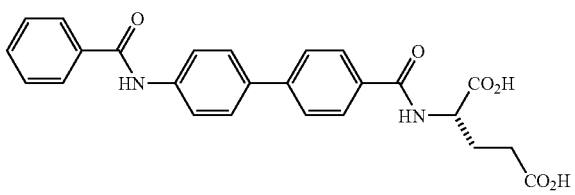

The title compound was prepared according to procedures similar to those described for Example 6B.

Step D: N-{[4'-(benzoylamino)-1,1'-biphenyl-4-yl] carbonyl}-L-glutamic acid

Hydrolysis of 2-[(4'-Benzoylamino-biphenyl-4-carbonyl)-amino]-pentanedioic acid di-tert-butyl ester (191 mg) was carried out according to procedures in step D of Example 6B to give N-{[4'-(benzoylamino)-1,1'-biphenyl-4-yl]carbonyl}-L-glutamic acid in 61.6% yield (93.7 mg). MS (ESI) m/z 445.

Example 31

N-({4'-[(1-benzofuran-2-ylcarbonyl)amino]-1,1'-biphenyl-4-yl}carbonyl)-L-α-glutamic acid

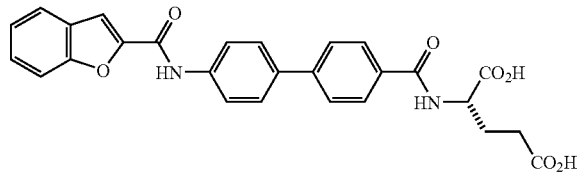

The title compound was prepared according to the procedures similar to that described for Example 28.

Step A: 2-({4'-[(Benzofuran-2-carbonyl)-amino]-biphenyl-4-carbonyl}-amino)-pentanedioic acid di-tert-butyl ester BOP coupling of 2-[(4'-Amino-biphenyl-4-carbonyl)-amino]-pentanedioic acid di-tert-butyl ester (349 mg, 0.77 mmol) with 2-Benzofuran carboxylic acid (124 mg, 0.77 mmol, 1 equiv.) was carried out according to procedures in step A of Example 6B to give 185 mg of 2-({4'-[(Benzofuran-2-carbonyl)-amino]-biphenyl-4-carbonyl}-amino)-pentanedioic acid di-tert-butyl ester in 40% yield. MS (ESI) m/z 597.

Step B: N-({4'-[(1-benzofuran-2-ylcarbonyl)amino]-1,1'-biphenyl-4-yl}carbonyl)-L-glutamic acid Hydrolysis of 2-({4'-[(Benzofuran-2-carbonyl)-amino]-biphenyl-4-carbonyl}-amino)-pentanedioic acid di-tert-butyl ester (185 mg, 0.31 mmol) was carried out according to procedures in step B of Example 6B to give N-({4'-[(1-benzofuran-2-ylcarbonyl)amino]-1,1'-biphenyl-4-yl}carbonyl)-L-glutamic acid in 82.5% yield (124 mg). MS (ESI) m/z 485.

Scheme 16

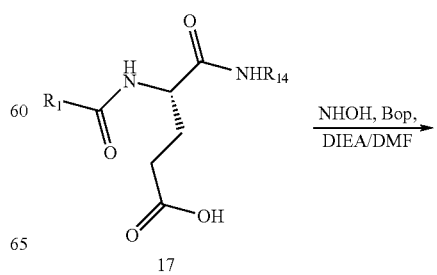

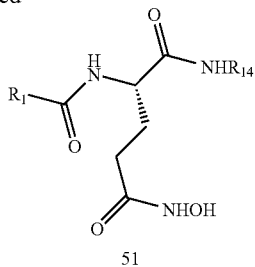

Example 32

$N^2$-(biphenyl-4-ylcarbonyl)-$N^1$-[2-(4-fluorophenyl)-1,1-dimethylethyl]-$N^5$-hydroxy-L-α-glutamamide

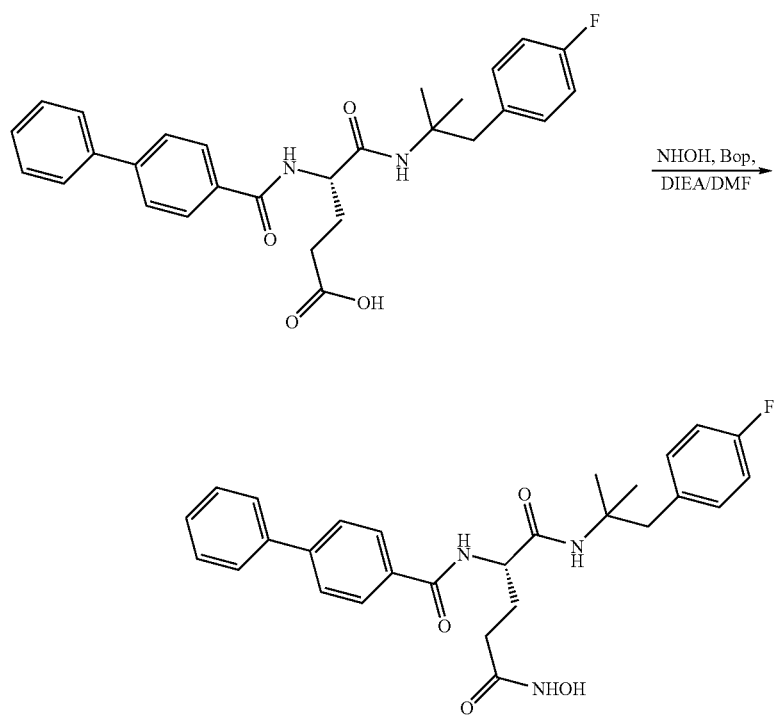

To a solution of the starting carboxylic acid (0.476 g, 1 mmol) in DMF (4 mL) under nitrogen is added BOP reagent (0.442 g, 1 mmol), followed by addition of hydroxylamine hydrochloride (0.076 g, 1.1 mmol), and DIEA (0.38 mL, 2.2 mmol). The reaction mixture was stirred for 24 hrs at room temperature. The mixture was then added slowly to 50 mL of water. The resulting white solid was collected, washed several times with water and dried under vacuum to give 350 mg of $N^2$-(biphenyl-4-ylcarbonyl)-$N^1$-[2-(4-fluorophenyl)-1,1-dimethylethyl]-$N^5$-hydroxy-L-glutamamide.

Example 33

The following compounds were prepared according to procedures similar to those described in Example 32.

Example 33A $N^2$-(1,1'-biphenyl-4-ylcarbonyl)-$N^5$-hydroxy-$N^1$-(3,4,5-trimethoxybenzyl)-L-α-glutamamide MS (ESI) m/z 522.2; HRMS: calcd for $C_{28}H_{31}N_3O_7$+H+, 522.22348. found (ESI_FTMS, [M+H]$^{1+}$), 522.22365.

Example 33B $N^2$-(1,1'-biphenyl-4-ylcarbonyl)-$N^1$-(3,4-dimethylbenzyl)-$N^5$-hydroxy-L-α-glutamamide MS (ESI) m/z 460.2; MS (ESI) m/z 919.4; HRMS: calcd for $C_{27}H_{29}N_3O_4$+H+, 460.22308. found (ESI_FTMS, [M+H]$^{1+}$), 460.22328.

Example 33C $N^2$-(1,1'-biphenyl-4-ylcarbonyl)-$N^5$-hydroxy-$N^1$-[2-(3-methoxyphenyl)ethyl]-L-α-glutamamide MS (ESI) m/z 476.2; MS (ESI) m/z 951.4; HRMS: calcd for $C_{27}H_{29}N_3O_5$+H+, 476.21800. found (ESI_FTMS, [M+H]$^{1+}$), 476.21792.

Example 33D $N^2$-(1,1'-biphenyl-4-ylcarbonyl)-$N^5$-hydroxy-$N^1$-[3-(trifluoromethoxy)benzyl]-L-α-glutamamide MS (ESI) m/z 516.2; MS (ESI) m/z 1031.4; HRMS: calcd for $C_{26}H_{24}F_3N_3O_5$+H+, 516.17408. found (ESI_FTMS, [M+H]$^{1+}$), 516.17389.

Example 34

In Vitro Fluorescence Screen for Aggrecanase-1 Inhibitors

Materials and Methods

This assay is a preliminary screen of potential aggrecanase-1 inhibitors at 11 concentrations to determine their ability to inhibit cleavage of a fluorescent peptide (Abz-TEGE-ARGSVI-Dap(Dnp)-KK). A GeminiXS fluorimeter (Molecular Devices) was turned on and the temperature was set to 30° C., ~30 min before setting up the assay. The following buffers were used: 50 mM HEPES, pH 7.5; 100 mM NaCl; 5 mM $CaCl_2$; 0.1% CHAPS; and 5% glycerol. The source of enzyme in the assay was purified recombinant human Aggrecanase-1-(rAgg1), used at 5 µg/ml (final concentration in the assay). The substrate used in the assay was the peptide (AnaSpec, MWT=1645.8, stored at 4° C.). A stock solution of peptide was prepared at 2 mg/ml in 100% DMSO. The absorbance at 354 nm ($\epsilon=18172\ M^{-1}\ cm^{-1}$) was measured to determine the exact concentration of the stock solution. The stock solution was then diluted to 62.5 µM in buffer. The unused 100% DMSO stock was stored at −80° C. The final concentration of the substrate in the assay was 25 µM. Inhibitor solutions were prepared in 100% DMSO with a 10× starting concentration, and serial dilutions were performed (in duplicate) across the dilution plate in 100% DMSO.

The assay was performed as follows: 96-well plates were set up so that the final column of wells was used for controls. The total reaction volume of each well was 100 µl. Each compound was assayed in duplicate. Buffer was added to the entire 96-well plate (30 µl/well). rAgg1 was diluted to 25 µg/ml buffer just prior to addition on the plate, and added to the wells at 20 µl/well. 10 µl/well of 10× inhibitors was added to the appropriate wells from the working plate, except for the control wells, to which are added 10 µl/well of a 10× reference control compound or 100% DMSO. The mixtures were incubated for 10-15 min at 30° C. 40 µl/well of 62.5 µM peptide substrate was then added to the appropriate wells.

Results

The reaction was monitored for 30-40 min at 30° C., with $\lambda ex=340$ nm and $\lambda\ em=420$ nm. The fluorescence was linear during this time and the slope of the line (Vmax/sec) represents the initial reaction rate, v. The maximal rate of cleavage of substrate was determined in the absence of inhibitor. The percent inhibition of activity in the presence of inhibitor was calculated as follows: % inhibition=(1−v(Rate, RFU/sec)/ Maximal Rate(RFU/sec))*100. The $IC_{50}$ was obtained by fitting the initial rate, v, or % inhibition at each concentration of inhibitor to the following equation: $y=(a-d)/(1+C/IC_{50})^n)+d$. The assay results are shown in Tables 1, 2, and 3 below.

This model describes a sigmoidal curve with an adjustable baseline, a. y is the % inhibition or initial rate of reaction, C is the concentration of inhibitor under test. A is the limiting response as C approaches zero. As C increases without bound, y tends toward its lower limit, d. y is halfway between the lower and upper asymptotes when $C=IC_{50}$. n is the Hill coefficient. The sign of n is positive when the response increases with increasing dose and is negative when the response decreases with increasing dose (inhibition). (See, Knight, C. G. *Methods Enzymol.* 1995, 248, 18-34; Knight, C. G. et al., *FEBS Lett.* 1992, 296, 263-266; Jin, G. et al., *Anal. Biochem.* 2002, 302, 269-275).

Example 35

In Vitro Fluorescence Screen for Aggrecanase-2 Inhibitors

Materials and Methods

A continuous assay was used in which the substrate is a synthetic peptide containing a fluorescent group that is quenched by energy transfer. Cleavage of the peptide by the enzyme results in a large increase in fluorescence. The initial rates of this reaction were compared to the initial rates of reactions containing inhibitors in order to assess the potency of small molecules. The source of enzyme in the assay was purified recombinant human Aggrecanase-2 prepared at Wyeth Research (Biological Chemistry, Cambridge). More specifically, the form used is denoted as Ag2t-$Phe_{628}$-Strep (MW=41,737). This form is truncated relative to the full-length enzyme and contains an affinity tag. Aliquots of this enzyme were stored at 80° C. in 25 mM Tris (pH 8.0), 100 mM NaCl, 5 mM $CaCl_2$, 10 µM $ZnCl_2$, 10% glycerol. The substrate in the assay was a synthetic peptide that is designed after a portion of brevican, one of the naturally occurring substrates of Aggrecanase-2. This peptide contains the fluorescent group 2-aminobenzoyl (Abz) that is quenched by energy transfer to a 2,4-dinitrophenyl group (Dnp). The peptide (mass=1740) is >95% pure based on HPLC analysis and has the sequence: Abz TESESRGAIY-Dap(Dnp)-KK—$NH_2$. Stock solutions of the substrate were prepared with MilliQ water and aliquots were stored at 80° C. The concentration of this substrate stock was spectrophotometrically determined using the extinction coefficient at 354 nm of 18,172 $M^{-1}\ cm^{-1}$. The $V_{max}$ and $K_m$ for this enzyme/substrate reaction were determined to be insensitive to DMSO up to at least 10% (v/v). The assay buffer (pH 7.4) consisted of 50 mM Hepes, 100 mM NaCl, 5 mM $CaCl_2$, 0.1% CHAPS, 5% glycerol.

Each well of the 96-well or 384-well plates contained a reaction consisting of assay buffer, purified Agg-2 (diluted with assay buffer), and varied concentrations of inhibitor (prepared by serial dilution in DMSO in 96-well polypropylene plates). The plates were then incubated at room temperature for 10 minutes. The enzymatic reactions were initiated by adding substrate to a final concentration of 25 µM and mixed by pipetting up and down. The initial rates of the cleavage reactions were determined at room temperature with a fluorescence plate reader immediately after substrate addition. The Agg-2 assays were run on a Tecan Safire with the following wavelength settings: excitation—316 nm, 12 nm bandwidth; emission—432 nm, 12 nm bandwidth.

Results

A plot of time vs. RFU, representing the progress curve of the reaction, was generated. The slope for the portion of the progress curve that is most linear was determined. This slope (RFU/min) is the initial rate of the reaction. Plots of the inhibitor concentration vs. the initial cleavage rate were fit to the following equation: $y=Vmax*(1-(x^n/(K^n+x^n)))$, whereby x=inhibitor concentration, y=initial rate, $V_{max}$=initial rate in the absence of inhibitor, n=slope factor, and $K=IC_{50}$ for the inhibition curve. The assay results are shown in Tables 1, 2, and 3 below.

Example 36

In Vitro Fluorescence Assay of MMP-13 Activity

Materials and Methods

A continuous assay was used in which the substrate is a synthetic peptide containing a fluorescent group (7-methoxycoumarin; Mca), which is quenched by energy transfer to a 2,4-dinitrophenyl group. When the peptide was cleaved by MMP, a large increase in fluorescence was observed. The source of enzyme in the assay was the recombinant human catalytic domain of MMP-13 (165 amino acids, residues 104-268, 19 kDa) prepared at Wyeth-Research in Cambridge. The substrate used was the peptide Mca-PQGL-(3-[2,4-dinitrophenyl]-L-2,3-diaminopropionyl)-AR-OH. The assay buffer consisted of 50 mM Hepes (pH 7.4), 100 mM NaCl, 5 mM $CaCl_2$, and 0.005% Brij-35. Each well of the 96-well plates contained a 200 µL reaction mixture consisting of assay buffer, purified MMP (final concentration of 0.5 nM, prepared by diluting with the assay buffer), and varied concentrations of inhibitor (prepared by serially diluting a given inhibitor in DMSO in 96-well polypropylene plate). The plates were then incubated at 30° C. for 15 minutes. The enzymatic reactions were initiated by adding the substrate to a final concentration of 20 µM, and mixing 10 times with a pipette. The final DMSO concentration in the assay was 6.0%. The initial rate of the cleavage reaction was determined at 30° C. temperature with a fluorescence plate reader (excitation filter of 330 nm and emission filter of 395 nm) immediately after substrate addition.

Results

Plots of the inhibitor concentration vs. the percent inhibition were fit to the following equation: $y=(a-d)/[1+(x/c)^b]+d$, a general sigmoidal curve with Hill slope, a to d. x is the inhibitor concentration under test. y is the percent inhibition. a is the limiting response as x approaches zero. As x increases without bound, y tends toward its limit d. c is the inflection point ($IC_{50}$) for the curve. That is, y is halfway between the lower and upper asymptotes when x=c. b is the slope factor or Hill coefficient. (See, Knight, C. G. et al., *FEBS Lett.* 1992, 296, 263-266). The assay results are shown in Tables 1, 2, and 3 below.

Example 37

In Vitro Fluorescence Assay of MMP-14 Activity

Materials and Materials

A continuous assay was used in which the substrate is a synthetic peptide containing a fluorescent group (7-methoxycoumarin; Mca), which is quenched by energy transfer to a 2,4-dinitrophenyl group. When the peptide was cleaved by MMP, a large increase in fluorescence was observed. The source of enzyme in the assay was the recombinant human catalytic domain of MMP-14 (177 amino acids corresponding to Tyr89-Gly265 of mature human enzyme; 20 kDa; Chemicon International, Inc. (catalog number CC1041)). The substrate used was the peptide Mca-PQGL-(3-[2,4-dinitrophenyl]-L-2,3-diaminopropionyl)-AR-OH. The assay buffer consisted of 50 mM Hepes (pH 7.4), 100 mM NaCl, 5 mM $CaCl_2$, and 0.005% Brij-35. Each well of the 96-well plates contained a 200 µL reaction mixture consisting of assay buffer, MMP (final concentration of 25 ng/ml, prepared by diluting with the assay buffer), and varied concentrations of inhibitor (prepared by serially diluting a given inhibitor in DMSO in 96-well polypropylene plate). The plates were then incubated at 30° C. for 15 minutes. The enzymatic reactions were initiated by adding the substrate to a final concentration of 20 µM, and mixing 10 times with a pipette. The final DMSO concentration in the assay was 6.0%. The initial rate of the cleavage reaction was determined at 30° C. temperature with a fluorescence plate reader (excitation filter of 330 nm and emission filter of 395 nm) immediately after substrate addition.

Results

Plots of the inhibitor concentration vs. the percent inhibition were fit to the following equation: $y=(a-d)/[1+(x/c)^b]+d$, a general sigmoidal curve with Hill slope, a to d. x is the inhibitor concentration under test. y is the percent inhibition. a is the limiting response as x approaches zero. As x increases without bound, y tends toward its limit d. c is the inflection point ($IC_{50}$) for the curve. That is, y is halfway between the lower and upper asymptotes when x=c. b is the slope factor or Hill coefficient. (See, Knight, C. G. et al., *FEBS Lett.* 1992, 296, 263-266). The assay results are shown in Tables 1, 2, and 3 below.

Example 38

In Vitro Fluorescence Assay of MMP-2 Activity

Materials and Methods

A continuous assay was used in which the substrate is a synthetic peptide containing a fluorescent group (7-methoxycoumarin; Mca), which is quenched by energy transfer to a 2,4-dinitrophenyl group. When the peptide was cleaved by MMP, a large increase in fluorescence was observed. The source of enzyme in the assay was the recombinant human MMP-2 (66 kDa; Oncogene Research Products (catalog number PF023 from Calbiochem)). The substrate used was the peptide Mca-PQGL-(3-[2,4-dinitrophenyl]-L-2,3-diaminopropionyl)-AR-OH. The assay buffer consisted of 50 mM Hepes (pH 7.4), 100 mM NaCl, 5 mM $CaCl_2$, and 0.005% Brij-35. Each well of the 96-well plates contained a 200 µL reaction mixture consisting of assay buffer, MMP (final concentration of 25 ng/ml, prepared by diluting with the assay buffer), and varied concentrations of inhibitor (prepared by serially diluting a given inhibitor in DMSO in 96-well polypropylene plate). The plates were then incubated at 30° C. for 15 minutes. The enzymatic reactions were initiated by adding the substrate to a final concentration of 20 µM, and mixing 10 times with a pipette. The final DMSO concentration in the assay was 6.0%. The initial rate of the cleavage reaction was determined at 30° C. temperature with a fluorescence plate reader (excitation filter of 330 nm and emission filter of 395 nm) immediately after substrate addition.

Results

Plots of the inhibitor concentration vs. the percent inhibition were fit to the following equation: $y=(a-d)/[1+(x/c)^b]+d$, a general sigmoidal curve with Hill slope, a to d. x is the inhibitor concentration under test. y is the percent inhibition. a is the limiting response as x approaches zero. As x increases without bound, y tends toward its limit d. c is the inflection point ($IC_{50}$) for the curve. That is, y is halfway between the lower and upper asymptotes when x=c. b is the slope factor or Hill coefficient. (See, Knight, C. G. et al., *FEBS Lett.* 1992, 296, 263-266). The assay results are shown in Tables 1, 2, and 3 below.

Example 39

In Vitro Articular Cartilage Model for the Inhibition of Degradation of Proteoglycan by Small Molecule Compounds: Bovine Articular Cartilage Explant Cultures This in vitro procedure was used to evaluate the effect and relative potencies of small molecule compounds to inhibit the degradation of proteoglycan in articular cartilage treated with Interleukin 1 alpha (IL-1α). Treatment of articular cartilage with IL 1α induces expression of a cascade of enzymes that initiates cartilage matrix degradation. This assay was utilized to select small molecule compounds that inhibit the enzyme activity and protects cartilage matrix degradation.

Materials and Methods

Articular cartilage: bovine metacarpal joints were disinfected with 10% Wescodyne followed by 70% ethanol. 6 mm articular cartilage discs were prepared and rinsed once in PBS and medium, respectively. The discs were cultured in a stirring flask with serum-free medium for 5 days for equilibrium with one medium change. Small molecule compounds: stock solutions of test small molecule compounds (usually at 5 mg/ml) were prepared in DMSO. Working solutions were diluted with DMSO and generally ranged from 0.1 µg/ml to 10 ug/ml. The DMSO stocks were stored at 20° C. Articular cartilage explant culture medium: DMEM, 2 mM glutamax, 100 U/ml of antibiotic and antimycotic, 50 µg/ml ascorbate and 10 mM Hepes (pH-7.0). Proteoglycan content-Dimethyl methylene blue (DMMB) solution: IL-16 mg DMMB, 10 ml 100% ethanol, 29.5 ml of 1M NaOH, 3.5 ml of 98% formic acid and water to 1 L. Chondroitin sulphate sodium salt: 1.56-200 ug/ml serial dilutions.

For the explant culture, cartilage discs were cultured in serum-free medium for 48 h or more. Discs were weighed and transferred to a 96-well plate, 1 disc per-well. 0.2 ml of medium containing 5 ng/ml of IL-1 and different concentrations of compounds were added to each well, with 3 wells allocated for each treatment. The medium was collected at days 1, 2, & 3 and replaced accordingly.

For the DMMB assay, conditioned medium (CM) samples were diluted with medium. 10 ul of each standard or diluted sample was added in duplicate into a 96-well-plate and 200 µl of DMMB solution was added into each well. Absorbance at 520 nm was measured for each well. Proteoglycan contents in CM were calculated daily.

Results

The proteoglycan contents are expressed as ug per mg of cartilage. The inhibitory effect of the compounds is expressed as percentage. (See, Tortorella, M. D. et al., *Science* 1999, 284, 1664-1666). The assay results are shown in Tables 1, 2, and 3 below.

TABLE 1

| Example | Agg1 IC$_{50}$ (nM) | K$_i$ (nM) | Agg 2 IC$_{50}$ (nM) | MMP-13 | MMP-2 | MMP-14 | MMP-1 | bovine | bovine |
|---|---|---|---|---|---|---|---|---|---|
| 8SSSS | >200,000 | | | | | | | | |
| 7 | 150 | | 1,800 | ~13,000 | 3,000 | ~13,000 | >100,000 | 61 | 28 |
| 8C | 110 | | 1,200 | ~50,000 | 6,000 | ~25,000 | >100,000 | 68 | 34 |
| 8B | 460 | | 1,900 | ~50,000 | 5,600 | ~25,000 | >100,000 | 54 | 22 |
| 8A | 150 | | 900 | ~40,000 | 4,400 | ~25,000 | >100,000 | 75 | 29 |
| 11 | 110 | | ~800 | ~5,000 | ~1,000 | ~2,000 | ~2,000 | 78 | 52 |
| 12A | 700 | | ~5,000 | ~6,000 | ~2,000 | ~2,000 | ~2,000 | 41 | 18 |
| 12B | 35000 | | | | | | | | |
| 8D | 220 | | 2,800 | ~25,000 | 4,400 | 17,000 | >100,000 | 67 | 27 |
| 8E | 90 | | 746 | ~25,000 | 3,700 | ~25,000 | >200,000 | 79 | 34 |
| 8NNNNNN | ~40,000 | | | | | | | | |
| 13B | ~50,000 | | | | | | | | |
| 8F | 30 | 12 | 304 | ~22,000 | 5,630 | ~25,000 | >200,000 | 81 | 56 |
| 17VV | 7900 | | | | | | | | |
| 13A | 1500 | | ~67,000 | >100,000 | ~67,000 | >100,000 | >100,000 | 37 | 18 |
| 13C | 9600 | | | | | | | | |
| 13D | 750 | | ~26,000 | >200,000 | >200,000 | >100,000 | >100,000 | 51 | 25 |
| 13E | ~25,000 | | | | | | | | |
| 13F | ~200 | | | | | | | | |
| 8G | 80 | | 614 | ~50,000 | ~50,000 | ~25,000 | >100,000 | 76 | 39 |
| 8OOOOOO | 670 | | | | | | | | |
| 8H | 200 | | 266 | ~50,000 | 3,310 | ~25,000 | >100,000 | 85 | 67 |
| 8I | 500 | | | | | | | | |
| 12E | 1800 | | | | | | | | |
| 12C | 25000 | | | | | | | | |
| 12D | >100,000 | | | | | | | | |
| 8K | 300 | | | | | | | | |
| 8L | 55 | | 189 | ~50,000 | 10,500 | 21,500 | >100,000 | 87 | 79 |
| 8J | 360 | | | | | | | | |
| 8M | 120 | | 856 | ~50,000 | 8,000 | 13,000 | >100,000 | 85 | 17 |
| 8N | 290 | | | | | | | | |
| 8O | 75 | 82 | 1,300 | 31,400 | 5,000 | ~22,000 | no inh | 69 | 34 |
| 8P | 290 | | | | | | | | |
| 8Q | 11 | 31 | 400 | 37,300 | 6,100 | ~22,000 | no inh | 66 | 24 |
| 8R | 16 | 5 | 50 | 42,400 | 10,400 | ~22,000 | no inh | 86 | 78 |
| 8S | 150 | 245 | 1,300 | >200,000 | 3,130 | ~25,000 | no inh | 51 | 40 |
| 8T | 300 | | | | | | | 51 | 20 |
| 8U | 200 | | | | | | | 63 | 26 |
| 8V | 160 | | 1,100 | ~67,000 | 3,430 | ~30,000 | >100,000 | 73 | 45 |
| 8W | 75 | | 971 | ~22,000 | ~2,500 | ~25,000 | no inh | | |
| 8X | 100 | | 1,100 | ~67,000 | 7,000 | ~25,000 | no inh | | |
| 8Y | 50 | | 520 | ~67,000 | 5,534 | ~25,000 | no inh | | |
| 8Z | 80 | | 680 | ~67,000 | 3,820 | ~25,000 | no inh | | |
| 8BB | 74 | | 650 | 19,000 | 2,300 | ~25,000 | no inh | | |
| 8AA | 370 | | | | | | | | |
| 33D | <10 | | 13.4 | 52 | 3.3 | 73.6 | ~1,560 | | |
| 33C | <10 | | 25 | 29 | 4.5 | 110 | 1,500 | | |
| Control (33A) | <10 | | 2.6 | 32 | 4.7 | 112 | 1,750 | | |

TABLE 1-continued

| Example | Agg1 IC$_{50}$ (nM) | K$_i$ (nM) | Agg 2 IC$_{50}$ (nM) | MMP-13 | MMP-2 | MMP-14 | MMP-1 | bovine | bovine |
|---|---|---|---|---|---|---|---|---|---|
| 8CC | 22 | 19 | 121 | ~22,000 | 5,655 | ~25,000 | no inh | 94 | 71 |
| 13G | ~2500 | | | | | | | | |
| 8DD | 94 | | 930 | ~22,000 | 4,580 | 16,200 | no inh | 89 | 50 |
| 14 | 60% @ 16,700 | | | | | | | | |
| 15A | >22,000 | | | | | | | | |
| 15B | 67% @ 7,500 | | | | | | | | |
| 15C | 50% @ 7,500 | | | | | | | | |
| 15D | 86% @ 7,500 | | | | | | | | |
| 15E | 3500 | | | | | | | | |
| 33B | <30 | | | | | | | | |
| 8PPPPPP | >33,000 | | | | | | | | |
| 23 | >6000 | | | | | | | | |
| 24A | 1100 | | | | | | | | |
| 24B | ~2200 | | | | | | | | |
| 24C | ~300 | | | | | | | | |
| 20 | ~22,000 | | | | | | | | |
| 21A | 2500-7500 | | | | | | | | |
| 21B | ~6700 | | | | | | | | |
| 21C | no inh | | | | | | | | |
| 21D | no inh | | | | | | | | |
| 22C | >50,000 | | | | | | | | |
| 8FFF | 200 | | 1000 | | | | | | |
| 8GGG, step D | 100 | | | | | | | 57 | 12 |
| 8AAAA | 100 | | | | | | | | |
| 8DDDD | 110 | | | | | | | | |
| 8HHHH | 200 | | | | | | | | |
| 8XX | 300 | | | | | | | | |
| 8FF | 26 | 28 | | | | | | 86 | 50 |
| 17WW | no inh | | | | | | | | |
| 17XX | no inh | | | | | | | | |
| 17YY | 2000 | | | | | | | | |
| 17ZZ | 200 | | | | | | | | |
| 17AAA | no inh | | | | | | | | |
| 8YY | 530 | | 4500 | | | | | | |
| 8ZZ | 210 | | | | | | | | |
| 8AAA | 48 | 44 | | | | | | 83 | 55 |
| 8EE | 200 | | | | | | | | |
| 15F | 600 | | | | | | | | |
| 15G | 2200 | | | | | | | | |
| 15H | 200 | | | | | | | | |
| 6A | 150 | | 740 | >50,000 | 29800 | >200,000 | >50,000 | | |
| 8HH | 160 | | | | | | | | |
| 8II | 44 | 39 | | | | | | 75 | 40 |
| 8QQQQQQ | 690 | | | | | | | | |
| 17BBB | 900 | | | | | | | | |
| 8III | 120 | | | | | | | | |
| 8NNN | 100 | 219 | 1750 | 14,000 | >10,000 | >50,000 | >50,000 | 60 | 0 |
| 8JJJ | 54 | 54 | 300 | 30,000 | >20,000 | >200,000 | >200,000 | 74 | 26 |
| 8JJ | 45 | 33 | 1100 | 17,000 | 27,000 | >200,000 | >200,000 | 70 | 17 |
| 10M | 43 | 54 | 1100 | ~20,000 | >20,000 | >200,000 | >50,000 | 67 | 35 |
| 10N | 19 | 28 | 970 | >50,000 | 7600 | >200,000 | >200,000 | 65 | 24 |
| 8OO | <30 | 6 | 44 | >50,000 | >20,000 | >200,000 | >200,000 | 87 | 40 |
| 22A | 1000 | | | | | | | | |
| 22B | 200 | | | | | | | | |
| 8KK | 180 | | | | | | | | |
| 8LL | 55 | | 990 | 24,000 | 50,000 | 200,000 | 200,000 | 40 | 0 |
| 10R | 77 | 187 | 1900 | >20,000 | >20,000 | >200,000 | >50,000 | 41 | 0 |
| 8BBB | 32 | 130 | 700 | >50,000 | | no inh | >200,000 | 35 | 0 |
| 8CCC | 100 | | | | | | | 74 | 26 |
| 8ZZZ | 100 | | 1600 | no inh | 13,000 | >200,000 | >50,000 | 72 | 34 |
| 8KKK | 120 | | 2000 | | | | | | |
| 10C | 240 | | >5000 | | | | | | |
| 10E | 370 | | | | | | | | |
| 10F | 130 | | >30000 | | | | | | |
| 10D | 480 | | 3200 | | | | | | |
| 10G | 1000 | | 4400 | | | | | | |
| 8BBBB | 100 | | | | | | | 40 | 0 |
| 8OOO | 280 | | 1000 | | | | | | |
| 8LLL | 230 | | | | | | | | |
| 8PPP | 130 | | | | | | | | |
| 8QQQ | 330 | | | | | | | | |

TABLE 1-continued

| Example | Agg1 IC$_{50}$ (nM) | K$_i$ (nM) | Agg 2 IC$_{50}$ (nM) | MMP-13 | MMP-2 | MMP-14 | MMP-1 | bovine | bovine |
|---|---|---|---|---|---|---|---|---|---|
| 8EEE | 7900 | | | | | | | | |
| 8MM | 58 | 126 | 980 | | | | | | |
| 9 | 200 | | | | | | | | |
| 10A | 840 | | 2100 | | | | | | |
| 10J | 260 | | | | | | | | |
| 10K | 380 | | >100000 | | | | | | |
| 10L | 130 | | 2000 | | | | | | |
| 10B | 150 | | | | | | | | |
| 8MMM | 40 | | 500 | | | | | | |
| 8RRR | 82 | | 680 | | | | | | |
| 10H | 300 | | | | | | | | |
| 8SSS | 64 | | 470 | >50,000 | 10300 | | | | |
| 10O | 470 | | | | | | | | |
| 8UUU | 61 | 60 | 660 | ~50,000 | 8900 | >200,000 | no inh | | |
| 10P | 700 | | | | | | | | |
| 10Q | 98 | | 3000 | ~50,000 | | >50,000 | no inh | | |
| 8PP | <30 | 10 | 85 | ~50,000 | 6000 | >66,600 | >200,000 | | |
| 8NN | <30 | 14 | 133 | ~50,000 | 9000 | no inh | >200,000 | | |
| 8VVV | 30 | 38 | 420 | ~50,000 | 5600 | >66,600 | no inh | | |
| 8TTT | >10000 | | | | | | | | |
| 6C | 150 | | | | | | | | |
| 8DDD | 300 | | | | | | | | |
| 6B | 300 | | | | | | | | |
| 8SS | 100 | | 800 | ~50,000 | 12400 | >66,600 | no inh | | |
| 8TT | 300 | | | | | | | | |
| 8UU | 200 | | | | | | | | |
| 8WW | 70 | | 350 | ~50,000 | 13300 | >66,600 | no inh | | |
| 8VV | 100 | | 1900 | ~50,000 | 9100 | >66,600 | no inh | | |
| 8XXX | 30 | | 930 | ~50,000 | 7900 | >200,000 | no inh | | |
| 8WWW | 36 | | 840 | ~200,000 | 7400 | >200,000 | no inh | | |
| 8YYY | 100 | | 1600 | >50,000 | 9400 | >200,000 | no inh | | |
| 8GGGG | 30 | | 160 | >50,000 | 18600 | no inh | no inh | | |
| 8FFFF | 3600 | | | | | | | | |
| 10I | 320 | | | | | | | | |
| 8RRRRRR | 3600 | | | | | | | | |
| 8KKKK | <30 | 4 | | | | | | | |
| 8LLLL | no inh | | | | | | | | |
| 8MMMM | 47 | 57 | | | | | | | |
| 8IIII | <30 | 9 | | | | | | | |
| 8JJJJ | >50000 | | | | | | | | |
| 8NNNN | 3400 | | | | | | | | |
| 8OOOO | 52 | 60 | | | | | | | |
| 8PPPP | >50000 | | | | | | | | |
| 8QQQQ | 9600 | | | | | | | | |
| 8RRRR | 122 | | | | | | | | |
| 8SSSSSS | 146 | | | | | | | | |
| 8TTTTTT | 17300 | | | | | | | | |
| 1 | 900 | | | | | | | | |
| 2 | 111 | | | | | | | | |
| 3 | 12700 | | | | | | | | |
| 4 | 1100 | | | | | | | | |
| 5 | 1800 | | | | | | | | |
| 8EEEE, step D | 400 | | | | | | | | |
| 8UUUUUU | 4000 | | | | | | | | |
| 26 | 5000 | | | | | | | | |
| 27 | 400 | | | | | | | | |
| 28 | 400 | | | | | | | | |
| 29 | 3000 | | | | | | | | |
| 30 | 500 | | | | | | | | |
| 31 | 1000 | | | | | | | | |
| 6D | 45 | | | | | | | | |
| 6E | 56 | | | | | | | | |
| 8VVVVVV | 46 | | | | | | | | |

TABLE 2

| Example | Agg1 IC$_{50}$ (nM) | K$_i$ (nM) | Agg 2 IC$_{50}$ (nM) | MMP-13 | MMP-2 | MMP-14 | MMP-1 |
|---|---|---|---|---|---|---|---|
| 8TTTT | >17,000 | | >22,000 | | | | |
| 8UUUU | >17,000 | | ~67,000 | | | | |

TABLE 2-continued

| Example | Agg1 IC$_{50}$ (nM) | K$_i$ (nM) | Agg 2 IC$_{50}$ (nM) | MMP-13 | MMP-2 | MMP-14 | MMP-1 |
|---|---|---|---|---|---|---|---|
| 8VVVV | >17000 | | >67,000 | | | | |
| 8WWWW | 8300 | | >67,000 | | | | |
| 8XXXX | >50,000 | | >200,000 | | | | |
| 8YYYY | 1500 | | >200,000 | | | | |
| 8ZZZZ | >17000 | | >22,000 | | | | |
| 8AAAAA | 372 | | 410 | | | | |
| 8BBBBB | >17000 | | 20900 | | | | |
| 8CCCCC | 107 | | 11000 | | | | |
| 8DDDDD | 315 | | 1100 | | | | |
| 8EEEEE | >50000 | | >200,000 | | | | |
| 8FFFFF | 92 | | 710 | >100,000 | | | |
| 8GGGGG | >50,000 | | | | | | |
| 8HHHHH | 357 | | | | | | |
| 8IIIII | 813 | | 1900 | | | | |
| 8JJJJJ | 191 | | 1100 | | | | |
| 8KKKKK | >50,000 | | >22,000 | | | | |
| 8LLLLL | >17,000 | | >200,000 | | | | |
| 8MMMMM | 20000 | | ~22,000 | | | | |
| 8NNNNN | 1200 | | 1,893 +/− 76 | | | | |
| 8OOOOO | >50,000 | | >200,000 | | | | |
| 8PPPPP | 157 | | 2967 | | | | |
| 8QQQQQ | 108 | | 1165 | | | | |
| 8RRRRR | 129 | | 2905 | | | | |
| 8SSSSS | 208 | | 2470 | | | | |
| 8TTTTT | 389 | | 2011 | | | | |
| 8UUUUU | 317 | | 2119 | | | | |
| 8VVVVV | 221 | | 1558 | | | | |
| 8WWWWW | >17,000 | | >67,000 | | | | |
| 8XXXXX | 246 | | 1450 | | | | |
| 8YYYYY | 87 | | 2800 | ~20,000 | | | |
| 8ZZZZZ | <30 | | 63 | >100,000 | | | |
| 16 | <30 nM | | 467 | | | | |
| 17A | 116 | | 1123 | | | | |
| 17B | 204 | | 1020 | | | | |
| 18D | 4400 | | >22,000 | | | | |
| 17C | <30 nM | | 80 | | | | |
| 17D | >17,000 nM | | >200,000 | | | | |
| 17E | 251 | | 1040 | | | | |
| 12F | ~3,000 nM | | 3,000-8,000 | | | | |
| 17F | 1700 | | ~8,300 | | | | |
| 17G | 1600 | | 3,000-8,000 | | | | |
| 17H | 1000 | | ~22,000 | | | | |
| 8AAAAAA | 534 | | 1759 | — | | | |
| 17I | <30 | | 217 +/− 8 | ~100,000 | | | |
| 17J | ~5,600 | | ~30,000 | — | | | |
| 17K | 1200 | | ~3,700 | — | | | |
| 17L | 133 | | 226 | — | | | |
| 18E | 2200 | | >11,000 | — | | | |
| 17M | ~310 | | >11,000 | — | | | |
| 17N | 40 | | 42 | 11,200 +/− 1,200 | | | |
| 8MMMMMM | 550 | | 5100 | — | | | |
| 8BBBBBB | 470 | | 2671 | — | | | |
| 18F | >67,000 | | >67,000 | — | | | |
| 17O | 8500 | | ~22,000 | — | | | |
| 17P | 126 | | 58 | — | | | |
| 17Q | ~13,000 | | >30,000 | — | | | |
| 17R | 73 | | 142 | 6,000 +/− 400 | | | |
| 18 | 49 | | 50 | ~1,600 nM | | | |
| 19A | 930 | | 1020 | | | | |
| 19B | 3200 | | 590 | | | | |
| 8CCCCCC | 2400 | | >22000 | | | | |
| 17S | 4600 | | 10100 | | | | |
| 17T | 3200 | | 7200 | | | | |
| 17U | 1800 | | ~6700 | | | | |
| 19C | 140 +/− 20 | | 75 | | | | |
| 17V | 90 | | 1800 | | | | |
| 17W | >25,000 | | ~67000 | | | | |
| 17X | 2000 | | ~22,000 | | | | |
| 8DDDDDD | 2400 | | >22000 | | | | |
| 17Y | <30 | | 156 | | | | |
| 19D | 210 | | 223 | | | | |
| 19E | 49 | | 1120 | | | | |
| 17Z | 170 | | 3140 | | | | |
| 17AA | 3500 | | 5700 | | | | |
| 17BB | 3600 | | 2900 | | | | |

TABLE 2-continued

| Example | Agg1 IC$_{50}$ (nM) | K$_i$ (nM) | Agg 2 IC$_{50}$ (nM) | MMP-13 | MMP-2 | MMP-14 | MMP-1 |
|---|---|---|---|---|---|---|---|
| 17CC | 2900 | | 2970 | | | | |
| 17DD | <30 nM | | 1190 | | | | |
| 17EE | <30 nM | | 194 | | | | |
| 17FF | 690 | | 13900 | | | | |
| 17GG | 34 | | 113 | | | | |
| 17HH | 2200 | | 6320 | | | | |
| 17II | ~1000-3000 | | ~10,000 | | | | |
| 17JJ | 2400 | | 19454 | | | | |
| 15I | 430 | | 1593 | | | | |
| 15J | 510 | | ~3,125 | | | | |
| 12G | >25000 | | 11700 | | | | |
| 12H | 1200 | | 1635 | | | | |
| 12I | >25000 | | >20,000 | | | | |
| 17KK | >25000 | | >67,000 | | | | |
| 19F | 68 | | 163 | | | | |
| 17LL | 87 | | 1193 | | | | |
| 17MM | 46 | | 2707 | | | | |
| 19G | 270 | | 146 | | | | |
| 19H | 69 | | 158 | | | | |
| 18G | ~8300 | | | | | | |
| 17NN | 200 | | 729 | | | | |
| 8EEEEEE | 5000 | | | | | | |
| 17OO | <30 | | 1677 | | | | |
| 8FFFFFF | 3900 | | 18131 | | | | |
| 8GGGGGG | 4200 | | | | | | |
| 8HHHHHH | 38 | | 46 | | | | |
| 8IIIIII | 2900 | | 11908 | | | | |
| 8JJJJJJ | 300 | | 943 | | | | |
| 8KKKKKK | 350 | | 1674 | | | | |
| 17QQ | >25,000 | | ~22000 | | | | |
| 12J | ~8,000 | | ~22000 | | | | |
| 12K | ~25,000 | | >22000 | | | | |
| 12L | ~22,000 | | >22000 | | | | |
| 17RR | <30 | | 26 | | | | |
| 17SS | 450 | | 3959 | | | | |
| 17TT | 120 | | 173 | | | | |
| 8LLLLLL | >25000 | | >100000 | | | | |
| 15Y | 220 | | 841 | | | | |
| 15Z | 1400 | | 6036 | | | | |
| 15AA | 44 | | 327 | | | | |
| 15BB | 53 | | 527 | | | | |
| 17UU | <30 | | 39 | | | | |

TABLE 3

| Example | Agg1 IC$_{50}$ (nM) | K$_i$ Agg1 (nM) | Agg 2 IC$_{50}$ (nM) | K$_i$ Agg2 (nM) | MMP-13 | MMP-2 | MMP-14 | MMP-8 | MMP-12 |
|---|---|---|---|---|---|---|---|---|---|
| 8WWWWWW | <03 | 7.1 | 50 | 72 | | 2600 | 1000 | | 5800 |
| 8XXXXXX | <30 | <3 | 20 | 60 | | 7500 | 4100 | | 1600 |
| 8YYYYYY | <30 | 13.5 | 30 | 160 | | 4700 | 737 | | 365 |
| 8ZZZZZZ | <30 | | 120 | | | | | | |
| 8AAAAAAA | 80 | | 550 | | | | | | |
| 8BBBBBBB | 110 | | 1000 | | | | | | |
| 8CCCCCCC | 50 | | 680 | | | | | | |
| 8DDDDDDD | <30 | | 220 | | | | | | |
| 8EEEEEEE | 37 | | 510 | | | | | | |
| 8FFFFFFF | 200 | | 4200 | | | | | | |
| 8GGGGGGG | 60 | | 160 | | | | | | |
| 8HHHHHHH | 50 | | 180 | | | | | | |
| 8IIIIIII | <30 | | 42 | | | | | | |
| 8JJJJJJJ | <30 | | 53 | | | | | | |
| 8KKKKKKK | <30 | | <30 | | | | | | |
| 8LLLLLLL | 228 | | 3380 | | | | | | |
| 8MMMMMMM | 198 | | 614 | | | | | | |
| 8NNNNNNN | <30 | <3 | <30 | 37 | | 2150 | 1210 | | 680 |
| 8OOOOOOO | <30 | | 100-400 | | | | | | |
| 8PPPPPPP | 3116 | | 48% 16700 | | | | | | |
| 8QQQQQQQ | NT | | NT | | | | | | |
| 8RRRRRRR | 70-210 | | 48% 1200 | | | | | | |

TABLE 3-continued

| Example | Agg1 IC$_{50}$ (nM) | K$_i$ Agg1 (nM) | Agg 2 IC$_{50}$ (nM) | K$_i$ Agg2 (nM) | MMP-13 | MMP-2 | MMP-14 | MMP-8 | MMP-12 |
|---|---|---|---|---|---|---|---|---|---|
| 8SSSSSSS | 57 | 22 | 230 | 356 | | | | | |
| 8TTTTTTT | 707 | | 20% 11000 | | | | | | |
| 8UUUUUUU | <30 | <3 | 60 | 60 | | 5180 | | 2030 | 410 |
| 8VVVVVVV | <30 | 7 | 51% 140 | 305 | | 570 | | 410 | 770 |
| 8WWWWWWW | <30 | <3 | 50 | 42 | | 1080 | | 370 | 630 |
| 8XXXXXXX | <30 | 4.5 | 20-70 | 56 | | | | | |
| 8YYYYYYY | <30 | 27 | 200-600 | 197 | | | | | |
| 8ZZZZZZZ | <30 | 12.7 | 200-600 | 290 | | | | | |
| 8AAAAAAAA | <30 | 86 | 600-1800 | 1147 | | | | | |
| 8BBBBBBBB | 300 | | 200-600 | | | | | | |
| 8CCCCCCCC | 140 | | 5200 | | | | | | |
| 8DDDDDDDD | 50 | | 1000 | | | | | | |
| 8EEEEEEEE | <30 | 3.8 | 60-200 | 79 | | | | | |
| 8FFFFFFFF | <30 | | 200 | | | | | | |
| 8GGGGGGGG | 40 | | 3400 | | | | | | |
| 8HHHHHHHH | 60 | | 3000 | | | | | | |
| 8IIIIIIII | 65% 200 | | 90-270 | | | | | | |
| 8JJJJJJJJ | <30 | | 800-2500 | | | | | | |
| 8KKKKKKKK | 70 | | 270-800 | | | | | | |
| 8LLLLLLLL | <30 | <3 | 60-200 | 156 | | | | | |
| 8MMMMMMMM | <30 | <3 | 60-200 | 38 | | | | | |
| 8NNNNNNNN | <30 | <3 | 70-200 | 151 | | | | | |
| 8OOOOOOOO | <30 | | 200-600 | | | | | | |
| 8PPPPPPPP | <30 | | 200-600 | | | | | | |
| 8QQQQQQQQ | <30 | | 3300 | | | | | | |
| 8RRRRRRRR | 57% 70 | | 7200 | | | | | | |
| 8SSSSSSSS | <30 | 5.4 | 70-200 | 51 | | | | | |
| 8TTTTTTTT | 20-70 | 37.6 | 100-300 | 359 | | | | | |
| 8UUUUUUUU | 100 | | 700 | | | | | | |
| 8VVVVVVVV | 60% 16700 | | 50% 50000 | | | | | | |
| 8WWWWWWWW | 20-70 | 40.6 | 100-300 | 526 | | | | | |
| 8XXXXXXXX | 100 | | 1700 | | | | | | |
| 8YYYYYYYY | <30 | 6.2 | 100-300 | 143 | | | | | |
| 8ZZZZZZZZ | 20-70 | | 9900 | | | | | | |
| 8AAAAAAAAA | <30 | 6.7 | 98 | 45 | | | | | |
| 8BBBBBBBBB | <30 | 11.5 | 100-300 | 681 | | | | | |
| 8CCCCCCCCC | <30 | | 900 | | | | | | |
| 8DDDDDDDDD | 2400 | | 50% 7400 | | | | | | |
| 8EEEEEEEEE | 1200 | | 50% 2500 | | | | | | |
| 8FFFFFFFFF | 270 | | 62% 25000 | | | | | | |
| 8GGGGGGGGG | 30% 8300 | | 28% 25000 | | | | | | |
| 8HHHHHHHHH | <30 | | 500 | | | | | | |
| 8IIIIIIIII | 300-900 | | 5% 2500 | | | | | | |
| 8JJJJJJJJJ | 25% 25000 | | 10% 25000 | | | | | | |
| 8KKKKKKKKK | 16% 25000 | | 10% 25000 | | | | | | |
| 8LLLLLLLLL | <30 | | >300 | | | | | | |
| 8MMMMMMMMM | <30 | <3 | 30-100 | 87 | | | | | |
| 8NNNNNNNNN | <30 | 8.3 | 30-100 | 69 | | | | | |
| 8OOOOOOOOO | <30 | 2.7 | ~30 | 66 | | 718 | | 349 | 372 |
| 8PPPPPPPPP | <30 | 11.5 | 30-300 | 126 | | 7240 | | 2550 | 2890 |
| 8QQQQQQQQQ | >900 | | >8300 | | | | | | |
| 8RRRRRRRRR | >8300 | | 100000 | | | | | | |
| 8SSSSSSSSS | <30 | 8.8 | 200 | 157 | | | | | |
| 8TTTTTTTTT | <30 | 6.7 | 59 | 54 | | | | | |
| 8UUUUUUUUU | <30 | 6.9 | 83 | 75 | | | | | |
| 8VVVVVVVVV | <30 | 4.5 | 77 | 81 | | | | | |
| 8WWWWWWWWW | >25000 | | >100000 | | | | | | |
| 8XXXXXXXXX | <30 | 18.2 | 25 | 71.6 | | 2610 | | 1790 | 597 |
| 8YYYYYYYYY | <30 | 39.6 | 250 | 349 | | 25500 | | 13200 | 3710 |
| 8ZZZZZZZZZ | <30 | 4.7 | 30-90 | 123 | | 8280 | | 2440 | 2860 |
| 8AAAAAAAAAA | <30 | 28.9 | 100-300 | 204 | | 6970 | | 2230 | 2240 |
| 8BBBBBBBBBB | 22000 | | >200000 | | | | | | |
| 8CCCCCCCCCC | 1040 | | 7400 | | | | | | |
| 8DDDDDDDDDD | <30 | 27.2 | 90 | 218 | | 4000 | | 763 | 628 |
| 8EEEEEEEEEE | <30 | 23.2 | 80 | 180 | | 6400 | | 2500 | 1070 |
| 8FFFFFFFFFF | >400 | | >2700 | | | | | | |
| 8GGGGGGGGGG | <30 | 42 | >300 | 723 | | 1300 | | >5000 | >10,000 |

TABLE 3-continued

| Example | Agg1 IC$_{50}$ (nM) | K$_i$ Agg1 (nM) | Agg 2 IC$_{50}$ (nM) | K$_i$ Agg2 (nM) | MMP-13 | MMP-2 | MMP-14 | MMP-8 | MMP-12 |
|---|---|---|---|---|---|---|---|---|---|
| 8HHHHHHHHHH 8IIIIIIIII | <30 | 11.7 | >100 | 405 | | 8000 | | 3400 | >10,000 |
| 15O | 52 | | 3132 | | | | | | |
| 15P | <30 | | 255 | | | | | | |
| 15K | <30 | | 379 | | | | | | |
| 15L | 47 | | 413 | | | | | | |
| 15M | <30 | | 789 | | | | | | |
| 15N | 91 | | 103 | | | | | | |
| 15U | 53% 100 | | 600 | | | | | | |
| 15V | 47% 40 | | 700 | | | | | | |
| 15Q | 158 | | 1939 | | | | | | |
| 15R | 560 | | 48% 11000 | | | | | | |
| 15S | 30% 1850 | | 41% 33000 | | | | | | |
| 15U | 53% 1000 | | 30% 11000 | | | | | | |
| 15W | 56% 1900 | | 59% 11000 | | | | | | |
| 15X | 46% 1900 | | 52% 11000 | | | | | | |

Example 40

Aggrecanase Inhibitors in Human Osteoarthritic Cartilage Explant Studies and Effect on Aggrecan Metabolism in Human Osteoarthritic Cartilage The loss of cartilage matrix in osteoarthritis (OA) is associated with increased loss of type II collagen by collagenases and aggrecan loss by aggrecanases. Depletion of aggrecan is one of the earliest changes observed in osteoarthritis (Lohmander, L S et al., *Arthritis & Rheum* 1993, 36, 1214-1222). Aggrecan is a chondroitin sulfate and keratan sulfate-bearing proteoglycan. Aggrecanase 1 and Aggrecanase 2 cleave aggrecan within the interglobular domain at the aggrecanase site between residues Glu$^{373}$ and Ala$^{374}$ (Sandy, J D et al., *J Clin Invest.* 1992, 89, 1512-1516). Aggrecan cleavage by aggrecanase results in the release of a large sulfated glycosaminoglycan (sGAG)-containing aggrecan fragments which diffuse out of the cartilage matrix. Neoepitope antibodies have been generated to recognize these aggrecanase generated aggrecan fragments (Hughes, C E et al., *Biochem J.* 1995, 305, 799-804). Aggrecan fragments in inflammatory and OA synovial fluid have been reported as being generated by cleavage at the aggrecanase site (Malfait, A-M et al., *J Biol Chem.* 2002, 277, 22201-22208). Inhibiting aggrecanase activity is an attractive therapeutic target for OA. In this example, we investigated the effects of a selective aggrecanase inhibitor on the fate of existing and newly synthesized aggrecan in human OA cartilage.

Materials and Methods

Human OA Cartilage Explant Culture: Discarded tissues from consented knee replacement patients were obtained from New England Baptist Hospital (Brookline, Mass.) in sterile phosphate buffered saline (PBS) after about 2-4 hrs post surgery. Cartilage slices were harvested from the knee specimens and washed several times in PBS. These cartilage slices were cut into appropriate pieces (6-8 mm) and rinsed in PBS and then in media and further cultured for additional days as cartilage explants. The medium consisted of Dulbecco's Modified Eagle's medium (DMEM, JRH Biosciences, Lenexa, Kans.), 50 µg/ml ascorbic acid (Wako, Osaka, Japan), 10 mM HEPES, pH 7.0 (Mediatech, Herndon, Va.), 2 mM L-glutamine (Mediatech), 100 U/ml antibiotic-antimycotic solution (Mediatech).

Test compounds: The test compounds are described in Examples 8OO, 8NNNNNNN, and 8WWWWWWW. Stock solutions of the compounds were prepared at 1 mg/ml in DMSO, aliquoted and stored at −20° C. Working solutions of the compounds were made in DMSO and added to the culture for efficacy studies.

Efficacy study: Cartilage explants were cultured for 2-3 days in DMEM medium in a 37° C. and 5% CO$_2$ environment to equilibrate the tissue. Explants were weighed (~250 mg) and placed in wells of a 24-well culture dish in 1 ml of medium and 3 replicates per treatment group. For the efficacy study, cartilage explants were cultured for 6 days in the presence or absence of various concentrations of the test compound. The media was replaced on day 3 and the experiment was terminated on day 6. Total aggrecan content of conditioned media was measured by a colorimetric assay with DMMB (Farndale, R W et al., *Biochim Biophys Acta.* 1986, 883, 173-177).

Cartilage aggrecan metabolism study: Cartilage metabolism study was performed with test compound 8OO. Cartilage explants immediately after harvest were cultured in the presence or absence of test compound 8OO. On day 3, media was collected and replaced with media, test compound and labeled sulfate ($^{35}$SO$_4$, 5 mCi, Perkin Elmer, Boston, Mass.). On day 6, media was collected, explants washed and replaced with media and test compound 8OO. On Day 9, media was collected, explants washed and the remaining tissue was digested with Proteinase K (Sigma). Samples were separated on NAP10 columns (Pharmacia, Uppsala, Sweden) to separate free label and newly synthesized labeled aggrecan. Labeled aggrecan molecules were counted using Opti-Fluor (Perkin Elmer) and a liquid scintillation-measuring instrument (Beckman Coulter, Fullerton, Calif.). The percentage of newly synthesized aggrecan in cartilage and media was estimated.

Western analysis: Aggrecan fragments in conditioned medium were analyzed by western analysis using neoepitope antibody, BC-3 designed to recognize the Aggrecanase-generated N-terminal interglobular neoepitope $^{374}$ARGS. Equal cartilage weight equivalent conditioned media from each replicate well per treatment group was pooled and digested with Chondroitinase ABC (Sigma, St Louis, Mo.), Keratinase I (Seikagaku America, Falmouth, Mass.) and Keratinase II (Seikagaku America, Falmouth, Mass.) for 2 h at 37° C. Samples were concentrated by YM-10 centrifugal filter device (Millipore Corp., Bedford, Mass.), lyophilized and reconstituted with equal volume of water. Samples were separated under reducing conditions on 4-12% gradient Tris-glycine gels (Invitrogen, Carlsbad, Calif.). Proteins from the gels were transferred to nitrocellulose membranes. Immunoblots were probed using Mab BC-3 (Abcam, Cambridge, Mass.). Incubation with primary and alkaline-phosphatase-conjugated secondary goat anti-mouse IgG (Promega Corp., Madison, Wis.) was performed overnight at 4° C. and at room temperature for 1 h, respectively. The immunoblots were incubated with NBT/BCIP substrate (Promega Corp., Madison, Wis.) at room temperature to achieve optimum color development. The aggrecan fragments containing the ARGS neoepitope were quantitated by densitometry analysis and the percentage inhibition of aggrecan degradation by test compounds was determined.

Results

Efficacy of test compounds 8OO, 8NNNNNNN, and 8WWWWWWW:

Information on human donors including age and sex are shown in Table 4b, 5b, and 6b. Cartilage from all the donors when placed in culture exhibited Aggrecanase-mediated aggrecan cleavage and when treated with test compounds showed dose dependent inhibition of Aggrecanase-mediated aggrecan cleavage. Results of the inhibition of aggrecanase activity in terms of inhibition of aggrecanase generated aggrecan fragments by test compounds are shown in Table 4a, 5a, and 6a. Based on these results, $EC_{50}$ of test compound 8OO was determined to be about 150 ng/ml (FIG. 1), $EC_{50}$ for test compound 8WWWWWWW was around 40-160 ng/ml; and EC50 for test compound 8NNNNNNN was less than 40 ng/ml. However, test compound 8WWWWWWW and test compound 8NNNNNNN were tested in only 8 and 4 donors, respectively. Test compound 8OO was tested in a total of 15 donors.

Effect of test compound 8OO on Aggrecan Metabolism: Articular cartilage from 3 human OA donors was analyzed for the effect of test compound 8OO on newly synthesized aggrecan. Cartilage from all 3 donors showed the ability to synthesize new aggrecan molecules that was either in the cartilage matrix or released into conditioned medium. Cartilage from all 3 donors when treated with compound 8OO showed dose dependent increase in newly synthesized aggrecan content of the cartilage matrix and an equivalent decrease in aggrecan released into the medium (FIG. 2).

Aggrecanase activity is a characteristic of human osteoarthritis throughout the disease process. Analysis of aggrecan released from human osteoarthritic articular cartilage revealed significant ongoing degradation of aggrecan by Aggrecanases in human donors tested. Inhibition of Aggrecanase activity by Aggrecanase selective inhibitors reduced release of aggrecan degradation products from the articular cartilage matrix.

Since newly synthesized aggrecan appeared to be susceptible to degradation by Aggrecanases, selective Aggrecanase inhibition resulted in a net increase in aggrecan incorporation into the cartilage matrix. These results indicate that inhibition of Aggrecanases will reduce aggrecan degradation in human osteoarthritic articular cartilage throughout the disease process, and also result in a net increase in extracellular matrix aggrecan.

TABLE 4

A) Efficacy of test compound 8OO in human explant studies
Compound 8OO (BC3 analysis)

| Conc. of compound (ug/ml) | Average of 15 donors | |
|---|---|---|
| | % inhibition | SDM |
| 0.02 | 8.52 | |
| 0.04 | 26.16 | 5.33 |
| 0.08 | 42.93 | 7.86 |
| 0.15 | 49.03 | 7.87 |
| 0.3 | 56.40 | 5.95 |
| 0.6 | 73.92 | 5.24 |
| 1.25 | 83.36 | 5.59 |
| 2.5 | 100.94 | 4.12 |
| 5 | 98.88 | 1.32 |
| 10 | 101.60 | 0.99 |

B) Human donor information for test compound 8OO studies
Compound 8OO (Donor info)

| Sex | Age |
|---|---|
| F | 65 |
| M | 83 |
| M | 70 |
| F | 56 |
| F | 76 |
| M | 53 |
| F | 77 |
| F | 74 |
| F | 75 |
| M | 79 |
| M | 61 |
| F | 57 |
| M | 72 |
| M | 70 |
| M | 62 |

~EC50 = 150 ng/ml

TABLE 5

A) Efficacy of test compound 8WWWWWWW
in human explant studies
Compound 8WWWWWWW (BC3 analysis)

| Conc. of compound (ug/ml) | Average of 8 donors | |
|---|---|---|
| | % inhibition | SDM |
| 0.01 | 2.85 | 2.85 |
| 0.02 | 46.39 | 15.95 |
| 0.04 | 23.50 | 10.57 |
| 0.08 | 76.91 | 5.99 |
| 0.15 | 88.47 | 3.25 |
| 0.3 | 95.03 | 1.70 |
| 0.6 | 98.03 | 0.90 |
| 1.25 | 100.30 | 0.55 |

B) Human donor information for test compound
8WWWWWWW studies
Test compound (Donor info)

| Sex | Age |
|---|---|
| F | 69 |
| F | 69 |
| F | 63 |
| M | 60 |
| M | 57 |
| F | 72 |
| F | 65 |
| F | 75 |

~EC50 = 40-160 ng/ml

TABLE 6

A) Efficacy of test compound 8NNNNNNN in human explant studies
Test compound 8NNNNNNN (BC3 analysis)

| Conc. of compound (ug/ml) | Average of 4 donors | |
|---|---|---|
| | % inhibition | SDM |
| 0.04 | 70.22 | |
| 0.08 | 84.46 | |
| 0.15 | 66.74 | 10.97 |
| 0.3 | 73.14 | 19.73 |
| 0.6 | 98.93 | 0.92 |
| 1.25 | 99.43 | 1.44 |
| 2.5 | 98.66 | 2.20 |
| 5 | 100.21 | 1.15 |
| 10 | 101.15 | 0.42 |

B) Human donor information for test compound 8NNNNNNN studies
Test compound (Donor info)

| Sex | Age |
|---|---|
| M | 63 |
| F | 68 |
| F | 72 |
| F | 60 |

~EC50 = less than 40 ng/ml

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A compound of the formula (I):

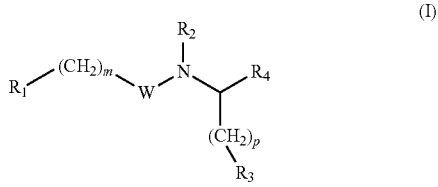

or a pharmaceutically acceptable salt thereof,
wherein
W is —C(O)—;
$R_1$ is biphenyl optionally substituted with one or more of $R_5$ or $R_6$, and when $R_1$ is substituted with more than one of $R_5$ or $R_6$, the substituents can be identical or different;
$R_2$ is hydrogen;
$R_3$ is —$CO_2H$;
$R_4$ is —$CONR_9R_{10}$;
$R_5$ is aryl, heteroaryl, —$(CH_2)_n$-aryl, —$(CH_2)_n$-heteroaryl, —O-aryl, —O-heteroaryl, —S-aryl, —S-heteroaryl, —NH-aryl, —NH-heteroaryl, —CO—($C_1$-$C_6$) alkyl, —CO-aryl, —CO-heteroaryl, —$SO_2$($C_1$-$C_6$) alkyl, —$SO_2$-aryl, —$SO_2$-heteroaryl, —$SO_2$NH-aryl, —$SO_2$NH-heteroaryl, —$NHSO_2$($C_1$-$C_6$) alkyl, —$NHSO_2$-aryl, —$NHSO_2$-heteroaryl, —NHCO-aryl, —NHCO-heteroaryl, —CONH-aryl, —CONH-heteroaryl, ($C_1$-$C_6$) alkyl, —O—($C_1$-$C_6$) alkyl, —S—($C_1$-$C_6$) alkyl, —NH—($C_1$-$C_6$) alkyl, —NHCO—($C_1$-$C_6$) alkyl, —CONH—($C_1$-$C_6$) alkyl, —O—($C_3$-$C_6$) cycloalkyl, —S—($C_3$-$C_6$) cycloalkyl, —NH—($C_3$-$C_6$) cycloalkyl, —NHCO—($C_3$-$C_6$) cycloalkyl, or —CONH—($C_3$-$C_6$ cycloalkyl; each alkyl, aryl, cycloalkyl, or heteroaryl optionally substituted with one or more of $R_6$, and when $R_5$ is substituted with more than one $R_6$ the substituents can be identical or different;
$R_6$ is hydrogen, halogen, —CN, —$OCF_3$, —$CF_3$, —OH, —SH, —$NR_7R_8$, —$CONR_7R_8$—$NR_8COR_7$— $NR_8CO_7R_7$—$CO_7R_7$—$SO_2(C_1$-$C_6$) alkyl, —$SO_2$-aryl, —$SO_2$-heteroaryl, —$SO_2R_7$—$NR_7SO_2R_8$, —$SO_7NR_7R_8$; ($C_1$-$C_6$) alkyl, —O—($C_1$-$C_6$) alkyl, —S—($C_1$-$C_6$) alkyl, —NH—($C_1$-$C_6$) alkyl, —NHCO—($C_1$-$C_6$) alkyl, —CONH—($C_1$-$C_6$) alkyl, —O—($C_3$-$C_6$) cycloalkyl, —S—($C_3$-$C_6$) cycloalkyl, —NH—($C_3$-$C_6$) cycloalkyl, —NHCO—($C_3$-$C_6$) cycloalkyl, —CONH—($C_3$-$C_6$) cycloalkyl, heterocycloalkyl, —($C_1$-$C_6$) ($C_7$-$C_6$) alkynyl, ($C_2$-$C_6$) alkenyl, —O—($C_1$-$C_6$) alkyl-($C_3$-$C_6$) cycloalkyl, —O-alkenyl, —O—($C_1$-$C_6$) alkyl substituted with aryl, aryl, heteroaryl, —$(CH_2)_n$-aryl, —$(CH_2)_n$-heteroaryl, —O-aryl, —O-heteroaryl, —S-aryl, or —S-heteroaryl; each alkyl, aryl, cycloalkyl, heterocycloalkyl, heteroaryl, alkenyl, or alkynyl optionally substituted with one or more of $R_{13}$;
$R_{12}$ is —$SO_2$-heteroaryl, heterocycloalkyl, heteroaryl, —$(CH_2)_n$-heteroaryl, —O-heteroaryl, or —S-heteroaryl; each heterocycloalkyl, or heteroaryl optionally substituted with one or more of $R_{13}$;
$R_7$ and $R_8$ are each independently hydrogen, ($C_1$-$C_6$) alkyl, aryl, heteroaryl, ($C_2$-$C_6$) alkenyl, ($C_7$-$C_6$) alkynyl, cycloalkyl, —$(CH_2)_n$-heteroaryl; or $R_7$ and $R_8$ together with the atom to which they are attached may form a five- to seven-membered cyclic group containing up to 3 heteroatoms selected from N, O, or S;
$R_9$ and $R_{10}$ are each independently hydrogen, ($C_1$-$C_6$) alkyl, ($C_1$-$C_6$) alkyl-OH, ($C_1$-$C_6$) alkyl-O—($C_1$-$C_6$) alkyl, aryl, cycloalkyl, heteroaryl, ($C_2$-$C_6$) alkenyl, ($C_2$-$C_6$) alkynyl, bicyclic aryl, tricyclic aryl, bicyclic heteroaryl, or tricyclic heteroaryl, each alkyl, aryl, cycloalkyl, or heteroaryl optionally substituted with one or more $R_{12}$; or $R_9$ and $R_{10}$ together may form a five- to seven-membered cyclic group containing up to 3 heteroatoms selected from N, O, or S;
$R_{11}$ is aryl, heteroaryl, or cycloalkyl;
$R_{13}$ is halogen, —O—($C_1$-$C_6$) alkyl, —$CO_2H$, —OH, —$CF_3$, hydrogen, ($C_1$-$C_6$) alkyl, aryl, heteroaryl, ($C_2$-$C_6$) alkenyl, ($C_2$-$C_6$) alkynyl, cycloalkyl, cycloalkyl substituted with —OH, aryl substituted with —$NH_2$, aryl substituted with —O—($C_1$-$C_6$) alkyl, —$(CH_2)_n$-aryl, or —$(CH_2)_n$-heteroaryl;
m is 0;
n is 0-4; and
p is 2.

2. The compound of claim 1 of the formula (Ia):

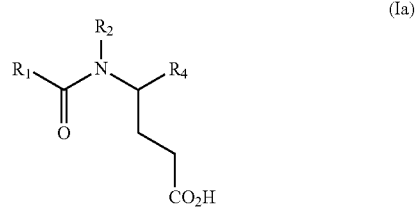

or a pharmaceutically acceptable salt thereof, wherein $R_1$, $R_2$, and $R_4$ are defined as in claim 1.

3. The compound of claim 1 of the formula (Id):

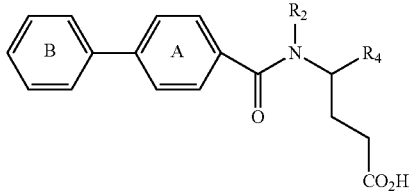

(Id)

or a pharmaceutically acceptable salt thereof,
wherein
ring A and ring B are each independently optionally substituted with one or more of $R_5$ and $R_6$; and
$R_2$, $R_4$, $R_5$, and $R_6$ are defined as in claim 1.

4. The compound of claim 3 of the formula (Id-1):

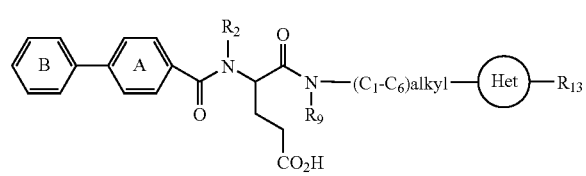

(Id-1)

or a pharmaceutically acceptable salt thereof, wherein
ring A and ring B are defined as in claim 3,
Het is —$SO_2$-heteroaryl, heterocycloalkyl, heteroaryl, —$(CH_2)_n$-heteroaryl, —O-heteroaryl, or —S-heteroaryl, and
$R_2$, $R_4$, $R_5$, $R_6$, $R_9$ and $R_{13}$ are defined as in claim 3.

5. The compound of claim 3 or a pharmaceutically acceptable salt thereof, wherein $R_2$ is hydrogen;
$R_4$ is ![structure showing acyl group connected to NH-C(CH3)2-CH2-thienyl-R13]

and
$R_{13}$ is defined as in claim 3.

6. The compound of claim 5 or a pharmaceutically acceptable salt thereof, wherein $R_{13}$ is halogen.

7. A compound selected from:
$N^2$-(1,1'-biphenyl-4-ylcarbonyl)-$N^1$-(2-furylmethyl)-L-α-glutamine,
$N^2$-biphenyl-4-ylcarbonyl)-$N^1$-(pyridin-4-ylmethyl)-L-α-glutamine,
$N^2$-biphenyl-4-ylcarbonyl)-$N^1$-(2-morpholin-4-ylethyl)-L-α-glutamine
$N^2$-(biphenyl-4-ylcarbonyl)-$N^1$-[2-(2-thienyl)ethyl]-L-α-glutamine,
N-[2-(5-chloro-2-thienyl)-1,1-dimethylethyl]-$N^2$-[(3-fluorobiphenyl-4-yl)carbonyl]-L-α-glutamine,
N-[2-(5-chloro-2-thienyl)-1,1-dimethylethyl]-$N^2$-[(3',4'-difluorobiphenyl-4-yl)carbonyl]-L-α-glutamine, and
$N^2$-(biphenyl-4-ylcarbonyl)-N-[2-(5-chloro-2-thienyl)-1,1-dimethylethyl]-L-α-glutamine,
or a pharmaceutically acceptable salt thereof.

8. A composition comprising the compound or a pharmaceutically acceptable salt of the compound of claim 1 and a pharmaceutically acceptable carrier.

9. The composition of claim 8, wherein the pharmaceutically acceptable carrier is suitable for oral administration and the composition comprises an oral dosage form.

10. A method for treating a disorder, in an animal in need thereof, wherein the disorder is osteoarthritis, wherein the method comprises administering an effective dose of the compound of claim 1, or a pharmaceutically acceptable salt.

* * * * *